United States Patent
Monenschein et al.

(10) Patent No.: US 12,370,192 B2
(45) Date of Patent: Jul. 29, 2025

(54) AZOLE-FUSED PYRIDAZIN-3(2H)-ONE DERIVATIVES

(71) Applicant: TAKEDA PHARMACEUTICAL COMPANY LIMITED, Osaka (JP)

(72) Inventors: Holger Monenschein, San Diego, CA (US); Sean Murphy, San Diego, CA (US); Scott Olsen, San Diego, CA (US); Natasha O'Rourke, San Diego, CA (US); Holly Reichard, San Diego, CA (US); Melinda Davis, San Diego, CA (US); Betty Lam, San Diego, CA (US)

(73) Assignee: Takeda Pharmaceutical Company Limited, Osaka (JP)

( * ) Notice: Subject to any disclaimer, the term of this patent is extended or adjusted under 35 U.S.C. 154(b) by 806 days.

(21) Appl. No.: 17/753,803

(22) PCT Filed: Sep. 15, 2020

(86) PCT No.: PCT/US2020/050823
§ 371 (c)(1),
(2) Date: Mar. 15, 2022

(87) PCT Pub. No.: WO2021/055326
PCT Pub. Date: Mar. 25, 2021

(65) Prior Publication Data
US 2023/0028114 A1   Jan. 26, 2023

Related U.S. Application Data

(60) Provisional application No. 62/901,052, filed on Sep. 16, 2019.

(51) Int. Cl.
*A61K 31/5025* (2006.01)
*C07D 471/04* (2006.01)

(52) U.S. Cl.
CPC ........ *A61K 31/5025* (2013.01); *C07D 471/04* (2013.01); *C07B 2200/05* (2013.01)

(58) Field of Classification Search
CPC .............. A61K 31/5025; C07D 471/04; C07D 487/04; C07B 2200/05; A61P 25/00
See application file for complete search history.

(56) References Cited

U.S. PATENT DOCUMENTS

| | | |
|---|---|---|
| 3,794,726 A | 2/1974 | Ariyan |
| 4,959,367 A | 9/1990 | King |
| 4,959,368 A | 9/1990 | Awaya et al. |
| 6,106,864 A | 8/2000 | Dolan et al. |
| 6,894,043 B1 | 5/2005 | Pirotte et al. |
| 7,253,164 B2 | 8/2007 | Molteni et al. |
| 7,262,190 B2 | 8/2007 | Desos et al. |
| 8,642,660 B2 | 2/2014 | Goldfarb |
| 9,150,591 B2 | 10/2015 | Kori et al. |
| 9,499,568 B2 | 11/2016 | Kori et al. |
| 9,556,130 B2 | 1/2017 | Hitchcock et al. |
| 9,770,450 B2 | 9/2017 | Hitchcock et al. |
| 9,884,875 B2 | 2/2018 | Kori et al. |
| 10,159,677 B2 | 12/2018 | Hitchcock et al. |
| 10,561,662 B2 | 2/2020 | Hitchcock et al. |
| 11,173,161 B2 | 11/2021 | Hitchcock et al. |
| 2004/0242571 A1 | 12/2004 | Gouliaev et al. |
| 2005/0065146 A1 | 3/2005 | Cordi et al. |
| 2005/0165008 A1 | 7/2005 | Francotte et al. |
| 2005/0165064 A1 | 7/2005 | Kajino et al. |
| 2006/0079696 A1 | 4/2006 | Masson et al. |

(Continued)

FOREIGN PATENT DOCUMENTS

| | | |
|---|---|---|
| EP | 1500658 A1 | 1/2005 |
| JP | 2-085851 | 3/1990 |

(Continued)

OTHER PUBLICATIONS

"A Randomized, Double-Blind, Placebo Controlled, Two-Period Cross-Over, Proof of Activity Study to Evaluate the Effects of TAK-041 on Motivational Anhedonia as Add-On to Antipsychotics in Participants With Stable Schizophrenia," <ClinicalTrials.gov,>, Oct. 24, 2017.

Kunugi et al., "TAK-137, an AMPA-R Potentiator with Little Agonistic Effect, Has a Wide Therapeutic Window," Neuropsychopharmacology, vol. 44, No. 5, Sep. 12, 2018, pp. 961-970.

Almarsson and M. J. Zaworotko, Chem. Commun. (2004) 17:1889-1896.

Berge et al., J. Pharm. Sci. (1997) 66:1-19.

Bettler, et al., "Review: Neurotransmitter Receptors II AMPA and Kainate Receptors", Neuropharmacology, vol. 34, pp. 123-139, 1995.

(Continued)

*Primary Examiner* — Adam C Milligan
*Assistant Examiner* — Sophia P Hirakis
(74) *Attorney, Agent, or Firm* — Finnegan, Henderson, Farabow, Garrett & Dunner LLP

(57) ABSTRACT

Disclosed are compounds of Formula (1) and pharmaceutically acceptable salts thereof, wherein α, β, n, $R^4$, $R^5$, $R^6$, $R^8$, $R^9$, $R^{10}$, $R^{11}$, $X^1$, $X^2$, $X^3$ and $X^7$ are defined in the specification. This disclosure also relates to materials and methods for preparing compounds of Formula (1), to pharmaceutical compositions comprising them, and to their use for treating diseases, disorders, and conditions associated with GPR139.

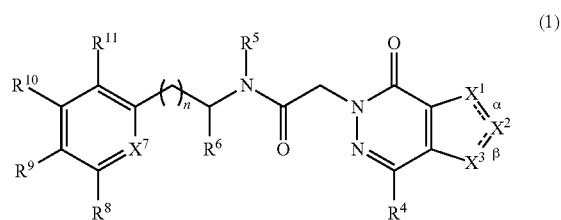

28 Claims, No Drawings

(56) References Cited

U.S. PATENT DOCUMENTS

| | | |
|---|---|---|
| 2006/0128697 A1 | 6/2006 | Desos et al. |
| 2007/0004709 A1 | 1/2007 | Francotte et al. |
| 2009/0163545 A1 | 6/2009 | Goldfarb |
| 2009/0281107 A1 | 11/2009 | Congy et al. |
| 2010/0009974 A1 | 1/2010 | Francotte et al. |
| 2010/0010090 A1 | 1/2010 | Dominguez-Manzanares |
| 2010/0240635 A1 | 9/2010 | Cordi et al. |
| 2011/0034451 A1 | 2/2011 | Heinelt et al. |
| 2011/0118236 A1 | 5/2011 | Mochizuki et al. |
| 2012/0142672 A1 | 6/2012 | Koike et al. |
| 2016/0145218 A1 | 5/2016 | Hitchcock et al. |
| 2023/0002318 A1 | 1/2023 | Ikeda et al. |
| 2023/0134307 A1 | 5/2023 | Ikeda et al. |
| 2023/0150934 A1 | 5/2023 | Ikeda et al. |
| 2023/0227416 A1 | 7/2023 | Bowlin et al. |
| 2023/0310441 A1 | 10/2023 | Arkilo et al. |

FOREIGN PATENT DOCUMENTS

| | | |
|---|---|---|
| JP | 4-37742 | 2/1992 |
| JP | 4-119890 | 4/1992 |
| JP | 7-137462 | 5/1995 |
| JP | 2009-119088 A1 | 6/2009 |
| JP | 2009-248543 | 10/2009 |
| WO | WO 1991/11172 A1 | 8/1991 |
| WO | WO 1994/02518 A1 | 2/1994 |
| WO | WO 1998/055148 A1 | 12/1998 |
| WO | WO 1999/042456 A2 | 8/1999 |
| WO | WO 2001/030330 A2 | 5/2001 |
| WO | WO 2001/032013 A1 | 5/2001 |
| WO | WO 2001/040210 A1 | 6/2001 |
| WO | WO 2004/022521 A1 | 3/2004 |
| WO | WO 2004/099217 A1 | 11/2004 |
| WO | WO 2004/108673 A2 | 12/2004 |
| WO | WO 2007/073303 A2 | 6/2007 |
| WO | WO 2007/075387 A1 | 7/2007 |
| WO | WO 2007/147208 A1 | 12/2007 |
| WO | WO 2008/018827 A1 | 2/2008 |
| WO | WO 2008/085682 A2 | 7/2008 |
| WO | WO 2008/089005 A2 | 7/2008 |
| WO | WO 2008/094556 A3 | 8/2008 |
| WO | WO 2009/004430 A1 | 1/2009 |
| WO | WO 2009/061699 A1 | 5/2009 |
| WO | WO 2009/147167 A1 | 12/2009 |
| WO | WO 2010/054067 A1 | 5/2010 |
| WO | WO 2010/083141 A1 | 7/2010 |
| WO | WO 2010/098495 A1 | 9/2010 |
| WO | WO 2010/106249 A1 | 9/2010 |
| WO | WO 2010/140339 A1 | 12/2010 |
| WO | WO 2011/036885 A1 | 3/2011 |
| WO | WO 2011/036889 A1 | 3/2011 |
| WO | WO 2011/138265 A2 | 11/2011 |
| WO | WO 2012/020848 A1 | 2/2012 |
| WO | WO 2014/152917 A2 | 9/2014 |
| WO | WO 2016/020786 | 2/2016 |
| WO | WO 2016/081736 A1 | 5/2016 |
| WO | WO 2020/081999 A1 | 4/2020 |
| WO | WO 2020/097609 A1 | 5/2020 |
| WO | WO 2020/198710 A1 | 10/2020 |
| WO | WO 2021/055295 | 3/2021 |
| WO | WO 2021/055326 A1 | 3/2021 |
| WO | WO 2021/094832 A1 | 5/2021 |
| WO | WO 2021/224680 | 11/2021 |
| WO | WO 2022/058791 | 3/2022 |
| ZA | 981019 | 8/1998 |

OTHER PUBLICATIONS

Boraei et al., "Design and Synthesis of New Phthalazin Based Derivatives as Potential EGFR Inhibitors for the Treatment of Hepatocellular Carcinoma", Bioorganic Chemistry, vol. 85, Dec. 31, 2018, pp. 293-307.

Bowie, et al., "Ionotropic Glutamate Receptors & CNS Disorders", CNS & Neurological Disorders—Drug Targets, vol. 7, pp. 129-143, 2008.

Burk, M. J. et al., "A Convenient Asymmetric Synthesis of Alpha-1-Arylalkylamines Through the Enantioselective Hydrogenation of Enamides," Journal of the American Chemical Society, , vol. 118, Jan. 1, 1996, pp. 5142-5143.

Caddy, C. et al., "Ketamine as the prototype glutamatergic antidepressant: pharmacodynamic actions, and a systematic review and meta-analysis of efficacy," Therapeutic Advances in Psychopharmacology, vol. 4, p. 75-99, 2014.

Carlson et al., "Neural Correlates of Rapid Antidepressant Response to Ketamine in Treatment-Resistant Unipolar Depression: A Preliminary Positron Emission Tomography Study," Biol Psychiatry, 2013, 73(12):1213-1221.

Castellani et al., "Copy Number Variation Distribution in Six Monozygotic Twin Pairs Discordant for Schizophrenia," Twin Research and Human Genetics Apr. 2014; 17(2):108-120.

Castellani et al., "Biological relevance of CNV calling methods using familial relatedness including monozygotic twins," BMC Bioinformatics, 2014, 15:114 (eight pages).

Cecil Textbook of Medicine, edited by Bennet, J.C. and Plum F., 20$^{th}$ edition, vol. 1, pp. 1004-1010, 1996.

Chabchoub, F. et al., "New Method for the Synthesis of Hydrazonates. Reaction of Primary Amines With N-1-Ethoycarbonyl Hydrazonates: Synthesis of 1,2,4-Triazol-5-Ones," Journal De La Societe Chimique De Tunisie, vol. 4, No. 3, 1998, pp. 171-178.

'Chemical Encyclopedia', vol. 4, p. 499-501, scientific publishing house 'The Great Russian Encyclopedia', Moscow, 1995 (English Translation).

Cilibrizzi et al., "6-Methyl-2,4-Disubstituted Pyridazin-3-ones: A Novel Class of Small-Molecule Agonists for Formyl Peptide Receptors," Journal of Medicinal Chemistry, vol. 52, Jul. 29, 2009, pp. 5044-5057.

Database CA [Online] Chemical Abstracts Service, Columbus, Ohio, US; Goldfarb, David Scott: "Method using lifespan-altering compounds for altering the lifespan of eukaryotic organisms, and screening for such compounds," Jun. 25, 2009, XP002754170 (four pages).

Database Registry [Online] Chemical Abstracts Service, Columbus, Ohio, US; Aug. 24, 2008, XP002754167, retrieved from STN; Database accession No. 1043204-06-03 (eight pages).

Database Registry [Online] Chemical Abstracts Service, Columbus, Ohio, US; Mar. 26, 2014, XP002754168, retrieved from STN; Database accession No. 1574302-61-6 (eighteen pages).

Database Registry [Online] Chemical Abstracts Service, Columbus, Ohio, US; Aug. 4, 2010, XP002754169, retrieved from STN; Database accession No. 1234906-37-6 (eighteen pages).

Database Registry [Online], "Benzenesulfonic acid, 3-[8-[5-[2,2-dioxido-7-(3-sulfophenyl)-8Hpyrazolo[5,1-c][1,2,4]thiadiazin-8-ylidene]-1,3-pentadien-1-yl]-2,2-dioxido-1H-pyrazolo[5,1-c][1,2,4]thiadiazin-7-yl]-"Chemical Abstracts Service, Columbus, Ohio, US; 2004, XP002661033 (one page).

Dermer et al., Bio/Technology, 1994, 12:320.

Devonshire, Ian M. et al., "Effects of urethane anaesthesia on sensory processing in the rat barrel cortex revealed by combined optical imaging and electrophysiology," European Journal of Neuroscience (Eur. J. Neurosci.) vol. 32, p. 786-797, 2010.

Diethelm et al., "Amine-Selective Bioconjugation Using Arene Diazonium Salts," Organic Letters, 2014, 16(15), pp. 3908-3911.

Dingledine, et al., "The Glutamate Receptor Ion Channels", Pharmacological Reviews, vol. 51, No. 1, pp. 7-61, 1999.

Dvorak et al., "Identification and SAR of glycine benzamides as potent agonists for the GPR139 receptor," ACS Medicinal Chemistry Letters, Jul. 20, 2015, 6(9), pp. 1015-1018.

Ebejer et al., "Genome-Wide Association Study of Inattention and Hyperactivity-Impulsivity Measured as Quantitative Traits," Twin Research and Human Genetics Apr. 2013; 16(2):560-574.

Farley S. et al., "Antidepressant-like effects of an AMPA Receptor Potentiator Under a Chronic Mild Stress Paradigm," International Journal of Neuropsychopharmacology, Cambridge Univ. Press, Cambridge, vol. 13, No. 9, Oct. 1, 2010, pp. 1207-1218.

Finnin and Morgan, J. Pharm. Sci. 88(10):955-958 (1999).

(56) References Cited

OTHER PUBLICATIONS

Francotte, et al., "Synthesis and pharmacological evaluation of a second generation of pyridothiadiazine 1,1-dioxides acting as AMPA potentiators", Bioorganic & Medicinal Chemistry, vol. 16, pp. 9948-9956, 2008.
Freshney et al., Culture of Animal Cells, A manual of Basic Technique, Alan R. Liss, Inc. 1983, New York (seven pages).
Greene and P. G. Wuts, Protecting Groups in Organic Chemistry (1999).
Hald, et el., "Distinct Structural Features of Cyclothiazide Are Responsible for Effects on Peak Current Amplitude and Desensitization Kinetics at iGluR2", Journal of Molecular Biology, vol. 391, pp. 906-917, 2009.
Haleblian, J. Pharm. Sci. (1975) 64(8):1269-88.
Higuchi and V. Stella "Pro-drugs as Novel Delivery Systems," ACS Symposium Series 14 (1975).
Hitchcock, Stephen A., "Structural Modifications that Alter the P-Glycoprotein Efflux Properties of Compounds," *Journal of Medicinal Chemistry*, 2012, vol. 55, pp. 4877-4895.
Howlett, D. et al., Inhibition of fibril formation in b-amyloid peptide by a novel series of benzofurans, Biochem. J. vol. 340 (1), p. 283-289, 1999.
Hu et al., "Identification of Surrogate Agonists and Antagonists for Orphan G-Protein-Coupled Receptor GPR139," Journal of Biomolecular Screening, 2009, 14:789-797.
Hunter et al., Negative symptoms and psychosocial functioning in schizophrenia: Neglected but important targets for treatment. European Psychiatry, 27(6), 432-436.
Isberg et al., "Computer-Aided Discovery of Aromatic L-a-Amino Acids as Agonists of the Orphan G Protein-Coupled Receptor GPR139", Journal of Chemical Information Modeling, 2014, vol. 54, pp. 1553-1557.
Kandiah, N. et al., "Cerebral white matter disease is independently associated with BPSD in Alzheimer's disease," Journal of the Neurological Sciences (J. Neurol. Sci.) vol. 337, p. 162-166, 2014.
Kattimani, Pramod P. et al., "C 5-Alkyl-1,3,4-Oxadiazol-2-ones Undergo Dealkylation upon Nitrogen Insertion to Form 2H-1,2,4-Triazol-3-ones: Synthesis of 1,2,4-Triazol-3-one Hybrids with Triazolothiadiazoles and Triazolothiadiazines," *J. Heterocyclic Chem*, 54, 2258-2265 (2017).
Kim Y, Cho HY, Ahn YJ, et al. "Effect of NMDA NR2B antagonist on neuropathic pain in two spinal cord injury models," Pain, vol. 153, p. 1022-1029, 2012.
L'abbe, et al., "Synthesis of Fused Dihydro-1,2,4-thiadiazolimines from Cyano-substituted Azides and Acyl Isothiocyanates", Journal of the Chemical Society, Perkin Transactions 1: Organic and Bio-Organic Chemistry, vol. 1, pp. 27-29, 1993.
Liang and Chen, "Fast-dissolving intraoral drug delivery systems," Expert Opinion in Therapeutic Patents (2001) 11(6):981-986.
Lieberman et al. (ed.), Pharmaceutical Dosage Forms: Tablets, vol. 1-3 (2d ed., 1990).
Asgharnejad et al., "M148. Pharmacokinetic and Pharmacodynamic Properties of the Investigational AMPA Receptor Positive Allosteric Modulator TAK-653 After Single and Multiple Rising Doses in Healthy Volunteers," ACP 57th Annual Meeting: Poster Session I (one page).
Xu, et al., "Safety, Pharmacokinetics, and Pharmacodynamics of TAK-831, a Selective D-Amino Acid Oxidase Inhibitor, in Healthy Volunteers," ACNP 57th Annual Meeting: Poster Session III (two pages).
Maidment, I. D. et al., "Efficacy of Memantine on Behavioral and Psychological Symptoms Related to Dementia: A Systematic Meta-Analysis," The Annals of Pharmacotherapy (Ann. Pharmacother.) vol. 42, p. 32-38, 2007.
Malinow, et al., "AMPA Receptor Trafficking and Synaptic Plasticity", Ann. Rev. Neurosci, vol. 25, pp. 103-126, 2002.
Matsuo et al., "Molecular cloning and characterization of a novel Gq-coupled orphan receptor GPRg1 exclusively expressed in the central nervous system," Biochemical and Biophysical Research Communications 331 (2005) 363-369.

Morrow, et al., "Recent advances in positive allosteric modulators of the AMPA receptor", Current Opinion in Drug Discovery and Development, vol. 9, pp. 571-579, 2006.
Nesaragi, Aravind R. et al., "Microwave assisted regioselective synthesis of quinoline appended triazoles as potent anti-tubercular and antifungal agents via copper (I) catalyzed cycloaddition," Bioorganic & Medicinal Chemistry Letters, 41, (2021) (ten pages).
Nisenbaum Eric S. et al., "Positive Allosteric Modulation of AMPA Receptors: A Novel Potential Antidepressant Therapy,Glutamate-Based Therapeutics for Psychiatric Disorders," Jan. 1, 2010, pp. 39-56.
O'Roak et al., "Exome sequencing in sporadic autism spectrum disorders identifies severe de novo mutations," Nature Genetics Jun. 2011; 43(6):585-589.
Okuzumi, et al., "Efficient solid-phase synthesis of diverse 1,2,3-benzotriazin-4-ones using tert-butyl nitrite", Tetrahedron Letters, 2003, vol. 44, pp. 5539-5542.
Peeters, M. et al., "Effects of Pan- and Subtype-Selective N-Methyl-D-aspartate Receptor Antagonists on Cortical Spreading Depression in the Rat: Therapeutic Potential for Migraine," The Journal of Pharmacology and Experimental Therapeutics, vol. 321, No. 2, pp. 564-572 (2007).
"Phase 1 TAK-041 First-in-Human Safety, Tolerability, and Pharmacokinetics Study," <ClinicalTrialsgov>, Apr. 22, 2016.
Phillips, et al., "50-Alkyl-benzothiadiazides: A New Subgroup of AMPA Receptor Modulators with Improved Affinity", Bioorganic & Medicinal Chemistry, vol. 10, pp. 1229-1248, 2002.
Preskorn et al., "An Innovative Design to Establish Proof of Concept of the Antidepressant Effects of the NR2B Subunit Selective N-Methyl-D-Aspartate Antagonist, CP-101,606, in Patients With Treatment- Refractory Major Depressive Disorder," *J. Clin. Psychopharmacol.*, 28, pp. 631-637 (2008).
Reichard et al.: "Discovery of TAK-041: a Potent and Selective GPR139 Agonist Explored for the Treatment of Negative Symptoms Associated with Schizophrenia", Journal of Medicinal Chemistry, vol. 64, No. 15, pp. 11527-11542 (2021).
Sartorius et al., "Remission of Major Depression Under Deep Brain Stimulation of the Lateral Habenula in a Therapy-Refractory Patient," Biol Psychiatry 2010 67: e9-e11.
Schiffer, Hans et al.: "The Selective GPR139 Agonist TAK041 Reverses Anhedonia and Social Interaction Deficits In Rodent Models Related To Negative Symptoms In Schizophrenia," Abstract S180 in SIRS 2020 Abstracts.
Schiffer, Hans, et al., "The Selective GPR139 Agonist TAK-041 Reverses Anhedonia and Social Interaction Deficits in Rodent Models Related to Negative Symptoms in Schizophrenia," poster (one page).
Schmidt et al., "Mass spectroscopy of natural products. 20-Quinazoline carboxylic acids 4-Comparative positive and negative ion mass spectroscopic studies of 3,4-dihydroquinazolin-4-on-3-ylalkanoic acids and 3,4-dihydro-1,2,3-benzotriazin-4-on-3-ylal kanoic acids," *Organic Mass Spectrometry*, vol. 20, No. 3, Mar. 1, 1985, pp. 184-188.
Shi, et al., "Discovery and SAR of a Series of Agonists at Orphan G Protein-Coupled Receptor 139" ACS Medicinal Chemistry Letters, Apr. 14, 2011, vol. 2, No. 4, pp. 303-306.
Smith et al., "Advances in functional and structural MR image analysis and implementation as FSL" In NeuroImage (vol. 23, pp. S208-S219).
Somagond et al., "Microwave-Assisted Synthesis of November Symmetric Bis-1,2,4-triazolin-3-ones as Potent Inhibitors of CYP51: An Antifungal Activity Study", *Arch. Pharm. Chem. Life Sci.*, 2019;352:1900013.
Strauss et al., "A New Perspective on Anhedonia in Schizophrenia," *Am J Psychiatry* 2012; 169:364-373.
Thompson et al., "7-Chloro-3-methyl-3 ,4-dihydro-2H-1,2,4-benzothiadiazine-S,S-dioxide (IDRA 21), a congener of aniracetam, potently abates pharmacologically induced cognitive impairments in patas monkeys", Proc. Natl. Acad. Sci. USA, vol. 92, pp. 7667-7671 (1995).
Treadway et al., "Reconsidering Anhedonia in Depression: Lessons from Translational Neuroscience," *Neurosci. Biobehav. Rev.*, 35(3): 537-555 (2011).

(56) References Cited

OTHER PUBLICATIONS

Vaisburg et al., "(2-Amino-phenyl)-amides of-omega—substituted alkanoic acids as new histone deacetylase inhibitors," Bioorganic & Medicinal Chemistry Letters, vol. 14, No. 1, Jan. 5, 2004, pp. 283-287.
Verma et al., "Current Status of Drug Delivery Technologies and Future Directions," *Pharmaceutical Technology On-line*, (2001) 25(2):1-14.
Ward et al., "Recent Advances in the Discovery of Selective AMPA Receptor Positive Allosteric Modulators", *Current Medicinal Chemistry*, vol. 17, No. 30, pp. 3503-3513 (2010).
Yang et al., "Ketamine blocks bursting in the lateral habenula to rapidly relieve depression," *Nature*, 2018 554, 317-322.
Anthony Bouillon, et al., "*In silico* screening on the three-dimensional model of the *Plasmodium vivax* SUB1 protease leads to the validation of a novel antiparasite compound," *J Biol Chem.*, vol. 288, pp. 18561-18573 (2013).
A. Boraei et al., "Design and Synthesis of New Phthalazin Based Derivatives as Potential EGFR Inhibitors for the Treatment of Hepatocellular Carcinoma", Bioorganic Chemistry, vol. 85, Dec. 31, 2018 (Dec. 31, 2018), pp. 293-307, XP002800723, DOI: 10.1016/j.bioorg.2018.12.039.
A. Cilibrizzi et al., "6-Methyl-2,4-Disubstituted Pyridazin-3-ones: A Novel Class of Small-Molecule Agonists for Formyl Peptide Receptors," Journal of Medicinal Chemistry, vol. 52, Jul. 29, 2009 (Jul. 29, 2009), pp. 5044-5057, XP002800722, DOI: 10.1021/jm900592h.
International Search Report for International Application No. PCT/US2020/050823, dated Nov. 2, 2020 (three pages).
Written Opinion for International Application No. PCT/US2020/050823 (five pages).

AZOLE-FUSED PYRIDAZIN-3(2H)-ONE DERIVATIVES

This application is a national stage filing under 35 U.S.C. § 371 of International Application No. PCT/US2020/050823, filed Sep. 15, 2020, which claims priority to U.S. Provisional Application No. 62/901,052, filed Sep. 16, 2019, the contents of each of which are incorporated by reference herein in their entirety.

This disclosure relates to azole-fused pyridin-3(2H)-one derivatives which are agonists of GPR139, to pharmaceutical compositions which comprise them; and to their use to treat diseases, disorders, and conditions associated with GPR139, including schizophrenia, depression and substance use disorder.

GPR139 is an orphan G-protein coupled receptor. GPR139 may be coupled with Gs, Gq and Gi signaling and appears to be constitutively active when recombinantly expressed in mammalian cells. GPR139 is expressed in the central nervous system (CNS) and to a lesser extent in the pancreas and pituitary and at low levels in other peripheral tissues.

GPR139 is highly conserved among different species. For example, human, mouse, and rat GPR139 protein sequences share greater than 94% identity at the amino acid level. The predominant expression in the brain and high degree of sequence homology across different species, suggest GPR139 has an important role in physiology.

We have discovered that GPR139 has its strongest expression in the medial habenular nucleus of mice. The habenula receives inputs from the basal ganglia and the limbic system and sends outputs to midbrain and forebrain structures which contain dopaminergic and serotonergic neurons. Habenular nuclei are involved in reward, pain processing, reproductive behavior, nutrition, sleep-wake cycles, stress responses, cognition and learning.

Several findings suggested a role of the habenula in schizophrenia. Large calcifications in the pineal gland and habenula are more common in people suffering from schizophrenia, and an fMRI study has shown altered activation of the habenula in patients with schizophrenia. Also, following an error in a difficult matching-to-sample task, the habenula was activated in control subjects, but not in patients with schizophrenia. Chronic treatment with cocaine or amphetamine are damaging to the output pathways of the habenula in rats resulting in a schizophrenic-like state. Modulators of GPR139 are expected to be useful for treating schizophrenia and other CNS disorders such as depression, autism and substance use disorder.

Published PCT applications WO 2016/081736 and WO 2014/152917 describe activators of GPR139. In addition, Vignir Isberg, Kirsten B. Andersen, Christoph Bisig, et al., *J. Chem. Model.* 54:1553-57 (2014) and Feng Shi, Jing Kang Shen, Danqi Chen, et al., *Med. Chem. Lett.* 2, 303-06 (2011) describe agonists of GPR139.

This disclosure provides azole-fused pyridin-3(2H)-one derivatives, tautomers thereof, and pharmaceutically acceptable salts of any of the foregoing. This disclosure also provides pharmaceutical compositions comprising azole-fused pyridin-3(2H)-one derivatives, tautomers thereof; and pharmaceutically acceptable salts of any of the foregoing, and provides for the use of azole-fused pyridin-3(2H)-one derivatives, tautomers thereof, and pharmaceutically acceptable salts of any of the foregoing to treat diseases, disorders and conditions associated with GPR139, including schizophrenia and depression.

One aspect of the disclosure provides a compound of Formula 1:

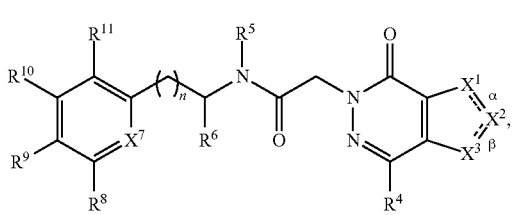

a tautomer thereof, or a pharmaceutically acceptable salt of the compound or tautomer, wherein:

α is a single bond, β is a double bond, $X^1$ is $NR^{1N}$, and either (i) $X^2$ is N and $X^3$ is $CR^{3C}$ or (ii) $X^2$ is $CR^2$ and $X^3$ is selected from N and $CR^{3C}$; or α is a double bond, β is a single bond, $X^3$ is $NR^{3N}$ and either (i) $X^1$ is N and $X^2$ is $CR^2$ or (ii) $X^1$ is $CR^{1C}$ and $X^2$ is selected from N and $CR^2$;

n is selected from 0 and 1;

$R^{1C}$, $R^2$, $R^{3C}$ and $R^4$ are each independently selected from
  (a) hydrogen; and
  (b) $C_{1-6}$ alkyl and $C_{3-8}$ cycloalkyl, each unsubstituted or substituted with 1 to 3 substituents independently selected from halo;

$R^{1N}$ and $R^{3N}$ are each independently selected from $C_{1-6}$ alkyl, $C_{3-8}$ cycloalkyl and $C_{6-10}$ aryl, each unsubstituted or substituted with 1 to 3 substituents independently selected from halo;

$R^5$ is selected from hydrogen and $C_{1-6}$ alkyl; and $R^6$ is selected from $C_{1-6}$ alkyl and $C_{3-8}$ cycloalkyl; or $R^5$ and $R^6$, together with the nitrogen and carbon atoms to which they are each respectively attached, form a $C_{3-6}$ heterocyclic ring; the heterocyclic ring being monocyclic and having one ring atom which is a heteroatom;

$X^7$ is selected from N and $CR^7$;

$R^7$ is selected from
  (a) hydrogen, halo, cyano, hydroxy and amino; and
  (b) $C_{1-6}$ alkyl and $C_{1-6}$ alkoxy, each unsubstituted or substituted with 1 to 3 substituents independently selected from halo;

$R^8$ and $R^9$ are each independently selected from
  (a) hydrogen, halo, cyano, hydroxy and amino; and
  (b) $C_{1-6}$ alkyl and $C_{1-6}$ alkoxy, each unsubstituted or substituted with 1 to 3 substituents independently selected from halo; or $R^8$ and $R^9$, together with the carbon atoms to which they are attached, form a
  $C_{4-5}$ heterocyclic ring, the heterocyclic ring having one or two ring atoms that are heteroatoms, each of heteroatoms being independently selected from N, O and S;

$R^{10}$ and $R^{11}$ are each independently selected from
  (a) hydrogen, halo; cyano, hydroxy and amino; and
  (b) $C_{1-6}$ alkyl and $C_{1-6}$ alkoxy, each unsubstituted or substituted with 1 to 3 substituents independently selected from halo.

Another aspect of the disclosure provides a compound which is selected from the example compounds, their tautomers, and pharmaceutically acceptable salts of any of the foregoing.

A further aspect of the disclosure provides a pharmaceutical composition comprising a compound of Formula 1, a tautomer thereof, or a pharmaceutically acceptable salt of the compound of Formula 1 or tautomer thereof; and a pharmaceutically acceptable excipient.

An additional aspect of the disclosure provides a compound of Formula 1, a tautomer thereof, or a pharmaceutically acceptable salt of the compound of Formula 1 or tautomer thereof, for use as a medicament.

Another aspect of the disclosure provides a compound of Formula 1, a tautomer thereof, or a pharmaceutically acceptable salt of the compound of Formula 1 or tautomer thereof, for treating a disease, disorder or condition associated with GPR139.

A further aspect of the disclosure provides a compound of Formula 1, a tautomer thereof, or a pharmaceutically acceptable salt of the compound of Formula 1 or tautomer thereof, for use in treating a disease, disorder or condition selected from schizophrenia, autism spectrum disorder, sleep disorders, depression, bipolar disorder, cognitive impairment, attention deficit hyperactivity disorder, post-traumatic stress disorder, substance use disorder, substance abuse, drug addiction, eating disorders, obsessive compulsive disorder, anxiety disorders, epilepsy, pain, fibromyalgia, Alzheimer's disease and Parkinson's disease.

An additional aspect of the disclosure provides a compound of Formula 1, a tautomer thereof, or a pharmaceutically acceptable salt of the compound of Formula 1 or tautomer thereof, for the manufacture of a medicament for the treatment of a disease, disorder or condition associated with GPR139.

Another aspect of the disclosure provides a method for activating GPR139 in a subject, the method comprising administering to the subject a compound of Formula 1, a tautomer thereof, or a pharmaceutically acceptable salt of the compound of Formula 1 or tautomer thereof.

A further aspect of the disclosure provides a method for treating a disease, disorder or condition associated with GPR139, the method comprising administering to the subject an effective amount of a compound of Formula 1, a tautomer thereof, or a pharmaceutically acceptable salt of the compound of Formula 1 or tautomer thereof.

An additional aspect of the disclosure provides a method for treating a disease, disorder or condition in a subject, the method comprising administering to the subject an effective amount of a compound of Formula 1, a tautomer thereof; or a pharmaceutically acceptable salt of the compound of Formula 1 or tautomer thereof, wherein the disease, disorder or condition is selected from schizophrenia, autism spectrum disorder, sleep disorders, depression, bipolar disorder, cognitive impairment, attention deficit hyperactivity disorder, post-traumatic stress disorder, substance use disorder, substance abuse, drug addiction, eating disorders, obsessive compulsive disorder, anxiety disorders, epilepsy, pain, fibromyalgia, Alzheimer's disease and Parkinson's disease.

A further aspect of the disclosure provides a compound of Formula 1, a tautomer thereof, or a pharmaceutically acceptable salt of the compound of Formula 1 or tautomer thereof; and at least one additional pharmacologically active agent.

Unless otherwise indicated, this disclosure uses definitions provided below.

"Substituted," when used about a chemical substituent or moiety (e.g., a $C_{1-6}$ alkyl group), means that one or more hydrogen atoms of the substituent or moiety have been replaced with one or more non-hydrogen atoms or groups, provided valence requirements are met and a chemically stable compound results from the substitution.

"About" or "approximately," when used about a measurable numerical variable, refers to the indicated value of the variable and to all values of the variable that are within the experimental error of the indicated value or within ±10 percent of the indicated value, whichever is greater.

"Agonist" refers to both full agonists and partial agonists.

"Alkyl" refers to straight chain and branched saturated hydrocarbon groups, generally having a specified number of carbon atoms (e.g., $C_{1-4}$ alkyl refers to an alkyl group having 1 to 4 (i.e., 1, 2, 3 or 4) carbon atoms, $C_{1-6}$ alkyl refers to an alkyl group having 1 to 6 carbon atoms, and so on). Examples of alkyl groups include methyl, ethyl, n-propyl, n-butyl, s-butyl, i-butyl, t-butyl, pent-1-yl, pent-2-yl, pent-3-yl, 3-methylbut-1-yl, 3-methylbut-2-yl, 2-methylbut-2-yl, 2,2,2-trimethyleth-1-yl, n-hexyl, and the like.

"Alkanediyl" refers to divalent alkyl groups, where alkyl is defined above, and generally having a specified number of carbon atoms (e.g., $C_{1-4}$ alkanediyl refers to an alkanediyl group having 1 to 4 (i.e., 1, 2, 3 or 4) carbon atoms, $C_{1-6}$ alkanediyl refers to an alkanediyl group having 1 to 6 carbon atoms, and so on). Examples of alkanediyl groups include methylene, ethane-1,1-diyl, ethane-1,2-diyl, propane-1,3-diyl, propane-1,2-diyl, propane-1,1-diyl, propane-2,2-diyl, butane-1,4-diyl, butane-1,3-diyl, butane-1,2-diyl, butane-1,1-diyl, isobutane-1,3-diyl, isobutane-1,1-diyl, isobutane-1,2-diyl, and the like.

"Alkenyl" refers to straight chain and branched hydrocarbon groups having one or more carbon-carbon double bonds, and generally having a specified number of carbon atoms. Examples of alkenyl groups include ethenyl, 1-propen-1-yl, 1-propen-2-yl, 2-propen-1-yl, 1-buten-1-yl, 1-buten-2-yl, 3-buten-1-yl, 3-buten-2-yl, 2-buten-1-yl, 2-buten-2-yl, 2-methyl-1-propen-1-yl, 2-methyl-2-propen-1-yl, 1,3-butadien-1-yl, 1,3-butadien-2-yl, and the like.

"Alkynyl" refers to straight chain or branched hydrocarbon groups having one or more triple carbon-carbon bonds, and generally having a specified number of carbon atoms. Examples of alkynyl groups include ethynyl, 1-propyn-1-yl, 2-propyn-1-yl, 1-butyn-1-yl, 3-butyn-1-yl, 3-butyn-2-yl, 2-butyn-1-yl, and the like.

"Alkoxy" refers to straight chain and branched saturated hydrocarbon groups attached through an oxygen atom, generally having a specified number of carbon atoms (e.g., $C_{1-4}$ alkoxy refers to an alkoxy group having 1 to 4 (i.e., 1, 2, 3 or 4) carbon atoms, $C_{1-6}$ alkoxy refers to an alkoxy group having 1 to 6 carbon atoms, and so on). Examples of alkoxy groups include methoxy, ethoxy, n-propoxy, i-propoxy, n-butoxy, s-butoxy, i-butoxy, t-butoxy, pent-1-yloxy, pent-2-yloxy, pent-3-yloxy, 3-methylbut-1-yloxy, 3-methylbut-2-yloxy, 2-methylbut-2-yloxy, 2,2,2-trimethyleth-1-yloxy, n-hexoxy, and the like.

"Halo," "halogen" and "halogeno" may be used interchangeably and refer to fluoro, chloro, bromo, and iodo.

"Haloalkyl," "haloalkenyl," and "haloalkynyl," refer, respectively, to alkyl, alkenyl, and alkynyl groups substituted with one or more halogen atoms, where alkyl, alkenyl, and alkynyl are defined above, and generally having a specified number of carbon atoms. Examples of haloalkyl groups include fluoromethyl; difluoromethyl, trifluoromethyl, chloromethyl, dichloromethyl, trichloromethyl, 1-fluoroethyl, 1,1-difluoroethyl, 1-chloroethyl, 1,1-dichloroethyl, 1-fluoro-1-methylethyl, 1-chloro-1-methylethyl, and the like.

"Cycloalkyl" refers to saturated monocyclic and bicyclic hydrocarbon groups, generally having a specified number of carbon atoms that comprise the ring or rings (e.g., $C_{3-8}$ cycloalkyl refers to a cycloalkyl group having 3 to 8 carbon atoms as ring members) Bicyclic hydrocarbon groups may include isolated rings (two rings sharing no carbon atoms), Spiro rings (two rings sharing one carbon atom), fused rings (two rings sharing two carbon atoms and the bond between the two common carbon atoms), and bridged rings (two rings sharing two carbon atoms, but not a common bond). The cycloalkyl group may be attached through any ring atom unless such attachment would violate valence requirements, and where indicated, may optionally include one or more non-hydrogen substituents unless such substitution would violate valence requirements.

Examples of monocyclic cycloalkyl groups include cyclopropyl, cyclobutyl, cyclopentyl, cyclohexyl, and the like. Examples of fused bicyclic cycloalkyl groups include bicyclo[2.1.0]pentanyl (i.e., bicyclo[2.1.0]pentan-1-yl, bicyclo[2.1.0]pentan-2-yl, and bicyclo[2.1.0]pentan-5-yl), bicyclo[3.1.0]hexanyl, bicyclo[3.2.0]heptanyl, bicyclo[4.1.0]heptanyl, bicyclo[3.3.0]octanyl, bicyclo[4.2.0]octanyl, bicyclo[4.3.0]nonanyl, bicyclo[4.4.0]decanyl, and the like. Examples of bridged cycloalkyl groups include bicyclo[2.1.1]hexanyl, bicyclo[2.2.1]heptanyl, bicyclo[3.1.1]heptanyl, bicyclo[2.2.2]octanyl, bicyclo[3.2.1]octanyl; bicyclo[4.1.1]octanyl, bicyclo[3.3.1]nonanyl, bicyclo[4.2.1]nonanyl, bicyclo[3.2.1]decanyl, bicyclo[4.2.2]decanyl, bicyclo[4.3.1]decanyl, bicyclo[3.3.3]undecanyl, bicyclo[4.3.2]undecanyl, bicyclo[4.3.3]dodecanyl, and the like. Examples of Spiro cycloalkyl groups include spiro[3.3]heptanyl, spiro[2.4]heptanyl, spiro[3.4]octanyl, spiro[2.5]octanyl, spiro[3.5]nonanyl, and the like. Examples of isolated bicyclic cycloalkyl groups include those derived from bi(cyclobutane), cyclobutanecyclopentane, bi(cyclopentane), cyclobutanecyclohexane, cyclopentanecyclohexane, bi(cyclohexane), etc.

"Cycloalkanediyl" refers to divalent cycloalkyl groups, where cycloalkyl is defined above, and generally having a specified number of carbon atoms (e.g., $C_{3-4}$ cycloalkanediyl refers to a cycloalkanediyl group having 3 to 4 (i.e., 3 or 4) carbon atoms, $C_{3-6}$ cycloalkanediyl refers to a cycloalkanediyl group having 3 to 6 carbon atoms, and so on). Examples of cycloalkanediyl groups include cyclopropan-1,1-diyl, cyclopropan-1,2-diyl, cyclobutan-1,1-diyl, cyclobutan-1,2-diyl, and the like.

"Cycloalkylidene" refers to divalent monocyclic cycloalkyl groups, where cycloalkyl is defined above, which are attached through a single carbon atom of the group, and generally having a specified number of carbon atoms that comprise the ring (e.g., $C_{3-6}$ cycloalkylidene refers to a cycloalkylidene group having 3 to 6 carbon atoms as ring members). Examples include cyclopropylidene, cyclobutylidene, cyclopentylidene, and cyclohexylidene.

"Cycloalkenyl" refers to partially unsaturated monocyclic and bicyclic hydrocarbon groups, generally having a specified number of carbon atoms that comprise the ring or rings. As with cycloalkyl groups, the bicyclic cycloalkenyl groups may include isolated, spiro, fused, or bridged rings. Similarly, the cycloalkenyl group may be attached through any ring atom, and where indicated, may optionally include one or more non-hydrogen substituents unless such attachment or substitution would violate valence requirements. Examples of cycloalkenyl groups include the partially unsaturated analogs of the cycloalkyl groups described above, such as cyclobutenyl (i.e., cyclobuten-1-yl and cyclobuten-3-yl), cyclopentenyl, cyclohexenyl, bicyclo[2.2.1]hept-2-enyl, and the like.

"Aryl" refers to fully unsaturated monocyclic aromatic hydrocarbons and to polycyclic hydrocarbons having at least one aromatic ring, both monocyclic and polycyclic aryl groups generally having a specified number of carbon atoms that comprise their ring members (e.g., $C_{6-14}$ aryl refers to an aryl group having 6 to 14 carbon atoms as ring members). The group may be attached through any ring atom, and where indicated, may optionally include one or more non-hydrogen substituents unless such attachment or substitution would violate valence requirements. Examples of aryl groups include phenyl, biphenyl, cyclobutabenzenyl, indenyl, naphthalenyl, benzocycloheptanyl, biphenylenyl, fluorenyl, groups derived from cycloheptatriene cation, and the like.

"Arylene" refers to divalent aryl groups, where aryl is defined above. Examples of arylene groups include phenylene (i.e., benzene-1,2-diyl).

"Heterocycle" and "heterocyclyl" may be used interchangeably and refer to saturated or partially unsaturated monocyclic or bicyclic groups having ring atoms composed of carbon atoms and 1 to 4 heteroatoms independently selected from nitrogen, oxygen, and sulfur. Both the monocyclic and bicyclic groups generally have a specified number of carbon atoms in their ring or rings (e.g., $C_{2-8}$ heterocyclyl refers to a heterocyclyl group having 2 to 8 carbon atoms and 1 to 4 heteroatoms as ring members). As with bicyclic cycloalkyl groups, bicyclic heterocyclyl groups may include isolated rings, spiro rings, fused rings, and bridged rings in which at least one of the rings includes one or more heteroatoms. The heterocyclyl group may be attached through any ring atom, and where indicated, may optionally include one or more non-hydrogen substituents unless such attachment or substitution would violate valence requirements or result in a chemically unstable compound. Examples of heterocyclyl groups include oxiranyl, thiiranyl, aziridinyl (e.g., aziridin-1-yl and aziridin-2-yl), oxetanyl, thietanyl, azetidinyl, tetrahydrofuranyl, tetrahydrothienyl, pyrrolidinyl, tetrahydropyranyl, tetrahydrothiopyranyl, piperidinyl, 1,4-dioxanyl, 1,4-oxathianyl, morpholinyl, 1,4-dithianyl, piperazinyl, 1,4-azathianyl, oxepanyl, thiepanyl, azepanyl, 1,4-dioxepanyl, 1,4-oxathiepanyl, 1,4-oxaazepanyl, 1,4-dithiepanyl, 1,4-thiazepanyl, 1,4-diazepanyl, 3,4-dihydro-2H-pyranyl, 3,6-dihydro-2H-pyranyl, 2H-pyranyl, 1,2-dihydropyridinyl, 1,2,3,4-tetrahydropyridinyl, 1,2,56-tetrahydropyridinyl, 1,6-dihydropyrimidinyl, 1,2,3,4-tetrahydropyrimidinyl, and 1,2-dihydropyrazolo[1,5-d][1,2,4]triazinyl.

"Heterocycle-diyl" refers to heterocyclyl groups which are attached through two ring atoms of the group, where heterocyclyl is defined above. They generally have a specified number of carbon atoms in their ring or rings (e.g., $C_{2-8}$ heterocycle-diyl refers to a heterocycle-diyl group having 2 to 8 carbon atoms and 1 to 4 heteroatoms as ring members) Examples of heterocycle-diyl groups include the multivalent analogs of the heterocycle groups described above, such as morpholine-3,4-diyl, pyrrolidine-1,2-diyl, 1-pyrrolidinyl-2-ylidene, 1-pyddinyl-2-ylidene, 1-(4H)-pyrazolyl-5-ylidene, 1-(3H)-imidazolyl-2-ylidene, 3-oxazolyl-2-ylidene, 1-piperidinyl-2-ylidene, 1-piperazinyl-6-ylidene, and the like.

"Heteroaromatic" and "heteroaryl" may be used interchangeably and refer to unsaturated monocyclic aromatic groups and to polycyclic groups having at least one aromatic ring, each of the groups having ring atoms composed of carbon atoms and 1 to 4 heteroatoms independently selected from nitrogen, oxygen, and sulfur. Both the monocyclic and polycyclic groups generally have a specified number of carbon atoms as ring members (e.g., $C_{1-9}$ heteroaryl refers to a heteroaryl group having 1 to 9 carbon atoms and 1 to 4 heteroatoms as ring members) and may include any bicyclic group in which any of the above-listed monocyclic heterocycles are fused to a benzene ring. The heteroaryl group may be attached through any ring atom (or ring atoms for fused rings), and where indicated, may optionally include one or more non-hydrogen substituents unless such attachment or substitution would violate valence requirements or result in a chemically unstable compound. Examples of heteroaryl groups include monocyclic groups such as pyrrolyl (e.g., pyrrol-1-yl, pyrrol-2-yl, and pyrrol-3-yl), furanyl, thienyl, pyrazolyl, imidazolyl, isoxazolyl, oxazolyl, isothiazolyl, thiazolyl, 1,2,3-triazolyl, 1-oxa-2,3-diazolyl, 1-oxa-2,4-diazolyl, 1-oxa-2,5-diazolyl, 1-oxa-3,4-diazolyl, 1-thia-2,3-diazolyl, 1-thia-2,4-diazolyl, 1-thia-2,5-diazolyl, tetrazolyl, pyridinyl, pyridazinyl, pyrimidinyl, and pyrazinyl.

Examples of heteroaryl groups also include bicyclic groups such as benzofuranyl, isobenzofuranyl, benzothienyl, benzo[c]thienyl, isoindolyl, 1H-isoindolyl, indolinyl, isoindolinyl, benzimidazolyl, 1H-indazolyl, 2H-indazolyl, benzotriazolyl, 1H-pyrrolo[2,3-b]pyridinyl, 1H-pyrrolo[2,3-c]pyridinyl, 1H-pyrrolo[3,2-c]pyridinyl, 1H-pyrrolo[3,2-b]pyridinyl, 3H-imidazo[4,5-b]pyridinyl, 3H-imidazo[4,5-c]pyridinyl, 1H-pyrazolo[4,3-b]pyridinyl, 1H-pyrazolo[4,3-c]pyridinyl, 1H-pyrazolo[3,4-c]pyridinyl, 1H-pyrazolo[3,4-b]pyridinyl, 7H-purinyl, indolizinyl imidazo[1,2-d]pyridinyl, imidazo[1,5-d]pyridinyl, pyrazolo[1,5-d]pyridinyl, pyrrolo[1,2-b]pyridazinyl, imidazo[1,2-c]pyrimidinyl, quinolinyl, isoquinolinyl, cinnolinyl quinazolinyl, quinoxalinyl, phthalazinyl, 1,6-naphthyridinyl, 1,7-naphthyridinyl, 1,8-naphthyridinyl, 1,5-naphthyridinyl, 2,6-naphthyridinyl, 2,7-naphthyridinyl, pyrido[3,2-d]pyrimidinyl, pyrido[4,3-d]pyrimidinyl, pyrido[3,4-d]pyrimidinyl, pyrido[2,3-d]pyrimidinyl, pyrido[2,3-b]pyrazinyl, pyrido[3,4-b]pyrazinyl, pyrimido[5,4-d]pyrimidinyl, pyrazino[2,3-b]pyrazinyl, pyrimido[4,5-d]pyrimidinyl, 1,2,3,4-tetrahydropyrido[2,3-b]pyrazinyl, 2,3-dihydrobenzo[b][1,4]dioxinyl, 3,4-dihydro-2H-pyrido[3,2-b][1,4]oxazinyl, 2,3-dihydro-1H-benzo[d]imidazolyl, benzo[d]thiazolyl, 2,3-dihydro-1H-pyrrolo[2,3-b]pyridinyl, [1,2,4]triazolo[1,5-c]pyridinyl, 2,3-dihydro-1H-imidazo[4,5-b]pyridinyl, tetrazolo[1,5-c]pyridinyl, 7H-pyrrolo[2,3-d]pyrimidinyl, pyrazolo[1,5-d]pyrimidinyl, imidazo[1,2-d]pyrimidinyl, 4,5-dihydro-1H-pyrazolo[3,4-d]pyrimidinyl, 2,3,6,7-tetrahydro-1H-purinyl, 5H-pyrrolo[2,3-b]pyrazinyl, imidazo[1,2-c]pyrazinyl, imidazo[2-b]pyridazinyl, and 4,5,6,7-tetrahydropyrazolo[1,5-a]pyrazinyl.

"Heteroarylene" refers to heteroaryl groups which are attached through two ring atoms of the group, where heteroaryl is defined above. They generally have a specified number of carbon atoms in their ring or rings (e.g., $C_{3-5}$ heteroarylene refers to a heteroarylene group having 3 to 5 carbon atoms and 1 to 4 heteroatoms as ring members). Examples of heteroarylene groups include the multivalent analogs of the heteroaryl groups described above, such as pyridine-2,3-diyl, pyridine-3,4-diyl, pyrazole-4,5-diyl, pyrazole-3,4-diyl, and the like.

"Oxo" refers to a double bonded oxygen (=O).

"Leaving group" refers to any group that leaves a molecule during a fragmentation process, including substitution reactions, elimination reactions, and addition-elimination reactions. Leaving groups may be nucleofugal, in which the group leaves with a pair of electrons that formerly served as the bond between the leaving group and the molecule, or may be electrofugal, in which the group leaves without the pair of electrons. The ability of a nucleofugal leaving group to leave depends on its base strength, with the strongest bases being the poorest leaving groups. Common nucleofugal leaving groups include nitrogen (e.g., from diazonium salts); sulfonates, including alkylsulfonates (e.g., mesylate), fluoroalkylsulfonates (e.g., triflate, hexaflate, nonaflate, and tresylate and arylsulfonates (e.g., tosylate, brosylate, closylate, and nosylate). Others include carbonates, halide ions, carboxylate anions, phenolate ions, and alkoxides. Some stronger bases, such as $NE_2^-$ and $OH^-$ can be made better leaving groups by treatment with an acid. Common electrofugal leaving groups include the proton, $CO_2$, and metals.

"Opposite enantiomer" refers to a molecule that is a non-superimposable mirror image of a reference molecule, which may be obtained by inverting all the stereogenic centers of the reference molecule. For example, if the reference molecule has S absolute stereochemical configuration, then the opposite enantiomer has R absolute stereochemical configuration. Likewise, if the reference molecule has S,S absolute stereochemical configuration, then the opposite enantiomer has R,R stereochemical configuration, and so on.

"Stereoisomer" and "stereoisomers" of a compound with given stereochemical configuration refer to the opposite enantiomer of the compound and to any diastereoisomers, including geometrical isomers (Z/E) of the compound. For example, if a compound has S,R,Z stereochemical configuration, its stereoisomers would include its opposite enantiomer having R,S,Z configuration, and its diastereomers having S,S,Z configuration, R,R,Z configuration, S,R,E configuration, R,S,E configuration, S,S,E configuration, and R,R,E configuration. If the stereochemical configuration of a compound is not specified, then "stereoisomer" refers to any one of the possible stereochemical configurations of the compound.

"Substantially pure stereoisomer" and variants thereof refer to a sample containing a compound having a specific stereochemical configuration and which comprises at least about 95% of the sample.

"Pure stereoisomer" and variants thereof refer to a sample containing a compound having a specific stereochemical configuration and which comprises at least about 99.5% of the sample.

"Subject" refers to a mammal, including a human.

"Pharmaceutically acceptable" substances refer to those substances which are suitable for administration to subjects.

"Treating" refers to reversing, alleviating, inhibiting the progress of, or preventing a disease, disorder or condition to which such term applies, or to reversing, alleviating, inhibiting the progress of, or preventing one or more symptoms of such disease, disorder or condition.

"Treatment" refers to the act of "treating," as defined immediately above.

"Drug," "drug substance," "active pharmaceutical ingredient," and the like, refer to a compound (e.g., compounds of Formula 1, including subgeneric compounds and compounds specifically named in the specification) that may be used for treating a subject in need of treatment.

"Effective amount" of a drug, "therapeutically effective amount" of a drug, and the like, refer to the quantity of the drug that may be used for treating a subject and may depend on the weight and age of the subject and the route of administration, among other things.

"Excipient" refers to any diluent or vehicle for a drug.

"Pharmaceutical composition" refers to the combination of one or more drug substances and one or more excipients.

"Drug product," "pharmaceutical dosage form," "dosage form," "final dosage form" and the like, refer to a pharmaceutical composition suitable for treating a subject in need of treatment and generally may be in the form of tablets, capsules, sachets containing powder or granules, liquid solutions or suspensions, patches, films, and the like.

"Condition associated with GPR139" and similar phrases relate to a disease, disorder or condition in a subject for which activation (agonism) of GPR139 may provide a therapeutic or prophylactic benefit.

The following abbreviations may be used in the specification: Ac (acetyl); ACN (acetonitrile); AIBN (azo-bis-isobutyronitrile); API (active pharmaceutical ingredient); aq (aqueous); B$_2$pin$_2$ (4,4,4',4',5,5,5',5'-octamethyl-2,2'-bi(1,3,2-dioxaborolane)); BINAP (2,2'-bis(diphenylphosphino)-1,1'-binaphthyl); Boc (tert-butoxycarbonyl); Cbz (carbobenzyloxy); CDI (1,1'-carbonyldiimidazole); dba (dibenzylideneacetone); DAST (N,N-diethylaminosuflur trifluoride); DCC (1,3-dicyclohexylcarbodiimide); DCE (1,1-dichloroethane); DCM (dichloromethane); DIAD (diisopropyl azodicarboxylate); DIPEA sopropylethyl-amine, Hünig's Base); DMA (N,N-dimethylacetamide); DMAP (4-dimethylaminopyridine); DME (1,2-dimethoxyethane); DMF (N,N-dimethylformamide); DMSO (dimethylsulfoxide); dppf (1,1'-bis(diphenylphosphino)ferrocene); DTT (dithiothreitol); EC$_{50}$ (effective concentration at half maximal response); EDA (ethoxylated dodecyl alcohol, Brj®35); EDC (N-(3-dimethylaminopropyl)-N'-ethylcarbodiimide); EDTA (ethylenediaminetetraacetic acid); ee (enantiomeric excess); eq (equivalents); Et (ethyl); Et$_3$N (triethylamine); EtOAc (ethyl acetate); EtOH (ethanol); HATU (2-(3H-[1,2,3]triazolo[4,5-b]pyridin-3-yl)-1,1,3,3, tetramethyluronium hexafluorophosphate (V)); HEPES (4-(2-hydroxyethyl)piperazine-1-ethanesulfonic acid); HOAc (acetic acid); HOBt (1H-benzo[d][1,2,3]triazol-1-ol); IC$_{50}$ (concentration at 50% inhibition); IPA (isopropanol); IPAc (isopropyl acetate); IPE (isopropylether); Ki (inhibition constant); KOt-Bu (potassium tertiary butoxide); IDA (lithium diisopropylamide); LiHMDS (lithium bis(trimethylsilyl)amide); mCPBA (m-chloroperoxybenzoic acid); Me (methyl); MeOH (methanol); MTBE (methyl tert-butyl ether); mp (melting point); n-BuLi (n-butyl lithium); NaOt-Bu (sodium tertiary butoxide); NBS (N-bromosuccinimide); NCS (N-chlorosuccinimide); MS (N-iodosuccinimide); NMM (N-methylmorpholine); NMP (N-methyl-pyrrolidone); OTf (triflate); PdCl$_2$(dtbpf) (dichloro[1,1'-bis(di-tert-butylphosphino)ferrocene]palladium(II)); PE (petroleum ether); Ph (phenyl); pEC$_{50}$ (−log$_{10}$(EC$_{50}$), where EC$_{50}$ is given in molar (M) units); pIC$_{50}$ (−log$_{10}$(IC$_{50}$), where IC$_{50}$ is given in molar (M) units); pKi (−log$_{10}$(Ki), where Ki is given in molar (M) units); Pr (propyl); c-Pr (cyclopropyl); i-Pr (isopropyl); PTFE (polytetrafluoroethylene); Rae (racemic); RT (room temperature; approximately 20° C. to 25° C.); SEM (2-(trimethylsilyl)ethoxymethyl); SEM-Cl ((2-chloromethoxyethyl)trimethylsilane); SFC (supercritical fluid chromatography); T3P (2,4,6-tripropyl-1,3,5,2,4,6-trioxatriphosphinane 2,4,6-trioxide); TBAF (tetrabutylammonium fluoride); TBS (tert-butyldimethylsilyl); TBSCl (Cert-butylchlorodimethylsilane); TCEP (tris(2-carboxyethyl)phosphine); TFA (trifluoroacetic acid); TFAA (2,2,2-trifluoroacetic anhydride); THE (tetrahydrofuran); TLC (thin layer chromatography); TMEDA (tetramethylethylenediamine); TMS (trimethylsilyl); and Tris buffer (2-amino-2-hydroxymethyl-propane-1,3-diol buffer).

As described; below, this disclosure provides compounds of Formula 1, tautomers thereof, or pharmaceutically acceptable salts of the compounds of Formula 1 or their tautomers. This disclosure also provides materials and methods for preparing compounds of Formula 1, pharmaceutical compositions comprising them, and the use of compounds of Formula 1 and their tautomers and pharmaceutically acceptable salts (optionally in combination with other pharmacologically active agents) for treating diseases, disorders or conditions associated with GPR139.

In addition to the specific compounds in the examples; the compounds of Formula 1,

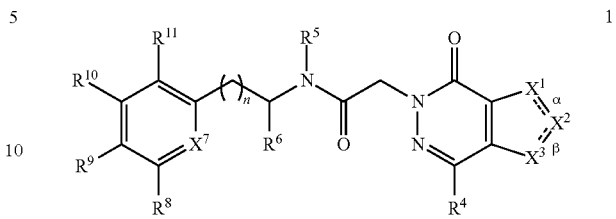

tautomers thereof, or pharmaceutically acceptable salts of the compounds of Formula 1 or tautomers thereof, include those in which:

(1) α is a single bond, β is a double bond, X$^1$ is NR$^{1N}$, and either (i) X$^2$ is N and X$^3$ is CR$^{3C}$ or (ii) X$^2$ is CR$^2$ and X$^3$ is selected from N and CR$^{3C}$; or α is a double bond, β is a single bond, X$^3$ is NR$^{3N}$ and either (i) X$^1$ is N and X$^2$ is CR$^2$ or (ii) X$^1$ is CR$^{1C}$ and X$^2$ is selected from N and CR$^2$;

n is selected from 0 and 1;

R$^{1C}$, R$^2$, R$^{3C}$ and R$^4$ are each independently selected
  (a) hydrogen; and
  (b) C$_{1-6}$ alkyl and C$_{3-8}$ cycloalkyl, each unsubstituted or substituted with 1 to 3 substituents independently selected from halo;

R$^{1N}$ and R$^{3N}$ are each independently selected from C$_{1-6}$ alkyl, C$_{3-8}$ cycloalkyl and C$_{6-10}$ aryl, each unsubstituted or substituted with 1 to 3 substituents independently selected from halo;

R$^5$ is selected from hydrogen and C$_{1-6}$ alkyl, and R$^6$ is selected from C$_{1-6}$ alkyl and C$_{3-8}$ cycloalkyl; or R$^5$ and R$^6$, together with the nitrogen and carbon atoms to which they are each respectively attached, form a C$_{3-6}$ heterocyclic ring, the heterocyclic ring being monocyclic and having one ring atom which is a heteroatom;

X$^7$ is selected from N and CR$^7$;

R$^7$ is selected from
  (a) hydrogen, halo, cyano, hydroxy and amino; and
  (b) C$_{1-6}$ alkyl and C$_{1-6}$ alkoxy, each unsubstituted or substituted with 1 to 3 substituents independently selected from halo;

R$^8$ and R$^9$ are each independently selected from
  (a) hydrogen, halo, cyano, hydroxy and amino; and
  (b) C$_{1-6}$ alkyl and C$_{1-6}$ alkoxy, each unsubstituted or substituted with 1 to 3 substituents independently selected from halo; or R$^8$ and R$^9$, together with the carbon atoms to which they are attached, form a C$_{4-5}$ heterocyclic ring, the heterocyclic ring having one or two ring atoms that are heteroatoms, each of heteroatoms being independently selected from N, O and S;

R$^{10}$ and R$^{11}$ are each independently selected from
  (a) hydrogen, halo, cyano, hydroxy and amino; and
  (b) C$_{1-6}$ alkyl and C$_{1-6}$ alkoxy, each unsubstituted or substituted with 1 to 3 substituents independently selected from halo.

In addition to embodiment (I) in the preceding paragraph, the compounds of Formula 1 include those in which:

(2) α is a single bond, β is a double bond, X$^1$ is NR$^{1N}$, and either (i) X$^2$ is N and X$^3$ is CR$^{3C}$ or (ii) X$^2$ is CR$^2$ and X$^3$ is selected from N and CR$^{3C}$.

In addition to embodiment (2) in the preceding paragraph, the compounds of Formula 1 include those in which $R^{1N}$ is selected from:
- (3) $C_{1-6}$ alkyl, $C_{3-8}$ cycloalkyl and phenyl, each unsubstituted or substituted with 1 to 3 substituents independently selected from halo;
- (4) $C_{1-6}$ alkyl, $C_{3-6}$ cycloalkyl and phenyl, each unsubstituted or substituted with 1 to 3 substituents independently selected from halo;
- (5) $C_{1-4}$ alkyl, $C_{3-6}$ cycloalkyl and phenyl, each unsubstituted or substituted with 1 to 3 substituents independently selected from halo;
- (6) $C_{1-4}$ alkyl, cyclopropyl and phenyl, each unsubstituted or substituted with 1 to 3 substituents independently selected from halo; or
- (7) $C_{1-4}$ alkyl and cyclopropyl, each unsubstituted or substituted with 1 to 3 substituents independently selected from halo.

In addition to any one of embodiments (3) to (7) in the preceding paragraph, the compounds of Formula 1 include those in which:
- (8) the substituents for $R^{1N}$ are each unsubstituted or substituted with 1 to 3 substituents selected from fluoro; or
- (9) the substituents for $R^{1N}$ are each unsubstituted.

In addition to any one of embodiments (2) to (9) in the preceding paragraphs, the compounds of Formula 1 include those in which:
- (10) $X^2$ is N and $X^3$ is $CR^{3C}$.

In addition to any one of embodiments (2) to (10) in the preceding paragraphs, the compounds of Formula 1 include those in which $R^{3C}$ is selected from:
- (11) hydrogen, $C_{1-6}$ alkyl and $C_{3-6}$ cycloalkyl, wherein $C_{1-6}$ alkyl and $C_{3-6}$ cycloalkyl are each unsubstituted or substituted with 1 to 3 substituents independently selected from halo;
- (12) hydrogen, $C_{1-4}$ alkyl and $C_{3-6}$ cycloalkyl, wherein $C_{1-4}$ alkyl and $C_{3-6}$ cycloalkyl are each unsubstituted or substituted with 1 to 3 substituents independently selected from halo; or
- (13) hydrogen, $C_{1-4}$ alkyl and cyclopropyl, wherein $C_{1-4}$ alkyl and cyclopropyl are each unsubstituted or substituted with 1 to 3 substituents independently selected from halo.

In addition to any one of embodiments (11) to (13) in the preceding paragraph, the compounds of Formula 1 include those in which:
- (14) the substituents for $R^{3C}$ are each unsubstituted or substituted with 1 to 3 substituents selected from fluoro; or
- (15) the substituents for $R^{3C}$ are each unsubstituted.

In addition to any one of embodiments (2) to (9) in the preceding paragraphs, the compounds of Formula 1 include those in which:
- (16) $X^2$ is $CR^2$ and $X^3$ is selected from N and $CR^{3C}$.

In addition to any one of embodiments (2) to (9) in the preceding paragraphs, the compounds of Formula 1 include those in which:
- (17) $X^2$ is $CR^2$ and $X^3$ is $CR^{3C}$.

In addition to any one of embodiments (16) to (17) in the preceding paragraphs; the compounds of Formula 1 include those in which $R^{3C}$ is selected from:
- (18) hydrogen, $C_{1-6}$ alkyl and $C_{3-6}$ cycloalkyl, wherein $C_{1-6}$ alkyl and $C_{3-6}$ cycloalkyl are each unsubstituted or substituted with 1 to 3 substituents independently selected from halo;
- (19) hydrogen, $C_{1-4}$ alkyl and $C_{3-6}$ cycloalkyl, wherein $C_{1-4}$ alkyl and $C_{3-6}$ cycloalkyl are each unsubstituted or substituted with 1 to 3 substituents independently selected from halo; or
- (20) hydrogen, $C_{1-4}$ alkyl and cyclopropyl, wherein $C_{1-4}$ alkyl and cyclopropyl each unsubstituted or substituted with 1 to 3 substituents independently selected from halo.

In addition to any one of embodiments (18) to (20) in the preceding paragraph, the compounds of Formula 1 include those in which:
- (21) the substituents for $R^{3C}$ are each unsubstituted or substituted with 1 to 3 substituents selected from fluoro; or
- (22) the substituents for $R^{3C}$ are each unsubstituted.

In addition to any one of embodiments (2) to (9) in the preceding paragraphs, the compounds of Formula 1 include those in which:
- (23) $X^2$ is $CR^2$ and $X^3$ is N.

In addition to embodiment (1), the compounds of Formula 1 include those in which:
- (24) α is a double bond, β is a single bond, $X^3$ is $NR^{3N}$ and either (i) $X^1$ is N and $X^2$ is $CR^2$ or (ii) $X^1$ is $CR^{1C}$ and $X^2$ is selected from N and $CR^2$.

In addition to embodiment (24) in the preceding paragraph, the compounds of Formula 1 include those in which $R^{3N}$ is selected from:
- (25) $C_{1-6}$ alkyl, $C_{3-8}$ cycloalkyl and phenyl, each unsubstituted or substituted with 1 to 3 substituents independently selected from halo;
- (26) $C_{1-6}$ alkyl, $C_{3-6}$ cycloalkyl and phenyl, each unsubstituted or substituted with 1 to 3 substituents independently selected from halo;
- (27) $C_{1-4}$ alkyl, $C_{3-6}$ cycloalkyl and phenyl, each unsubstituted or substituted with 1 to 3 substituents independently selected from halo;
- (28) $C_{1-4}$ alkyl and $C_{3-6}$ cycloalkyl, each unsubstituted or substituted with 1 to 3 substituents independently selected from halo; or
- (29) $C_{1-4}$ alkyl and cyclopropyl, each unsubstituted or substituted with 1 to 3 substituents independently selected from halo.

In addition to any one of embodiments (25) to (29) in the preceding paragraph, the compounds of Formula 1 include those in which:
- (30) the substituents for $R^{3N}$ are each unsubstituted or substituted with 1 to 3 substituents selected from fluoro; or
- (31) the substituents for $R^{3N}$ are each unsubstituted.

In addition to any one of embodiments (24) to (31) in the preceding paragraphs, the compounds of Formula 1 include those in which:
- (32) $X^1$ is N and $X^2$ is $CR^2$;
- (33) $X^1$ is $CR^{1C}$ and $X^2$ is selected from N and $CR^2$; or
- (34) $X^1$ is $CR^{1C}$ and $X^2$ is $CR^2$.

In addition to any one of embodiments (32) to (34) in the preceding paragraph, the compounds of Formula 1 include those in which $R^{1C}$ is selected from:
- (35) hydrogen, $C_{1-6}$ alkyl and $C_{3-6}$ cycloalkyl, wherein $C_{1-6}$ alkyl and $C_{3-6}$ cycloalkyl are each unsubstituted or substituted with 1 to 3 substituents independently selected from halo;
- (36) hydrogen, $C_{1-4}$ alkyl and $C_{3-6}$ cycloalkyl, wherein $C_{1-4}$ alkyl and $C_{3-6}$ cycloalkyl are each unsubstituted or substituted with 1 to 3 substituents independently selected from halo; or

(37) hydrogen, $C_{1-4}$ alkyl and cyclopropyl, wherein $C_{1-4}$ alkyl and cyclopropyl are each unsubstituted or substituted with 1 to 3 substituents independently selected from halo.

In addition to any one of embodiments (35) to (37) in the preceding paragraph, the compounds of Formula 1 include those in which:
(38) the substituents for $R^{1C}$ are each unsubstituted or substituted with 1 to 3 substituents selected from fluoro; or
(39) the substituents for $R^{1C}$ are each unsubstituted.

In addition to any one of embodiments (24) to (31) in the preceding paragraphs, the compounds of Formula 1 include those in which:
(40) $X^1$ is $CR^{1C}$ and $X^2$ is N.

In addition to embodiment (40) in the preceding paragraph, the compounds of Formula 1 include those in $R^{1C}$ is selected from:
(41) hydrogen, $C_{1-6}$ alkyl and $C_{3-6}$ cycloalkyl, wherein $C_{1-6}$ alkyl and $C_{3-6}$ cycloalkyl are each unsubstituted or substituted with 1 to 3 substituents independently selected from halo;
(42) hydrogen, $C_{1-4}$ alkyl and $C_{3-6}$ cycloalkyl, wherein $C_{1-4}$ alkyl and $C_{3-6}$ cycloalkyl are each unsubstituted or substituted with 1 to 3 substituents independently selected from halo; or
(43) hydrogen, $C_{1-4}$ alkyl and cyclopropyl, wherein $C_{1-4}$ alkyl and cyclopropyl are each unsubstituted or substituted with 1 to 3 substituents independently selected from halo.

In addition to any one of embodiments (41) to (43) in the preceding paragraph, the compounds of Formula 1 include those in which the $R^{1C}$ substituent is:
(44) the substituents for $R^{1C}$ are each unsubstituted or substituted with 1 to 3 substituents selected from fluoro; or
(45) the substituents for $R^{1C}$ are each unsubstituted.

In addition to any one of embodiments (1) to (9) and (16) to in the preceding paragraphs, the compounds of Formula 1 include those in which $R^2$ is selected from:
(46) hydrogen, $C_{1-6}$ alkyl and $C_{3-6}$ cycloalkyl, wherein $C_{1-6}$ alkyl and $C_{3-6}$ cycloalkyl are each unsubstituted or substituted with 1 to 3 substituents independently selected from halo;
(47) hydrogen, $C_{1-4}$ alkyl and $C_{3-6}$ cycloalkyl, wherein $C_{1-4}$ alkyl and $C_{3-6}$ cycloalkyl are each unsubstituted or substituted with 1 to 3 substituents independently selected from halo;
(48) hydrogen; $C_{1-4}$ alkyl and cyclopropyl, wherein $C_{1-4}$ alkyl and cyclopropyl are each unsubstituted or substituted with 1 to 3 substituents independently selected from halo;
(49) hydrogen and $C_{1-4}$ alkyl which is unsubstituted or substituted with 1 to 3 substituents independently selected from halo; or
(50) hydrogen.

In addition to any one of embodiments (46) to (49) in the preceding paragraph, the compounds of Formula 1 include those in which:
(51) the substituents for $R^1$ are each unsubstituted or substituted with 1 to 3 substituents selected from fluoro; or
(52) the substituents for $R^2$ are each unsubstituted.

In addition to any one of embodiments (1) to (52) in the preceding paragraphs, the compounds of Formula 1 include those in which $R^4$ is selected from:

(53) hydrogen, $C_{1-6}$ alkyl and $C_{3-6}$ cycloalkyl, wherein $C_{1-6}$ alkyl and $C_{3-6}$ cycloalkyl are each unsubstituted or substituted with 1 to 3 substituents independently selected from halo;
(54) hydrogen, $C_{1-4}$ alkyl and $C_{3-6}$ cycloalkyl, wherein $C_{1-4}$ alkyl and $C_{3-6}$ cycloalkyl are each unsubstituted or substituted with 1 to 3 substituents independently selected from halo;
(55) hydrogen, $C_{1-4}$ alkyl and cyclopropyl, wherein $C_{1-4}$ alkyl and cyclopropyl are each unsubstituted or substituted with 1 to 3 substituents independently selected from halo;
(56) hydrogen, methyl, ethyl, isopropyl and cyclopropyl, wherein the methyl, ethyl, isopropyl and cyclopropyl substituents are each unsubstituted or substituted with 1 to 3 substituents independently selected from halo;
(57) hydrogen and methyl which is unsubstituted or substituted with 1 to 3 substituents independently selected from halo; or
(58) hydrogen.

In addition to any one of embodiments (53) to (57) in the preceding paragraph, the compounds of Formula 1 include those in which:
(59) the substituents for $R^4$ are each unsubstituted or substituted with 1 to 3 substituents selected from fluoro; or
(60) the substituents for $R^4$ are each unsubstituted.

In addition to any one of embodiments (1) to (60) in the preceding paragraphs, the compounds of Formula 1 include those in which $R^5$ is selected from:
(61) hydrogen and $C_{1-6}$ alkyl;
(62) hydrogen and $C_{1-4}$ alkyl;
(63) hydrogen, methyl, ethyl and isopropyl;
(64) hydrogen and methyl; or
(65) hydrogen.

In addition to any one of embodiments (1) to (65) in the preceding paragraphs, the compounds of Formula 1 include those in which $R^6$ is selected from:
(66) $C_{1-4}$ alkyl and $C_{3-8}$ cycloalkyl;
(67) $C_{1-4}$ alkyl and $C_{3-6}$ cycloalkyl,
(68) methyl, ethyl, propyl, isopropyl and cyclopropyl;
(69) methyl and ethyl; or
(70) methyl.

In addition to any one of embodiments (1) to (60) in the preceding paragraphs, the compounds of Formula 1 include those in which wherein $R^5$ and $R^6$, together with the nitrogen and carbon atoms to which they are each respectively attached; form a:
(71) $C_{3-5}$ heterocyclic ring, the heterocyclic ring being monocyclic and having one ring atom which is a heteroatom;
(72) $C_{3-4}$ heterocyclic ring, the heterocyclic ring being monocyclic and having one ring atom which is a heteroatom;
(73) pyrrolidine; or
(74) pyrrolidin-1,2-diyl.

In addition to any one of embodiments (1) to (74), compounds of Formula 1 include those in which:
(75) n is 0.

In addition to any one of embodiments (1) to (75), compounds of Formula 1 include those in which:
(76) $X^7$ is N.

In addition to any one of embodiments (1) to (75), compounds of Formula 1 include those in which:
(77) $X^7$ is $CR^7$.

In addition to embodiment (77) in the preceding paragraph, the compounds of Formula 1 include those in which $R^7$ is selected from:

(78) (a) hydrogen; halo, cyano and hydroxy; and
  (b) $C_{1-6}$ alkyl and $C_{1-6}$ alkoxy, each unsubstituted or substituted with 1 to 3 substituents independently selected from halo;
(79) (a) hydrogen, halo and hydroxy; and
  (b) $C_{1-6}$ alkyl and $C_{1-6}$ alkoxy, each unsubstituted or substituted with 1 to 3 substituents independently selected from halo;
(80) (a) hydrogen and halo; and
  (b) $C_{1-6}$ alkyl and $C_{1-6}$ alkoxy, each unsubstituted or substituted with 1 to 3 substituents independently selected from halo;
(81) (a) hydrogen and halo; and
  (b) $C_{1-4}$ alkyl and $C_{1-3}$ alkoxy, each unsubstituted or substituted with 1 to 3 substituents independently selected from halo;
(82) (a) hydrogen and halo; and
  (b) methyl, ethyl and methoxy, each unsubstituted or substituted with 1 to 3 substituents independently selected from halo;
(83) (a) hydrogen and halo; and
  (b) methyl, ethyl and methoxy, each unsubstituted or substituted with 1 to 3 substituents independently selected from fluoro;
(84) hydrogen, halo, methyl, ethyl and methoxy;
(85) hydrogen, halo, methyl and methoxy;
(86) hydrogen, fluoro, chloro, methyl and methoxy; or
(87) hydrogen.

In addition to any one of embodiments (1) to (87) in the preceding paragraphs, the compounds of Formula 1 include those in which $R^8$ is selected from:

(88) (a) hydrogen; halo, cyano, hydroxy and amino; and
  (b) $C_{1-6}$ alkyl and $C_{1-6}$ alkoxy, each unsubstituted or substituted with 1 to 3 substituents independently selected from halo;
(89) (a) hydrogen, halo, cyano and hydroxy; and
  (b) $C_{1-6}$ alkyl and $C_{1-6}$ alkoxy, each unsubstituted or substituted with 1 to 3 substituents independently selected from halo;
(90) (a) hydrogen, halo and hydroxy; and
  (b) $C_{1-6}$ alkyl and $C_{1-6}$ alkoxy, each unsubstituted or substituted with 1 to 3 substituents independently selected from halo;
(91) (a) hydrogen and halo; and
  (b) $C_{1-6}$ alkyl and $C_{1-6}$ alkoxy, each unsubstituted or substituted with 1 to 3 substituents independently selected from halo;
(92) (a) hydrogen and halo; and
  (b) $C_{1-4}$ alkyl and $C_{1-3}$ alkoxy, each unsubstituted or substituted with 1 to 3 substituents independently selected from halo;
(93) (a) hydrogen and halo; and
  (b) methyl, ethyl, and methoxy, each unsubstituted or substituted with 1 to 3 substituents independently selected from halo;
(94) (a) hydrogen and halo; and
  (b) methyl; ethyl and methoxy, each unsubstituted or substituted with 1 to 3 substituents independently selected from fluoro;
(95) hydrogen, halo, methyl, ethyl and methoxy;
(96) hydrogen; halo, methyl and methoxy;
(97) hydrogen, fluoro, methyl and methoxy; or
(98) hydrogen.

In addition to any one of embodiments (1) to (98) in the preceding paragraphs, the compounds of Formula 1 include those in which $R^9$ is selected from:

(99) (a) hydrogen, halo, cyano, hydroxy and amino; and
  (b) $C_{1-6}$ alkyl and $C_{1-6}$ alkoxy, each unsubstituted or substituted with 1 to 3 substituents independently selected from halo;
(100) (a) hydrogen, halo, cyano and hydroxy; and
  (b) $C_{1-6}$ alkyl and $C_{1-6}$ alkoxy, each unsubstituted or substituted with 1 to 3 substituents independently selected from halo;
(101) (a) hydrogen, halo and hydroxy; and
  (b) $C_{1-6}$ alkyl and $C_{1-6}$ alkoxy, each unsubstituted or substituted with 1 to 3 substituents independently selected from halo;
(102) (a) hydrogen and halo; and
  (b) $C_{1-6}$ alkyl and $C_{1-6}$ alkoxy, each unsubstituted or substituted with 1 to 3 substituents independently selected from halo;
(103) (a) hydrogen and halo; and
  (b) $C_{1-4}$ alkyl and $C_{1-3}$ alkoxy, each unsubstituted or substituted with 1 to 3 substituents independently selected from halo;
(104) (a) hydrogen and halo; and
  (b) methyl, ethyl and methoxy, each unsubstituted or substituted with 1 to 3 substituents independently selected from halo;
(105) (a) hydrogen and halo; and
  (b) methyl, ethyl and methoxy, each unsubstituted or substituted with 1 to 3 substituents independently selected from fluoro;
(106) hydrogen, halo, methyl, trifluoromethyl, methoxy and trifluoromethoxy;
(107) hydrogen, chloro, fluoro, methyl, trifluoromethyl, methoxy and trifluoromethoxy;
(108) hydrogen, methyl, trifluoromethyl, methoxy and trifluoromethoxy; or
(109) methyl, trifluoromethyl, methoxy and trifluoromethoxy.

In addition to any one of embodiments (1) to (87) in the preceding paragraphs, the compounds of Formula 1 include those in which $R^8$ and $R^9$, together with the carbon atoms to which they are attached, form a $C_{4-5}$ heterocyclic ring; the heterocyclic ring having one or two ring atoms that are heteroatoms, each of heteroatoms being independently selected from:

(110) N, O and S;
(111) N and O; or
(112) O.

In addition to any one of embodiments (110) to (112) in the preceding paragraph, the compounds of Formula 1 include those in which $R^8$ and $R^9$, together with the carbon atoms to which they are attached, form a $C_{4-5}$ heterocyclic ring having:

(113) six ring atoms;
(114) six ring atoms in which 2 of the ring atoms are heteroatoms; or
(115) six ring atoms in which 1 of the ring atoms is a heteroatom.

In addition to any one of embodiments (1) to (115) in the preceding paragraphs, the compounds of Formula 1 include those in which $R^{10}$ is selected from:

(116) (a) hydrogen, halo, cyano and hydroxy; and
  (b) $C_{1-6}$ alkyl and $C_{1-6}$ alkoxy, each unsubstituted or substituted with 1 to 3 substituents independently selected from halo;
(117) (a) hydrogen, halo and hydroxy; and (b) $C_{1-6}$ alkyl and $C_{1-6}$ alkoxy, each unsubstituted or substituted with 1 to 3 substituents independently selected from halo;
(118) (a) hydrogen and halo; and
(b) $C_{1-6}$ alkyl and $C_{1-6}$ alkoxy, each unsubstituted or substituted with 1 to 3 substituents independently selected from halo;
(119) (a) hydrogen and halo; and
(b) $C_{1-4}$ alkyl and $C_{1-3}$ alkoxy, each unsubstituted or substituted with 1 to 3 substituents independently selected from halo;
(120) hydrogen, halo and $C_{1-4}$ alkyl which is unsubstituted or substituted with 1 to 3 substituents independently selected from halo;
(121) hydrogen, halo and $C_{1-4}$ alkyl;
(122) hydrogen, halo and methyl;
(123) hydrogen, fluoro and methyl; or
(124) hydrogen.

In addition to any one of embodiments (1) to (124) in the preceding paragraphs, the compounds of Formula 1 include those in which is selected from:
(125) (a) hydrogen, halo, cyano and hydroxy; and
(b) $C_{1-6}$ alkyl and $C_{1-6}$ alkoxy, each unsubstituted or substituted with 1 to 3 substituents independently selected from halo;
(126) (a) hydrogen, halo and hydroxy; and
(b) $C_{1-6}$ alkyl and $C_{1-6}$ alkoxy, each unsubstituted or substituted with 1 to 3 substituents independently selected from halo;
(127) (a) hydrogen and halo; and
(b) $C_{1-6}$ alkyl and $C_{1-6}$ alkoxy, each unsubstituted or substituted with 1 to 3 substituents independently selected from halo;
(128) (a) hydrogen and halo; and
(b) $C_{1-4}$ alkyl and $C_{1-3}$ alkoxy, each unsubstituted or substituted with 1 to 3 substituents independently selected from halo;
(129) hydrogen, halo and $C_{1-4}$ alkyl which is unsubstituted or substituted with 1 to 3 substituents independently selected from halo;
(130) hydrogen, halo and $C_{1-4}$ alkyl;
(131) hydrogen, halo and methyl;
(132) hydrogen, chloro, fluoro and methyl; or
(133) hydrogen.

Compounds of Formula 1 include embodiments (1) through (133) described in the preceding paragraphs and all compounds specifically named in the examples, and may exist as salts, complexes, solvates, hydrates; and liquid crystals. Likewise; compounds of Formula 1 that are salts may exist as complexes, solvates, hydrates, and liquid crystals.

Compounds of Formula 1 may form pharmaceutically acceptable complexes, salts, solvates and hydrates. These salts include acid addition salts (including di-acids) and base salts. Pharmaceutically acceptable acid addition salts include salts derived from inorganic acids such as hydrochloric acid, nitric acid, phosphoric acid, sulfuric acid, hydrobromic acid, hydroiodic acid, hydrofluoric acid, and phosphorous acids, as well nontoxic salts derived from organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts include acetate, adipate, aspartate, benzoate, besylate, bicarbonate, carbonate, bisulfate, sulfate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulfate, naphthylate, 2-napsylate, nicotinate, nitrate, orotate; oxalate; palmitate, pamoate, phosphate, hydrogen phosphate, dihydrogen phosphate, pyroglutamate, saccharate, stearate, succinate, tannate, tartrate, tosylate, trifluoroacetate and xinofoate salts.

Pharmaceutically acceptable base salts include salts derived from bases, including metal cations, such as an alkali or alkaline earth metal cation, as well as amines. Examples of suitable metal cations include sodium, potassium, magnesium, calcium, zinc, and aluminum. Examples of suitable amines include arginine, N,N'-dibenzylethylenediamine, chloroprocaine, choline, diethylamine; diethanolamine, dicyclohexylamine, ethylenediamine, glycine, lysine, N-methylglucamine, olamine, 2-amino-2-hydroxymethyl-propane-1,3-diol, and procaine. For a discussion of useful acid addition and base salts; see S. M. Berge et al., *J. Pharm. Sci.* (1977) 66:1-19; see also Stahl and Wermuth, *Handbook of Pharmaceutical Salts: Properties, Selection, and Use* (2002).

Pharmaceutically acceptable salts may be prepared using various methods. For example, a compound of Formula 1 may be reacted with an appropriate acid or base to give the desired salt. Alternatively, a precursor of the compound of Formula 1 may be reacted with an acid or base to remove an acid- or base-labile protecting group or to open a lactone or lactam group of the precursor. Additionally, a salt of the compound of Formula 1 may be converted to another salt (or free form) through treatment with an appropriate acid or base or through contact with an ion exchange resin. Following reaction, the salt may be isolated by filtration if it precipitates from solution, or by evaporation to recover the salt. The degree of ionization of the salt may vary from completely ionized to almost non-ionized.

Compounds of Formula 1 may exist in a continuum of solid states ranging from fully amorphous to fully crystalline. The term "amorphous" refers to a state in which the material lacks long range order at the molecular level and, depending upon temperature, may exhibit the physical properties of a solid or a liquid. Typically, such materials do not give distinctive X-ray diffraction patterns and, while exhibiting the properties of a solid, are more formally described as a liquid. Upon heating, a change from solid to liquid properties occurs which is characterized by a change of state, typically second order ("glass transition"). The term "crystalline" refers to a solid phase in which the material has a regular ordered internal structure at the molecular level and gives a distinctive X-ray diffraction pattern with defined peaks. Such materials when heated sufficiently will also exhibit the properties of a liquid, but the change from solid to liquid is characterized by a phase change, typically first order ("melting point").

Compounds of Formula 1 may also exist in unsolvated and solvated forms. The term "solvate" describes a molecular complex comprising the compound and one or more pharmaceutically acceptable solvent molecules (e.g., ethanol). The term "hydrate" is a solvate in which the solvent is water. Pharmaceutically acceptable solvates include those in which the solvent may be isotopically substituted (e.g., $D_2O$, acetone-$d_6$, DMSO-$d_6$).

A currently accepted classification system for solvates and hydrates of organic compounds is one that distinguishes between isolated site, channel, and metal-ion coordinated solvates and hydrates. See, e.g., K. R. Morris (H. G. Brittain ed.) *Polymorphism in Pharmaceutical Solids* (1995). Isolated site solvates and hydrates are ones in which the solvent (e.g., water) molecules are isolated from direct contact with each other by intervening molecules of the organic compound. In channel solvates, the solvent molecules lie in lattice channels where they are next to other solvent molecules. In metal-ion coordinated solvates, the solvent molecules are bonded to the metal ion.

When the solvent or water is tightly bound, the complex will have a well-defined stoichiometry independent of humidity. When, however, the solvent or water is weakly bound, as in channel solvates and in hygroscopic compounds, the water or solvent content will depend on humidity and drying conditions. In such cases, non-stoichiometry will typically be observed.

Compounds of Formula 1 may also exist as multi-component complexes (other than salts and solvates) in which the compound (drug) and at least one other component are present in stoichiometric or non-stoichiometric amounts. Complexes of this type include clathrates (drug-host inclusion complexes) and co-crystals. The latter are typically defined as crystalline complexes of neutral molecular constituents which are bound together through non-covalent interactions but could also be a complex of a neutral molecule with a salt. Co-crystals may be prepared by melt crystallization, by recrystallization from solvents, or by physically grinding the components together. See, e.g., O. Almarsson and M, J. Zaworotko, *Chem. Commun.* (2004) 17:1889-1896. For a general review of multi-component complexes, see J. K. Haleblian, *J. Pharm, Sci.* (1975) 64(8):1269-88.

When subjected to suitable conditions, compounds of Formula 1 may exist in a mesomorphic state (mesophase or liquid crystal). The mesomorphic state lies between the true crystalline state and the true liquid state (either melt or solution). Mesomorphism arising as the result of a change in temperature is described as "thermotropic" and mesomorphism resulting from the addition of a second component, such as water or another solvent, is described as "lyotropic." Compounds that have the potential to form lyotropic mesophases are described as "amphiphilic" and include molecules which possess a polar ionic moiety (e.g., —COO$^-$Na$^+$, —COO$^-$K$^+$, —SO$_3^-$Na$^+$) or polar non-ionic moiety (such as —N$^-$N$^+$(CH$_3$)$_3$). See, e.g., N. H. Hartshorne and A. Stuart, *Crystals and the Polarizing Microscope* (4th ed, 1970).

Each compound of Formula 1 may exist as polymorphs, stereoisomers, tautomers, or some combination thereof, may be isotopically-labeled, may result from the administration of a prodrug, or form a metabolite following administration.

"Prodrugs" refer to compounds having little or no pharmacological activity that can, when metabolized in vivo, undergo conversion to compounds having desired pharmacological activity. Prodrugs may be prepared by replacing appropriate functionalities present in pharmacologically active compounds with "pro-moieties" as described, for example, in H. Bundgaar, *Design of Prodrugs* (1985). Examples of prodrugs include ester, ether or amide derivatives of compounds of Formula 1 having carboxylic acid, hydroxy, or amino functional groups, respectively. For further discussions of prodrugs, see e.g., T. Higuchi and V. Stella "Pro-drugs as Novel Delivery Systems," *ACS Symposium Series* 14 (1975) and E. B. Roche ed., *Bioreversible Carriers in Drug Design* (1987).

"Metabolites" refer to compounds formed in vivo upon administration of pharmacologically active compounds. Examples include hydroxymethyl, hydroxy, secondary amino, primary amino, phenol, and carboxylic acid derivatives of compounds of Formula 1 having methyl, alkoxy, tertiary amino, secondary amino, phenyl, and amide groups, respectively.

Compounds of Formula 1 may exist as stereoisomers that result from the presence of one or more stereogenic centers, one or more double bonds, or both. The stereoisomers may be pure, substantially pure, or mixtures. Such stereoisomers may also result from acid addition or base salts in which the counter-ion is optically active, for example, when the counter-ion is D-lactate or L-lysine.

Compounds of Formula 1 may exist as tautomers, which are isomers resulting from tautomerization. Tautomeric isomerism includes, for example, imine-enamine, keto-enol, oxime-nitroso, and amide-imidic acid tautomerism.

Compounds of Formula. I may exhibit more than one type of isomerism.

Geometrical (cis/trans) isomers may be separated by conventional techniques such as chromatography and fractional crystallization.

Conventional techniques for preparing or isolating a compound having a specific stereochemical configuration include chiral synthesis from a suitable optically pure precursor or resolution of the racemate (or the racemate of a salt or derivative) using, for example, chiral high-pressure liquid chromatography (HPLC). Alternatively, the racemate (or a racemic precursor) may be reacted with a suitable optically active compound, for example, an alcohol; or, in the case where the compound of Formula 1 contains an acidic or basic moiety, an acid or base such as tartaric acid or 1-phenylethylamine. The resulting diastereomeric mixture may be separated by chromatography, fractional crystallization, etc., and the appropriate diastereoisomer converted to the compound having the requisite stereochemical configuration. For a further discussion of techniques for separating stereoisomers, see E. L. Eliel and S. H. Wilen, *Stereochemistry of Organic Compounds* (1994).

Compounds of Formula 1 may possess isotopic variations, in which at least one atom is replaced by an atom having the same atomic number, but an atomic mass different from the atomic mass usually found in nature. Isotopes suitable for inclusion in compounds of Formula 1 include, for example, isotopes of hydrogen, such as $^2$H and $^3$H; isotopes of carbon, such as $^{11}$C, $^{13}$C and $^{14}$C; isotopes of nitrogen, such as $^{13}$N and $^{15}$N; isotopes of oxygen, such as $^{15}$O, $^{17}$O and $^{18}$O; isotopes of sulfur, such as $^{35}$S; isotopes of fluorine, such as $^{18}$F; isotopes of chlorine, such as $^{36}$Cl, and isotopes of iodine, such as $^{123}$I and $^{125}$I. Use of isotopic variations (e.g., deuterium, $^2$H) may afford certain therapeutic advantages resulting from greater metabolic stability; for example; increased in vivo half-life or reduced dosage requirements. Additionally, certain isotopic variations of the disclosed compounds may incorporate a radioactive isotope (e.g., tritium, $^3$H, or $^{14}$C), which may be useful in drug and/or substrate tissue distribution studies. Substitution with positron emitting isotopes, such as $^{11}$C, $^{15}$F, $^{15}$O and $^{13}$N, may be useful in Positron Emission Topography (PET) studies for examining substrate receptor occupancy.

Isotopically-labeled compounds may be prepared by processes analogous to those described elsewhere in the disclosure using an appropriate isotopically-labeled reagent in place of a non-labeled reagent. Thus, for example, the compounds of Formula 1 include those in which one or more R$^7$, R$^8$, R$^9$, R$^{10}$ and R$^{11}$ may optionally be deuterium, or one or more of R$^7$, R$^8$, R$^9$, R$^{10}$ and R$^{11}$ may include a substituent having one or more hydrogen atoms that are deuterium. Unless otherwise stated, when a substituent is designated specifically as "D" or "deuterium," it is understood to have deuterium at an abundance that is at least 3000 times greater than the natural abundance of deuterium, which is 0.015% (i.e., at least 45% incorporation of deuterium).

The compounds of Formula 1 may be prepared using the techniques described below. Some of the schemes and examples may omit details of common reactions, including oxidations, reductions, and so on, separation techniques (extraction, evaporation, precipitation, chromatography, filtration, trituration, crystallization, and the like), and analytical procedures, which are known to persons of ordinary skill in the art of organic chemistry. The details of such reactions and techniques can be found in several treatises, including Richard Larock, *Comprehensive Organic Transformations* (1999), and the multi-volume series edited by Michael B. Smith and others, *Compendium of Organic Synthetic Methods* (1974 et seq.). Starting materials and reagents may be obtained from commercial sources or may be prepared using literature methods. Some of the reaction schemes may omit minor products resulting from chemical transformations (e.g., an alcohol from the hydrolysis of an ester, $CO_2$ from the decarboxylation of a di-acid, etc.). In addition, in some instances, reaction intermediates may be used in subsequent steps without isolation or purification in situ).

In some of the reaction schemes and examples below, certain compounds can be prepared using protecting groups, which prevent undesirable chemical reaction at otherwise reactive sites. Protecting groups may also be used to enhance solubility or otherwise modify physical properties of a compound. For a discussion of protecting group strategies, a description of materials and methods for installing and removing protecting groups, and a compilation of useful protecting groups for common functional groups, including amines, carboxylic acids, alcohols, ketones, aldehydes, and so on, see T. W. Greene and P. G. Wuts, *Protecting Groups in Organic Chemistry* (1999) and P. Kocienski, *Protective Groups* (2000).

Generally, the chemical transformations described throughout the specification may be carried out using substantially stoichiometric amounts of reactants, though certain reactions may benefit from using an excess of one or more of the reactants. Additionally, many of the reactions disclosed throughout the specification may be carried out at about room temperature (RT) and ambient pressure, but depending on reaction kinetics, yields, and so on, some reactions may be run at elevated pressures or employ higher temperatures (e.g., reflux conditions) or lower temperatures (e.g., −78° C. to 0° C.). Any reference in the disclosure and claims to a stoichiometric range, a temperature range, a pH range, etc., whether expressly using the word "range," also includes the indicated endpoints.

Many of the chemical transformations may also employ one or more compatible solvents, which may influence the reaction rate and yield. Depending on the nature of the reactants, the one or more solvents may be polar protic solvents (including water), polar aprotic solvents, non-polar solvents, or some combination. Representative solvents include saturated aliphatic hydrocarbons (e.g., n-pentane, n-hexane, n-heptane, n-octane, cyclohexane, methylcyclohexane); aromatic hydrocarbons (e.g., benzene, toluene, xylenes); halogenated hydrocarbons (e.g., methylene chloride, chloroform, carbon tetrachloride); aliphatic alcohols (e.g., methanol, ethanol, propan-1-ol, propan-2-ol, butan-1-ol, 2-methyl-propan-1-ol, butan-2-ol, 2-methyl-propan-2-ol, pentan-1-ol, 3-methyl-butan-1-ol, hexan-1-ol, 2-methoxy-ethanol, 2-ethoxy-ethanol, 2-butoxy-ethanol, 2-(2-methoxy-ethoxy)-ethanol, 2-(2-ethoxy-ethoxy)-ethanol, 2-(2-butoxy-ethoxy)-ethanol); ethers (e.g., diethyl ether, di-isopropyl ether, dibutyl ether, 1,2-dimethoxy-ethane, 1,2-di ethoxy-ethane, 1-methoxy-2-(2-methoxy-ethoxy)-ethane, 1-ethoxy-2-(2-ethoxy-ethoxy)-ethane, tetrahydrofuran, 1,4-dioxane); ketones (e.g., acetone, methyl ethyl ketone); esters (methyl acetate, ethyl acetate); nitrogen-containing solvents (e.g., formamide, N,N-dimethylformamide, acetonitrile, N-methyl-pyrrolidone, pyridine, quinoline, nitrobenzene); sulfur-containing solvents (e.g., carbon disulfide, dimethyl sulfoxide, tetrahydro-thiophene-1,1-dioxide); and phosphorus-containing solvents (e.g., hexamethylphosphoric triamide).

In the scheme, below, substituent identifiers ($\alpha$, $\beta$, n, $R^4$, $R^5$, $R^6$, $R^8$, $R^9$, $R^{10}$, $R^{11}$, $X^1$, $X^2$, $X^3$ and $X^7$) are as defined above for Formula 1. As mentioned earlier, some of the starting materials and intermediates may include protecting groups, which are removed prior to the final product. In such cases, the substituent identifier refers to groups defined in Formula 1 and to those groups with appropriate protecting groups (unless explicitly shown). For example, a starting material or intermediate in the schemes may include a substituent ($X^3$=$NR^{3N}$) with a potentially reactive amine ($R^{3N}$=H). In such cases, the $R^{3N}$ substituent would also include benzyl, Boc, Cbz, etc.

Scheme A shows a general method for preparing compounds of Formula 1. In accordance with the method, appropriately substituted secondary amine (A-1) and alkyl halide (A-2, X=Cl, Br, I) are reacted in the presence of a non-nucleophilic or inorganic base (e.g., $K_2CO_3$, NaH, etc.) and a polar aprotic solvent (e.g., DMF, NMP, ACN, etc.), at a temperature which may range from about RT to about 60° C., to give the compound of Formula 1. The secondary amine (A-1) and alkyl halide (A-2) may be obtained using procedures described in (or analogous to) specific preparations provided in the Examples section, below.

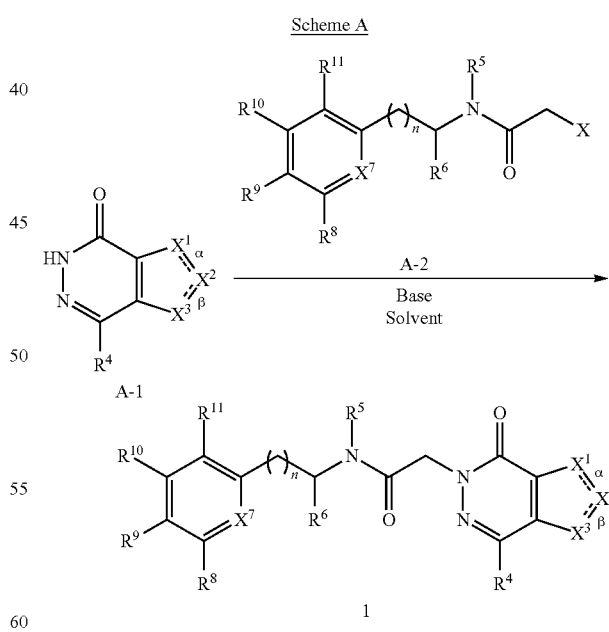

Scheme A

The methods depicted in the schemes may be varied as desired. For example, protecting groups may be added or removed, and intermediates or products may be further elaborated via, for example, alkylation, acylation, halogenation, hydrolysis, oxidation, reduction, amidation, sulfonation, alkynation, transition metal catalyzed cross-coupling reactions, and the like to give the desired final product. Furthermore, any intermediate or final product which comprises mixture of stereoisomers may be optionally purified by chiral column chromatography (e.g., supercritical fluid chromatography) or by derivatization with optically-pure reagents as described above to give a desired stereoisomer.

Compounds of Formula 1, which include compounds named above, and their pharmaceutically acceptable complexes, salts, solvates and hydrates, should be assessed for their biopharmaceutical properties, such as solubility and solution stability across pH, permeability, and the like, to select an appropriate dosage form and route of administration. Compounds that are intended for pharmaceutical use may be administered as crystalline or amorphous products, and may be obtained, for example, as solid plugs, powders, or films by methods such as precipitation, crystallization, freeze drying, spray drying; evaporative drying, microwave drying, or radio frequency drying.

Compounds of Formula 1 may be administered alone or in combination with one another or with one or more pharmacologically active compounds which are different than the compounds of Formula 1. Generally, one or more of these compounds are administered as a pharmaceutical composition (a formulation) in association with one or more pharmaceutically acceptable excipients. The choice of excipients depends on the mode of administration, the effect of the excipient on solubility and stability, and the nature of the dosage form, among other things. Useful pharmaceutical compositions and methods for their preparation may be found; for example, in A. R. Gennaro (ed.), *Remington: The Science and Practice of Pharmacy* (20th ed., 2000).

Compounds of Formula 1 may be administered orally. Oral administration may involve swallowing in which case the compound enters the bloodstream via the gastrointestinal tract. Alternatively, or additionally, oral administration may involve mucosal administration (e.g., buccal, sublingual, supralingual administration) such that the compound enters the bloodstream through the oral mucosa.

Formulations suitable for oral administration include solid, semi-solid and liquid systems such as tablets; soft or hard capsules containing multi- or nano-particulates, liquids, or powders; lozenges which may be liquid-filled; chews; gels; fast dispersing dosage forms; films; ovules; sprays; and buccal or mucoadhesive patches. Liquid formulations include suspensions, solutions, syrups and elixirs. Such formulations may be employed as fillers in soft or hard capsules (made, e.g., from gelatin or hydroxypropylmethylcellulose) and typically comprise a carrier (e.g., water, ethanol, polyethylene glycol, propylene glycol, methylcellulose, or a suitable oil) and one or more emulsifying agents, suspending agents or both. Liquid formulations may also be prepared by the reconstitution of a solid (e.g., from a sachet).

Compounds of Formula 1 may also be used in fast-dissolving, fast-disintegrating dosage forms such as those described in Liang and Chen, *Expert Opinion in Therapeutic Patents* (2001) 11(6):981-986.

For tablet dosage forms, depending on dose, the active pharmaceutical ingredient (API) may comprise from about 1 wt % to about 80 wt % of the dosage form or more typically from about 5 wt % to about 60 wt % of the dosage form. In addition to the API, tablets may include one or more disintegrants, binders, diluents, surfactants, glidants, lubricants, anti-oxidants, colorants, flavoring agents, preservatives, and taste-masking agents. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, $C_{1-6}$ alkyl-substituted hydroxypropylcellulose, starch, pregelatinized starch, and sodium alginate. Generally, the disintegrant will comprise from about 1 wt % to about 25 wt % or from about 5 wt % to about 20 wt % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinized starch, hydroxypropylcellulose and hydroxypropylmethylcellulose. Tablets may also contain diluents, such as lactose (monohydrate, spray-dried monohydrate, anhydrous), mannitol, xylitol, dextrose, sucrose, sorbitol, microcrystalline cellulose, starch and dibasic calcium phosphate dihydrate.

Tablets may also include surface active agents, such as sodium laurel sulfate and polysorbate 80, and glidants such as silicon dioxide and talc. When present, surface active agents may comprise from about 0.2 wt % to about 5 wt % of the tablet, and glidants may comprise from about 0.2 wt % to about 1 wt % of the tablet.

Tablets may also contain lubricants such as magnesium stearate, calcium stearate, zinc stearate, sodium stearyl fumarate, and mixtures of magnesium stearate with sodium lauryl sulfate. Lubricants may comprise from about 0.25 wt % to about 10 wt % or from about 0.5 wt % to about 3 wt % of the tablet.

Tablet blends may be compressed directly or by roller compaction to form tablets. Tablet blends or portions of blends may alternatively be wet-, dry-, or melt-granulated, melt congealed, or extruded before tableting. If desired, prior to blending one or more of the components may be sized by screening or milling or both. The final dosage form may comprise one or more layers and may be coated, uncoated, or encapsulated. Exemplary tablets may contain up to about 80 wt % of API, from about 10 wt % to about 90 wt % of binder, from about 0 Wt % to about 85 wt % of diluent, from about 2 wt % to about 10 wt % of disintegrant, and from about 0.25 wt % to about 10 wt % of lubricant. For a discussion of blending, granulation, milling, screening, tableting, coating, as well as a description of alternative techniques for preparing drug products, see A. R. Gennaro (ed.), *Remington: The Science and Practice of Pharmacy* (20th ed., 2000); H. A. Lieberman et al. (ed.), *Pharmaceutical Dosage Forms: Tablets, Vol.* 1-3 (2d ed., 1990); and D. K. Parikh & C. K. Parikh, *Handbook of Pharmaceutical Granulation Technology, Vol.* 81 (1997).

Consumable oral films for human or veterinary use are pliable water-soluble or water-swellable thin film dosage forms which may be rapidly dissolving or mucoadhesive. In addition to the API, a typical film includes one or more film-forming polymers, binders, solvents, humectants, plasticizers, stabilizers or emulsifiers, viscosity-modifying agents, and solvents. Other film ingredients may include anti-oxidants, colorants, flavorants and flavor enhancers, preservatives, salivary stimulating agents, cooling agents, co-solvents (including oils), emollients, bulking agents, antifoaming agents, surfactants, and taste-masking agents. Some components of the formulation may perform more than one function.

In addition to dosing requirements, the amount of API in the film may depend on its solubility. If water soluble; the API would typically comprise from about 1 wt % to about 80 wt % of the non-solvent components (solutes) in the film or from about 20 wt % to about 50 wt % of the solutes in the film. A less soluble API may comprise a greater proportion of the composition, typically up to about 88 wt % of the non-solvent components in the film.

The film-forming polymer may be selected from natural polysaccharides, proteins, or synthetic hydrocolloids and typically comprises from about 0.01 wt % to about 99 wt % or from about 30 wt % to about 80 wt % of the film.

Film dosage forms are typically prepared by evaporative drying of thin aqueous films coated onto a peelable backing support or paper, which may be carried out in a drying oven or tunnel (e.g., in a combined coating-drying apparatus), in lyophilization equipment, or in a vacuum oven.

Useful solid formulations for oral administration may include immediate release formulations and modified release formulations, Modified release formulations include delayed-, sustained-, pulsed-, controlled-, targeted-, and programmed-release. For a general description of suitable modified release formulations, see U.S. Pat. No. 6,106,864. For details of other useful release technologies, such as high energy dispersions and osmotic and coated particles, see Verma et al., *Pharmaceutical Technology On-line* (2001) 25(2):1-14.

Compounds of Formula 1 may also be administered directly into the blood stream, muscle, or an internal organ of the subject. Suitable techniques for parenteral administration include intravenous, intraarterial, intraperitoneal, intrathecal, intraventricular, intraurethral, intrasternal, intracranial, intramuscular, intrasynovial, and subcutaneous administration. Suitable devices for parenteral administration include needle injectors, including microneedle injectors, needle-free injectors, and infusion devices.

Parenteral formulations are typically aqueous solutions which may contain excipients such as salts, carbohydrates and buffering agents (e.g., pH of from about 3 to about 9). For some applications, however, compounds of Formula 1 may be more suitably, formulated as a sterile non-aqueous solution or as a dried form to be used in conjunction with a suitable vehicle such as sterile, pyrogen-free water. The preparation of parenteral formulations under sterile conditions (e.g., by lyophilization) may be readily accomplished using standard pharmaceutical techniques.

The solubility of compounds which are used in the preparation of parenteral solutions may be increased through appropriate formulation techniques, such as the incorporation of solubility-enhancing agents. Formulations for parenteral administration may be formulated to be immediate or modified release. Modified release formulations include delayed, sustained, pulsed, controlled, targeted, and programmed release. Thus, compounds of Formula 1 may be formulated as a suspension, a solid, a semi-solid, or a thixotropic liquid for administration as an implanted depot providing modified release of the active compound. Examples of such formulations include drug-coated stents and semi-solids and suspensions comprising drug-loaded poly(DL-lactic-coglycolic)acid (PGLA) microspheres.

Compounds of Formula 1 may also be administered topically, intradermally, or transdermally to the skin or mucosa. Typical formulations for this purpose include gels, hydrogels, lotions, solutions, creams, ointments, dusting powders, dressings, foams, films, skin patches, wafers, implants, sponges, fibers, bandages and microemulsions. Liposomes may also be used. Typical carriers may include alcohol, water, mineral oil, liquid petrolatum, white petrolatum, glycerin, polyethylene glycol and propylene glycol. Topical formulations may also include penetration enhancers. See, e.g., Finnin and Morgan, *J. Pharm. Sci.* 88(10): 955-958 (1999).

Other means of topical administration include delivery by electroporation, iontophoresis, phonophoresis, sonophoresis and microneedle or needle-free (e.g. Powderject™ and Bioject™) injection. Formulations for topical administration may be formulated to be immediate or modified release as described above.

Compounds of Formula 1 may also be administered intranasally or by inhalation, typically in the form of a dry powder, an aerosol spray, or nasal drops. An inhaler may be used to administer the dry powder, which comprises the API alone, a powder blend of the API and a diluent, such as lactose, or a mixed component particle that includes the API and a phospholipid, such as phosphatidylcholine. For intranasal use, the powder may include a bioadhesive agent, e.g., chitosan or cyclodextrin. A pressurized container, pump, sprayer, atom/zer, or nebulizer, may be used to generate the aerosol spray from a solution or suspension comprising the API, one or more agents for dispersing, solubilizing, or extending the release of the API (e.g., EtOH with or without water), one or more solvents (e.g., 1,1,1,2-tetrafluoroethane or 1,1,1,2,3,3,3-heptafluoropropane) which serve as a propellant, and an optional surfactant, such as sorbitan trioleate, oleic acid, or an oligolactic acid. An atom/zer using electrohydrodynamics may be used to produce a fine mist.

Prior to use in a dry powder or suspension formulation, the drug product is usually comminuted to a particle size suitable for delivery by inhalation (typically 90% of the particles, based on volume, having a largest dimension less than 5 microns). This may be achieved by any appropriate size reduction method, such as spiral jet milling, fluid bed jet milling, supercritical fluid processing, high pressure homogenization, or spray drying.

Capsules, blisters and cartridges (made, for example, from gelatin or hydroxypropylmethyl cellulose) for use in an inhaler or insufflator may be formulated to contain a powder mixture of the active compound, a suitable powder base such as lactose or starch, and a performance modifier such as L-leucine, mannitol, or magnesium stearate. The lactose may be anhydrous or monohydrated. Other suitable excipients include dextran, glucose, maltose, sorbitol, xylitol, fructose, sucrose, and trehalose.

A suitable solution formulation for use in an atom/zer using electrohydrodynamics to produce a fine mist may contain from about 1 µg to about 20 mg of the API per actuation and the actuation volume may vary from about 1 µL to about 100 µL. A typical formulation may comprise one or more compounds of Formula 1, propylene glycol, sterile water, EtOH, and NaCl. Alternative solvents, which may be used instead of propylene glycol, include glycerol and polyethylene glycol.

Formulations for inhaled administration, intranasal administration, or both, may be formulated to be immediate or modified release using, for example, PGLA. Suitable flavors, such as menthol and levomenthol, or sweeteners, such as saccharin or sodium saccharin, may be added to formulations intended for inhaled/intranasal administration.

In the case of dry powder inhalers and aerosols, the dosage unit is determined by means of a valve that delivers a metered amount. Units are typically arranged to administer a metered dose or "puff" containing from about 10 µg to about 1000 µg of the API. The overall daily dose will typically range from about 100 µg to about 10 mg which may be administered in a single dose or, more usually, as divided doses throughout the day.

The active compounds may be administered rectally or vaginally, e.g., in the form of a suppository, pessary, or enema. Cocoa butter is a traditional suppository base, but various alternatives may be used as appropriate. Formulations for rectal or vaginal administration may be formulated to be immediate or modified release as described above.

Compounds of Formula 1 may also be administered directly to the eye or ear, typically in the form of drops of a micronized suspension or solution in isotonic, pH-adjusted, sterile saline. Other formulations suitable for ocular and aural administration include ointments, gels, biodegradable implants (e.g. absorbable gel sponges, collagen), non-biodegradable implants (e.g. silicone), wafers, lenses, and particulate or vesicular systems, such as niosomes or liposomes. The formulation may include one or more polymers and a preservative, such as benzalkonium chloride. Typical polymers include crossed-linked polyacrylic acid, polyvinyl alcohol, hyaluronic acid, cellulosic polymers (e.g., hydroxypropylmethylcellulose, hydroxyethyl cellulose, methyl cellulose), and heteropolysaccharide polymers (e.g., gelan gum). Such formulations may also be delivered by iontophoresis. Formulations for ocular or aural administration may be formulated to be immediate or modified release as described above.

To improve their solubility, dissolution rate, taste-masking, bioavailability, or stability, compounds of Formula 1 may be combined with soluble macromolecular entities, including cyclodextrin and its derivatives and polyethylene glycol-containing polymers. For example, API-cyclodextrin complexes are generally useful for most dosage forms and routes of administration. Both inclusion and non-inclusion complexes may be used. As an alternative to direct complexation with the API, the cyclodextrin may be used as an auxiliary additive, i.e. as a carrier, diluent, or solubilizer. Alpha-, beta- and gamma-cyclodextrins are commonly used for these purposes. See, e.g., WO 91/11172, WO 94/02518, and WO 98/55148.

As noted above, one or more compounds of Formula 1, including compounds specifically named above, and their pharmaceutically active complexes, salts, solvates and hydrates, may be combined with each other or with one or more other active pharmaceutically active compounds to treat various diseases, conditions and disorders. In such cases, the active compounds may be combined in a single dosage form as described above or may be provided in the form of a kit which is suitable for coadministration of the compositions. The kit comprises (1) two or more different pharmaceutical compositions, at least one of which comprises a compound of Formula 1; and (2) a device for separately retaining the two pharmaceutical compositions, such as a divided bottle or a divided foil packet. An example of such a kit is the familiar blister pack used for the packaging of tablets or capsules. The kit is suitable for administering different types of dosage forms (e.g., oral and parenteral) or for administering different pharmaceutical compositions at separate dosing intervals, or for titrating the different pharmaceutical compositions against one another. To assist with patient compliance, the kit typically comprises directions for administration and may be provided with a memory aid.

For administration to human patients, the total daily dose of the claimed and disclosed compounds is typically in the range of about 0.1 mg to about 3000 mg depending on the route of administration. For example, oral administration may require a total daily dose of from about 1 mg to about 3000 mg, while an intravenous dose may only require a total daily dose of from about 0.1 mg to about 300 mg. The total daily dose may be administered in single or divided doses and, at the physician's discretion, may fall outside of the typical ranges given above. Although these dosages are based on an average human subject having a mass of about 60 kg to about 70 kg, the physician will be able to determine the appropriate dose for a patient (e.g., an infant) whose mass falls outside of this weight range.

As noted above, the compounds of Formula 1 may be used to treat diseases, disorders or conditions for which activation of GPR139 is indicated. Such diseases, disorders or conditions generally relate to any unhealthy or abnormal state in a subject for which the activation of GPR139 provides a therapeutic benefit. More particularly, the compounds of Formula 1 may be used to treat diseases, disorders or conditions of the CNS, including schizophrenia, autism spectrum disorder, sleep disorders, depression, bipolar disorder, cognitive impairment, attention deficit hyperactivity disorder, post-traumatic stress disorder, substance use disorder, substance abuse, drug addiction, eating disorders (including anorexia nervosa), obsessive compulsive disorder, anxiety disorders, epilepsy, pain and fibromyalgia.

In addition, the compounds of Formula 1 may be used to treat Alzheimer's disease, and other forms of dementia (i.e., major or mild neurocognitive disorders) associated with one or more medical conditions, including frontotemporal lobar degeneration, Lewy body disease, vascular disease, traumatic brain injury, substance or medication use, HA infection, prion disease; Parkinson's disease, and Huntington's disease. The compounds of Formula 1 may also be used to treat major or mild neurocognitive disorders associated with depression, schizophrenia, bipolar disorder, and autism.

The claimed and disclosed compounds may be combined with one or more other pharmacologically active compounds or therapies to treat one or more disorders, diseases or conditions for which GPR139 is indicated. Such combinations may offer significant therapeutic advantages, including fewer side effects; improved ability to treat underserved patient populations, or synergistic activity. For example, compounds of Formula 1, which include compounds specifically named above, and their pharmaceutically acceptable complexes; salts; solvates and hydrates, may be administered simultaneously, sequentially or separately in combination with one or more compounds or therapies for treating Alzheimer's disease, including beta-secretase inhibitors, gamma-secretase inhibitors, HMG-CoA reductase inhibitors, nonsteroidal anti-inflammatory drugs (NSAIDs, such as apazone, aspirin, celecoxib, diclofenac (with and without misoprostol), diflunisal, etodolac, fenoprofen, flurbiprofen, ibuprofen, indomethacin, ketoprofen, meclofenamate sodium, mefenamic acid, meloxicam, nabumetone, naproxen, oxaprozin, phenylbutazone; piroxicam, choline and magnesium salicylates, salsalate, and sulindac), vitamin E, and anti-amyloid antibodies. Specific examples of compounds used to treat Alzheimer's disease include donepezil, rivastigmine, memantine, and galantamine.

In addition to drugs used to improve cognition, the compounds of Formula 1 may be combined with sedatives, hypnotics, anxiolytics, antipsychotics, tranquilizers, and other medications. For example, the compounds of Formula 1 may be combined with one or more agents for treating depression (antidepressants) and/or schizophrenia (atypical or typical antipsychotics) including amitriptyline, amoxapine, aripiprazole, asenapine, bupropion, chlordiazepoxide, citalopram, chlorpromazine, clozapine, desipramine, desvenlafaxine, doxepin, duloxetine, escitalopram, fluoxetine, fluoxetine, fluphenazine, haloperidol, iloperidone, imipramine, isocarboxazid, lamotrigine, levomilnacipran; lurasidone, mirtazapine, nefazodone, nortriptyline; olanzapine; paliperidone, paroxetine; perphenazine, phenelzine, protriptyline, quetiapine, risperidone, selegiline, sertraline, tranylcypromine, trazodone, trimipramine, venlafaxine, vilazodone, and vortioxetine, and ziprasidone.

Likewise, the compounds of Formula 1 may be combined with one or more agents for treating anxiety (anxiolytics) including benzodiazepines (alprazolam, chlordiazepoxide, clobazepam, clonazepam, clorazepate, diazepam, estazolam, flurazepam, lorazepam, midazolam, oxazepam, prazepam, quazepam, temazepam, and triazolam), antihistamines (hydroxyzine), non-benzodiazepines (eszopiclone, zaleplon, zolpidem, and zopiclone) and buspirone.

The compounds of Formula 1 may also be combined with one or more agents for treating epilepsy (antiepileptics or anticonvulsants) including acetazolamide, carbamazepine, clobazam, clonazepam, eslicarbazepine acetate, ethosuximide, gabapentin, lacosamide, lamotrigine, levetiracetam, nitrazepam, oxcarbazepine, perampanel, piracetam, phenobarbital, phenytoin, pregabalin, primidone retigabine, ralfinamide, sodium valproate, stiripentol, tiagabine, topiramate, vigabatrin, and zonisamide.

The compounds of Formula 1 may be combined with one or more agents for treating movement disorders, including Parkinson's disease. These compounds include levodopa; DOPA decarboxylase inhibitors such as carbidopa, benserazide, methyldopa, difluoromethyl-DOPA, and 3',4',5,7-tetrahydroxy-8-methoxyisoflavone; dopamine agonists, such as apomorphine hydrochloride, bromocriptine, rotigotine, pramipexole, and ropinirole; anticholinergics, such as trihexyphenidyl and benztropine mesylate; B-selective monoamine oxidase (MAO-B) inhibitors, such as selegiline and rasagiline; A2A receptor antagonists, such as istradefylline and preladenant; and catechol O-methyl transferase (COMT) inhibitors, such as entacapone and tolcapone.

BIOLOGICAL ACTIVITY

One may determine the activity of the compounds of Formula 1 using a variety of methods, including in vitro and in vivo methods.

OPR139 Competition Binding

This membrane-based assay measures the ability of compounds to competitively bind GPR139 in stably transfected TREx™-CHO membranes. To prepare the membranes, T-REx™-CHO (Thermo Fisher Scientific®) cells are stably expressed with human GPR139 receptor, whose expression is controlled by a tetracycline-inducible element. The cells are cultured in medium containing F-12K nutrient mixture-Kaighn's modification, 10% tetracycline-free FBS, Blasticidin S HCl (10 µg/mL) and Hygromycin B (200 µg/mL). GPR139 receptor expression is induced for 18 hours with 2 µg/mL doxycycline (Sigma D9891) in growth media. After addition of doxycycline, cells are harvested in PBS and pelleted by centrifugation for 5 minutes at 200×G. Liquid is aspirated off and cells are resuspended in ice cold lysis buffer (20 mM HEPES/5 mM EDTA pH 7.4/1× Roche® protease inhibitor). Samples are vortexed until homogenous and then placed on ice and homogenized using a Dounce homogenizer at 50% power (3 cycles, 10 strokes per cycle). Lysate is centrifuged at 4° C. for 10 minutes in a tabletop Sorvall® centrifuge at 2000×G. The supernatant is recovered and centrifuged in a Sorvall® ultracentrifuge at 35,000 rpm for 30 minutes at 4° C. The supernatant is discarded, and the remaining pellet resuspended in lysis buffer (20 mM HEPES/0.1 mM EGTA/Roche® protease inhibitor). Membrane protein concentration is determined using Thermo Fisher® BCA quantification kit and is aliquoted into microtubes. Tubes are snap frozen in liquid nitrogen and stored at −80° C. Prior to use, the membranes are removed from cold storage, thawed to room temperature, vortexed until homogenous and diluted in assay buffer (20 mM HEPES pH 7.3, 5 mM $MgCl_2$, 1 mM $CaCl_2$), 1× Thermo Scientific® Halt™ protease inhibitor (78429)).

The assay is run in 96-well, polypropylene, v-bottom plates (Greiner Bio-One® 651201). Test compound in DMSO is added to the wells of each plate (11-point dose response curve, 30 µM maximum concentration, 3-fold serial dilution). A fixed amount of tritium-labeled ligand, (S)-2-(2,3-dimethyl-7-oxothieno[2,3-d]pyridazin-6(7H)-yl)-N-(1-(4-methoxyphenyl-2-t)propan-2-yl)acetamide (Quotient Bioresearch) in assay buffer (6.5 nM assay concentration) is added to each well of the assay plate, which is then agitated on a plate shaker for 30 seconds. Next, a fixed amount of membranes in assay buffer (2 µg membranes) is added to each well of the assay plate, which is then spun for 30 seconds at 300 rpm in a tabletop Eppendorf centrifuge, and then incubated at room temperature for 20 minutes. Using a Tomtec harvester, the contents of the assay plate are transferred to Filtermat A (PerkinElmer® No. 1450-421) which prior to use is pre-soaked in 0.5% PEI (Sigma P3143) for 3 hours and dried at room temperature overnight. Following transfer, the Filtermat is washed 5 times with cold wash buffer (20 mM HEPES pH 7.3, 100 mM NaCl). The Filtermat is dried using a microwave oven and placed in a sample bag (PerkinElmer® No. 1450-432) with a scintillator sheet (PerkinElmer® No. 1450-411). The scintillator sheet is melted to the Filtermat using a heat block set to 65° C., placed in a MicroBeta® cartridge and read using a MicroBeta® scintillation counter. Binding curves are generated with a four-parameter logistic equation using GraphPad Prism® 6 and the inhibition constant Ki is reported as pKi.

Measurement of GPR139 Activation Via Calcium Signaling

This cell-based assay measures the ability of compounds to activate GPR139 in stably transfected T-REx™-CHO cells. T-REx™-CHO cells (Thermo Fisher Scientific®) are stably expressed with human GPR139 receptor, whose expression is controlled by a tetracycline-inducible element. The cells are cultured in medium containing F-12K nutrient mixture-Kaighn's modification, TripleLE™ Express (1×)-phenol red, Dulbecco's phosphate-buffered saline (1×), 10% tetracycline-free FBS, Blasticidin S HCl (10 µg/mL) and Hygromycin B (200 µg/mL). The cells are introduced into the wells of a 384-well black clear bottom plate (Costar®) at 10,000 cells/well. GPR139 receptor expression is induced with 2 µg/mL doxycycline (Sigma D9891). The plate is allowed to stand at room temperature for 10-30 minutes and then incubated at 37° C. and 5% $CO_2$ for 17 hours prior to assay.

Culture media is removed from cells and 45 µL of 1× calcium dye (2.5 mM) is added to each well and incubated at 37° C. and 5% $CO_2$ for 40 minutes. The plate is removed from the incubator and allowed to stand at RT for 20 minutes without a plate cover prior to measurement of calcium signaling. The calcium dye is prepared by adding 10 mL of assay buffer (Hank's Balanced Salt Solution (1×), 1 mM HEPES at pH 7.4) to one vial of calcium dye (FLIPR® Calcium 5 Assay Kit; Molecular Devices) at room temperature, vortexing the mixture until homogenous, and transferring the dye to a 250 mL flask using 10 mL of assay, buffer to rinse the vial. The dye is subsequently transferred to a conical flask, which is filled to the 200 mL mark with assay buffer, and 1 mL of 500 nM probenecid solution (142.68 mg/mL in 1M NaOH aq) is added.

Example compounds suspended in DMSO are received from compound management in microtiter plates (0.25 µL/well) and are diluted in assay buffer (25 µL). Following incubation of the cell plate, the Example compounds are added to the cells (11-point dose response, 10 μM maximum concentration) using a FLIPR® Tetra system (Molecular Devices) and fluorescence is measured continuously for 1 minute. $EC_{50}$ curves are generated with a four-parameter logistic equation using GraphPad Prism® 6, and activation of GPR139 for each example compound is reported as $pEC_{50}$.

EXAMPLES

The following examples are intended to be illustrative and non-limiting and represent specific embodiments of the present disclosure.

$^1$H Nuclear magnetic resonance (NMR) spectra were obtained for many of the compounds in the following examples. Characteristic chemical shifts (δ) are given in parts-per-million downfield from tetramethylsilane using conventional abbreviations for designation of major peaks, including s (singlet), d (doublet), t (triplet), q (quartet), m (multiplet), and br (broad). The following abbreviations are used for common solvents: $CDCl_3$ (deuterochloroform), DMSO-$d_6$ (deuterodimethylsulfoxide), $CD_3OD$ (deuteromethanol), $CD_3CN$ (deuteroacetonitrile), and TEIF-$d_8$ (deuterotetrahydrofuran). The mass spectra (m/z for $[M+H]^+$) were recorded using either electrospray ionization (ESI-MS) or atmospheric pressure chemical ionization (APCI-MS) mass spectrometry.

Where indicated, intermediate preparations and example compounds are purified by HPLC. Tables 1 to 4 list equipment, materials, and conditions for some of the Fine, separations.

TABLE 1

HPLC Method A

| | |
|---|---|
| Pump | Shimadzu LC-8A or LC-20AP |
| UV/Vis | Shimadzu SPD-20A |
| Software | LCSolution |
| Column | Phenomenex Gemini® C18, 5 μm, ID 30 mm × 150 mm |
| Mobile Phases | ACN (0.035% TFA) in water (0.05% TFA) |
| Gradient | 10% to 100% ACN (unless indicated otherwise) |

TABLE 2

HPLC Method B

| | |
|---|---|
| Pump | Shimadzu LC-8A or LC-20AP |
| UV/Vis | Shimadzu SPD-20A |
| Software | LCSolution |
| Column | Phenomenex Gemini® C18, 5 μm, ID 30 mm × 150 mm |
| Mobile Phases | Water/ACN (10 mM $NH_4HCO_3$ in 20/80 water/ACN, pH 9.5-10) in water (10 mM $NH_4HCO_3$, pH 9.5-10) |
| Gradient | 10% to 100% ACN (unless indicated otherwise) |

TABLE 3

HPLC Method C

| | |
|---|---|
| Pump | Gilson 322 |
| UV/Vis | Gilson 156 UV |
| Software | Trilution 2.1 |
| Column | Phenomenex Gemini® 5 μm, ID 25 mm × 150 mm |
| Mobile Phases | water (0.05% ammonia hydroxide v/v)/ACN |
| Gradient | 30% to 60% ACN, 10 minutes (unless indicated otherwise) |

TABLE 4

HPLC Method D

| | |
|---|---|
| Pump | Gilson 322 |
| UV/Vis | Gilson 156 UV |
| Software | Trilution 2.1 |
| Column | Phenomenex Gemini® 10 μm, ID 25 mm × 150 mm |
| Mobile Phases | Water (0.05% HCl)/ACN |
| Gradient | 10% to 40% ACN, 10 minutes (unless indicated otherwise) |

Besides HPLC, some of the preparations and examples may employ flash chromatography or preparative thin layer chromatography (TLC). Preparative TLC is typically carried out on silica gel 60 $F_{254}$ plates. The preparations and examples may employ SFC to separate enantiomers.

After isolation by chromatography, the solvent may be removed and the product dried in a centrifugal evaporator (e.g., GeneVac™), rotary evaporator, evacuated flask, etc. Reactions in an inert (e.g., nitrogen) or reactive (e.g., $H_2$) atmosphere are typically carried out at a pressure of about 1 atmosphere (14.7 psi).

Preparation 1: 1-methyl-1,5-dihydro-4H-pyrazolo[3,4-d]pyridazin-4-one

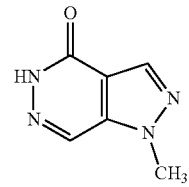

Step 1:
4-chloro-5-(1-methylhydrazinyl)pyridazin-3(2H)-one

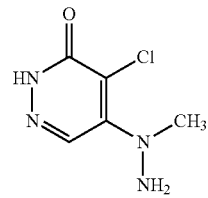

To a solution of 4,5-di chloropyridazin-3(2H)-one (500 mg, 3.03 mmol) in MeOH (12.1 mL) was added methylhydrazine (479 μL, 9.09 mmol) dropwise. The reaction mixture was stirred at RT for 16 hours and then filtered. The filter cake was washed with EtOH to provide the title compound as a pale yellow solid (443 mg, 84%).

Step 2: 4-chloro-5-(1-methyl-2-methylenehydrazineyl)pyridazin-3(2H)-one

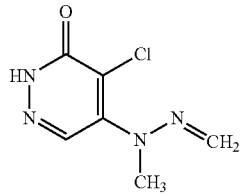

To a solution of 4-chloro-5-(1-methylhydrazinyl)pyridazin-3(2H)-one (220 mg, 1.260 mmol) in EtOH (6301 µL) was added formaldehyde (118 µL, 1.512 mmol) dropwise. The reaction mixture was heated at reflux for 2 hours and then filtered. The filter cake was washed with cold. EtOH to give the title compound as a pale yellow solid (245 mg, 104%).

Step 3: 1-methyl-1,5-dihydro-4H-pyrazolo[3,4-d]pyridazin-4-one

A solution of 4-chloro-5-(1-methyl-2-methylenehydrazineyl)pyridazin-3(2H)-one (245 mg, 1.313 mmol) in acetone (26.3 mL) was irradiated with a 120V lamp for 15 hours. The reaction mixture was concentrated, dissolved in DCM and purified using an ISCO® automated purification system, eluting with a gradient of 0-100% EtOAc in heptanes. The product-containing fractions were collected and combined, concentrated in a rotary evaporator at 35° C., and dried in vacuo to provide the title compound as a white solid (43 mg, 22%).

Preparation 2: 1,4-dimethyl-1,6-dihydro-7H-pyrazolo[3,4-d]pyridazin-7-one

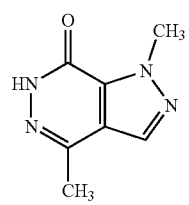

Step 1: ethyl (E)-3-(ethoxymethylene)-2,4-dioxopentanoate

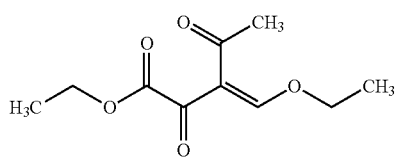

To a solution of ethyl 2,4-dioxopentanoate (0.888 mL, 6.32 mmol) and acetic anhydride (1.195 mL, 12.65 mmol) was added triethoxymethane (1.052 mL, 6.32 mmol). The reaction mixture was heated at 120° C. for 1 hour and then at 140° C. for 1 hour. The reaction mixture was concentrated under reduced pressure to give the title compound as a dark brown oil, which was used directly in the next step.

Step 2: ethyl 4-acetyl-1-methyl-1H-pyrazole-5-carboxylate

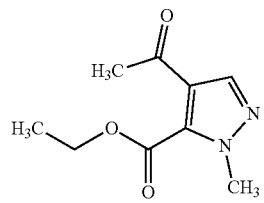

To a solution of ethyl (E)-3-(ethoxymethylene)-2,4-dioxopentanoate (1.354 g, 6.32 mmol) in ether (126 mL) at 0° C. was added methylhydrazine (0.333 mL, 6.32 mmol) dropwise. The reaction mixture was dried over MgSO₄, filtered and concentrated to give the title compound as an orange-brown oil, which was used in the step without further purification.

Step 3: 1,4-dimethyl-1,6-dihydro-7H-pyrazolo[3,4-d]pyridazin-7-one

To a solution of ethyl 4-acetyl-1-methyl-1H-pyrazole-5-carboxylate (1240 mg, 6.32 mmol) in ethanol (13 mL) was added hydrazine hydrate (884 µL, 6.32 mmol) dropwise. The reaction mixture was heated at reflux for 2 hours and then concentrated. The resulting crude material was dissolved in DCM and purified using an ISCO® automated purification system (NH column) eluting with a gradient of 0-100% EtOAc in heptanes. The product-containing fractions were collected and combined, concentrated in a rotary evaporator at 35° C. and dried in vacuo to give the title compound as a tan solid (25 mg, 2.4%).

Preparation 3: 3-cyclopropyl-1-isopropyl-1,5-dihydro-4H-pyrazolo[3,4-d]pyridazin-4-one

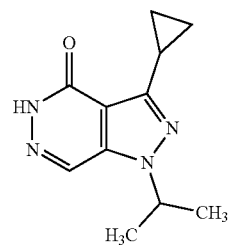 [SMILES: CC(C)n1nc(C2CC2)c2c(=O)[nH]ncc21]

Step 1: ethyl 4,4-diethoxy-3-oxobutanoate

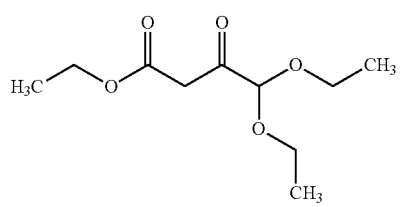

To a mixture of NaH (7.87 g, 196.64 mmol, 60% in mineral oil) in THF (250 mL) was added dropwise a mixture of ethyl 2,2-diethoxyacetate (24.75 g, 140.46 mmol, 25 mL) and EtOAc (13.74 g, 155.91 mmol, 15.26 mL) at 50° C. under $N_2$. The reaction mixture was stirred at 70° C. for 4 hours and then at 25° C. for 12 hours, quenched with aq HOAc (15%, 150 mL) and extracted with EtOAc (100 mL×2). The combined organic layers were washed with aq $NaHCO_3$ (100 mL×2) and brine (100 mL), dried over anhydrous $Na_2SO_4$ and filtered. The filtrate was concentrated in vacuo to give the title compound as a yellow oil (36 g, crude) which was used into the next step without further purification.

Step 2: ethyl (Z)-2-((dimethylamino)methylene)-4,4-diethoxy-3-oxobutanoate

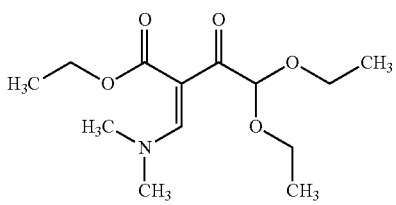 [SMILES: CCOC(=O)/C(=C\N(C)C)C(=O)C(OCC)OCC]

A mixture of ethyl 4,4-diethoxy-3-oxo-butanoate (36 g, 164.95 mmol) and DMF-DMA (23.59 g, 197.94 mmol, 26.21 mL) in toluene (200 mL) was stirred at 100° C. for 12 hours. The reaction mixture was concentrated in vacuo and purified by column chromatography ($SiO_2$) eluting with petroleum ether/EtOAc (10:1 to 0:1) to give the title compound as a yellow oil (31 g, 69%).

Step 3: ethyl 1-benzyl-5-(diethoxymethyl)-1H-pyrazole-4-carboxylate

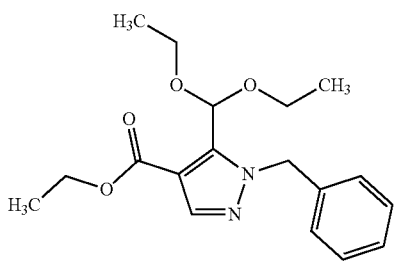 [SMILES: CCOC(=O)c1cnn(Cc2ccccc2)c1C(OCC)OCC]

To a solution of benzylhydrazine (23.55 g, 120.74 mmol, 2 HCl) in EtOH (50 mL) was added $Et_3N$ (33.32 g, 329.28 mmol, 45.64 mL) at 25° C. The mixture was stirred for 0.2 hours and then added to a solution of ethyl (Z)-2-((dimethylamino)methylene)-4,4-diethoxy-3-oxobutanoate (30.00 g, 109.76 mmol) in EtOH (150 mL) at 0° C. The reaction mixture was stirred at 25° C. for 0.8 hours and then diluted with water (500 mL) and extracted with EtOAc (250 mL×3). The combined organic layers were washed with brine (800 mL×2), dried over anhydrous $Na_2SO_4$, filtered and concentrated in vacuo. The resulting residue was purified by column chromatography ($SiO_2$) eluting with petroleum ether/EtOAc (30:1 to 10:1) to give the title compound as a yellow oil (28 g, 77%).

Step 4: 1-benzyl-1,5-dihydro-4H-pyrazolo[3,4-d]pyridazin-4-one

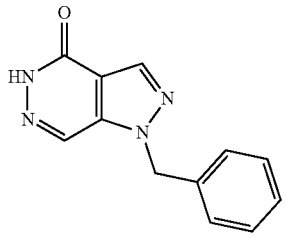 [SMILES: O=c1[nH]ncc2c1cnn2Cc1ccccc1]

To a solution of ethyl 1-benzyl-5-(diethoxymethyl)-1H-pyrazole-4-carboxylate (28 g, 84.24 mmol) in HOAc (200 mL) were added $N_2H_4 \cdot H_2O$ (14.88 g, 252.72 mmol, 14.45 mL, 85%) and HCl aq (12 M, 702.00 μL). The mixture was stirred at 90° C. for 12 hours and then poured into ice water (400 mL) and filtered. The filter cake was washed with water (200 mL) and dried in vacuo to give title compound as a white solid (16.5 g, 87%).

Step 5: 1-benzyl-4-chloro-1H-pyrazolo[3,4-d]pyridazine

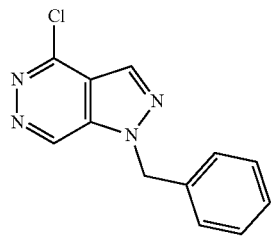 [SMILES: Clc1nncc2c1cnn2Cc1ccccc1]

A solution of 1-benzyl-1,5-dihydro-4H-pyrazolo[3,4-d]pyridazin-4-one (13.00 g, 57.46 mmol) in $POCl_3$ (204.50 g, 1.33 mol, 123.94 mL) was stirred at 100° C. for 2 hours. The reaction mixture was concentrated in vacuo, and the resulting residue was diluted with EtOAc (500 mL), washed with $NaHCO_3$ (400 mL) and brine (500 mL), dried over anhydrous $Na_2SO_4$ and filtered. The filtrate was concentrated in vacuo to give the title compound as a yellow gum (15 g, crude) which was used without further purification.

Step 6: 1-benzyl-4-methoxy-1H-pyrazolo[3,4-d]pyridazine

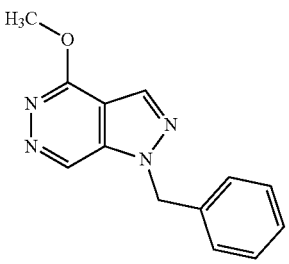 [SMILES: COc1nncc2c1cnn2Cc1ccccc1]

A mixture of 1-benzyl-4-chloro-1H-pyrazolo[3,4-d]pyridazine (14.00 g, 57.22 mmol) and NaOMe (9.27 g, 171.66 mmol) in MeOH (200.00 mL) was stirred at 70° C. for 0.5 hours and then diluted with water (400 mL) and extracted with EtOAc (200 mL×2). The combined organic layers were washed with brine (400 mL), dried over anhydrous Na₂SO₄, filtered and concentrated in vacuo. The resulting residue was purified by column chromatography (SiO₂) eluting with petroleum ether/EtOAc (10/1 to 0:1) to give the title compound as a yellow solid (8 g, 58%).

Step 7: 4-methoxy-1H-pyrazolo[3,4-d]pyridazine

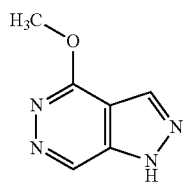

A solution of 1-benzyl-4-methoxy-1H-pyrazolo[3,4-d]pyridazine (7.00 g, 29.14 mmol) in H₂SO₄ (40.00 mL) was stirred at 50° C. for 12 hours and then slowly added to act NaHCO₃ (400 mL) and extracted with DCM/MeOH (10:1, 500 mL×8). The combined organic layers were dried over anhydrous Na₂SO₄, filtered and concentrated in vacuo to give the title compound as a yellow solid (3.10 g, 71%).

Step 8: 3-bromo-4-methoxy-1H-pyrazolo[3,4-d]pyridazine

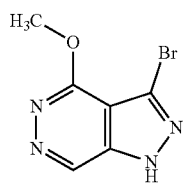

To a mixture of 4-methoxy-1H-pyrazolo[3,4-d]pyridazine (1.00 g, 6.66 mmol) and NaOAc (3.82 g, 46.62 mmol) in EtOH (20 mL) and water (20 mL) was added Br₂ (4.26 g, 26.64 mmol, 1.37 mL). The mixture was stirred at 25° C. for 2 hours and then diluted with EtOAc (80 mL), washed with saturated aq Na₂S₂O₃ (30 mL) and brine (40 mL), dried over anhydrous Na₂SO₄, filtered and concentrated in vacuo. The resulting residue was triturated with petroleum ether/EtOAc (5:1, 30 mL) for 30 minutes and filtered. The filter cake was dried in vacuo to give the title compound as a yellow solid (1 g, 66%).

Step 9: 3-bromo-1-isopropyl-4-methoxy-1H-pyrazolo[3,4-d]pyridazine

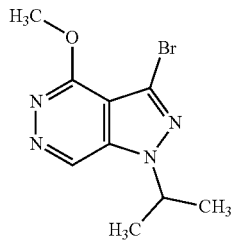

A mixture of 3-bromo-4-methoxy-1H-pyrazolo[3,4-d]pyridazine (1 g, 4.37 mmol), 2-iodopropane (1.49 g, 8.74 mmol, 873.95 μL) and K₂CO₃ (1.81 g, 13.11 mmol) in DMF (30 mL) was stirred at 25° C. for 12 hours and then diluted with water (100 mL) and extracted with EtOAc (50 mL×3). The combined organic layers were washed with brine (100 mL), dried over anhydrous Na₂SO₄, filtered and concentrated in vacuo. The resulting residue was purified by column chromatography (SiO₂) eluting with DCM/MeOH (100:1 to 40:1) to give the title compound which was used without further purification.

Step 10: 3-cyclopropyl-1-isopropyl-4-methoxy-1H-pyrazolo[3,4-d]pyridazine

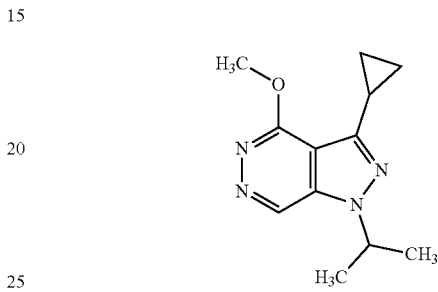

A mixture of regioisomers, 3-bromo-1-isopropyl-4-methoxy-iii-pyrazolo[3,4-d]pyridazine and 3-bromo-2-isopropyl-4-methoxy-2H-pyrazolo[3,4-d]pyridazine (total 550 mg, 2.03 mmol), cyclopropylboronic acid (348.75 mg, 4.06 mmol), Na₂CO₃ (430.32 mg, 4.06 mmol) and Pd(dppf)Cl₂ (148.54 mg, 203.00 μmol) in dioxane (10 mL) and water (2 mL) was stirred at 90° C. for 12 hours under N₂. The mixture was diluted with water (20 mL) and extracted with DCM (20 mL×2). The combined organic layers were washed with brine (20 mL), dried over anhydrous Na₂SO₄, filtered and concentrated in vacuo to afford a residue which was purified by column chromatography (Sift) eluting with DCM/MeOH (100:1 to 40:1). The resulting product was further purified by preparative TLC (Sift) eluting with petroleum ether/EtOAc (1:3) to give the title compound as a yellow solid (180 mg).

Step 11: 3-cyclopropyl-1-isopropyl-1,5-dihydro-4H-pyrazolo[3,4-d]pyridazin-4-one A solution of 3-cyclopropyl-1-isopropyl-4-methoxy-1H-pyrazolo[3,4-d]pyridazine (160.00 mg, 688.82 μmol) in dioxane (5 mL) and HCl aq (2 M, 5.00 Ml) was stirred at 90° C. for 2 hours and then concentrated in vacuo. The resulting residue was purified by HPLC (Method C) to give the title compound as a white solid (102.40 mg, 67% yield, 99% purity).

Preparation 4: 1-isopropyl-3-methyl-1,5-dihydro-4H-pyrazolo[3,4-d]pyridazin-4-one

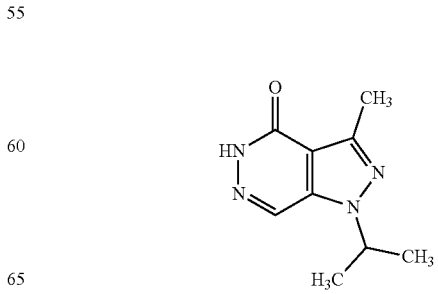

Step 1: 1-isopropyl-4-methoxy-3-methyl-1H-pyrazolo[3,4-d]pyridazine

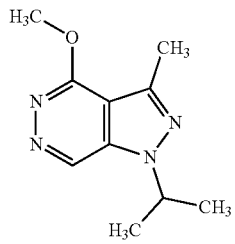

A mixture of regioisomers, 3-bromo-1-isopropyl-4-methoxy-1H-pyrazolo[3,4-d]pyridazine and 3-bromo-2-isopropyl-4-methoxy-2H-pyrazolo[3,4-d]pyridazine (total 400 mg, 1.48 mmol), methylboronic acid (180.00 mg, 3.01 mmol), Na$_2$CO$_3$ (319.03 mg, 3.01 mmol) and Pd(dppf)Cl$_2$ (110.12 mg, 150.50 mop in dioxane (10 mL) and water (2 mL) was stirred at 90° C. for 12 hours under N$_2$. The mixture was diluted with water (20 mL) and extracted with DCM (20 mL×2). The combined organic layers were washed with brine (20 mL), dried over anhydrous Na$_2$SO$_4$, filtered and concentrated in vacuo to afford a residue which was purified by column chromatography (Sift) eluting with DCM/MeOH (100:1 to 40:1). The resulting product was further purified by preparative TLC (SiO$_2$) eluting with petroleum ether/EtOAc (1:3) to give the title compound as a yellow solid (120 mg).

Step 2: 1-isopropyl-3-methyl-1,5-dihydro-4H-pyrazolo[3,4-d]pyridazin-4-one

A solution of 1-isopropyl-4-methoxy-3-methyl-1H-pyrazolo[3,4-d]pyridazine (120 mg, 581.85 μmol) in dioxane (5 mL) and HCl aq (2 M, 5.00 mL) was stirred at 90° C. for 2 hours and then concentrated in vacuo. The resulting residue was triturated with petroleum ether/EtOAc (10:1, 10 mL) for 30 minutes and filtered. The filter cake was dried in vacuo to give the title compound as a light-yellow solid (84.10 mg, 75%).

Preparation 5: 1-cyclopropyl-1,5-dihydro-4H-pyrazolo[3,4-d]pyridazin-4-one

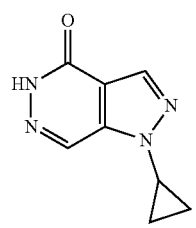 [SMILES: O=c1[nH]ncc2c1cnn2C1CC1]

Step 1: ethyl 5-(diethoxymethyl)-1H-pyrazole-4-carboxylate

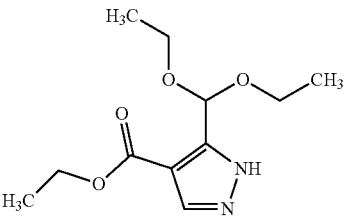 [SMILES: CCOC(=O)c1cn[nH]c1C(OCC)OCC]

To a solution of ethyl (Z)-2-((dimethylamino)methylene)-4,4-diethoxy-3-oxobutanoate (5.00 g, 18.29 mmol) in EtOH (100.00 mL) was added N$_2$H$_4$·H$_2$O (1.29 g, 21.95 mmol, 1.25 mL, 85% purity) at 0° C. The mixture was stirred at 25° C. for 1 hour and then diluted with water (200 mL) and extracted with EtOAc (150 mL×3). The combined organic layers were washed with brine (600 mL), dried over anhydrous Na$_2$SO$_4$, filtered and concentrated in vacuo. The resulting residue was purified by column chromatography (SiO$_2$) eluting with petroleum ether/EtOAc (10:1 to 2:1) to give the title compound as a yellow oil (3 g, 68%).

Step 2: ethyl 1-cyclopropyl-5-(diethoxymethyl)-1H-pyrazole-4-carboxylate

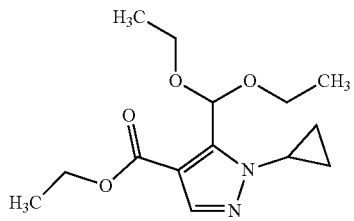 [SMILES: CCOC(=O)c1cnn(C2CC2)c1C(OCC)OCC]

A mixture of ethyl 5-(diethoxymethyl)-1H-pyrazole-4-carboxylate (1.00 g, 4.13 cyclopropylboronic acid (709.13 mg, 8.26 mmol), Cu(OAc)$_2$ (1.13 g, 6.20 mmol), Na$_2$CO$_3$ (874.97 mg, 8.26 mmol) and 2-(2-pyridyl)pyridine (966.98 mg, 6.20 mmol) in DCE (20 mL) was stirred at 70° C. for 12 hours under 02 (15 psi). The mixture was diluted with DCM (20 ML), washed with water (20 mL) and brine (20 mL), dried over anhydrous Na$_2$SO$_4$, filtered and concentrated in vacuo. The resulting residue was purified by column chromatography (SiO$_2$) eluting with petroleum ether/EtOAc (30:1 to 10:1) to give the title compound as a colorless oil (600 mg, 51%).

Step 3: 1-cyclopropyl-1,5-dihydro-4H-pyrazolo[3,4-d]pyridazin-4-one

To a solution of ethyl 1-cyclopropyl-5-(diethoxymethyl)-1H-pyrazole-4-carboxylate (500.00 mg, 1.77 mmol) in HOAc (10 mL) were added N$_2$H$_4$·H$_2$O (312.90 mg, 5.31 mmol, 303.79 μL, 85% purity) and HCl (12 M, 6.32 μL). The mixture was stirred at 90° C. for 12 hours and then poured into ice water (30 mL) and extracted with DCM/MeOH (10:1, 15 mL×3). The combined organic layers were washed with aq NaHCO$_3$ (20 mL) and brine (20 mL), dried over anhydrous Na$_2$SO$_4$, filtered and concentrated in vacuo. The resulting residue was triturated with MTBE (15 mL) for 30 minutes and filtered. The filter cake was dried in vacuo to give the title compound as a white solid (130 mg, 42% yield, 100% purity).

Preparation 6: 1-isopropyl-1,5-dihydro-4H-pyrazolo[3,4-d]pyridazin-4-one

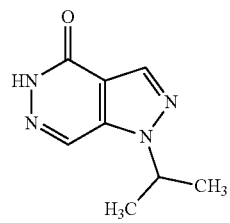

Step 1: 1-isopropyl-4-methoxy-1H-pyrazolo[3,4-d]pyridazine

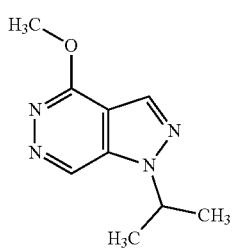

A mixture of 4-methoxy-1H-pyrazolo[3,4-d]pyridazine (400 mg, 2.66 mmol), 2-iodopropane (904.35 mg, 5.32 mmol, 531.97 μL) and K₂CO₃ (1.10 g, 7.98 mmol) in DMF (50 mL) was stirred at 25° C. for 12 hours and then diluted with water (100 mL) and extracted with EtOAc (50 mL×3). The combined organic layers were washed with brine (100 mL), dried over anhydrous Na₂SO₄, filtered and concentrated in vacuo to afford a residue which was purified by column chromatography (Sift) eluting with DCM/MeOH (100:1 to 40:1). The product was further purified by preparative TLC (SiO₂) eluting with petroleum ether/EtOAc (1:3) to give the title compound as yellow solid (80 mg, 16%).

Step 2: 1-isopropyl-1,5-dihydro-4H-pyrazolo[3,4-d]pyridazin-4-one

A solution of 1-isopropyl-4-methoxy-1H-pyrazolo[3,4-d]pyridazine (160 mg, 832.38 μmol) in dioxane (5 mL) and HCl (2 M, 357.34 μL) was stirred at 90° C. for 2 hours and then concentrated in vacuo. The resulting residue was triturated with MTBE/MeOH (50:1, 30 mL) for 30 minutes and filtered. The filter cake was dried in vacuo to give the title compound as a light-yellow solid (100 mg, 67% yield, 99% purity).

Preparation 7: 3-cyclopropyl-1-methyl-1,5-dihydro-4H-pyrazolo[3,4-d]pyridazin-4-one

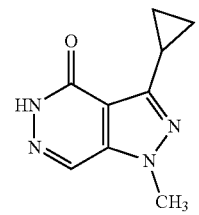

Step 1: 3-bromo-4-methoxy-1-methyl-1H-pyrazolo[3,4-d]pyridazine

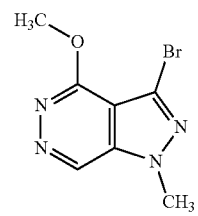

A mixture of 3-bromo-4-methoxy-1H-pyrazolo[3,4-d]pyridazine (3.00 g, 13.10 mmol), iodomethane (2.23 g, 15.72 mmol, 978.07 and K₂CO₃ (5.43 g, 39.30 mmol) in DMF (50 mL) was stirred at 25° C. for 2 hours and then diluted with water (100 mL) and extracted with EtOAc (50 mL×3). The combined organic layers were washed with brine (200 mL), dried over anhydrous Na₂SO₄, filtered and concentrated in vacuo. The resulting residue was purified by column chromatography (SiO₂) eluting with petroleum ether/EtOAc (5:1 to 0:1) to give the title compound as a yellow solid (1.10 g, crude).

Step 2: 3-cyclopropyl-4-methoxy-1-methyl-1H-pyrazolo[3,4-d]pyridazine

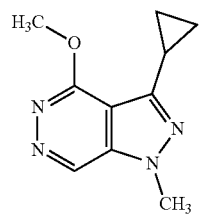

A mixture of 3-bromo-4-methoxy-1-methyl-1H-pyrazolo[3,4]pyridazine (600 mg 2.47 mmol), cyclopropylboronic acid (636.14 mg, 7.41 mmol), Na₂CO₃ (784.92 mg, 7.41 mmol) and Pd(dppf)Cl₂ (361.25 mg, 493.71 mop in dioxane (10 mL) and water (2 mL) was stirred at 90° C. for 12 hours under N₂ and then diluted with water (20 mL) and extracted with DCM (20 ML×2). The combined organic layers were dried over anhydrous Na₂SO₄, filtered and concentrated in vacuo to afford a residue which was purified by column chromatography (SiO₂) eluting with DCM/MeOH (1:0 to 40:1). The resulting product was further purified by preparative TLC (Sift) eluting with petroleum ether/EtOAc (3:1) to give the title compound as a yellow solid.

Step 3: 3-cyclopropyl-1-methyl-1,5-dihydro-4H-pyrazolo[3,4-d]pyridazin-4-one A solution of 3-cyclopropyl-4-methoxy-1-methyl-1H-pyrazolo[3,4-d]pyridazine (370 mg, 1.81 mmol) in dioxane (5 mL) and HCl aq M, 5 mL) was stirred at 90° C. for 2 hours. The reaction mixture was concentrated in vacuo, and the resulting residue was triturated with petroleum ether/EtOAc (10:1, 10 mL) for 30 minutes and filtered. The filter cake was dried in vacuo to give the title compound as a yellow solid (191.1 mg, 56% yield, 100% purity).

Preparation 8: 1,3-dimethyl-1,5-dihydro-4H-pyrazolo[3,4-d]pyridazin-4-one

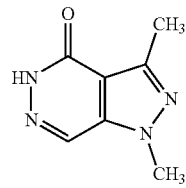

Step 1: 4-methoxy-1,3-dimethyl-1H-pyrazolo[3,4-d]pyridazine

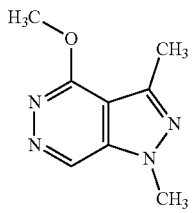

A mixture of 3-bromo-4-methoxy-1-methyl-1H-pyrazolo[3,4-d]pyridazine (900 mg, 3.70 mmol), methylboronic acid (443.3 mg, 7.40 mmol), $Na_2CO_3$ (1.18 g, 11.1 mmol) and Pd(dppf)$Cl_2$ (541.87 mg, 740.00 μmol) in dioxane (15 mL) and water (2 mL) was stirred at 90° C. for 12 hours under $N_2$ and then diluted with water (20 mL) and extracted with DCM (20 mL×2), The combined organic layers were dried over anhydrous $Na_2SO_4$, filtered and concentrated in vacuo. The resulting residue was purified by column chromatography (Sift) eluting with petroleum ether/EtOAc (10:1 to 0:1) to give the title compound as a yellow solid (200 mg, 30%).

Step 2: 1,3-dimethyl-1,5-dihydro-4H-pyrazolo[3,4-d]pyridazin-4-one

A solution of 4-methoxy-1,3-dimethyl-1H-pyrazolo[3,4-d]pyridazine (200 mg, 1.12 mmol) in dioxane (2 mL) and HCl aq (4 M, 2 mL) was stirred at 90° C. for 2 hours and then concentrated in vacuo to give the title compound as a yellow solid (156 mg, 82% yield, 97% purity).

Preparation 9: 3-isopropyl-1-methyl-1,5-dihydro-4H-pyrazolo[3,4-d]pyridazin-4-one

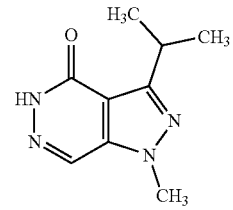

Step 1: 4-methoxy-1-methyl-3-(prop-1-en-2-yl)-1H-pyrazolo[3,4-d]pyridazine

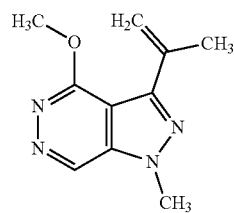

A mixture of 3-bromo-4-methoxy-1-methyl-1H-pyrazolo[3,4-d]pyridazine (900 mg, 3.70 mmol), 2-isopropenyl-4,4,5,5-tetramethyl-1,3,2-dioxaborolane (1.24 g, 7.40 mmol), $Na_2CO_3$ (1.18 g, 11.10 mmol) and Pd(dppf)$Cl_2$ (270.94 mg, 370 μmol) in dioxane (20 mL) and water (2 mL) was stirred at 90° C. for 12 hours under $N_2$ and then filtered. The filtrate was concentrated in vacuo and purified by column chromatography (Sift) eluting with DCM/MeOH (100:1 to 50:1) to give the title compound as a yellow solid (400 mg, 49% yield, 92% purity).

Step 2: 3-isopropyl-4-methoxy-1-methyl-1H-pyrazolo[3,4-d]pyridazine

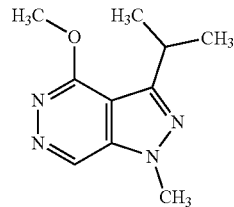

A mixture of 4-methoxy-1-methyl-3-(prop-1-en-2-yl)-1H-pyrazolo[3,4-d]pyridazine (350 mg, 1.71 mmol) and Pd/C (wet basis) (100.00 mg, 10% purity) in THF (10 mL) was purged with $H_2$ several times. The reaction mixture was stirred at 10° C. for 12 hours under $H_2$ (15 psi) and then filtered. The filtrate was concentrated in mew) and purified by HPLC (Method D) to give the title compound as a white solid (120 mg, 34%).

Step 3: 3-isopropyl-1-methyl-1,5-dihydro-4H-pyrazolo[3,4-d]pyridazin-4-one

A solution of 3-isopropyl-4-methoxy-1-methyl-1H-pyrazolo[3,4-d]pyridazine (120 mg, 581.85 μmol) in dioxane (2 mL) and HCl act (4 M, 2 mL) was stirred at 90° C. for 1 hour and then concentrated in vacuo, triturated with petroleum ether/EtOAc (10:1, 10 mL) for 30 minutes, and filtered. The filter cake was dried in vacuo to give the title compound as a yellow solid (89.3 mg, 80% yield, 100% purity).

Preparation 10: 1-cyclopropyl-3-methyl-1,5-di-hydro-4/1-pyrazolo[3,4-d]pyridazin-4-one

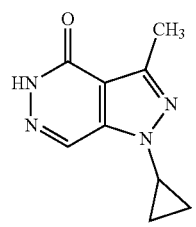

Step 1: 3-bromo-1-cyclopropyl-4-methoxy-1H-pyrazolo[3,4-d]pyridazine

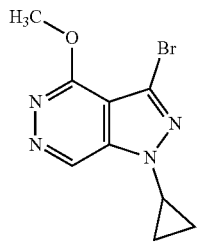

A mixture of 3-bromo-4-methoxy-1H-pyrazolo[3,4-d]pyridazine (1.00 g, 4.37 mmol), cyclopropylboronic acid (750.12 mg, 8.74 mmol), Cu(OAc)$_2$ (1.19 g, 6.56 mmol), Na$_2$CO$_3$ (925.56 mg, 8.74 mmol) and 2-(2-pyridyl)pyridine (1.02 g, 6.56 mmol) in DCE (20 mL) was stirred at 70° C. for 12 hours under O$_2$ (15 psi) and then filtered. The filtrate was concentrated in vacuo and purified by column chromatography (SiO$_2$) eluting with petroleum ether/EtOAc (10:1 to 0:1) to give the title compound as a yellow solid (500 mg) which was used without further purification.

Step 2: 1-cyclopropyl-4-methoxy-3-methyl-1H-pyrazolo[3,4-d]pyridazine

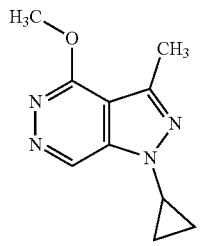

A mixture of 3-bromo-1-cyclopropyl-4-methoxy-1H-pyrazolo[3,4-d]pyridazine (450 mg, 1.67 mmol), methylboronic acid (200.2 mg, 3.34 mmol), Na$_2$CO$_3$ (354.48 mg, 3.34 mmol) and Pd(dppf)Cl$_2$ (122.36 mg, 167.22 mop in dioxane (10 mL) and water (2 mL) was stirred at 90° C. for 12 hours under N$_2$ and then diluted with water (20 mL) and extracted with DCM (20 mL×2). The combined organic layers were dried over anhydrous Na$_2$SO$_4$, filtered and concentrated in vacuo. The resulting residue was purified by column chromatography (SiO$_2$) eluting with petroleum ether/EtOAc (10:1 to 0:1) to give the title compound as a white solid (130 mg, 38%).

Step 3: 1-cyclopropyl-3-methyl-1,5-dihydro-4H-pyrazolo[3,4-d]pyridazin-4-one

A solution of 1-cyclopropyl-4-methoxy-3-methyl-1H-pyrazolo[3,4-d]pyridazine (120 mg, 587.57 μmol) in dioxane (5 mL) and HCl (4 M, 5 mL) was stirred at 90° C. for 2 hours and then concentrated in vacuo. The resulting residue was triturated with petroleum ether/EtOAc (10:1, 10 mL) for 30 minutes and filtered. The filter cake was dried in vacuo to give the title compound as a light-yellow solid (85.1 mg, 75% yield, 98% purity).

Preparation 11: 1-cyclopropyl-7-methyl-1,5-di-hydro-4H-pyrazolo[3,4-d]pyridazin-4-one

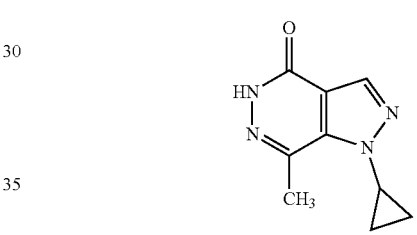

Step 1: ethyl 5-iodo-1H-pyrazole-4-carboxylate

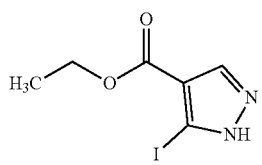

Ethyl 5-amino-1H-pyrazole-4-carboxylate (34 g, 219.14 mmol) was added portion-wise to a solution of H$_2$SO$_4$ (21.93 g, 219.14 mmol, 72.00 mL, 98% purity) in water (60 mL) at 0° C. The mixture was stirred at 0° C. for 30 minutes. A solution of NaNO$_2$ (22.68 g, 328.71 mmol, 17.86 mL) in water (100 mL) was added dropwise at 0° C., and the mixture was stirred at 0° C. for an additional hour. Next, a solution of KI (72.76 g, 438.28 mmol) in water (100 mL) was added dropwise at 0° C. The mixture was stirred at 25° C. for 14.5 hours and then diluted with EtOAc (500 mL). The organic phase was washed with saturated aq Na$_2$SO$_3$ (200 mL×3) and brine (100 mL×3), dried over Na$_2$SO$_4$, filtered and concentrated in vacuo. The resulting residue was purified by column chromatography (Sift) eluting with petroleum ether/EtOAc (50:1 to 4:1) to give the title compound as a white solid (38.10 g, 65%).

Step 2: ethyl 1-cyclopropyl-5-iodo-1H-pyrazole-4-carboxylate

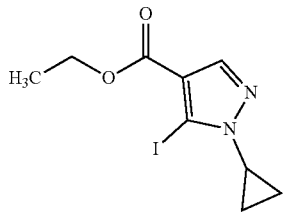

A mixture of ethyl 5-iodo-1H-pyrazole-4-carboxylate (1.00 g, 3.76 mmol), cyclopropylboronic acid (645.77 mg, 7.52 mmol), Cu(OAc)₂ (1.02 g, 5.64 mmol) and pyridine (594.83 mg, 7.52 mmol, 606.97 μL) in DCE (20 mL) was stirred at 50° C. for 12 hours under air and then diluted with DCM (20 mL), washed with brine (30 mL×3), dried over Na₂SO₄ and concentrated under reduced pressure. The resulting residue was purified by column chromatography (SiO₂) eluting with petroleum ether/EtOAc (50:1 to 10:1) to give the title compound as a colorless oil (150 mg, 13%).

Step 3: ethyl 5-acetyl-1-cyclopropyl-1H-pyrazole-4-carboxylate

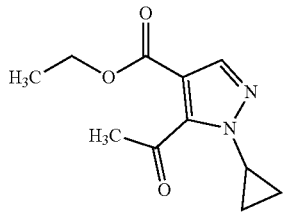 [SMILES: CCOC(=O)c1cnn(C2CC2)c1C(C)=O]

A mixture of ethyl 1-cyclopropyl-5-iodo-1H-pyrazole-4-carboxylate (500 mg, 1.63 mmol), tributyl(1-ethoxyvinyl)stannane (883.01 mg, 2.45 mmol, 825.24 μL) and Pd(PPh₃)₂Cl₂ (114.41 mg, 163.00 mop in toluene (12 mL) was degassed and purged with N₂ (3×). The reaction mixture was stirred at 110° C. for 2 hours under N₂ atmosphere and then concentrated under reduced pressure. The resulting residue was dissolved in a solution of THF (5 mL) and HCl (2 M, 5 mL). The mixture was stirred at 25° C. for 14 hours and then diluted with saturated aq KF (5 mL) and extracted with EtOAc (20 mL×3). The combined organic layers were dried over Na₂SO₄, filtered and concentrated under reduced pressure. The resulting residue was purified by column chromatography (SiO₂) eluting with petroleum ether/EtOAc (50:1 to 5:1) to give the title compound as a yellow oil (550 mg, crude).

Step 4: 1-cyclopropyl-7-methyl-1,5-dihydro-4H-pyrazolo[3,4-d]pyridazin-4-one To a solution of ethyl 5-acetyl-1-cyclopropyl-1H-pyrazole-4-carboxylate (550 mg, 2.47 mmol) in EtOH (10 mL) was added N₂H₄·H₂O (436.41 mg, 7.41 mmol, 423.70 The mixture was stirred at 80° C. for 16 hours and then concentrated under reduced pressure. The resulting residue was purified by column chromatography (SiO₂) eluting with DCM/MeOH (50:1 to 30:1) to give the title compound as a white solid (87 mg, 18% yield, 97% purity).

Preparation 12: 1,7-dimethyl-1,5-dihydro-4H-pyrazolo[3,4-d]pyridazin-4-one

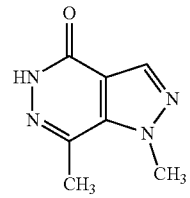

Step 1: ethyl 5-iodo-1-methyl-1H-pyrazole-4-carboxylate

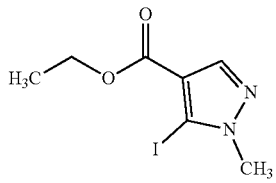

To a suspension of ethyl 5-iodo-III-pyrazole-4-carboxylate (1.00 g, 3.76 mmol) and K₂CO₃ (1.04 g, 7.52 mmol) in DMF (15 mL) was added MeI (1.60 g, 11.28 mmol, 701.75 μL). The reaction mixture was stirred at 28° C. for 3 hours and then diluted with EtOAc (50 mL), washed with brine (3×30 mL), dried over Na₂SO₄, filtered and concentrated under reduced pressure. The resulting residue was purified by column chromatography (SiO₂) eluting with petroleum ether/EtOAc (50:1 to 10:1) to give the title compound as a white solid (42.0 mg, 40%).

Step 2: ethyl 5-acetyl-1-methyl-1H-pyrazole-4-carboxylate

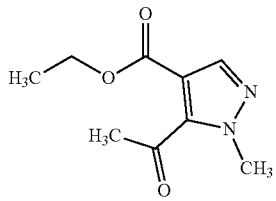

A mixture of ethyl 5-iodo-1-methyl-1H-pyrazole-4-carboxylate (400 mg, 1.43 mmol), tributyl(1-ethoxyvinyl)stannane (774.67 mg, 2.14 mmol, 723.99 μL) and Pd(PPh₃)₂Cl₂ (100.37 mg, 143.00 μmol) in toluene (15 mL) was stirred at 100° C. for 2 hours under N₂ and then evaporated in vacuo, diluted with THF (5 mL) and HCl (2 M, 5 mL) and stirred at 28° C. for 12 hours. The reaction mixture was diluted with EtOAc (50 mL), washed with saturated aq KF solution (20 mL) and brine (20 mL), dried over Na₂SO₄, filtered and concentrated in vacuo. The resulting residue was purified by column chromatography (SiO$_2$) eluting with petroleum ether/EtOAc (50:1 to 10:1) to give the title compound as yellow oil (270 mg, 96%).

Step 3: 1,7-dimethyl-1,5-dihydro-4H-pyrazolo[3,4-d]pyridazin-4-one

A mixture of ethyl 5-acetyl-1-methyl-1H-pyrazole-4-carboxylate (250 mg, 1.27 mmol) and NH$_2$NH$_2$·H$_2$O (150.09 mg, 2.55 mmol, 145.72 µL, 85% purity) in HOAc (5 mL) was stirred at 110° C. for 12 hours and then concentrated in vacuo, poured into water (10 mL) and extracted with DCM (30 mL×3). The combined organic layers were washed with brine (30 mL), dried over Na$_2$SO$_4$, filtered and concentrated in vacuo. The resulting residue was triturated with MTBE (10 mL) for 15 minutes and filtered to isolate a solid product, which was dried in vacuo to give the title compound as white solid (78 mg, 37% yield, 98% purity).

Preparation 13: 1-isopropyl-7-1,5-dihydro-4H-pyrazolo[3,4-d]pyridazin-4-one

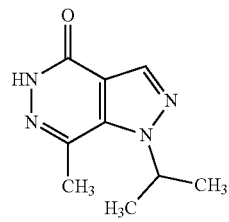

Step 1: ethyl 5-iodo-1-isopropyl-1H-pyrazole-4-carboxylate

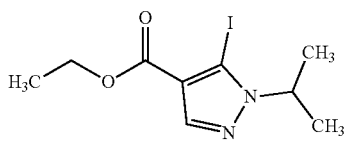

To a solution of ethyl 5-iodo-1H-pyrazole-4-carboxylate (3.10 g, 11.65 mmol) and K$_2$CO$_3$ (4.83 g, 34.96 mmol) in DMF (40 mL) was added 2-iodopropane (7.92 g, 46.61 mmol, 4.66 mL). The reaction mixture was stirred at 25° C. for 1 hour and then diluted with brine (100 mL) and extracted with EtOAc (100 mL×3). The combined organic layers were dried over Na$_2$SO$_4$, filtered and concentrated under reduced pressure. The resulting residue was purified by column chromatography (Sift) eluting with petroleum ether/EtOAc (20:1 to 15:1) to give the title compound as a yellow oil (1.25 g, 35%).

Step 2: ethyl 5-acetyl-1-isopropyl-1H-pyrazole-4-carboxylate

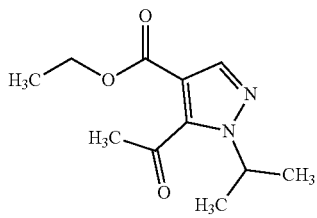

A mixture of ethyl 5-iodo-1-isopropyl-1H-pyrazole-4-carboxylate (1.20 g, 3.89 mmol), tributyl(1-ethoxyvinyl)stannane (2.11 g, 5.84 mmol, 1.97 mL) and Pd(PPh$_3$)$_2$Cl$_2$ (273.04 mg, 389.00 µmol) in toluene (20 mL) was stirred at 100° C. for 2 hours under N$_2$ and then concentrated in vacuo. THF (10 mL) and HCl (2 M, 10 mL) were added. The mixture was stirred at 28° C. for 12 hours and then diluted with EtOAc (100 mL) and washed with saturated KF solution (50 mL) and brine (50 mL×2). The organic layer was dried over Na$_2$SO$_4$, filtered, concentrated in vacuo, and purified by column chromatography (silica gel) eluting with petroleum ether/EtOAc (20:1 to 10:1) to give the title compound as light-yellow oil (700 mg, 80%).

Step 3: 1-isopropyl-7-methyl-1,5-dihydro-4H-pyrazolo[3,4-d]pyridazin-4-one

A mixture of ethyl 5-acetyl-1-isopropyl-1H-pyrazole-4-carboxylate (200.00 mg, 891.82 µmol) and N$_2$H$_4$·H$_2$O (52.52 mg, 891.82 µmol, 50.99 µL) in EtOH (5 mL) was stirred at 80° C. for 16 hours and then concentrated under reduced pressure. The resulting residue was triturated with MTBE (10 mL) for 15 minutes and filtered to isolate a solid product, which was dried in vacuo to give the title compound as a white solid (116 mg, 68% yield, 95% purity).

Preparation 14: 1,3,7-trimethyl-1,5-dihydro-4H-pyrazolo[3,4-d]pyridazin-4-one

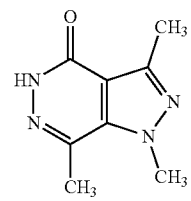

Step 1: ethyl 5-acetyl-pyrazole-4-carboxylate

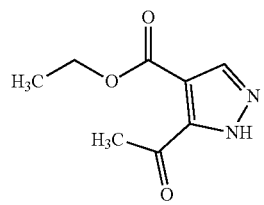

To a solution of ethyl 5-iodo-1H-pyrazole-4-carboxylate (23.00 g, 86.45 mmol) and Pd(PPh₃)₂Cl₂ (6.07 g, 8.65 mmol) in toluene (200 mL) was added tributyl(1-ethoxyvinyl)stannane (46.83 g, 129.67 mmol, 43.77 mL), The mixture was degassed and purged with N₂ (3×), stirred at 100° C. for 14 hours under N₂ atmosphere, and then concentrated under reduced pressure. The resulting residue was dissolved in THF (100 mL) and HCl (2 M, 100 mL) and stirred at 25° C. for 2 hours. The mixture was diluted with saturated KF solution (200 mL) and extracted with EtOAc (300 mL×3). The combined organic layers were washed with brine (200 mL×2), dried over Na₂SO₄, filtered and concentrated under reduced pressure. The resulting residue was purified by column chromatography (Sift) eluting with petroleum ether/EtOAc (20:1 to 5:1) to give the title compound as a light-yellow solid.

Step 2: ethyl 5-acetyl-3-bromo-1H-pyrazole-4-carboxylate

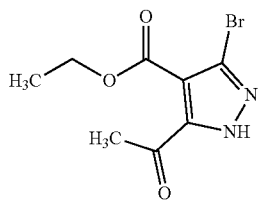

To a solution of ethyl 5-acetyl-1H-pyrazole-4-carboxylate (25.00 g, 137.23 mmol) in EtOH (150 mL) was added NaOAc (90.05 g, 1.10 mol) followed by Br₂ (109.65 g, 686.15 mmol, 35.37 mL) dropwise. The reaction mixture was stirred at 20° C. for 16 hours and then filtered. The filter cake was washed with EtOAc (300 mL) and the filtrate was evaporated under reduced pressure. The resulting residue was purified by column chromatography (Sift) eluting with petroleum ether/EtOAc (100:1 to 10:1) to give the title compound as a yellow solid.

Step 3: ethyl 5-acetyl-3-bromo-1-methyl-1H-pyrazole-4-carboxylate

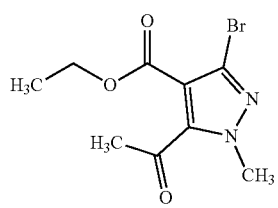

To a solution of ethyl 5-acetyl-3-bromo-1H-pyrazole-4-carboxylate (15.00 g, 57.46 mmol) and K₂CO₃ (23.82 g, 172.38 mmol) in DMF (50 mL) was added MeI (32.62 g, 229.84 mmol, 14.31 mL). The reaction mixture was stirred at 20° C. for 2 hours and then filtered. The filtrate was diluted with brine (100 mL) and extracted with EtOAc (50 mL×3). The combined organic layers were dried over Na₂SO₄ and concentrated under reduced pressure. The resulting residue was purified by column chromatography (Sift) eluting with petroleum ether/EtOAc (50:1 to 10:1) to give the title compound as a light-yellow solid (6 g, 38%).

Step 4: ethyl 5-acetyl-1,3-dimethyl-1H-pyrazole-4-carboxylate

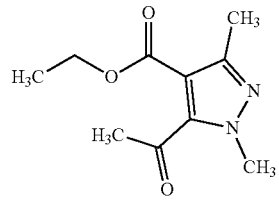

To a solution of ethyl 5-acetyl-3-bromo-1-methyl-1H-pyrazole-4-carboxylate (500 mg, 1.82 mmol), Pd(dppf)Cl₂·CH₂Cl₂ (297.26 mg, 364.00 µmol) and Cs₂CO₃ (1.78 g, 5.46 mmol) in water (1 mL) and toluene (10 mL) was added methylboronic acid (217.89 mg, 3.64 mmol). The mixture was degassed and purged with N₂ (3×) and then stirred at 100° C. for 16 hours under N₂ atmosphere, and filtered, washing the filter cake with EtOAc (10 mL). The filtrate was diluted with brine (20 mL) and extracted with EtOAc (15 mL×3). The combined organic layers were dried over Na₂SO₄, filtered and evaporated under reduced pressure. The resulting residue was purified by silica gel flash chromatography, eluting with EtOAc/petroleum ether (0:100 to 15:85). The product was purified further by HPLC (Method C) to give the title compound as a white solid (78 mg, 20%).

Step 5: 1,3,7-trimethyl-1,5-dihydro-4H-pyrazolo[3,4-d]pyridazin-4-one

To a solution of ethyl 5-acetyl-1,3-dimethyl-1H-pyrazole-4-carboxylate (78 mg, 371.02 µmol) in EtOH (1.0 mL) was added N₂H₄·H₂O (55.72 mg, 1.11 mmol, 54.10 µL). The reaction mixture was stirred at 80° C. for 16 hours and then evaporated under reduced pressure. The resulting residue was purified by HPLC (Method C) to give the title compound as a white solid (58 mg, 88%).

Preparation 15: 3-cyclopropyl-1,7-dimethyl-1,5-dihydro-4H-pyrazolo[3,4-d]pyridazin-4-one

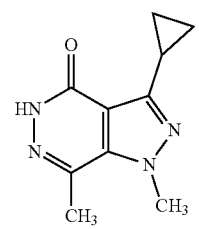

Step 1: ethyl 5-acetyl-3-cyclopropyl-1-methyl-1H-pyrazole-4-carboxylate

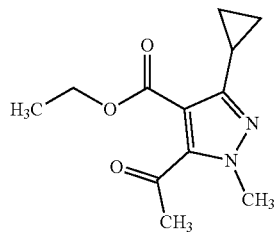 [SMILES: CCOC(=O)c1c(C2CC2)nn(C)c1C(C)=O]

To a solution of ethyl 5-acetyl-3-bromo-1-methyl-1H-pyrazole-4-carboxylate (500 mg, 1.82 mmol), Pd(dppf)Cl$_2$·CH$_2$Cl$_2$ (297.26 mg, 364.00 µmol) and Cs$_2$CO$_3$ (1.78 g, 5.46 mmol) in dioxane (20 mL) and water (1 mL) was added cyclopropylboronic acid (312.68 mg, 3.64 mmol), The mixture was degassed and purged with N$_2$ (3×) and then stirred at 100° C. for 16 hours under N$_2$ atmosphere. The mixture was diluted with brine (40 mL) and extracted with EtOAc (30 mL×3). The combined organic layers were dried over Na$_2$SO$_4$, filtered and concentrated under reduced pressure. The residue was purified by preparative TLC (SiO$_2$) eluting with petroleum ether/EtOAc (5:1) to give the title compound as a yellow oil (200 mg, 47%).

Step 2: 3-cyclopropyl-1,7-dimethyl-1,5-dihydro-4H-pyrazolo[3,4-d]pyridazin-4-one To a solution of ethyl 5-acetyl-3-cyclopropyl-1-methyl-1H-pyrazole-4-carboxylate (270 mg, 1.14 mmol) in EMI (10 mL) was added N$_2$H$_4$·H$_2$O (20191 mg, 3.43 mmol, 196.02 µL). The reaction mixture was stirred at 80° C. for 16 hours and then concentrated under reduced pressure and purified by HPLC (Method C) to give the title compound as a white solid (80 mg, 34%).

Preparation 16: 3-isopropyl-1,7-di methyl-1,5-dihydro-4H-pyrazolo[3,4-d]pyridazin-4-one

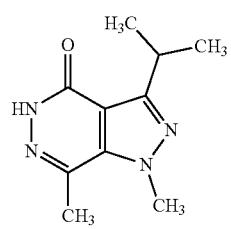

Step 1: ethyl 5-iodo-1-(4-methoxybenzyl)-1H-pyrazole-4-carboxylate

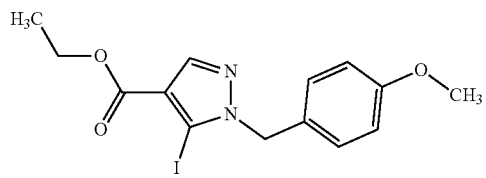

A mixture of ethyl 5-iodo-1H-pyrazole-4-carboxylate (72 g, 270.64 mmol), 4-methoxybenzyl chloride (50.86 g, 324.77 mmol, 44.23 mL) and K$_2$CO$_3$ (74.81 g, 541.28 mmol) in IMF (700 mL) was stirred at 10° C. for 12 hours and then diluted with water (1.4 L) and extracted with EtOAc (700 mL×2). The combined organic layers were washed with brine (1.5 L), dried over anhydrous Na$_2$SO$_4$, filtered and concentrated in vacuo. The resulting residue was purified by column chromatography (SiO$_2$) eluting with petroleum ether/EtOAc (20:1 to 5:1) to give the title compound as a yellow oil (105 g, crude).

Step 2: ethyl 5-acetyl-1-(4-methoxybenzyl)-1H-pyrazole-4-carboxylate

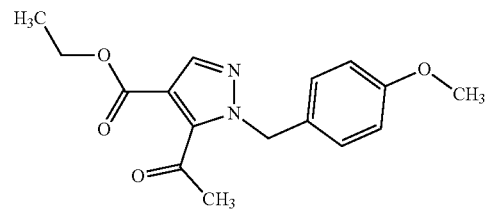

A mixture of ethyl 5-iodo-1-(4-methoxybenzyl)-1H-pyrazole-4-carboxylate (50 g, 129.47 mmol), tributyl(1-ethoxyvinyl)stannane (66.5 g, 184.13 mmol, 62.15 mL) and Pd(PPh$_3$)$_2$Cl$_2$ (18.18 g, 25.89 mmol) in toluene (600 mL) was stirred at 100° C. for 12 hours under N$_2$. The mixture was concentrated in vacuo. The resulting residue was diluted with THF (300 mL) and HCl (2 M, 400 mL), stirred at 10° C. for 2 hours and then diluted with aqueous KF (500 mL) and extracted with EtOAc (800 mL×2). The organic layers were combined and concentrated in vacuo. The resulting residue was purified by column chromatography (SiO$_2$) eluting with petroleum ether/EtOAc (10:1 to 4:1) to give the title compound as a yellow oil.

Step 3: 1-(4-oxybenzyl)-7-methyl-1,5-dihydro-4H-pyrazolo[3,4-d]pyridazin-4-one

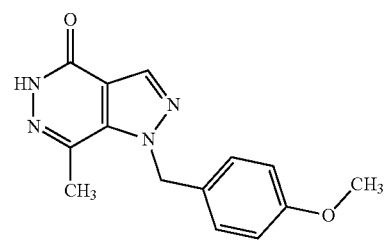

A mixture of ethyl 5-acetyl-1-(4-methoxybenzyl)-1H-pyrazole-4-carboxylate (50.00 g, 165.38 mmol) and N$_2$H$_4$·H$_2$O (29.22 g, 496.15 mmol, 28.37 mL, 85% purity) in EtOH L) was stirred at 80° C. for 12 hours. The reaction mixture was concentrated in vacuo and the resulting residue triturated with petroleum ether/EtOAc (2:1, 300 mL) for 30 minutes and filtered. The filter cake was dried in vacuo to give the title compound as an off-white solid (50 g, crude).

Step 4: 4-chloro-1-(4-methoxybenzyl)-7-methyl-1-pyrazolo[3,4-d]pyridazine

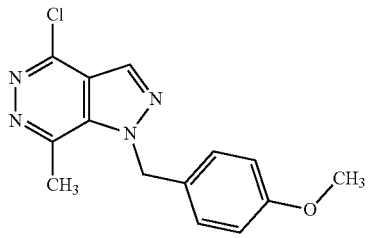 [SMILES: COc1ccc(Cn2ncc3c(Cl)nnc(C)c32)cc1]

A mixture of 1-(4-methoxybenzyl)-7-methyl-1,5-dihydro-4H-pyrazolo[3,4-d]pyridazin-4-one (50 g, 184.99 mmol) in POCl$_3$ (521.9 g, 3.40 mol, 316.30 mL) was stirred at 100° C. for 2 hours and then concentrated in vacuo. The resulting residue was diluted with DCM/MeOH (10:1, 800 mL), washed with water (300 mL) and aq NaHCO$_3$ (200 mL), dried over Na$_2$SO$_4$, filtered and concentrated in vacuo to give the title compound as a yellow oil (60 g, crude).

Step 5: 4-methoxy-1-(4-methoxybenzyl)-7-methyl-1H-pyrazolo[3,4-d]pyridazine

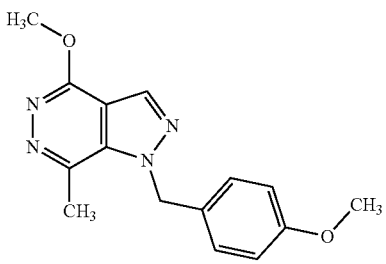 [SMILES: COc1ccc(Cn2ncc3c(OC)nnc(C)c32)cc1]

A mixture of 4-chloro-1-(4-methoxybenzyl)-7-methyl-1H-pyrazolo[3,4-d]pyridazine (60 g, 207.81 mmol) and NaOMe (33.68 g, 623.42 mmol) in MeOH (500 mL) was stirred at 70° C. for 2 hours and then concentrated in vacuo. The resulting residue was diluted with water (400 mL) and extracted with DCM/MeOH (10:1, 500 mL×2). The combined organic layers were dried over anhydrous Na$_2$SO$_4$, filtered and concentrated in vacuo. The residue was purified by column chromatography (Sift) eluting with petroleum ether/EtOAc (5:1 to 0:1) to give the title compound as a yellow solid (30 g, crude).

Step 6: 4-methoxy-7-methyl-1H-pyrazolo[3,4-d]pyridazine

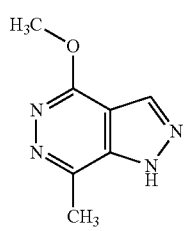

A solution of 4-methoxy-1-(4-methoxybenzyl)-7-methyl-1H-pyrazolo[3,4-d]pyridazine (28 g, 98.48 mmol) in H$_2$SO$_4$ (150 mL) was stirred at 50° C. for 5 hours. The mixture was added to a suspension of NaHCO$_3$ (500 g) in DCM/MeOH (10:1, 1.2 L) and filtered. The filter cake was washed with DCM/MeOH (10:1, 1.2 L×5) and the combined organic layers were concentrated in vacuo to give the title compound as a yellow solid (20 g, crude).

Step 7: 3-bromo-4-methoxy-7-methyl-1H-pyrazolo[3,4-d]pyridazine

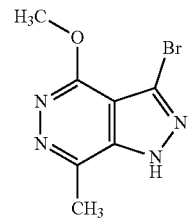

To a mixture of 4-methoxy-7-methyl-1H-pyrazolo[3,4-d]pyridazine (10 g, 60.91 mmol) and NaOAc (34.98 g, 426.40 mmol) in EtOH (100 mL) and water (100 mL) was added Br$_2$ (38.94 g, 243.66 mmol, 12.56 mL). The reaction mixture was stirred at 25° C.' for 12 hours and then quenched with aq Na$_2$S$_{O3}$ (200 mL) and extracted with DCM/MeOH (10:1, 300 mL×8). The combined organic layers were concentrated in vacuo. The resulting residue was triturated with petroleum ether/EtOAc (1:1, 100 mL) for 30 minutes and filtered. The filter cake was dried in vacuo to give the title compound as a white solid (4.2 g, 28%).

Step 8: 3-bromo-4-methoxy-1,7-dimethyl-1H-pyrazolo[3,4-d]pyridazine

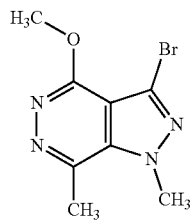

A mixture of 3-bromo-4-methoxy-7-methyl-1H-pyrazolo[3,4-d]pyridazine (5 g, 20.57 mmol), iodomethane (9.7 g, 68.34 mmol, 4.25 mL) and K$_2$CO$_3$ (8.53 g, 61.71 mmol) in DMF (100 mL) was stirred at 10° C. for 1 hour and then diluted with water (200 mL) and extracted with EtOAc (100 mL×3). The combined organic layers were washed with brine (200 mL), dried over anhydrous Na$_2$SO$_4$, filtered and concentrated in vacuo. The resulting residue was purified by column chromatography (SiO$_2$) eluting with petroleum ether/EtOAc (5:1 to 0:1) to give the title compound as a yellow solid (2.8 g, crude).

Step 9: 4-methoxy-1,7-dimethyl-3-(prop-1-en-2-yl)-1H-pyrazolo[3,4-d]pyridazine

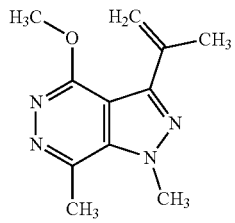

A mixture of 3-bromo-4-methoxy-1,7-dimethyl-1H-pyrazolo[3,4-d]pyridazine (2.8 g, 10.89 mmol), 2-isopropenyl-4,4,5,5-tetramethyl-1,3,2-dioxaborolane (3.66 g, 21.78 mmol), Na$_2$CO$_3$ (3.46 g, 32.67 mmol) and Pd(dppf)Cl$_2$ (796.92 mg, 1.09 mmol) in dioxane (20 mL) and water (2 mL) was stirred at 90° C. for 12 hours under N$_2$ and then filtered. The filtrate was concentrated in vacuo and the resulting residue was purified by column chromatography (SiO$_2$) eluting with DCM/MeOH (100:1 to 50:1) to give the title compound as a yellow solid (2.6 g, crude).

Step 10: 3-isopropyl-4-methoxy-1,7-dimethyl-1H-pyrazolo[3,4-d]pyridazine

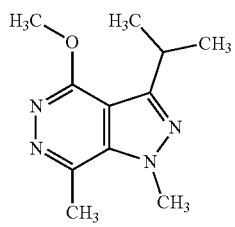 [SMILES: COc1nnc(C)c2c1c(C(C)C)nn2C]

A mixture of 4-methoxy-1,7-dimethyl-3-(prop-1-en-2-yl)-1H-pyrazolo[3,4-d]pyridazine (1.2 g, 5.50 mmol) and Pd/C (100 mg, 10% purity, wet basis) in THF (20 mL) was purged with 112 several times. The reaction mixture was stirred at 10° C. for 12 hours under H$_2$ (15 psi) and then filtered. The filtrate was concentrated in vacuo and the resulting residue was purified by column chromatography (Sift) eluting with petroleum ether/EtOAc (2:1 to 0:1). The product was further purified by HPLC (Method D) to give the title compound as a white solid (0.45 g, 37%).

Step 11: 3-isopropyl-1,7-dimethyl-1,5-dihydro-4H-pyrazolo[3,4-d]pyridazin-4-one A solution of 3-isopropyl-4-methoxy-1,7-dimethyl-1H-pyrazolo[3,4-d]pyridazine (0.45 g, 2.04 mmol) in dioxane (10 mL) and aq HCl (4 M, 10 mL) was stirred at 90° C. for 12 hours. The reaction mixture was concentrated in vacuo to give the title compound as a yellow solid (114.3 mg, 97%).

Preparation 17: 1-methyl-1,5-dihydro-4H-imidazo[4,5-d]pyridazin-4-one

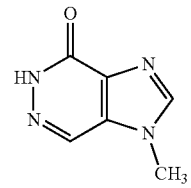

Step 1: diethyl 1-methyl-1H-imidazole-4,5-dicarboxylate

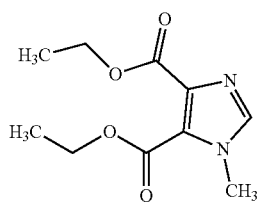 [SMILES: CCOC(=O)c1ncn(C)c1C(=O)OCC]

To a solution of diethyl 1H-imidazole-4,5-dicarboxylate (20 g, 94.25 mmol) in DMF (200 mL) were added K$_2$CO$_3$ (39.08 g, 282.75 mmol, 3 eq) and MeI (53.51 g, 377.00 mmol, 23.47 mL, 4 eq). The reaction mixture was stirred at 1.0° C. for 8 hours and then filtered. The filter cake was washed with EtOAc (80 mL) and the filtrate was evaporated in vacuo. The resulting residue that was purified by column chromatography (SiO$_2$) eluting with petroleum ether/EtOAc (1:0 to 1:1) to give the title compound as a yellow oil (14 g, 63% yield, 95% purity).

Step 2: 1-methyl-1H-imidazole-4,5-dicarbohydrazide

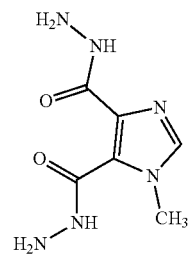

To a stirred solution of diethyl 1-methyl-1H-imidazole-4,5-dicarboxylate (14 g, 61.88 mmol) in EtOH (100 mL) was added N$_2$H$_4$·H$_2$O (12.64 g, 247.54 mmol, 12.28 mL). The reaction mixture was stirred at 80° C. for 16 hours and then evaporated in vacuo to give the title compound as a white solid (11.3 g, crude).

Step 3: 1-methyl-5,6-dihydro-1H-imidazo[4,5-d]
pyridazine-4,7-dione

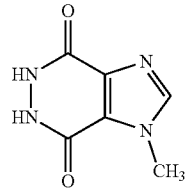

To aq HCl (4 M, 100 mL) was added 1-methyl-1H-imidazole-4,5-dicarbohydrazide (11.3 g, 57.02 mmol). The reaction mixture was stirred at 100° C. for 16 hours and then evaporated in vacuo to give the title compound as a white solid (18.3 g, crude).

Step 4: 4,7-dichloro-1-methyl-1H-imidazo[4,5-d]
pyridazine

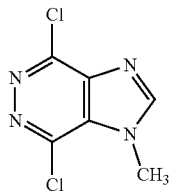

To POCl$_3$ (460.35 g, 3.00 mol, 279.00 mL) was added 1-methyl-5,6-dihydro-1H-imidazo[4,5-d]pyridazine-4,7-dione (9.3 g, 55.98 mmol) and DMF (981.67 mg, 13.43 mmol, 1.03 mL). The reaction mixture was stirred at 100° C. for 18 hours and then evaporated in vacuo. The resulting residue was diluted with saturated aq NaHCO$_3$ (100 mL) and extracted with DCM (50 mL×5). The combined organic layers were dried over Na$_2$SO$_4$, filtered and concentrated under reduced pressure. The residue was purified by silica gel flash chromatography (ISCO® 40 g SepaFlash®, column) eluting with MeOH/DCM (0:100 to 6:94) to give the title compound as a white solid (3.5 g, 29% yield, 95% purity).

Step 5: 7-chloro-4-methoxy-1-methyl-1H-imidazo
[4,5-d]pyridazine

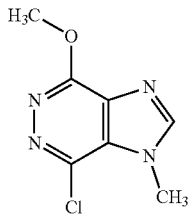

and 4-chloro-7-methoxy-1-methyl-1H-imidazo[4,5-d]
pyridazine

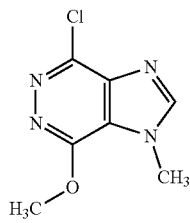

To a stirred solution of 4,7-di chloro-1-methyl-1H-imidazo[4,5-d]pyridazine (3.5 g, 17.24 mmol) in MeOH (50 mL) was added NaOMe (1.12 g, 20.69 mmol). The reaction mixture was stirred at 50° C. for 16 hours and then evaporated in vacuo. The resulting residue was purified by column chromatography (SiO$_2$) eluting with DCM/MeOH (15:1) to give a mixture of the title compounds as a white solid (total 3.3 g).

Step 6: 7-methoxy-1-methyl-1H-imidazo[4,5-d]
pyridazine

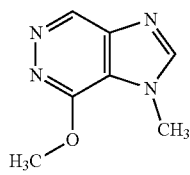

and 4-methoxy-1-methyl-1H-imidazo[4,5-d]pyridazine

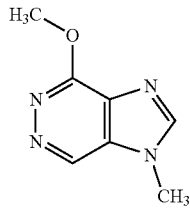

To a mixture of 7-chloro-4-methoxy-1-methyl-1H-imidazo[4,5-d]pyridazine and 4-chloro-7-methoxy-1-methyl-1H-imidazo[4,5-d]pyridazine (2.3 g total) in MeOH (100 mL) was added Pd/C (400 mg, 10% purity, wet basis). The mixture was purged with H$_2$ several times and then stirred at 10° C. for 16 hours under H$_2$ (15 psi) and filtered. The filter cake was washed with MeOH (40 mL) and the filtrate was evaporated in vacuo. The resulting residue was purified by silica gel flash chromatography (ISCO® 40 g SepaFlash® column) eluting with MeOH/DCM (0:100 to 6:94). The products were further purified by HPLC (Method C) to give 7-methoxy-1-methyl-1H-imidazo[4,5-d]pyridazine as a white solid (550 mg) and 4-methoxy-1-methyl-1H-imidazo[4,5-d]pyridazine as a yellow solid (1 g).

Step 7: 1-methyl-1,5-dihydro-4H-imidazo[4,5-d]pyridazin-4-one

A solution of 4-methoxy-1-methyl-1H-imidazo[4,5-d]pyridazine (170 mg, 1.04 mmol) in dioxane (10 mL) and HCl (4 M, 10 mL) was stirred at 90° C. for 2 hours and then concentrated in vacuo. The resulting residue was triturated with petroleum ether/EtOAc (1:1, 15 mL) for 30 minutes and filtered. The filter cake was dried in vacuo to give the title compound as a white solid (146.6 mg, 91%).

Preparation 18: 3-methyl-3,5-dihydro-4H-imidazo[4,5-d]pyridazin-4-one

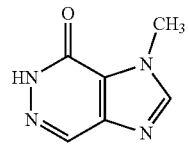

To 7-methoxy-1H-imidazo[4,5-d]pyridazine (550 mg, 3.35 mmol) dissolved in dioxane (10 mL) was added HO (4 M, 11.48 mL). The mixture was stirred at 100° C. for 16 hours and then evaporated in vacuo. The resulting residue was triturated with petroleum ether/EtOAc (5:1, 10 mL) for 10 minutes and filtered. The filter cake was dried in vacuo to give the title compound as a white solid (485 mg, 94%).

Preparation 19: 1,7-dimethyl-1,5-dihydro-4H-imidazo[4,5-d]pyridazin-4-one

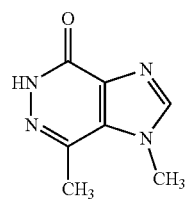

Step 1: 4-chloro-1,7-dimethyl-1H-imidazo[4,5-d]pyridazine

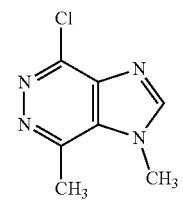

To a solution of 4,7-dichloro-1-methyl-1H-imidazo[4,5-d]pyridazine (500 mg, 2.46 mmol), CH$_3$B(OH)$_2$ (147.42 mg, 2.46 mmol) and Cs$_2$CO$_3$ (2.41 g, 7.39 mmol) in dioxane (20 mL) and water (1 mL) was added Pd(dppt)Cl$_2$·CH$_2$Cl$_2$ (402.23 mg, 492.54 μmol). The mixture was degassed and purged with N$_2$ (3×) and then stirred at 100° C. for 16 hours under N$_2$ atmosphere and filtered. The filter cake was washed with EtOAc (20 mL), and the filtrate was evaporated in vacuo and purified by silica gel flash chromatography (ISCO® 12 g SepaFlash® column) eluting with DCM/MeOH (0:100 to 10:90) to give the title compound as a brown solid (250 mg).

Step 2: 4-methoxy-7-dimethyl-1H-imidazo[4,5-d]pyridazine

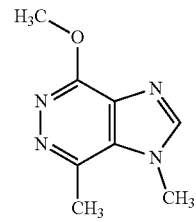

To a solution of 4-chloro-1,7-dimethyl-1H-imidazo[4,5-d]pyridazine (530 mg, 2.90 mmol) in MeOH (15 mL) was added NaOMe (470.39 mg, 8.71 mmol). The mixture was stirred at 60° C. for 16 hours and then evaporated in vacuo. The resulting residue was purified by column chromatography (SiO$_2$) eluting with DCM/MeOH (0:100 to 15:1) to give the title compound as a grey solid (520 mg, 96% yield, 95% purity).

Step 3: 1,7-dimethyl-1,5-dihydro-4H-imidazo[4,5-d]pyridazin-4-one

A solution of 4-methoxy-1,7-dimethyl-1H-imidazo[4,5-d]pyridazine (520 mg, 2.92 mmol) in dioxane (10 mL) and HCl (4 M, 10 mL) was stirred at 100° C. for 16 hours and then filtered. The filter cake was collected and dried in vacuo to give the title compound as a white solid (397.7 mg, 83%).

Preparation 20: 1,3,4-trimethyl-1,6-dihydro-7H-pyrazolo[3,4-d]pyridazin-7-one

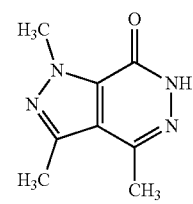

Step 1: ethyl 4-iodo-5-methyl-1H-pyrazole-3-carboxylate

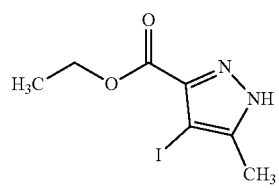

To a solution of ethyl 5-methyl-1H-pyrazole-3-carboxylate (20 g, 129.73 mmol) in DMF (250 mL) was added NIS (35.02 g, 155.68 mmol) in portions. The mixture was stirred at 18° C. for 16 hours and then diluted with water (250 mL) and extracted with EtOAc, (300 mL×4). The combined organic layers were washed with brine (300 mL×2), dried over Na₂SO₄, filtered and concentrated under reduced pressure. The product was purified by column chromatography (SiO₂) eluting with petroleum ether/EtOAc (20:1 to 4:1) to give the title compound as light-yellow solid.

Step 2: ethyl 4-iodo-1-(4-methoxybenzyl)-5-methyl-1H-pyrazole-3-carboxylate

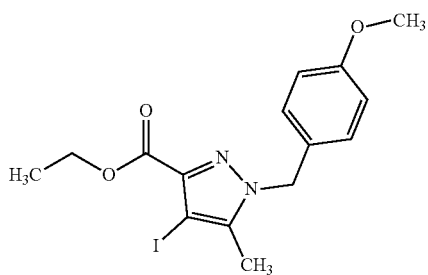 [SMILES: CCOC(=O)c1nn(Cc2ccc(OC)cc2)c(C)c1I]

To a mixture of ethyl 4-iodo-5-methyl-1H-pyrazole-3-carboxylate (42 g, 149.97 mmol) and K₂CO₃ (62.18 g, 449.90 mmol) in DMF (400 mL) was added 4-methoxybenzyl chloride (35.23 g, 224.95 mmol, 30.63 mL). The mixture was stirred at 18° C. for 16 hours and then filtered. The filtrate was concentrated under reduced pressure and purified by silica gel flash chromatography (NCO®, 220 g SepaFlash® column) eluting with EtOAc/petroleum ether (0:100 to 20:80) to give the title compound as yellow solid.

Step 3: ethyl 4-acetyl-1-(4-methoxybenzyl)-5-methyl-1H-pyrazole-3-carboxylate

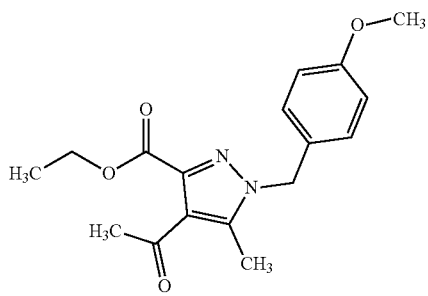 [SMILES: CCOC(=O)c1nn(Cc2ccc(OC)cc2)c(C)c1C(C)=O]

To a solution of ethyl 4-iodo-1-(4-methoxybenzyl)-5-methyl-1H-pyrazole-3-carboxylate (30 g, 74.96 mmol) and Pd(PPh₃)₂Cl₂ (5.26 g, 7.50 mmol) in toluene (300 mL) was added tributyl(1-ethoxyvinyl)stannane (40.61 g, 112.44 mmol, 37.95 mL). The mixture was degassed and purged with N₂ (3×) and then stirred at 100° C. under N₂ for 14 hours and evaporated under reduced pressure. The resulting residue was dissolved in THF (90 mL). Next, HCl (2 M, 90 mL) was added. The mixture was stirred at 25° C. for 2 hours and then quenched with saturated aq KF (200 mL) and filtered. The filtrate was extracted with DCM (200 mL×2). The combined organic layers were dried over Na₂SO₄, filtered, concentrated under reduced pressure, and purified by column chromatography (SiO₂) eluting with petroleum ether/EtOAc (10:1 to 3:1) to give the title compound as black brown oil (23 g, 97%).

Step 4: ethyl 4-acetyl-3-methyl-1H-pyrazole-5-carboxylate

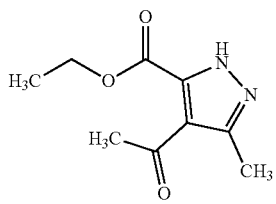

A mixture of ethyl 4-acetyl-1-(4-methoxybenzyl)-5-methyl-1H-pyrazole-3-carboxylate (23 g, 72.70 mmol) and H₂SO₄ (128.80 g, 1.29 mol, 70 mL, 98% purity) was stirred at 50° C. for 5 hours and then slowly added to a suspension of NaHCO₃ (240 g) in DCM/MeOH (10:1, 1500 mL). The mixture was stirred for 15 minutes and filtered. The filtrate was concentrated under reduced pressure and purified by column chromatography (SiO₂) eluting with petroleum ether/EtOAc (10:1 to 1:1) to give the title compound as yellow solid (4.3 g, 30%).

Step 5: ethyl 4-acetyl-1,3-dimethyl-1H-pyrazole-5-carboxylate

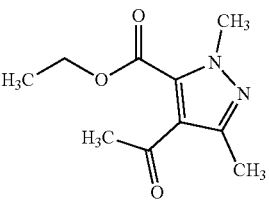

To a mixture of ethyl 4-acetyl-3-methyl-1H-pyrazole-5-carboxylate (1.8 g, 9.17 mmol) and K₂CO₃ (2.54 g, 18.35 mmol) in DMF (18 mL) was added MeI (3.91 g, 27.52 mmol, 1.71 mL), The mixture was stirred at 18° C. for 16 hours and then diluted with water (50 mL) and extracted with EtOAc (50 mL×3). The combined organic layers were washed with brine (50 mL×2), dried over Na₂SO₄, filtered and concentrated under reduced pressure. The product was purified by silica gel flash chromatography (ISCO® 12 g SepaFlash® column) eluting with EtOAc/petroleum ether (0:100 to 4:96)) to give the title compound as yellow oil (930 mg, 48%).

Step 6: 1,3,4-trimethyl-1,6-dihydro-7H-pyrazolo[3,4-d]pyridazin-7-one

To a solution ethyl 4-acetyl-1,3-dimethyl-1H-pyrazole-5-carboxylate (700 mg, 3.33 mmol) in EtOH (10 mL) was added N₂H₄·H₂O (510.26 mg, 9.99 mmol, 495.40 μL, 98% purity), The mixture was stirred at 80° C. for 14 hours and then concentrated under reduced pressure to give the title compound as white solid (507.1 mg, 85%).

Preparation 21: 1-isopropyl-3,4-dimethyl-1,6-dihydro-7H-pyrazolo[3,4-d]pyridazin-7-one

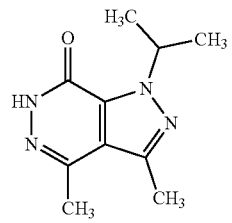

Step 1: ethyl 4-acetyl-1-isopropyl-3-methyl-1H-pyrazole-5-carboxylate

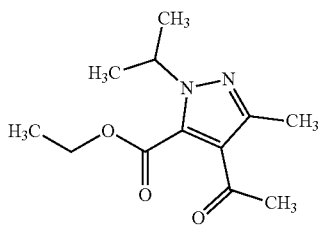 [SMILES: CCOC(=O)c1c(C(C)=O)c(C)nn1C(C)C]

To a solution of ethyl 4-acetyl-3-meth 4-1H-pyrazole-5-carboxylate (300 mg 1.53 mmol) in DMF (3 mL) was added $K_2CO_3$ (422.64 mg, 3.06 mmol, 2 eq) and 2-iodopropane (519.85 mg, 3.06 mmol, 305.79 μL). The mixture was stirred at 18° C. for 16 hours and then filtered. The filter cake was washed with EtOAc (20 mL) and the filtrate was concentrated under reduced pressure to afford a crude product, which was purified by preparative TLC ($SiO_2$) eluting with petroleum ether/EtOAc (3:1). The title compound was obtained as a colorless oil (200 mg, 55%).

Step 2: 1-isopropyl-3,4-dimethyl-1,6-dihydro-7H-pyrazolo[3,4-d]pyridazin-7-one

To a solution of ethyl 4-acetyl-1-isopropyl-3-methyl-1H-pyrazole-5-carboxylate (200 mg, 839.34 μmol) in EtOH (5 mL) was added $N_2H_4 \cdot H_2O$ (128.63 mg, 2.52 mmol, 124.88 μL, 98% purity). The mixture was stirred at 80° C. for 16 hours and then concentrated under reduced pressure to give the title compound as white solid (140 mg, 81%).

Preparation 22: 1-cyclopropyl-3,4-dimethyl-1,6-dihydro-7H-pyrazolo[3,4-d]pyridazin-7-one

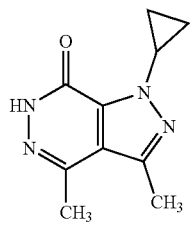

Step 1: 2-(4-methoxybenzyl)-3,4-dimethyl-2,6-dihydro-7H-pyrazolo[3,4-d]pyridazin-7-one

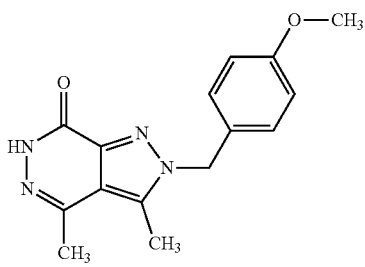 [SMILES: COc1ccc(Cn2nc3c(=O)[nH]nc(C)c3c2C)cc1]

To a solution of ethyl 4-acetyl-1-(4-methoxybenzyl)-5-methyl-1H-pyrazole-3-carboxylate (3 g, 9.48 mmol) in EtOH (40 mL) was added $N_2H_4 \cdot H_2O$ (1.45 g, 28.45 mmol, 1.41 mL, 98% purity). The reaction mixture was stirred at 80° C. for 16 hours and then concentrated under reduced pressure. The crude product was triturated with petroleum ether/EtOAc (3:1, 80 mL) for 15 minutes. The solids were collected by filtration and dried in vacuo to give the title compound as gray solid (3.1 g, crude).

Step 2: 7-chloro-2-(4-methoxybenzyl)-3,4-dimethyl-2H-pyrazolo[3,4-d]pyridazine

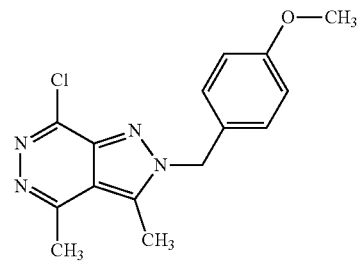 [SMILES: COc1ccc(Cn2nc3c(Cl)nnc(C)c3c2C)cc1]

Intermediate 2-(4-met oxybenzyl)-3,4-dimethyl-2,6-dihydro-7H-pyrazolo[3,4-d]pyridazin-7-one (25 g, 87.93 mmol) was added to $POCl_3$ (206.25 g, 1.35 mol, 125 mL). The mixture was stirred at 100° C. for 3 hours and then evaporated under reduced pressure, diluted with DCM/MeOH (10:1, 330 mL) and neutralized to pH 7~8 by addition of saturated aq $NaHCO_3$. The organic layer was dried over $Na_2SO_4$ and concentrated under reduced pressure to give the title compound as a yellow oil (29 g, crude).

Step 3: 7-methoxy-2-(4-methoxybenzyl)-3,4-dimethyl-2H-pyrazolo[3,4-d]pyridazine

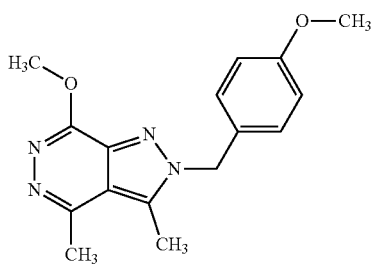 [SMILES: COc1ccc(Cn2nc3c(OC)nnc(C)c3c2C)cc1]

To a solution of 7-chloro-2-(4-methoxybenzyl)-3,4-dimethyl-2H-pyrazolo[3,4-d]pyridazine (29 g, 95.79 mmol) in MeOH (300 mL) was added NaOMe (20.70 g, 383.14 mmol). The mixture was stirred at 70° C. for 16 hours and then filtered. The filter cake was washed with DCM/MeOH (10:1, 55 mL) and the filtrate was evaporated under reduced pressure. The resulting crude product was purified by silica gel flash chromatography (ISCO® 60 g SepaFlash® column) eluting with EtOAc/petroleum ether (0:100 to 100:0) to give the title compound as a yellow solid (18 g, 63%).

Step 4: 7-methoxy-3,4-dimethyl-2H-pyrazolo[3,4-d]pyridazine

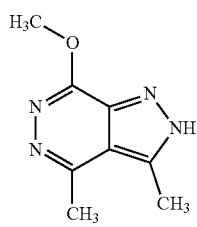

A mixture of 7-methoxy-2-(4-methoxybenzyl)-3,4-dimethyl-2H-pyrazolo[3,4-d]pyridazine (15 g, 50.28 mmol) and $H_2SO_4$ (82.80 g, 827.32 mmol, 45 mL, 98% purity) was stirred at 50° C. for 5 hours and then slowly added to a suspension of $NaHCO_3$ (150 g) in DCM/MeOH (10:1, 1000 mL). The mixture was stirred for 15 minutes and filtered. The filtrate was concentrated under reduced pressure to give the title compound as a yellow solid (12.9 g, crude).

Step 5: 1-cyclopropyl-7-methoxy-3,4-dimethyl-1H-pyrazolo[3,4-d]pyridazine

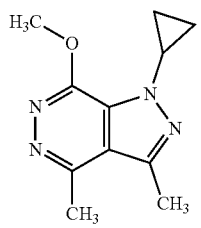 [SMILES: COc1nnc(C)c2c(C)nn(C3CC3)c12]

To a solution of 7-methoxy-3,4-dimethyl-2H-pyrazolo[3,4-d]pyridazine g, 14.03 mmol) in DCE (30 mL) was added $Cu(OAc)_2$ (3.82 g, 21.04 mmol), 2-(2-pyridyl)pyridine (3.29 g, 21.04 mmol), $Na_2CO_3$ (2.97 g, 28.06 mmol) and cyclopropylboronic acid (2.41 g, 28.06 mmol). The reaction mixture was stirred at 70° C. for 16 hours and then filtered. The filter cake was washed with DCM (300 mL) and the filtrate was washed with water (150 mL), dried over $Na_2SO_4$, filtered and concentrated under reduced pressure. The resulting crude product was purified by silica gel flash chromatography (ISCO® 8 g SepaFlash® column) eluting with EtOAc/petroleum ether (0:100 to 50:50) to give the title compound as a yellow solid (470 mg, 14%).

Step 6: 1-cyclopropyl-3,4-dimethyl-1,6-dihydro-7H-pyrazolo[3,4-d]pyridazin-7-one To a solution of 1-cyclopropyl-7-methoxy-3,4-dimethyl-H-pyrazolo[3,4-d]pyridazine (420 mg, 1.92 mmol) in DCM (6 mL) was added $BBr_3$ (2.41 g, 9.62 mmol, 927.11 μL) at 0° C. The reaction mixture was stirred at 25° C. for 16 hours and then quenched with water (30 mL) and extracted with EtOAc (20 mL×2). The combined organic layers were dried over $Na_2SO_4$, filtered, concentrated under reduced pressure and purified by silica gel flash chromatography (NCO® 4 g SepaFlash® column) eluting with EtOAc/petroleum ether (0:100 to 40:60). The resulting crude product was washed with DCM (5 mL×2) and filtered. The solids were dried in vacuo to give the title compound as white solid.

Preparation 23: 1,3-dimethyl-1,6-dihydro-7/1-pyrazolo[3,4-d]pyridazin-7-one

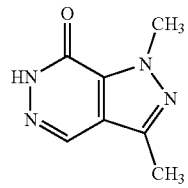

Step 1: ethyl 3-methyl-4-vinyl-1H-pyrazole-5-carboxylate

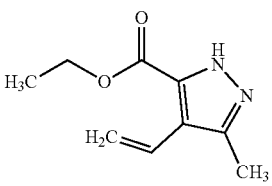

A mixture of ethyl 4-iodo-5-methyl-1H-pyrazole-3-carboxylate (20 g, 71.41 mmol), $Pd(dppf)Cl_2$ (5.23 g, 7.14 mmol), $Na_2CO_3$ (22.71 g, 214.24 mmol) and 4,4,5,5-tetramethyl-2-vinyl-1,3,2-dioxaborolane (22.00 g, 142.83 mmol, 24.23 mL) in dioxane (200 mL) and water (20 mL) was stirred at 100° C. for 14 hours under $N_2$. The reaction mixture was then diluted with water (500 mL) and extracted with DCM (500 mL×2). The combined organic layers were dried over $Na_2SO_4$, filtered and concentrated under reduced pressure. The crude product was purified by column chromatography (Sift) eluting with petroleum ether/EtOAc (100:1 to 10:1) to give the title compound as a yellow oil.

Step 2: ethyl 1,3-dimethyl-4-vinyl-1H-pyrazole-5-carboxylate

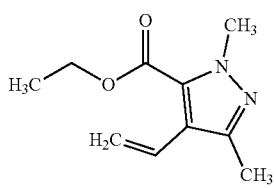

To a solution of ethyl 3-methyl-4-vinyl-1H-pyrazole-5-carboxylate (4 g, 22.20 mmol) in DMF (40 mL) were added MeI (9.45 g, 66.59 mmol, 4.15 mL) and K₂CO₃ (6.14 g, 44.39 mmol). The mixture was stirred at 18° C. for 2 hours and then diluted with water (200 mL) and extracted with EtOAc (200 mL×3). The combined organic layers were washed with brine (200 mL×2), dried over Na₂SO₄, filtered and concentrated under reduced pressure. The crude product was purified by silica gel flash chromatography (ISCO® 12 g SepaFlash® column) eluting with EtOAc/petroleum ether (0:100 to 1.5:98.5) to give the title compound as a white solid (2 g, 46%).

Step 3: ethyl 4-formyl-1,3-dimethyl-1H-pyrazole-5-carboxylate

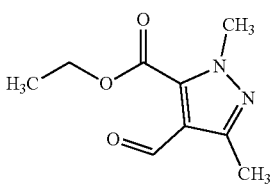

To a solution of ethyl 1,3-dimethyl-4-vinyl-1H-pyrazole-5-carboxylate (2 g, 10.30 mmol) in dioxane (20 mL) and water (5 mL) were added NaIO₄ (6.61 g, 30.89 mmol, 1.71 mL) and OsO₄ (0.1 M solution in water, 10.30 mL) at 0° C. The reaction mixture was stirred at 18° C. for 14 hours and then quenched with saturated aq Na₂S₂O₃·5H₂O (100 mL) and extracted with DCM (100 mL×2). The combined organic layers were dried over Na₂SO₄, filtered and concentrated under reduced pressure. The crude product was purified by column chromatography (Sift) eluting with petroleum ether/EtOAc (100:1 to 10:1) to give the title compound as a white solid (600 mg, 30%).

Step 4: 1,3-dimethyl-1,6-dihydro-7H-pyrazolo[3,4-d]pyridazin-7-one

To a solution of ethyl 4-formyl-1,3-dimethyl-1H-pyrazole-5-carboxylate (600 mg, 3.06 mmol) in EtOH (8 mL) was added N₂H₄·H₂O (468.64 mg, 9.17 mmol, 454.99 μL, 98% purity). The reaction mixture was stirred at 80° C. for 14 hours and then concentrated under reduced pressure. The crude product was purified by silica gel flash chromatography (NCO® 4 g SepaFlash® column) eluting with EtOAc/petroleum ether (0:100 to 20:80) to give the title compound as a white solid (315.6 mg, 62%).

Preparation 24: 1-isopropyl-3-methyl-1,6-dihydro-7H-pyrazolo[3,4-d]pyridazin-7-one

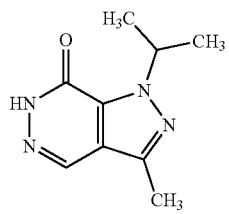

Step 1: ethyl 1-isopropyl-3-methyl-4-vinyl-1H-pyrazole-5-carboxylate

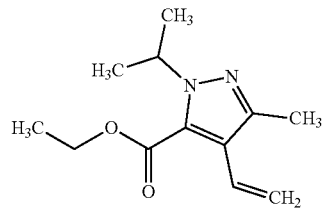 [SMILES: C=Cc1c(C)nn(C(C)C)c1C(=O)OCC]

To a solution of ethyl 3-methyl-4-vinyl-1H-pyrazole-5-carboxylate (1 g, 5.38 mmol) in DMF (10 mL) were added K₂CO₃ (1.49 g, 10.77 mmol) and 2-iodopropane (1.83 g, 10.77 mmol, 1.08 mL). The reaction mixture was stirred at 18° C. for 14 hours and then diluted with water (20 mL) and extracted with EtOAc (50 mL×2). The combined organic layers were washed with brine (50 mL×2), dried over Na₂SO₄, filtered and concentrated under reduced pressure. The crude product was purified by silica gel flash chromatography (ISCO® 8 g SepaFlash® column) eluting with EtOAc/petroleum ether (0:100 to 20:80) to give the title compound as a colorless oil (580 mg, 48%).

Step 2: ethyl 4-formyl-1-isopropyl-3-methyl-7H-pyrazole-5-carboxylate

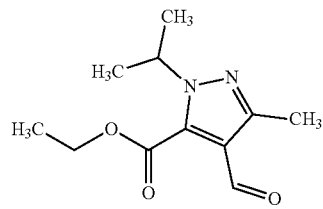 [SMILES: CCOC(=O)c1c(C=O)c(C)nn1C(C)C]

To a solution of ethyl 1-isopropyl-3-methyl-4-vinyl-1H-pyrazole-5-carboxylate (1.8 g, 8.10 mmol) in dioxane (20 mL) and water (5 mL) were added NaIO₄ (5.20 g, 24.29 mmol, 1.35 mL) and OsO4 (0.1 M solution in water, 12.15 mL) at 0° C. The reaction mixture was stirred at 18° C. for 16 hours and then quenched with saturated aq Na₂S₂O₃·5H₂O (80 mL) and extracted with EtOAc (100 mL×2). The combined organic layers were dried over Na₂SO₄, filtered and concentrated under reduced pressure. The crude product was purified by silica gel flash chromatography (ISCO® 12 g SepaFlash® column) eluting with EtOAc/petroleum ether (0:100 to 4:96) to give the title compound as a white solid (800 mg, 44%).

Step 3: 1-isopropyl-3-methyl-1,6-dihydro-7H-pyrazolo[3,4-d]pyridazin-7-one

To a solution of ethyl 4-formyl-1-isopropyl-3-methyl-1H-pyrazole-5-carboxylate (700 mg, 3.12 mmol) in EtOH (10 mL) was added N₂H₄·H₂O (478.35 mg, 9.36 mmol, 464.42 μL, 98% purity). The reaction mixture was stirred at 80° C. for 14 hours and then concentrated under reduced pressure. The crude product was purified by silica gel flash chromatography (NCO® 4 g SepaFlash® column) eluting with EtOAc/petroleum ether (0:100 to 12:88) to give the title compound as a white solid (228.3 mg, 37%).

Preparation 25: 1-cyclopropyl-3-methyl-1,6-di-hydro-7H-pyrazolo[3,4-d]pyridazin-7-one

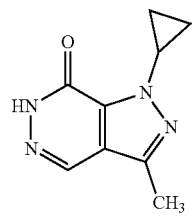

Step 1: ethyl 1-cyclopropyl-3-methyl-4-vinyl-1H-pyrazole-5-carboxylate

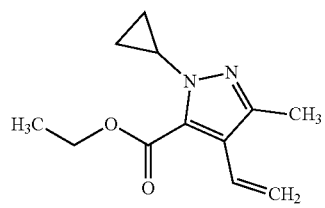

A mixture of ethyl 3-methyl-4-vinyl-1H-pyrazole-5-carboxylate (4 g, 22.20 mmol), cyclopropylboronic acid (3.81 g, 44.39 mmol), Na$_2$CO$_3$ (4.71 g, 44.39 mmol), Cu(OAc)$_2$ (6.05 g, 33.30 mmol) and 2-(2-pyridyl)pyridine (5.20 g, 33.30 mmol) in DCE (40 mL) was stirred at 70° C. for 14 hours. The reaction mixture was then diluted with water (300 mL) and acidified with HCl (1 M) until pH<7. The mixture was extracted with DCM (200 mL×3) and the combined organic layers were concentrated in vacuo. The resulting residue was purified by column chromatography (SiO$_2$) eluting with petroleum ether/EtOAc (500:1 to 200:1) to give the title compound as a light-yellow oil (3 g, 61%).

Step 2: ethyl 1-cyclopropyl-4-formyl-3-methyl-1H-pyrazole-5-carboxylate

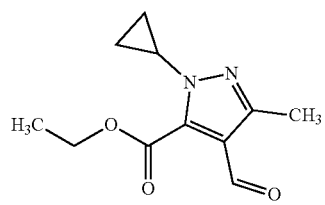 [SMILES: CCOC(=O)c1c(C=O)c(C)nn1C1CC1]

To a solution of ethyl 1-cyclopropyl-3-methyl-4-vinyl-1H-pyrazole-5-carboxylate (2.8 g, 12.71 mmol) in dioxane (32 mL) and water (8 mL) were added OsO$_4$ (0.1 M solution in water, 12.71 mL) and NaIO$_4$ (8.16 g, 38.14 mmol, 2.11 mL) at 0° C. The reaction mixture was stirred at 18° C. for 16 hours and then quenched with saturated aq Na$_2$S$_2$O$_3$.5H$_2$O (150 mL) and extracted with DCM (200 mL×2). The combined organic layers were dried over Na$_2$SO$_4$, filtered and concentrated under reduced pressure. The resulting residue was purified by column chromatography (Sift) eluting with petroleum ether/EtOAc (100:1 to 80:1) to give the title compound as a white solid (900 mg, 32%).

Step 3: 1-cyclopropyl-3-methyl-1,6-dihydro-7H-pyrazolo[3,4-d]pyridazin-7-one

To a solution of ethyl 1-cyclopropyl-4-formyl-3-methyl-1H-pyrazole-5-carboxylate (900 mg, 4.05 mmol) in EtOH (10 mL) was added N$_2$H$_4$·H$_2$O (620.60 mg, 12.15 mmol, 602.52 μL, 98% purity). The reaction mixture was stirred at 80° C. for 14 hours and then concentrated under reduced pressure. The crude product was purified by silica gel flash chromatography (ISCO® 12 g SepaFlash® column) eluting with EtOAc/petroleum ether (0:100 to 18:82) to give the title compound as a white solid (500.2 mg, 64%).

Preparation 26: 1-methyl-1,6-dihydro-7H-pyrrolo[2,3-d]pyridazin-7-one

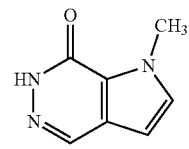

Step 1: methyl 3-bromo-1-methyl-1H-pyrrole-2-carboxylate

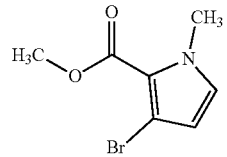

To a mixture of methyl 3-bromo-1H-pyrrole-2-carboxylate (3.5 g, 17.16 mmol) in DMF (40 mL) was added NaH (60% in mineral oil, 1.37 g, 34.31 mmol) at 0° C. After stirring at 0° C. for 30 minutes, MeI (5.2 g, 36.64 mmol, 2.28 mL) was added at 0° C. The mixture was stirred at 15° C. for 1 hour and then diluted with EtOAc (50 mL), poured into saturated aq NH$_4$Cl (100 mL) and extracted with EtOAc (50 mL). The combined organic layers were dried over Na$_2$SO$_4$, filtered and concentrated under reduced pressure to give the title compound as a yellow oil (3.75 g, crude).

Step 2: methyl 1-methyl-3-vinyl-1H-pyrrole-2-carboxylate

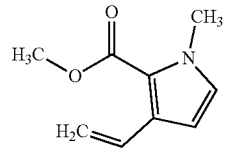

A mixture of methyl 3-bromo-1-methyl-1H-pyrrole-2-carboxylate (4.3 g, 19.72 mmol), tributyl(vinyl)stannane (27.8 g, 87.67 mmol, 25.50 mL) and Pd(PPh₃)₄ (2.28 g, 1.97 mmol) in DMF (60 mL) was degassed and purged with N₂ (3×) and stirred at 100° C. for 12 hours under N₂ atmosphere. Saturated ail KF (150 mL) was added. The mixture was stirred for 30 minutes and then extracted with EtOAc (100 mL×2). The combined organic layers were dried over Na₂SO₄, filtered and concentrated under reduced pressure. The crude product was purified by silica gel flash chromatography (ISCO® 40 g SepaFlash column) eluting with petroleum ether/EtOAc (0:100 to 3:97) to give the title compound as yellow oil.

Step 3: methyl 3-formyl-1-methyl-1H-pyrrole-2-carboxylate

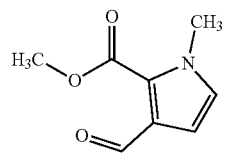

To a mixture of methyl 1-methyl-3-vinyl-1H-pyrrole-2-carboxylate (1.8 g, 10.79 mmol) and N-methylmorpholine-N-oxide (2.27 g, 19.42 mmol, 2.05 mL) in ACN (30 mL) and water (15 mL) was added dipotassium; dioxido(dioxo)osmium; dihydrate (198.74 mg, 539.38 µmol), After stirring for 3 hours at 15° C., NaIO₄ (4.95 g, 23.14 mmol, 1.28 mL) was added. The mixture was stirred for 0.25 hours and then quenched with Na₂S₂O₃ (100 mL) and extracted with EtOAc (50 mL×2). The combined organic layers were dried over Na₂SO₄, filtered and concentrated under reduced pressure. The crude product was purified by silica gel flash chromatography (ISCO® 40 g SepaFlash® column) eluting with petroleum ether/EtOAc (0:100 to 10:90) to give the title compound as a yellow oil (0.8 g, 44%).

Step 4: 1-methyl-1,6-dihydro-7H-pyrrolo[2,3-d]pyridazin-7-one

To a mixture of methyl 3-formyl-1-methyl-1H-pyrrole-2-carboxylate (800 mg, 4.71 mmol) in EtOH (20 mL) was added. N₂H₄·H₂O (722.40 mg, 14.14 mmol, 701.36 µL, 98% purity), The reaction mixture was stirred at 80° C. for 12 hours and then cooled to 5° C. and filtered. The filter cake was washed with EtOH (10 mL). The residue was collected to give the title compound as a white solid (460 mg, 64%).

Preparation 27: 1-cyclobutyl-5-(hydroxymethyl)-3-methyl-1,5-dihydro-4H-pyrazolo[3,4-d]pyridazin-4-one

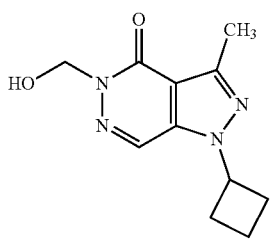 [SMILES: Cc1nn(C2CCC2)c2cnn(CO)c(=O)c12]

Step 1: 2-((benzyloxy)methyl)-5-chloropyridazin-3(2H)-one

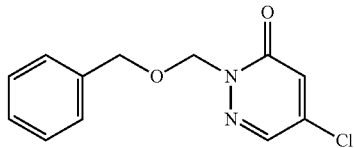 [SMILES: O=c1cc(Cl)cnn1COCc1ccccc1]

To a mixture of 5-chloropyridazin-3(2/1)-one (2 g, 15.32 mmol) and Cs₂CO₃ (6.49 g, 19.92 mmol) in DMF (30 mL) at 0° C. was added ((chloromethoxy)methyl)benzene (2.56 mL, 18.39 mmol) dropwise. The reaction mixture was stirred at 20° C. for 5 hours and then diluted with isopropyl acetate (400 mL) and washed with saturated aq NH₄Cl solution (400 mL) and brine (300 mL). The organic layer was dried over MgSO₄ and concentrated in vacuo. The product was purified by flash chromatography, eluting with 0 to 50% EtOAc in heptanes, to give the title compound as a yellow oil (2.08 g, 54%).

Step 2: 2-((benzyloxy)methyl)-4-bromo-5-chloropyridazin-3(2H)-one

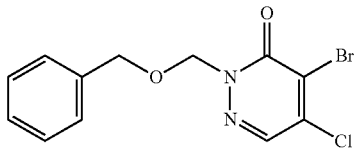 [SMILES: O=c1c(Br)c(Cl)cnn1COCc1ccccc1]

To a 1.0 M solution of (2,2,6,6-tetramethylpiperidin-1-yl)zinc(II) lithium chloride in THF (2.87 mL, 2.87 mmol) was added 2-((benzyloxy)methyl)-5-chloropyridazin-3(2H)-one (600 mg, 2.393 mmol) in THF (10 mL) dropwise over a 1-minute period. The solution was stirred at 20° C. for 1 minute. Bromine (0.247 mL, 4.79 mmol) was added in one portion and the solution was stirred at 2.0° C. for 3 hours. Sodium thiosulfate (378 mg, 2.393 mmol) and MeOH (1 mL) were added. The mixture was stirred at 20° C. for 18 hours and then concentrated on Celite® and purified by flash chromatography, eluting with 0 to 50% EtOAc in heptanes, to give the title compound as a white solid (620 mg, 79%).

Step 3: 2-((benzyloxy)methyl)-5-chloro-4-(prop-1-en-2-yl)pyridazin-3(2H)-one

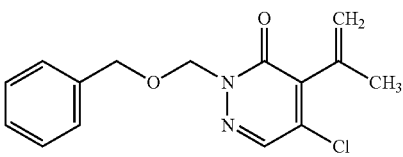 [SMILES: C=C(C)c1c(Cl)cnn(COCc2ccccc2)c1=O]

A mixture of 2-((benzyloxy)methyl)-4-bromo-5-chloropyridazin-3(2H)-one (300 mg, 0.910 mmol), 4,4,5,5-tetramethyl-2-(prop-1-en-2-yl)-1,3,2-dioxaborolane (0.428 mL, 2.276 mmol) and Pd(dppf)Cl₂·CH₂Cl₂, (37.2 nig, 0.046 mmol) in dioxane (3 mL) and saturated aq NaHCO₃ (3 mL, 3.30 mmol) was heated at 50° C. in an oil bath for 3 hours.

LCMS indicated the reaction was incomplete, so more Pd(dppf)Cl$_2$·CH$_2$Cl$_2$ (37.2 mg, 0.046 mmol) was added, and the reaction mixture was heated at 50° C. for 8 hours. The reaction was still incomplete, so additional Pd(dppf)Cl$_2$·CH$_2$Cl$_2$ (37.2 mg, 0.046 mmol), 4,4,5,5-tetramethyl-2-(prop-1-en-2-yl)-1,3,2-dioxaborolane (0.215 mL, 1.14 mmol) and saturated aq NaHCO$_3$ (124 mg, 1.821 mmol) were added. The reaction mixture was heated at 50° C. for 7 hours and then diluted with isopropyl acetate (60 mL), washed with saturated aq NH$_4$Cl (60 mL), vacuum filtered, washed with brine, dried over MgSO$_4$, and concentrated in vacuo. The product was purified by flash chromatography, eluting with 0 to 20% EtOAc in heptanes, to give the title compound as a white solid (169 mg, 64%).

Step 4: 4-acetyl-2-((benzyloxy)methyl)-5-chloro-pyridazin-3(2H)-one

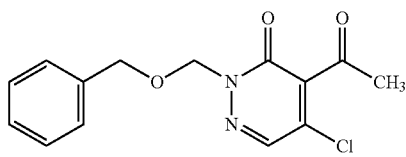 [SMILES: CC(=O)c1c(Cl)cnn(COCc2ccccc2)c1=O]

A solution of 2-((benzyloxy)methyl)-5-chloro-4-(prop-1-en-2-yl)pyridazin-3(2H)-one (0.275 g, 09946 mmol), ruthenium(III) chloride trihydrate (0,012 g, 0,047 mmol) and sodium periodate (0.415 g, 1.939 mmol) in THF (2 mL), acetone (2 mL) and water (2 mL) was stirred at 20° C. for 4 hours. LCMS indicated the reaction was incomplete, so more sodium periodate (220 mg, 1.01 mmol) was added, and the reaction mixture was stirred at 20° C. for 2 hours. The reaction was still incomplete, so additional sodium periodate (400 mg, 1.89 mmol) was added. The reaction mixture was stirred at 20° C. for 18 hours and then diluted with isopropyl acetate (50 mL), washed with a solution of sodium thiosulfate (8.2 g, 20.75 mmol) in water (50 mL) followed by brine (40 mL), dried over MgSO$_4$ and concentrated in vacuo. The product was purified by flash chromatography, eluting with 0 to 50% EtOAc in heptanes, to give the title compound as a clear, colorless oil (200 mg, 72%).

Step 5: 5-((benzyloxy)methyl)-1-cyclobutyl-3-methyl-5-dihydro-4H-pyrazolo[3,4-d]pyridazin-4-one

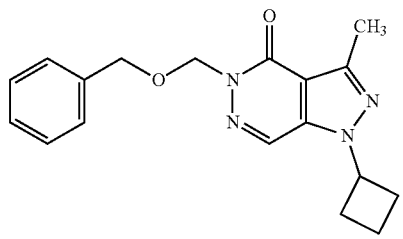 [SMILES: Cc1nn(C2CCC2)c2cnn(COCc3ccccc3)c(=O)c12]

To a solution of 4-acetyl-2-((benzyloxy)methyl)-5-chloropyridazin-3(2H)-one (60 mg, 0.205 mmol) and cyclobutylhydrazine hydrochloride (50.3 mg, 0.410 mmol) in DMF (1.5 mL) at −10° C. (salt/ice bath) was added DIPEA (0.179 mL, 1.025 mmol). The mixture was stirred at −10° C. for 10 minutes. The temperature of the mixture was raised to 0° C.' over a 20-minute period and the mixture was stirred at 0° C. for 2 hours. The mixture was allowed to warm to 20° C. and was then diluted with isopropenyl acetate (40 mL), washed with NH$_4$Cl solution (40 mL) and with brine, dried over MgSO$_4$ and concentrated in vacuo. The product was purified by flash chromatography, eluting with 0 to 60% EtOAc in heptanes, to give the title compound as a white solid (57 mg, 86%).

Step 6: 1-cyclobutyl-5-(hydroxymethyl)-3-methyl-1,5-dihydro-4H-pyrazolo[3,4-d]pyridazin-4-one To a solution of 5-((benzyloxy)methyl)-1-cyclobutyl-3-methyl-1,5-dihydro-4H-pyrazolo[3,4-d]pyridazin-4-one (54 mg, 0.166 mmol) in MeOH (2 mL) under nitrogen was added Pd/C (Degussa®, 10%) (30 mg, 0.028 mmol). The slurry was stirred under an atmosphere of hydrogen for 18 hours. Acetic acid (0.048 mL, 0.832 mmol) was added and the mixture stirred at 20° C. for 3 hours. The mixture was filtered through a pad of Celite®, rinsed with methanol and concentrated in vacuo to give the title compound as a white solid.

Preparation 28: 1-(bicyclo[1.1.1]pentan-1-yl)-5-(hydroxymethyl)-3-methyl-1,5-dihydro-4H-pyrazolo[3,4-d]pyridazin-4-one

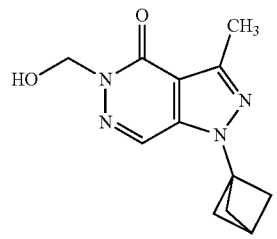 [SMILES: Cc1nn(C23CC(C2)C3)c2cnn(CO)c(=O)c12]

Step 1: 5-((benzyloxy)methyl)-1-(bicyclo[1.1.1]pentan-1-yl)-3-methyl-1,5-dihydro-4H-pyrazolo[3,4-d]pyridazin-4-one

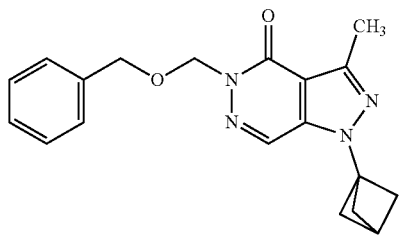 [SMILES: Cc1nn(C23CC(C2)C3)c2cnn(COCc3ccccc3)c(=O)c12]

To a solution of 4-acetyl-2-((benzyloxy)methyl)-5-chloropyridazin-3(2H)-one (60 mg, 0.205 mmol) and bicyclo[1.1.1]pentan-1-ylhydrazine dihydrochloride (70.1 nig, 0.410 mmol) in DMF (1.5 mL) at −10° C. (salt/ice bath) was added DIPEA (0.215 mL, 1.230 mmol). The mixture was stirred at −10° C. for 30 minutes, during which the temperature increased to 0° C., and then at 0° C. for another 30 minutes. The mixture was allowed to warm to 20° C. and was then diluted with isopropenyl acetate (40 mL), washed with NH$_4$Cl solution (40 mL) and with brine, dried over MgSO$_4$ and concentrated in vacuo. The product was purified by flash chromatography, eluting with 0 to 40% EtOAc in heptanes, to give the title compound as a white solid (33 mg, 48%).

Step 2: 1-(bicyclo[1.1.1]pentan-1-yl)-5-(hydroxymethyl)-3-methyl-1,5-dihydro-4H-pyrazolo[3,4-d]pyridazin-4-one To a solution of 5-((benzyloxy)methyl)-1-(bicyclo[1.1.1]pentan-1-yl)-3-methyl-1,5-dihydro-4H-pyrazolo[3,4-d]pyridazin-4-one (31 mg, 0.092 mmol) in MeOH (2 mL) (heated to completely dissolve solid) was added. Pd/C (Degussa®, 10%) (28 mg, 0.026 mmol) under nitrogen. The slurry was stirred under an atmosphere of hydrogen for 3 hours and then filtered through a pad of Celite®, rinsed with methanol and concentrated in metro to give the title compound as a white solid (21 mg, 93%).

Preparation 29: 1-(tert-butyl)-3-methyl-1,5-dihydro-4H-pyrazolo[3,4-d]pyridazin-4-one

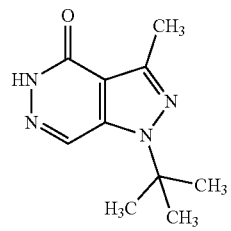

Step 1: ethyl 1-(tert-butyl)-5-(hydroxymethyl)-3-methyl-1H-pyrazole-4-carboxylate

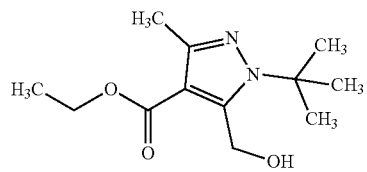 [SMILES: CCOC(=O)c1c(C)nn(C(C)(C)C)c1CO]

To a solution of ethyl 2-methyl-4-oxo-4,5-dihydrofuran-3-carboxylate (75 mg, 0.441 mmol) and tert-butylhydrazine hydrochloride (65.9 mg, 0.529 mmol) in ethanol (0.5 mL) was added DIPEA (0.185 mL, 1.058 mmol). The solution was stirred at 20° C. for 3 hours and then concentrated on Celite® and purified by flash chromatography, eluting with 0 to 50% EtOAc in heptanes, to give the title compound as a colorless oil (68 mg, 64%).

Step 2: ethyl 1-(tert-butyl)-5-formyl-3-methyl-1H-pyrazole-4-carboxylate

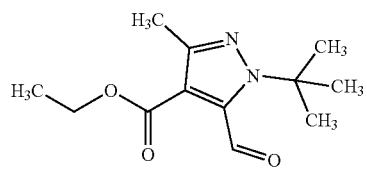 [SMILES: CCOC(=O)c1c(C)nn(C(C)(C)C)c1C=O]

A mixture of ethyl 1-(tert-butyl)-5-(hydroxymethyl)-3-methyl-1H-pyrazole-4-carboxylate (52 mg, 0.22 mmol) and Dess-Martin periodinane (138 mg, 0.32 mmol) in acetonitrile (2 mL) was stirred at 20° C. for 16 hours. The reaction mixture was concentrated on Celite® and purified by flash chromatography, eluting with 0 to 25% EtOAc in heptanes, to give the tide compound as a white solid (44 mg, 84%).

Step 3: 1-(tert-butyl)-3-methyl-1,5-dihydro-4H-pyrazolo[3,4-d]pyridazin-4-one

To a solution of ethyl 1-(tert-butyl)-5-formyl-3-methyl-1H-pyrazole-4-carboxylate (42 mg, 0.176 mmol) in ethanol (1.5 mL) was added anhydrous hydrazine (200 μL, 6.4 mmol) and acetic acid (500 μL, 8.73 mmol), The solution was heated at 70° C. for 16 hours and then concentrated on Celite® and purified by flash chromatography, eluting with 0 to 100% EtOAc in heptanes, to give the title compound as a white solid (31 mg, 85%).

Preparation 30: 3-cyclopropyl-1-methyl-1,6-dihydro-7H-pyrazolo[3,4-d]pyridazin-7-one

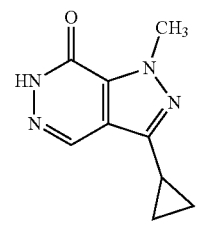

Step 1: ethyl 3-cyclopropyl-4-iodo-1-methyl-1H-pyrazole-5-carboxylate

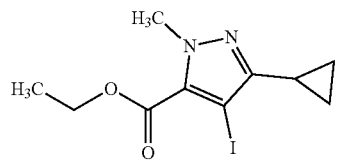

A solution of ethyl 3-cyclopropyl-1-methyl-1H-pyrazole-5-carboxylate (460 mg, 2.368 mmol) and 1-iodopyrrolidine-2,5-dione (799 mg, 3.55 mmol) in DMF (4 mL) was heated to 90° C. for 3 hours. Additional 1-iodopyrrolidine-2,5-dione (1.066 g, 4.736 mmol) was added and the reaction mixture was heated at 65° C. overnight. The reaction mixture was purified by column chromatography to give the title compound (325 mg, 43%).

Step 2: ethyl 3-cyclopropyl-1-methyl-4-vinyl-1H-pyrazole-5-carboxylate

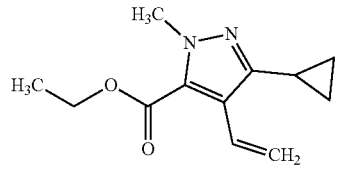 [SMILES: C=Cc1c(C2CC2)nn(C)c1C(=O)OCC]

A solution of ethyl 3-cyclopropyl-4-iodo-1-methyl-1H-pyrazole-5-carboxylate (325 mg, 1.015 mmol), 4,4,5,5-tetramethyl-2-vinyl-1,3,2-dioxaborolane (313 mg, 2.030 mmol) and triphenylphosphine palladium chloride (71.3 mg, 0.102 mmol) in dioxane (4 mL) and aq Na₂CO₃ (1.8 M, 2 mL) was heated to 90° C. overnight. The reaction mixture was purified by column chromatography to give the title compound (87 mg, 39%).

Step 3: ethyl 3-cyclopropyl-4-formyl-1-methyl-1H-pyrazole-5-carboxylate

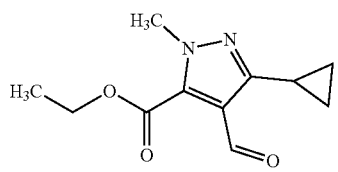 [SMILES: CCOC(=O)c1c(C=O)c(C2CC2)nn1C]

To a solution of ethyl 3-cyclopropyl-1-methyl-4-vinyl-1H-pyrazole-5-carboxylate (87 mg, 0,395 mmol) in dioxane (4 mL) at 0° C., was added osmium tetroxide (2.5 wt % solution in t-butanol) (0.149 mL, 0.012 mmol). Next, a solution of sodium periodate (169 mg, 0.790 mmol) in water (2 mL) was slowly added. The mixture was stirred at RT for 30 minutes and then diluted with aq Na₂S₂O₃ (1 M, 10 mL) and EtOAc (50 mL). The aqueous layer was washed with EtOAc (50 mL). The combined organic layers were washed with brine (50 mL). The organic layer was separated, dried over Na₂SO₄, filtered and evaporated in vacuo to give the title compound (88 mg, 100%).

Step 4: 3-cyclopropyl-1-methyl-1,6-dihydro-7H-pyrazolo[3,4-d]pyridazin-7-one

To a solution of ethyl 3-cyclopropyl-4-formyl-1-methyl-W-pyrazole-5-carboxylate (88 mg, 0,396 mmol) in EtOH (3 mL) was added hydrazine hydrate (99 mg, 0.096 mL, 1980 mmol). The mixture was stirred at 60° C. overnight and then concentrated under reduced pressure. The concentrate was diluted with sat NaHCO₃ (20 mL) and extracted with DCM (10 mL×3) to give the title compound as an off-white solid (74 mg, 98%).

Preparation 31: 1-cyclopropyl-3-methyl-1,5-dihydro-4H-pyrrolo[2,3-d]pyridazin-4-one

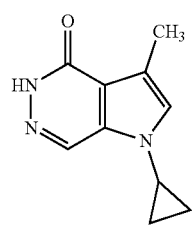

Step 1: ethyl 2-formyl-1-((2-(trimethylsilyl)ethoxy)methyl)-1H-pyrrole-3-carboxylate

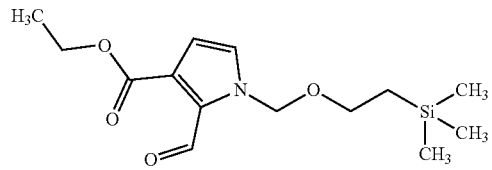 [SMILES: CCOC(=O)c1ccn(COCC[Si](C)(C)C)c1C=O]

To a solution of ethyl 2-formyl-1H-pyrrole-3-carboxylate (501 mg, 3.00 mmol) in DMF (7493 µL) was added sodium hydride (180 mg, 4.50 mmol). The mixture was stirred for 1 hour. Next, (2-(chloromethoxy)ethyl)trimethylsilane (532 µL, 3.00 mmol) was added. The reaction mixture was stirred for an additional hour and then quenched with water and extracted with EtOAc. The organic layer was washed with brine, dried over Na₂SO₄, and concentrated to give the title compound as an oil (766 mg, 86%).

Step 2: ethyl 4-bromo-2-formyl-1-((2-(trimethylsilyl)ethoxy)methyl)-1-pyrrole-3-carboxylate

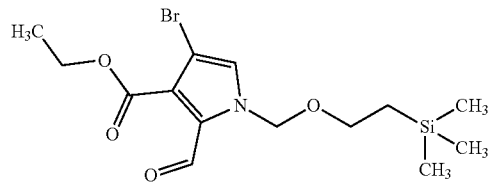 [SMILES: CCOC(=O)c1c(Br)cn(COCC[Si](C)(C)C)c1C=O]

To a solution of ethyl 2-formyl-1-((2-(trimethylsilyl)ethoxy)methyl)-1H-pyrrole-3-carboxylate (766 mg, 2.58 mmol) in acetonitrile (6.439 mL) was added N-bromosuccinimide (458 mg, 2.58 mmol). The mixture was stirred for 1 hour and then diluted with water and extracted with EtOAc. The organic layer was washed with brine, dried over Na₂SO₄, and concentrated. The product was purified by flash chromatography, eluting with 0 to 30% EtOAc in heptanes, to give the title compound as an oil (542 mg, 56%).

Step 3: ethyl 2-formyl-4-methyl-1-((2-(trimethylsilyl)ethoxy)methyl)-1H-pyrrole-3-carboxylate

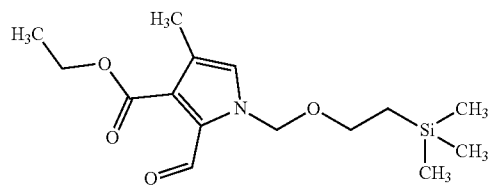 [SMILES: CCOC(=O)c1c(C)cn(COCC[Si](C)(C)C)c1C=O]

A solution of ethyl 4-bromo-2-formyl-1-((2-(trimethylsilyl)ethoxy)methyl)-1H-pyrrole-3-carboxylate (542 mg, 1.440 mmol), 2,4,6-trimethyl-1,3,5,2,4,6-trioxatriborinane (401 µL, 2.88 mmol), SPhos G1, methyl t-butyl ether adduct (110 mg, 0.144 mmol), and potassium phosphate (917 mg, 4.32 mmol) in THF (6.858 mL) and water (343 µL) was heated to 110° C. in a microwave reactor for 30 minutes. The reaction mixture was then concentrated on Celite® and purified by flash chromatography, eluting with 0 to 40% EtOAc in heptanes, to give the title compound as an oil (379 mg, 84%).

Step 4: ethyl 2-formyl-4-methyl-1H-pyrrole-3-carboxylate

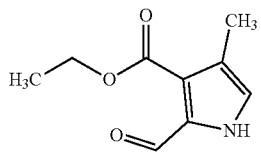

To a solution of ethyl 2-formyl-4-methyl-1-((2-(trimethylsilyl)ethoxy)methyl)-1H-pyrrole-3-carboxylate (369 mg, 1.185 mmol) in DCM (11.8 mL) was added boron trifluoride diethyl etherate (439 µL, 3.55 mmol). The reaction mixture was stirred at room temperature for 1 hour and then quenched with water and saturated NaHCO₃ and stirred for 2 hours. Ethyl acetate was added. The organic layer was separated, washed with brine, and concentrated to yield a light-red solid. The solid was dissolved in ethanol (9.272 mL) and water (1.854 mL). Potassium carbonate (1.538 g, 11.13 mmol) was added. The mixture was stirred at room temperature for 1 hour and evaporated to dryness under reduced pressure. The product was taken up in EtOAc, dried over anhydrous Na₂SO₄ and concentrated to give the title compound as an off-white solid (194 mg, 96%).

Step 5: ethyl 1-cyclopropyl-2-formyl-4-methyl-1H-pyrrole-3-carboxylate

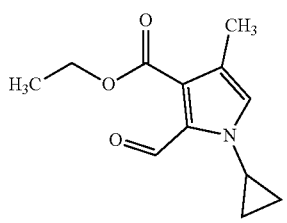 [SMILES: CCOC(=O)c1c(C)cn(C2CC2)c1C=O]

A solution of ethyl 2-formyl-4-methyl-1H-pyrrole-3-carboxylate (184 mg, 1.016 mmol), cyclopropylboronic acid (262 mg, 3.05 mmol), Na₂CO₃ (323 mg, 3.05 mmol), copper (II) acetate (277 mg, 1,523 mmol), and 2,2'-bipyridine (238 mg, 1.523 mmol) in DCE (5.078 mL) was stirred at 70° C. for 4 hours. The reaction mixture was concentrated on Celite® and purified by flash chromatography, eluting with 0 to 80% EtOAc in heptanes, to give the title compound (137 mg, 61%).

Step 6: 1-cyclopropyl-3-methyl-1,5-dihydro-4H-pyrrolo[2,3-d]pyridazin-4-one

A solution of ethyl 1-cyclopropyl-2-formyl-4-methyl-1H-pyrrole-3-carboxylate (127 mg, 0.574 mmol) and hydrazine hydrate (255 µL, 2.87 mmol) in acetic acid (1.435 mL) was heated at 80° C. for 30 minutes and then concentrated under vacuum. The resulting residue was partitioned between DCM and aqueous NaHCO₃. The organic layer was dried and concentrated to give the title compound (64 mg, 59%).

Preparation 32: 3-cyclopropyl-1-methyl-1,6-dihydro-7H-pyrrolo[2,3-d]pyridazin-7-one

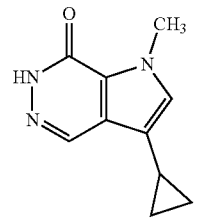

Step 1: ethyl 4-bromo-3-formyl-1H-pyrrole-2-carboxylate

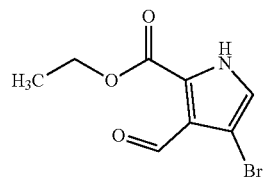

To an ice-cooled solution of ethyl 3-formyl-1H-pyrrole-2-carboxylate (702 mg, 4.20 mmol) in acetic acid (11.2 mL) and dioxane (5.599 mL), was added N-bromosuccinimide (860 mg, 4.83 mmol). The reaction mixture was stirred at 0° C. for 6 hours and then partitioned between brine and EtOAc. The organic layer was separated, washed with saturated aq Na₂CO₃, dried over Na₂SO₄ and purified by flash chromatography, eluting with 0 to 5% DCM in EtOAc, to give the title compound as a solid (348 mg, 34%).

Step 2: ethyl 4-bromo-3-formyl-1-methyl-1H-pyrrole-2-carboxylate

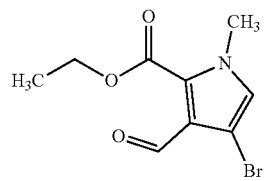

A solution of ethyl 4-bromo-3-formyl-1H-pyrrole-2-carboxylate (305 mg, 1.240 mmol) in DMF (4.958 mL) was cooled to 0° C. Sodium hydride (99 mg, 2.479 mmol) was added and the mixture was stirred for 30 minutes. Methyl iodide (116 µL, 1,859 mmol) was added, and the mixture was stirred for 1 hour at RT and then diluted with water. A precipitate was isolated by filtration to give the title compound as a solid (160 mg, 50%).

Step 3: ethyl 4-cyclopropyl-3-formyl-1-methyl-1H-pyrrole-2-carboxylate

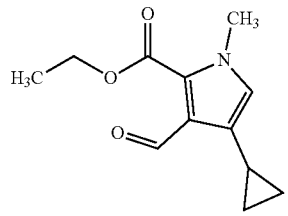 [SMILES: CCOC(=O)c1c(C=O)c(C2CC2)cn1C]

A solution of ethyl 4-bromo-3-formyl-1-methyl-1H-pyrrole-2-carboxylate (160 mg, 0.615 mmol), cyclopropylboronic acid (106 mg, 1230 mmol), SPhos G1, methyl t-butyl ether adduct (23.40 mg, 0.031 mmol), and potassium phosphate (392 mg, 1.846 mmol) in toluene (1.465 mL) and water (73.2 µL) was heated to 130° C. for 1 hour and then purified by HPLC (Method B) to give the title compound as an oil (39 mg, 29%).

Step 4: 3-cyclopropyl-1-methyl-1,6-dihydro-7H-pyrrolo[2,3-d]pyridazin-7-one

A solution of ethyl 4-cyclopropyl-3-formyl-1-methyl-1H-pyrrole-2-carboxylate (39 mg, 0.176 mmol) and hydrazine hydrate (47.0 µL, 0.529 mmol) in acetic acid (881 µL) was heated at 80° C. for 30 minutes. The reaction mixture was concentrated under vacuum and the residue partitioned between EtOAc and aqueous NaHCO$_3$. The organic layer was dried and concentrated to provide the title compound as a solid (30 mg, 90%).

Preparation 33: 1-methyl-3-(trifluoromethyl)-1,5-dihydro-4H-pyrazolo[3,4-d]pyridazin-4-one

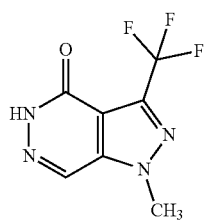

Step 1: ethyl 5-formyl-1-methyl-3-(trifluoromethyl)-1H-pyrazole-4-carboxylate

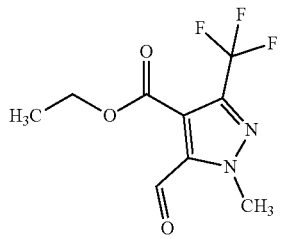 [SMILES: CCOC(=O)c1c(C(F)(F)F)nn(C)c1C=O]

A solution of 2.5 M n-butyl lithium in hexanes (1.58 mL, 3.96 mmol) was added dropwise via a syringe to a stirred solution of diisopropylamine (565 µL, 3.96 mmol) in anhydrous THF (2.57 mL) at −78° C. The resulting mixture was stirred at −78° C. for 10 minutes and then at 0° C. for 30 minutes. The resulting LDA solution was cooled to −78° C. and a solution of ethyl 1-methyl-3-(trifluoromethyl)-1H-pyrazole-4-carboxylate (400 mg, 1.80 mmol) in THF (2.57 mL) was added dropwise. The mixture was stirred at −78° C. for 5 minutes and then DMF (1.12 mL, 14.4 mmol) was added dropwise and the mixture was stirred at −78° C.' for 1 hour. The cooling bath was removed, and the reaction mixture was slowly warmed to room temperature. After 1 hour at 20° C., the reaction mixture was poured into a rapidly stirred solution of saturated aq NH$_4$Cl. The product was extracted with EtOAc (×3) and the combined organic phases were washed with saturated aq NH$_4$Cl, and then dried over anhydrous Na$_2$SO$_4$. The supernatant was decanted from the drying agent, and the solvents were removed in mow. The crude isolate was purified by flash column chromatography using an ISCO® automated purification system, eluting with a gradient of 0-20% EtOAc in heptanes. The product-containing fractions were collected and combined, concentrated on a rotary evaporator at 35° C., and dried in vacuo to give the title compound as a light-yellow oil (300 mg, 67%).

Step 2: 1-methyl-3-(trifluoromethyl)-1,5-dihydro-4H-pyrazolo[3,4-d]pyridazin-4-one To a flask charged with ethyl 5-formyl-1-methyl-3-(trifluoromethyl)-1H-pyrazole-4-carboxylate (300 mg, 1.20 mmol) in EtOH/HOAc (10:1 v/v, 4.00 mL) was added hydrazine hydrate (174 µL, 3.60 mmol) dropwise at room temperature with stirring. The flask was sealed, and the reaction mixture was heated at 80° C. for 20.5 hours before cooling to room temperature. A resulting white precipitate was collected by vacuum filtration over a fritted funnel to give the title compound as a white, crystalline solid (196 mg, 75N.

Preparation 34: 1-isopropyl-3,7-dimethyl-1,5-dihydro-4H-pyrazolo[3,4-d]pyridazin-4-one

Step 1: 3-bromo-1-isopropyl-4-methoxy-7-methyl-1H-pyrazolo[3,4-d]pyridazine and 3-bromo-2-isopropyl-4-methoxy-7-methyl-2H-pyrazolo[3,4-d]pyridazine

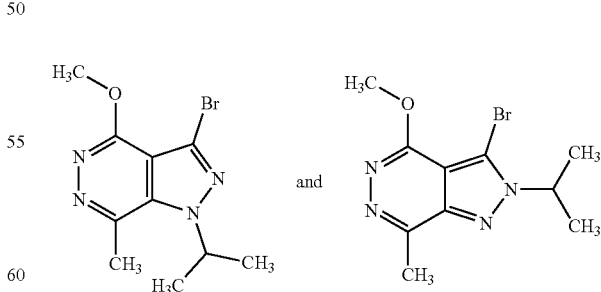

To a solution of 3-bromo-4-methoxy-7-methyl-1H-pyrazolo[3,4-d]pyridazine (1.00 g, 4.11 mmol) in DMF (10 mL) were added 2-iodopropane (2.79 g, 16.44 mmol, 1.64 mL) and K$_2$CO$_3$ (1.70 g, 12.33 mmol). The mixture was stirred at 15° C. for 3 hours and then filtered and washed with EtOAc (20 mL). The filtrate was evaporated under reduced pressure to give a residue, which was purified by column chromatography (SiO₂) eluting with petroleum ether/EtOAc (5:1 to 1:1) to give a mixture of the title compounds as a white solid (220 mg).

Step 2: 1-isopropyl-4-methoxy-3,7-dimethyl-1H-pyrazolo[3,4-d]pyridazine

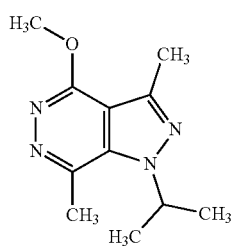

To a solution of 3-bromo-1-isopropyl-4-methoxy-7-methyl-1H-pyrazolo[3,4-d]pyridazine and 3-bromo-2-isopropyl-4-methoxy-7-methyl-2H-pyrazolo[3,4-d]pyridazine (1 g) in toluene (6 mL) and water (1 mL) were added methylboronic acid (314.9 mg, 5.26 mmol), Pd(dppf)Cl₂·CH₂Cl₂ (286.4 mg, 350.71 mot) and Cs₂CO₃ (3.43 g, 10.53 mmol). The mixture was degassed and purged with N₂ (3×) and then stirred at 100° C. for 16 hours under N₂ atmosphere. The reaction mixture was diluted with water (10 mL) and extracted with EtOAc (10 mL×3). The combined organic layers were dried over Na₂SO₄, filtered and concentrated under reduced pressure. The resulting residue was purified by silica gel flash chromatography (ISCO® 12 g SepaFlash® column) eluting with a gradient of 0-45% EtOAc in petroleum ether. The crude product was triturated with ACN/DMSO (20:1, 10 mL) in a dry ice/acetone bath and then filtered at sub-ambient temperature. The filter cake was dried under reduced pressure to give the title compound as a white solid (250 mg).

Step 3: 1-isopropyl-3,7-dimethyl-1,5-dihydro-4H-pyrazolo[3,4-d]pyridazin-4-one

To a solution of 1-isopropyl-4-methoxy-3,7-dimethyl-1H-pyrazolo[3,4-d]pyridazine (250 mg, 1.13 mmol) in dioxane (10 mL) was added HCl (4 M, 10.00 mL). The mixture was stirred at 90° C. for 16 hours and then concentrated under reduced pressure to give the title compound as a grey solid (172 mg, 72N.

Preparation 35: (S)-2-promo-N-(1-(p-tolyl)ethyl)acetamide

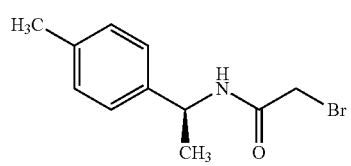

To a solution of (S)-1-(p-tolyl)ethanamine (16.32 mL, 111 mmol) and EON (15.46 mL, 111 mmol) in DCM (185 mL) at −10° C. was added 2-bromoacetyl bromide (9.66 mL, 111 mmol) dropwise. The reaction mixture was stirred at −10° C. for 1 hour and then diluted with water, extracted with DCM, washed with brine, dried over MgSO₄, filtered and concentrated. The crude product was dispersed in hexanes (200 mL), and the resulting slurry stirred for 30 minutes and filtered to give the title compound as a white solid (26.97 g, 95%).

Preparation 36: (S)-2-bromo-N-(1-(4-(trifluoromethyl)phenyl)ethyl)acetamide

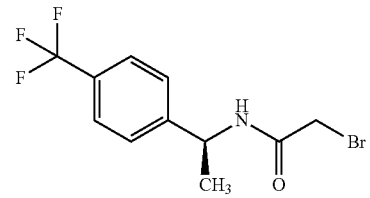

The title compound was prepared like PREPARATION 35, using (S)-1-(4-(trifluoromethyl)phenyl)ethanamine (21.00 g, 111 mmol) in place of (S)-1-(p-tolyl)ethanamine. The title compound was obtained as a white solid (30.4 g, 88%).

Preparation 37: (S)-2-bromo-N-(1-(4-methoxyphenyl)ethyl)acetamide

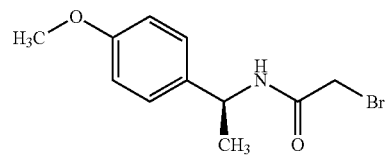

The title compound was prepared like PREPARATION 35, using (S)-1-(4-methoxyphenyl)ethanamine (48.8 mL, 331 mmol) in place of (S)-1-(p-tolyl)ethanamine. The title compound was obtained as an off-white solid (84.7 g, 94%).

Preparation 38: (S)-2-promo-N-(1-(4-chloro-2-methyl phenyl)ethyl)acetamide

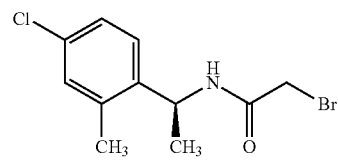

The title compound was prepared like PREPARATION 35, using (S)-1-(4-chloro-2-methylphenyl)ethan-1-amine (700 mg, 4.13 mmol) in place of (S)-1-(p-tolyl)ethanamine. The title compound was obtained as white solid (670 mg, 56%).

Preparation 39: (S)-2-bromo-N-(1-(4-chlorophenyl)ethyl)acetamide

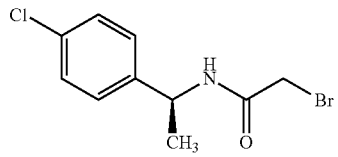

The title compound was prepared like PREPARATION 35, using (S)-1-(4-chlorophenyl)ethan-1-amine (5.68 mL, 40.5 mmol) in place of (S)-1-(p-tolyl)ethanamine. The title compound was obtained as an off-white solid (10.1 g, 90%).

Preparation 40: (S)-2-bromo-N-(1-(4-fluoro-3-methylphenyl)ethyl)acetamide

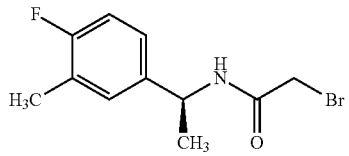

The title compound was prepared like PREPARATION 35, using (S)-1-(4-fluoro-3-methylphenyl)ethanamine (700 mg, 4.57 mmol) in place of (5)-1-(p-tolyl)ethanamine. The title compound was obtained as a white solid (1.1 g, 88%).

Preparation 41: (S)-2-bromo-N-(1-(3-fluorophenyl)ethyl)acetamide

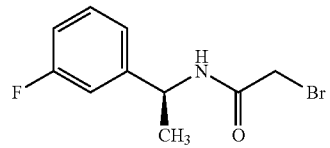

The title compound was prepared like PREPARATION 35, using (S)-1-(3-fluorophenyl)ethanamine (700 mg, 5.03 mmol) in place of (S)-1-(p-tolyl)ethanamine. The title compound was obtained as a pink solid (1.1 g, 86%).

Preparation 42: (S)-2-bromo-N-(1-phenylethyl)acetamide

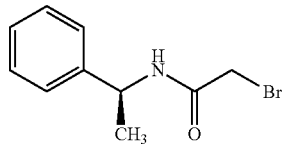

The title compound was prepared like PREPARATION 35, using (S)-1-phenylethan-1-amine (5.32 mL, 41.3 mmol) in place of (S)-1-(p-tolyl)ethanamine. The title compound was obtained as a tan solid (8.8 g, 88%).

Preparation 43: (S)-2-bromo-N-(1-(2-fluoro-4-methoxyphenyl)ethyl)acetamide

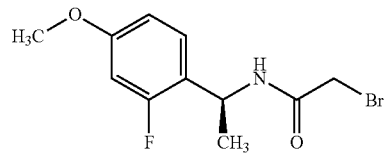 [SMILES: COc1ccc([C@H](C)NC(=O)CBr)c(F)c1]

The title compound was prepared like PREPARATION 35, using (S)-1-(2-fluoro-4-methoxyphenyl)ethanamine (6.338 g, 37.5 mmol) in place of (5)-1-(p-tolyl)ethanamine. The title compound was obtained as a tan solid (7.5 g, 69%).

Preparation 44: 2-bromo-N-(1-(chroman-6-yl)ethyl)acetamide

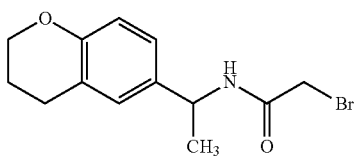 [SMILES: CC(NC(=O)CBr)c1ccc2c(c1)CCCO2]

The title compound was prepared like PREPARATION 35, using 1-(chroman-6-yl)ethan-1-amine (700 mg, 3.95 mmol) in place of (S)-1-(p-tolyl)ethanamine. The title compound was obtained as a brown oil (829 mg, 70%).

Preparation 45: 2-bromo-N-(1-(2,3-dihydrobenzo[b][1,4]dioxin-6-yl)ethyl)acetamide

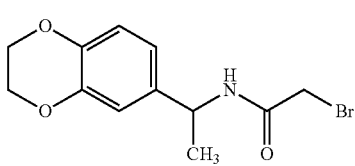 [SMILES: CC(NC(=O)CBr)c1ccc2c(c1)OCCO2]

The title compound was prepared like PREPARATION 35, using 1-(2,3-dihydrobenzo[b][1,4]dioxin-6-yl)ethan-1-amine (600 mg, 3.35 mmol) in place of (S)-1-(p-tolyl)ethanamine. The title compound was obtained as a white solid (590 mg, 59%).

Preparation 46: (S)-2-promo-N-(1-(2-fluoro-4-methylphenyl)ethyl)acetamide

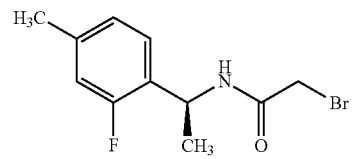

To a solution of (S)-1-(2-fluoro-4-methylphenyl)ethan-1-amine, HCl (10 g, 52.7 mmol) and Et$_3$N (14.70 mL, 105 mmol) in DCM (88 mL) at 0° C. was added 2-bromoacetyl bromide (4.58 mL, 52.7 mmol) dropwise. The reaction mixture was stirred at 0° C. for 1 hour and then diluted with water, extracted with DCM, washed with brine, dried over MgSO₄, filtered and concentrated. The crude product was slurried in hexanes (200 mL), stirred for 3 hours and then filtered to give the title compound as a white solid (12.37 g, 86%).

Preparation 47: (S)-2-bromo-N-(1-(3-fluoro-4-methyl phenyl)ethyl)acetamide

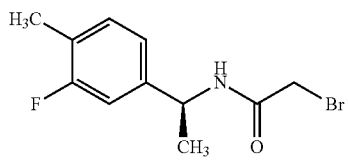

The title compound was prepared like PREPARATION 46, using (S)-1-(3-fluoro-4-methylphenyl)ethan-1-amine, HCl (4 g, 21.09 mmol) in place of (5)-1-(2-fluoro-4-methylphenyl)ethan-1-amine, HCl. The title compound was obtained as a white solid (5.14 g, 89%).

Preparation 48: (S)-2-bromo-N-(1-(4-methoxy-3-methylphenyl)ethyl)acetamide

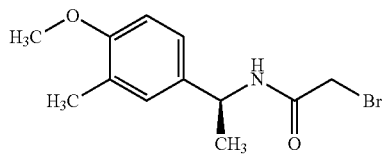 [SMILES: COc1ccc([C@H](C)NC(=O)CBr)cc1C]

The title compound was prepared like PREPARATION 46, using (S)-1-(4-methoxy-3-methylphenyl)ethanamine, HCl (700 mg, 3.47 mmol) in place of (S)-1-(2-fluoro-4-methylphenyl)ethan-1-amine, HCl. The title compound was obtained as a brown solid (260 mg, 26%).

Preparation 49: (S)-2-bromo-N-(1-(4-(trifluoromethoxy)phenyl)ethyl)acetamide

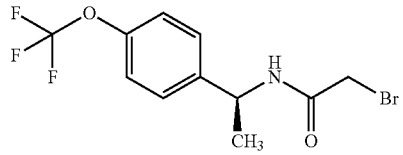 [SMILES: C[C@H](NC(=O)CBr)c1ccc(OC(F)(F)F)cc1]

The title compound was prepared like PREPARATION 46, using (5)-1-(4-(trifluoromethoxy)phenyl)ethan-1-amine, HCl (5 g, 20.69 mmol) in place of (S)-1-(2-fluoro-4-methylphenyl)ethan-1-amine, HCl. The title compound was obtained as a white solid (4.87 g, 72%).

Preparation 50: (S)-2-bromo-N-(1-(4-chloro-2-fluorophenyl)ethyl)acetamide

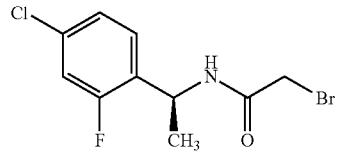

The title compound was prepared like PREPARATION 46, using (S)-1-(4-chloro-2-fluorophenyl)ethanamine, HCl (700 mg, 3.33 mmol) in place of (S)-1-(2-fluoro-4-methylphenyl)ethan-1-amine, HCl. The title compound was obtained as a white solid (660 mg, 67%).

Preparation 51: (S)-2-bromo-N-(1-(2,4-difluorophenyl)ethyl)acetamide

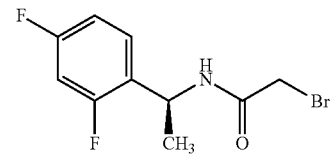

The title compound was prepared like PREPARATION 46, using (S)-1-(2,4-difluorophenyl)ethanamine, HCl (700 mg, 3.62 mmol) in place of (S)-1-(2-fluoro-4-methylphenyl) ethan-1-amine, HCl. The title compound was obtained as a white solid (439 mg 44%).

Preparation 52: (S)-2-promo-N-(1-(2-chloro-4-fluorophenyl)ethyl)acetamide

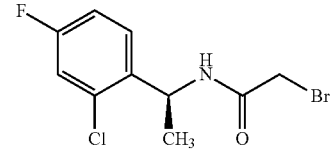

The title compound was prepared like PREPARATION 46, using (S)-1-(2-chloro-4-fluorophenyl)ethanamine, HCl (723 mg, 3.44 mmol) in place of (S)-1-(2-fluoro-4-methylphenyl)ethan-1-amine, HCl. The title compound was obtained as a white solid (424 mg, 42%).

Preparation 53: (S)-2-bromo-N-(1-(4-fluoro-3-methoxyphenyl)ethyl)acetamide

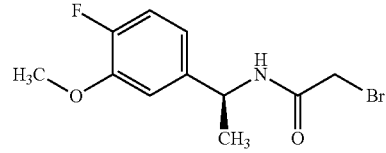 [SMILES: COc1cc([C@H](C)NC(=O)CBr)ccc1F]

The title compound was prepared like PREPARATION 46, using (S)-1-(4-fluoro-3-methoxyphenyl)ethanamine, HCl (1 g, 4.86 mmol) in place of (S)-1-(2-fluoro-4-methylphenyl)ethan-1-amine, HCl. The title compound was obtained as a white solid (639 mg, 45%).

Preparation 54: (S)-2-bromo-N-(1-(2,4,6-trifluorophenyl)ethyl)acetamide

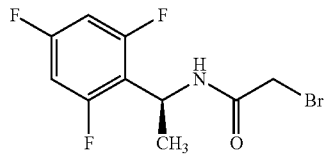

The title compound was prepared like PREPARATION 46, using (S)-1-(2,4,6-trifluorophenyl)ethanamine, HCl (700 mg, 3.31 mmol) in place of (S)-1-(2-fluoro-4-methylphenyl)ethan-1-amine, HCl. The title compound was obtained as an orange oil (596 mg, 61%).

Preparation 55: (S)-2-bromo-N-(1-(3,5-difluorophenyl)ethyl)acetamide

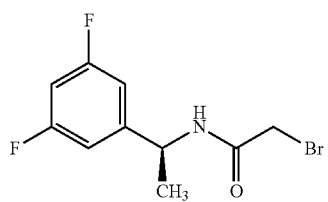

The title compound was prepared like PREPARATION 46, using (S)-1-(3,5-difluorophenyl)ethanamine, HCl (700 mg, 3.62 mmol) in place of (S)-1-(2-fluoro-4-methylphenyl)ethan-1-amine, HCl. The title compound was obtained as a white solid (594 mg 59%).

Preparation 56: (S)-2-promo-N-(1-(2-chloro-6-fluorophenyl)ethyl)acetamide

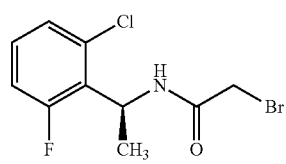

The title compound was prepared like PREPARATION 46, using (S)-1-(2-chloro-6-fluorophenyl)ethanamine, HCl (700 mg, 3.33 mmol) in place of (S)-1-(2-fluoro-4-methylphenyl)ethan-1-amine, HCl. The title compound was obtained as a colorless oil (800 mg, 82%).

Preparation 57: (S)-2-bromo-N-(1-(2,5-dimethylphenyl)ethyl)acetamide

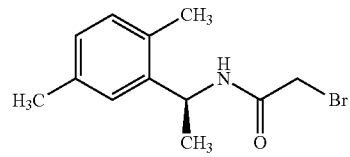

The title compound was prepared like PREPARATION 46, using (S)-1-(2,5-dimethylphenyl)ethanamine, HCl (700 mg, 3.77 mmol) in place of (S)-1-(2-fluoro-4-methylphenyl)ethan-1-amine, HCl. The title compound was obtained as a brown solid (620 mg, 61%).

Preparation 58: (S)-2-bromo-N-(1-(2,3-difluorophenyl)ethyl)acetamide

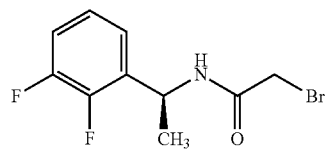

The title compound was prepared like PREPARATION 46, using (S)-1-(2,3-difluorophenyl)ethanamine, HCl (700 mg, 3.62 mmol) in place of (S)-1-(2-fluoro-4-methylphenyl)ethan-1-amine, HCl. The title compound was obtained as a white solid (595 mg, 59%).

Preparation 59: (S)-2-bromo-N-(1-(2,4-dimethylphenyl)ethyl)acetamide

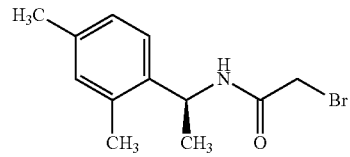

The title compound was prepared like PREPARATION 46, using (S)-1-(2,4-dimethylphenyl)ethan-1-amine hydrochloride (1 g, 5.39 mmol) in place of (S)-1-(2-fluoro-4-methylphenyl)ethan-1-amine, HCl. The title compound was obtained as a white solid (500 mg 34%).

Preparation 60: S)-2-bromo-N-(1-(5-(trifluoromethyl)pyri din-2-yl)ethyl)acetamide

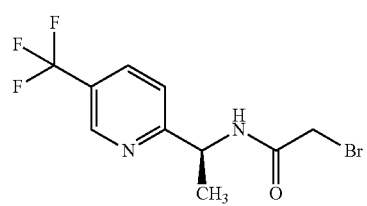 [SMILES: C[C@H](NC(=O)CBr)c1ccc(C(F)(F)F)cn1]

The title compound was prepared like PREPARATION 46, using (S)-1-(5-(trifluoromethyl)pyridin-2-yl)ethanamine, HCl (500 mg, 2.206 mmol) in place of (S)-1-(2-fluoro-4-methylphenyl)ethan-1-amine, HCl. The title compound was obtained as a green oil (412 mg, 60%).

Preparation 61:
(S)-2-bromo-N-(1-mesitylethyl)acetamide

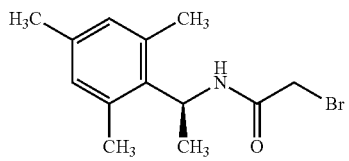 [SMILES: Cc1cc(C)c([C@H](C)NC(=O)CBr)c(C)c1]

To a solution of (S)-1-mesitylethan-1-amine, HCl (0.300 g, 1.502 mmol) and Et₃N (0.419 mL, 3.00 mmol) in anhydrous DCM (5 mL) at 0° C. was added 2-bromoacetyl bromide (0.130 mL, 1,502 mmol) dropwise. The reaction mixture was stirred at 0° C. for 3 hours and then quenched with saturated aq NH₄Cl and allowed to warm to 20° C. The mixture was diluted with EtOAc (45 mL), washed with saturated aq NH₄Cl (50 mL) and brine, dried over MgSO₄, filtered and concentrated in vacuo. The resulting crude material was purified by chromatography (40 g silica gel column) eluting with 0 to 50% EtOAc in heptane, to give the title compound as a white solid (268 mg, 63%).

Preparation 62: 2-bromo-1-(2-(4-chlorophenyl)pyrrolidin-1-yl)ethan-1-one

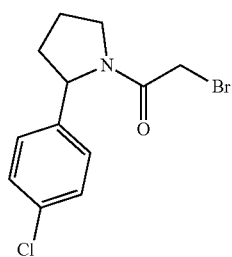 [SMILES: O=C(CBr)N1CCCC1c1ccc(Cl)cc1]

To a solution of 2-(4-chlorophenyl)pyrrolidine (1.7 g, 9.36 mmol) and Et₃N (1.304 mL, 9.36 mmol) in DCM (15.60 mL) at 0° C. was added 2-bromoacetyl bromide (0.813 mL, 9.36 mmol) dropwise. The reaction mixture was stirred at 0° C. for 1 hour and then diluted with water, extracted with DCM, washed with brine, dried over MgSO₄, filtered and concentrated. The resulting crude material was dissolved in DCM and purified by ISCO® automated purification system, eluting with 0 to 20% MeOH in DCM. The product-containing fractions were combined, and the solvent was removed via rotary evaporation at 35° C. The product was dried in vacuo to give the title compound as a colorless oil (2.62 g, 93%).

Preparation 63: (S)-2-bromo-N-(1-(2,6-difluorophenyl)ethyl)acetamide

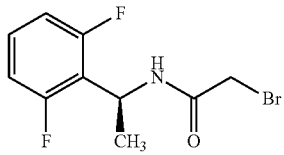

Step 1: (S)—N—((S)-1-(2,6-difluorophenyl)ethyl)-2-methylpropane-2-sulfinamide

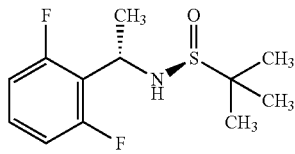

To a solution of (S)-2-methylpropane-2-sulfinamide (6.64 g, 54.8 mmol), tetraethoxytitanium (25.00 g, 110 mmol) and THF (110 mL) at RT was added 1-(2,6-difluorophenyl)ethanone (10.27 g, 65.8 mmol). The solution was stirred at 75° C. overnight and allowed to cool to RT. The solution was cooled to −45° C. in a dry ice/ACN/acetone bath, added dropwise to a suspension of sodium tetrahydroborate (8.29 g, 219 mmol) and THF (60 mL) at −45° C., and warmed to RT over several hours. After stirring at RT for 48 hours, the solution was cooled to 0° C. in an ice bath and MeOH (20 mL) was added dropwise until gas evolution ceased. The solution was allowed to warm to RT and saturated aq NaCl (about 100 mL) was added. The mixture was filtered and washed with EtOAc. The filtrate was diluted with brine and extracted with EtOAc (100 mL×3). The combined organic fractions were dried over anhydrous Na₂SO₄ and concentrated in vacuo. The resulting crude material was dissolved in DCM and purified by ISCO® automated purification system, eluting with 0 to 70% EtOAc in heptane. The product-containing fractions were combined, and solvent was removed via rotary evaporation at 35° C. The product was dried in vacuo to give the title compound as a clear oil as a clear oil (7.45 g, 52%).

Step 2: (S)-1-(2,6-difluorophenyl)ethan-1-amine

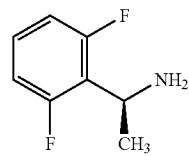

To a solution of (S)—N—((S)-1-(2,6-difluorophenyl)ethyl)-2-methylpropane-2-sulfinamide (365 mg, 1.397 mmol) in methanol (2.793 mL) was added 4 M HCl in dioxane (1.397 mL, 5.59 mmol), The reaction mixture was stirred at RT for 16 hours and then concentrated in vacuo to give an HCL salt of the title compound as a white solid (271 mg, 1.3996 mmol). The solid was dissolved in THF (6 mL)

and Et₃N (0.2 mL, 1.4 mmol) was added. A resulting white precipitate was filtered off and the filtrate was concentrated to give the free base of the title compound as an off-white solid (108 mg, 49%).

Step 3: (S)-2-bromo-N-(1-(2,6-difluorophenyl)ethyl)acetamide

To a solution of (S)-1-(2,6-difluorophenyl)ethan-1-amine (4.005 g, 25.5 mmol) and Et₃N (3.55 mL, 25.5 mmol) in DCM (42.5 mL) at −10° C. was added 2-bromoacetyl bromide (2.220 mL, 25.5 mmol) dropwise. The reaction mixture was stirred at −10° C. for 1 hour and then diluted with water, extracted with DCM, washed with brine, dried over Na₂SO₄, filtered and concentrated. The resulting crude material was dissolved in DCM and purified by ISCO® automated purification system, eluting with 0 to 100% EtOAc in heptane. The product-containing fractions were combined, and solvent was removed via rotary evaporation at 35° C. The product was dried in vacuo to give the title compound as an orange solid (3.204 g, 45.2%).

Preparation 64: (R)-2-chloro-N-(1-(4-(trifluoromethyl)phenyl)ethyl)acetamide

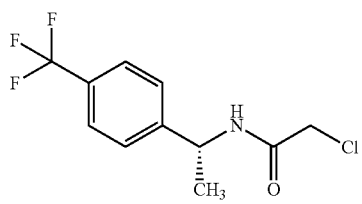 [SMILES: C[C@@H](NC(=O)CCl)c1ccc(C(F)(F)F)cc1]

To a 100 mL round-bottom flask charged with (R)-1-(4-(trifluoromethyl)phenyl)ethan-1-amine (2.0 g, 10.57 mmol), Et₃N (1.474 mL, 10.57 mmol) and ACN (20 mL) was added 2-chloroacetyl chloride (0,841 mL, 10.57 mmol) at a temperature less than 0° C. The reaction mixture was stirred at 0 to 5° C. for 1 hour and then diluted with water (40 mL) and extracted with DCM (2×). The combined organic layers were washed with water, dried over Na₂SO₄ and concentrated. The resulting solid was slurried in heptane (20 mL) at room temperature and filtered. The filter cake was washed with heptane (5 mL×2) and dried under reduced pressure at room temperature to give the title compound as an off-white solid (2.51 g, 89%).

Preparation 65: (S)-2-bromo-N-(cyclopropyl(phenyl)methyl)acetamide

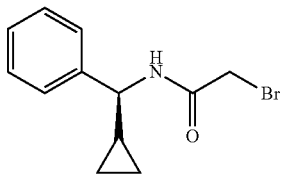 [SMILES: O=C(CBr)N[C@H](c1ccccc1)C1CC1]

To a solution of (S)-cyclopropyl(phenyl)methanamine hydrochloride (0.9743 g, 5.30 mmol) and Et₃N (1.479 mL, 10.61 mmol) in DCM (20.4 mL) at 0° C. was added 2-bromoacetyl bromide (0.462 mL, 5.30 mmol) dropwise via a syringe. The reaction mixture was stirred at 0° C. for 1 hour and then quenched with water (20 mL). The biphasic system was transferred to a separatory funnel and the two layers were separated. The aqueous phase was extracted with DCM (20 mL and then 10 mL). The combined organic phases were washed with brine (15 mL), dried over anhydrous Na₂SO₄, filtered and concentrated in vacuo to give the title compound as a pale-orange solid (1.3686 g, 96%).

Preparation 66: (S)-2-bromo-N-(1-(4-(methyl-d₃)phenyl)ethyl)acetamide

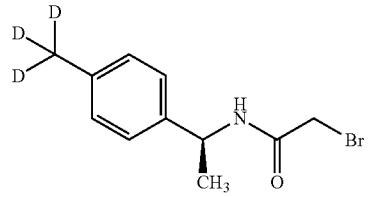 [SMILES: [2H]C([2H])([2H])c1ccc([C@H](C)NC(=O)CBr)cc1]

Step 1: (methyl-d₃)magnesium iodide

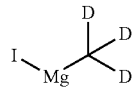

To a suspension of M, (3.27 g, 134.52 mmol) and 12 (131.32 mg, 517.39 μmol, 104.22 μL) in Et₂O (25 mL) was added dropwise a solution of iodomethane-d₃ (15 g, 103.48 mmol, 6.44 mL) in Et₂O (75 mL) at 15° C. under N₂. The mixture was stirred at 15° C. for 2 hours to give the title compound as a 0.97 M solution in Et₂O (100 mL).

Step 2: (S)-1-(4-(methyl-d₃)phenyl)ethan-1-amine

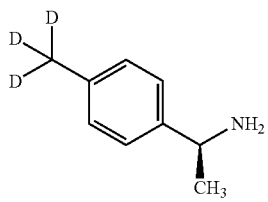

To a solution of (S)-1-(4-bromophenyl)ethan-1-amine (4.5 g, 22.49 mmol, 3.24 mL) and Pd(dppf)Cl₂·CH₂Cl₂ (3.67 g, 4.50 mmol) in THF (100 mL) was added dropwise (methyl-d₃)magnesium iodide (0.97 M, 100 mL, 4.31 eq) under N₂. The reaction mixture was stirred at 70° C. for 15 hours and then quenched with HCl (0.5 M, 300 mL) and extracted with EtOAc (300 mL×2). The organic layers were discarded. The aqueous layer was adjusted to PH 9 with Na₂CO₃ and extracted with DCM/MeOH (300 mL×3, 10:1). The combined organic phase was dried over anhydrous Na₂SO₄, filtered and concentrated in vacuo to give the title compound as a yellow oil (2.5 g, 80%).

Step 3: (S)-2-promo-N-(1-(4-(methyl-d₃)phenyl)ethyl)acetamide

To a solution of (S)-1-(4-(methyl-d₃)phenyl)ethan-1-amine (2.5 g, 18.09 mmol) and Et₃N (5.49 g, 54.26 mmol, 7.55 mL) in DCM (50 mL) was added dropwise 2-bromoacetyl bromide (4.38 g, 21.70 mmol, 1.89 mL, 1.2 eq) at 0° C. The reaction mixture was stirred at 0° C. for 0.5 hours and then washed with HCl (1.5 M, 50 mL) and concentrated under vacuum. The residue was purified by silica gel flash chromatography (ISCO® 40 g SepaFlash® column) eluting with a gradient of 0-20% EtOAc in petroleum ether to give the title compound as a white solid (2.11 g, 57%).

Preparation 67: (S)-2-bromo-N-(1-(4-chloro-2-methoxyphenyl)propan-2-yl)acetamide

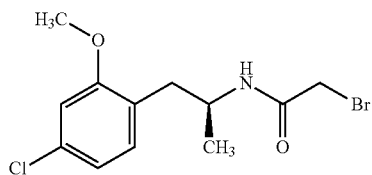 [SMILES: COc1cc(Cl)ccc1C[C@H](C)NC(=O)CBr]

To a solution of (S)-1-(4-chloro-2-methoxyphenyl)propan-2-amine hydrochloride (400 mg, 1.694 mmol) and Et$_3$N (472 µl, 3.39 mmol) in DCM (2,823 mL) at 0° C. was added 2-bromoacetyl bromide (147 µL, 1.694 mmol) dropwise. The reaction mixture was stirred at 0° C. for 1 hour and then diluted with water, extracted with DCM, washed with brine, dried over MgSO$_4$, filtered and concentrated. The crude product was slurried in heptanes (20 mL), stirred for 60 hours and then filtered to give the title compound as an off-white solid (349 mg, 64%).

Example 1: (S)-2-(4-methyl-7-oxo-1-phenyl-1,7-dihydro-6H-pyrazolo[3,4-d]pyridazin-6-yl)-N-(1-(p-tolylethyl)acetamide

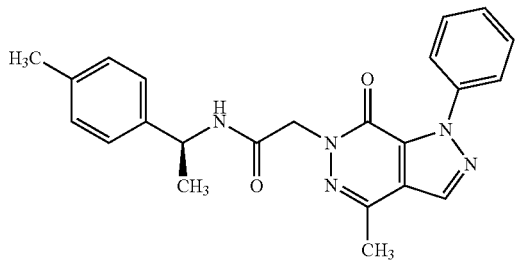 [SMILES: Cc1ccc([C@H](C)NC(=O)Cn2nc(C)c3cnn(-c4ccccc4)c3c2=O)cc1]

To a solution of (S)-2-bromo-N-(1-(p-tolyl)ethyl)acetamide (30 mg, 0.117 mmol) in DMF (586 µL) was added 4-methyl-1-phenyl-1,6-dihydro-7H-pyrazolo[3,4-d]pyridazin-7-one (29.1 mg, 0.129 mmol) and K$_2$CO$_3$ (32.4 mg, 0.234 mmol). The reaction mixture was heated at 50° C. for 3 hours and then poured into DMF, filtered through a hydrophilic PTFE 0.45 µm filter (Millipore® Millex-LCR) and purified by preparative HPLC (Method A). The product-containing fractions were combined, condensed in a rotary evaporator at 45° C., and dried in vacuo to give the title compound as a white solid (12.5 mg 27%). $^1$H NMR (500 MHz, DMSO-d$_6$) δ ppm 1.33 (d, J=6.8 Hz, 3H), 2.2.6 (s, 3H), 2.52 (s, 3H), 4.73 (s, 2H), 4.87 (quin, J=7.1 Hz, 1H), 7.11 (d, J=7.8 Hz, 2H), 7.19 (d, J=7.8 Hz, 2H), 7.46-7.58 (m, 3H), 7.64-7.69 (m, 2H), 8.45 (d, J=7.8 Hz, 1H), 8.48-8.51 (m, 1H); ESI-MS m/z [M+H]$^+$ 402.2.

Example 2: (S)—N-(1-(4-methoxyphenyl)ethyl)-2-(4-methyl-7-oxo-1-phenyl-1,7-dihydro-6H-pyrazolo[3,4-d]pyridazin-6-yl)acetamide

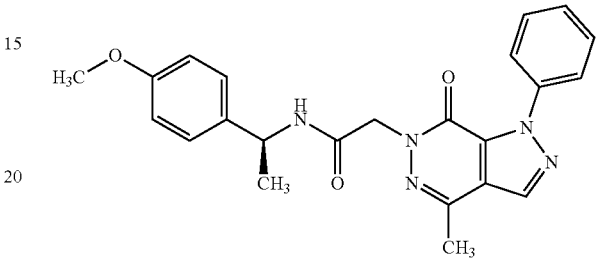

The title compound was prepared like EXAMPLE 1, using 4-methyl-1-phenyl-1,6-dihydro-7H-pyrazolo[3,4-d]pyridazin-7-one and (S)-2-bromo-N-(1-(4-methoxyphenyl)ethyl)acetamide, and was obtained as a white solid (28 mg, 62%). $^1$H NMR (500 MHz, DMSO-d$_6$) δ ppm 1.29-1.36 (m, 3H), 2.94 (s, 3H), 3.69-3.75 (m, 3H), 4.72 (s, 2H), 4.86 (quin, J=7.2 Hz, 1H), 6.81-6.88 (m, 2H), 7.19-7.26 (m, 2H), 7.45-7.57 (m, 3H), 7.62-7.71 (m, 2H), 8.43 (d, J=7.8 Hz, 1H), 8.46-8.50 (m, 1H); ESI-MS m/z [M+H]$^+$ 418.2.

Example 3: (S)-2-(4-isopropyl-7-oxo-1-phenyl-1,7-dihydro-6H-pyrazolo[3,4-d]pyridazin-6-yl)-N-(1-(p-tolyl)ethyl)acetamide

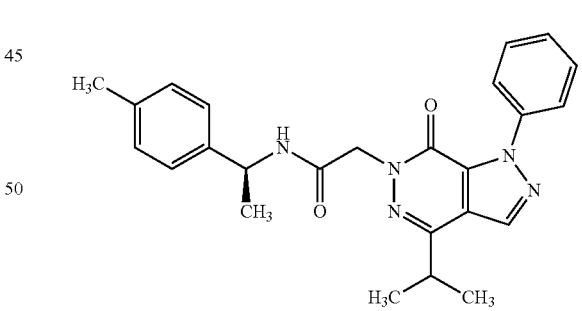

The title compound was prepared like EXAMPLE 1, using 4-isopropyl-1-phenyl-1,6-dihydro-7H-pyrazolo[3,4-d]pyridazin-7-one and (S)-2-bromo-N-(1-(p-tolyl)ethyl)acetamide, and was obtained as a white solid (37 mg, 55%). $^1$H NMR (500 MHz, DMSO-d$_6$) δ ppm 1.30-1.37 (m, 10H), 2.24-2.29 (m, 3H), 3.24-3.30 (m, 1H), 4.71-4.76 (m, 2H), 4.89 (quin, J=7.2 Hz, 1H), 7.10 (d, J=8.3 Hz, 2H), 7.19 (d, J=7.8 Hz, 2H), 7.46-7.57 (m, 3H), 7.63-7.68 (m, 2H), 8.42 (d, J=8.3 Hz, 1H), 8.60 (s, 1H); ESI-MS m/z [M+H]$^+$ 430.3.

Example 4: (S)-2-(4-isopropyl-7-oxo-1-phenyl-1,7-dihydro-6H-pyrazolo[3,4-d]pyridazin-6-yl)-N-(1-(4-(trifluoromethyl)phenyl)ethyl)acetamide

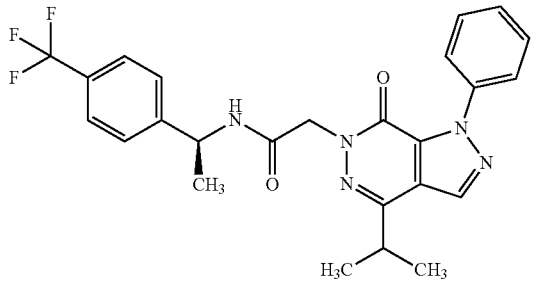 [SMILES: CC(C)c1nn(CC(=O)N[C@@H](C)c2ccc(C(F)(F)F)cc2)c(=O)c2c1cnn2-c1ccccc1]

The title compound was prepared like EXAMPLE 1, using 4-isopropyl-1-phenyl-1,6-dihydro-7H-pyrazolo[3,4-d]pyridazin-7-one and (S)-2-bromo-N-(1-(4-(trifluoromethyl)phenyl)ethyl)acetamide, and was obtained as a white solid (51 mg, 81%). $^1$H NMR (500 MHz, DMSO-$d_6$) δ ppm 1.32 (dd, J=6.8, 4.9 Hz, 6H), 1.38 (d, J=6.8 Hz, 3H), 3.24-3.30 (m, 1H), 4.76 (s, 2H), 4.98 (quin, J=7.2 Hz, 1H), 7.47-7.57 (m, 5H), 7.63-7.67 (m, 4H), 8.59-8.65 (m, 2H); ESI-MS m/z [M+H]$^+$ 484.2.

Example 5: (S)-2-(4-methyl-7-oxo-1-phenyl-1,7-dihydro-6H-pyrazolo[3,4-d]pyridazin-6-yl)-N-(1-(4-(trifluoromethoxy)phenyl)ethyl)acetamide

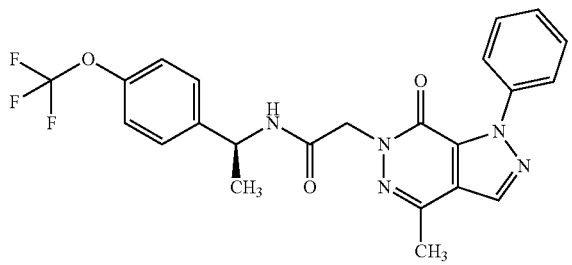 [SMILES: Cc1nn(CC(=O)N[C@@H](C)c2ccc(OC(F)(F)F)cc2)c(=O)c2c1cnn2-c1ccccc1]

To a vial containing 4-methyl-1-phenyl-1,6-dihydro-7H-pyrazolo[3,4-d]pyridazin-7-one (30 mg, 0.133 mmol) in DMF (553 μL) was added (S)-2-bromo-N-(1-(4-(trifluoromethoxy)phenyl)ethyl)acetamide (40.1 mg, 0.111 mmol) and K$_2$CO$_3$ (18.33 mg, 0:133 mmol). The mixture was stirred for 1 hour at 60° C. After cooling, 1 M HCl was added (200 mL). A resulting precipitate was filtered and dried in vacuo to give the title compound as a white solid (28.4 mg, 55%). $^1$H NMR (500 MHz, CD$_3$OD) δ ppm 1.49 (d, J=7.32 Hz, 3H), 2.58 (s, 3H), 4.88 (s, 2H), 5.07 (q, J=7.00 Hz, 1H), 7.22 (d, J=8.79 Hz, 2H), 7.42-7.57 (m, 6H), 7.66-7.72 (m, 2H), 8.31 (s, 1H); ESI-MS m/z [M+H]$^+$ 472.3.

Example 6: (S)—N-(1-(2-fluoro-4-methylphenyl)ethyl)-2-(4-methyl-7-oxo-1-phenyl-1,7-dihydro-6H-pyrazolo[3,4-d]pyridazin-6-yl)acetamide

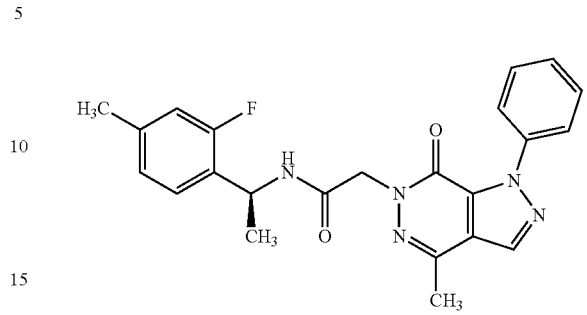

The title compound was prepared like EXAMPLE 5, using 4-methyl-1-phenyl-1,6-dihydro-7H-pyrazolo[3,4-d]pyridazin-7-one and (S)-2-bromo-N-(1-(2-fluoro-4-methylphenyl)ethyl)acetamide, and was obtained as a white solid (36 mg, 79%). $^1$H NMR (500 MHz, CD$_3$OD) δ ppm 1.46 (d, J=7.08 Hz, 3H), 2.32 (s, 3H), 2.58 (s, 3H), 4.86-4.88 (m, 2H), 5.23 (d, J=7.08 Hz, 1H), 6.88 (d, J=12.20 Hz, 1H), 6.95 (d, J=8.05 Hz, 1H), 7.26 (t, J=7.93 Hz, 1H), 7.48-7.55 (m, 3H), 7.66-7.70 (m, 2H), 8.30 (s, 1H); ESI-MS m/z [M+H]$^+$ 420.3.

Example 7: (S)-2-(4-isopropyl-7-oxo-1-phenyl-1,7-dihydro-6H-pyrazolo[3,4-d]pyridazin-6-yl)-N-(1-(4-(trifluoromethoxy)phenyl)ethyl)acetamide

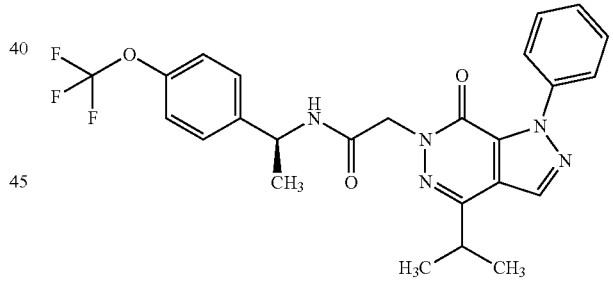

To a vial were added 4-isopropyl-1-phenyl-1,6-dihydro-7H-pyrazolo[3,4-d]pyridazin-7-one (0.025 g, 0.096 mmol), (S)-2-bromo-N-(1-(4-(trifluoromethoxy)phenyl)ethyl)acetamide (0.03 g, 0.092 mmol) and K$_2$CO$_3$ (0.036 g, 0.263 mmol) in DMF (0.438 mL). The reaction mixture was stirred for 4 hours at RT and then 1 N HCl (1 mL) and methanol (1 mL) were added. The crude material was purified by HPLC (Method B) to give the title compound as a white solid (9.0 mg, 21%). $^1$H NMR (500 MHz, CDCl$_3$) δ ppm 1.40 (dd, J=7.08, 4.15 Hz, 6H), 1.47 (d, J=7.32 Hz, 3H), 3.27 (spt, J=6.92 Hz, 1H), 4.82-4.96 (m, 2H), 5.14 (quin, J=7.08 Hz, 1H), 6.33 (d, J=7.81 Hz, 1H), 7.14 (d, J=7.81 Hz, 2H), 7.29-7.33 (m, 2H), 7.46-7.58 (m, 3H), 7.63-7.70 (m, 2H), 8.15 (s, 1H); ESI-MS m/z [M+H]$^+$ 500.3.

Example 8: (S)—N-(1-(2-fluoro-4-methylphenyl)ethyl)-2-(4-isopropyl-7-oxo-1-phenyl-1,7-dihydro-6H-pyrazolo[3,4-d]pyridazin-6-yl)acetamide

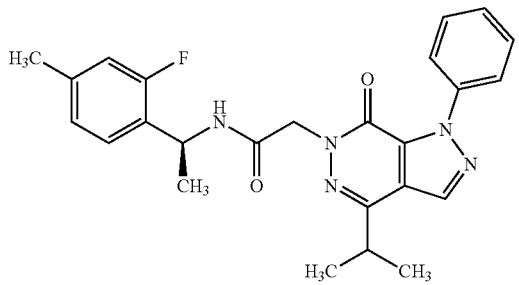 [SMILES: Cc1ccc([C@H](C)NC(=O)Cn2nc(C(C)C)c3cnn(-c4ccccc4)c3c2=O)c(F)c1]

The title compound was prepared like EXAMPLE 7, using 4-isopropyl-1-phenyl-1,6-dihydro-7H-pyrazolo[3,4-d]pyridazin-7-one and (S)-2-bromo-N-(1-(2-fluoro-4-methylphenyl)ethyl)acetamide, and was obtained as a white solid (9 mg, 20%). $^1$H NMR (500 MHz, CDCl$_3$) δ ppm 1.41 (dd, J=6.83, 2.93 Hz, 6H), 1.46 (d, J=6.83 Hz, 3H), 2.31 (s, 3H), 3.27 (spt, J=6.92 Hz, 1H), 4.73-4.98 (m, 2H), 5.23 (quin, J=7.32 Hz, 1H), 6.51 (d, J=8.30 Hz, 1H), 6.77-6.92 (m, 2H), 7.12 (t, J=7.81 Hz, 1H), 7.43-7.56 (m, 3H), 7.66-7.71 (m, 2H), 8.15 (s, 1H); ESI-MS m/z [M+H]$^+$ 448.4.

Example 9: (S)-2-(1-(tert-butyl)-4-methyl-7-oxo-1,7-dihydro-6H-pyrazolo[3,4-d]pyridazin-6-yl)-N-(1-(4-methoxyphenyl)ethyl)acetamide

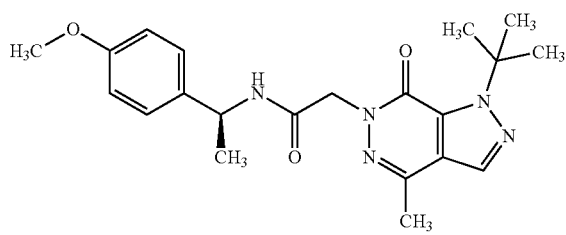 [SMILES: COc1ccc([C@H](C)NC(=O)Cn2nc(C)c3cnn(C(C)(C)C)c3c2=O)cc1]

The title compound was prepared like EXAMPLE 7, using 1-(tert-butyl)-4-methyl-1,6-dihydro-7H-pyrazolo[3,4-d]pyridazin-7-one and (S)-2-bromo-N-(1-(4-methoxyphenyl)ethyl)acetamide, and was obtained as a white solid (2.0 mg, 45%). $^1$H NMR (500 MHz, CDCl$_3$) δ ppm 1.46 (d, J=6.83 Hz, 3H), 1.81 (s, 9H), 2.50 (s, 3H), 3.77 (s, 3H), 4.80-4.92 (m, 2H), 5.09 (quin, J=7.20 Hz, 1H), 6.40 (d, J=7.81 Hz, 1H), 6.74-6.86 (m, 2H), 7.15-7.24 (m, 2H), 7.78 (s, 1H); ESI-MS m/z [M+H]$^+$ 398.3.

Example 10: (S)—N-(1-(3-fluoro-4-methoxyphenyl)ethyl)-2-(3-isopropyl-1,7-dimethyl-4-oxo-1H-pyrazolo[3,4-d]pyridazin-5(4H)-yl)acetamide

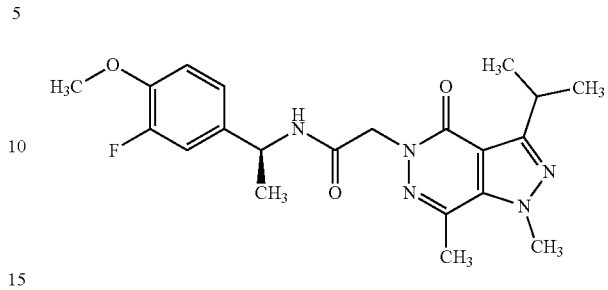

The title compound was prepared like EXAMPLE 7, using 3-isopropyl-1,7-dimethyl-1,5-dihydro-4H-pyrazolo[3,4-d]pyridazin-4-one and (S)-2-bromo-N-(1-(3-fluoro-4-methoxyphenyl)ethyl)acetamide, and was obtained as a white solid (11 mg, 30%). $^1$H NMR (500 MHz, CDCl$_3$) δ ppm 1.38 (d, J=6.83 Hz, 6H) 1.43 (d, 0.1-6.83 Hz, 3H) 2.65 (s, 3H) 3.57 (quin, J=6.96 Hz, 1H) 3.85 (s, 3H) 4.17 (s, 3H) 4.73-4.89 (m, 2H) 4.99-5.09 (m, 1H) 6.68 (d, J=7.81 Hz, 1H) 6.86 (t, J=8.79 Hz, 1H) 6.94-7.03 (m, 2H); m/z [M+H]$^+$ 416.3.

Example 11: (S)-2-(1-(tert-butyl)-4-isopropyl-7-oxo-1,7-dihydro-6H-pyrazolo[3,4-d]pyridazin-6-yl)-N-(1-(p-tolyl)ethyl)acetamide

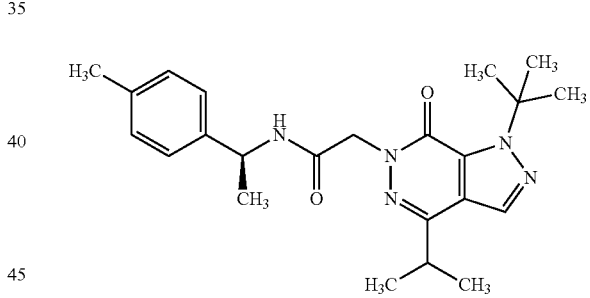

To a solution of (S)-2-bromo-N-(1-(p-tolyl)ethyl)acetamide (40 mg, 0,156 mol) in DMF (781 μL) were added 1-(tert-butyl)-4-isopropyl-1,6-dihydro-7H-pyrazolo[3,4-d]pyridazin-7-one (36.6 mg, 0.156 mmol) and K$_2$CO$_3$ (43.2 mg, 0.312 mmol). The reaction mixture was stirred at RT for 18 hours and then diluted in DMF, filtered through a hydrophilic PTFE 0.45 μm filter (Millipore® Millex-LCR) and purified by preparative HPLC (Method A), The product-containing fractions were combined, concentrated in a rotary, evaporator at 45° C., and dried in vacuo to give the title compound as a white solid (18.4 mg, 76%). $^1$H NMR (500 MHz, DMSO-d$_6$) δ ppm 1.28 (dd, J=6.8, 3.4 Hz, 6H), 1.36 (d, J=7.3 Hz, 3H), 1.75 (s, 9H), 2.27 (s, 3H), 3.16-3.25 (m, 1H), 4.71-4.80 (m, 2H), 4.90 (quin, J=7.3 Hz, 1H), 7.10 (d, J=7.8 Hz, 2H), 7.22 (d, J=8.3 Hz, 2H), 8.23 (s, 1H), 8.49 (d, J=8.3 Hz, 1H); ESI-MS m/z [M+H]$^+$ 410.3.

Example 12: (S)-2-(1-(tert-butyl)-4-isopropyl-7-oxo-1,7-dihydro-6/1-pyrazolo[3,4-d]pyridazin-6-yl)-N-(1-(4-(trifluoromethyl)phenyl)ethyl)acetamide

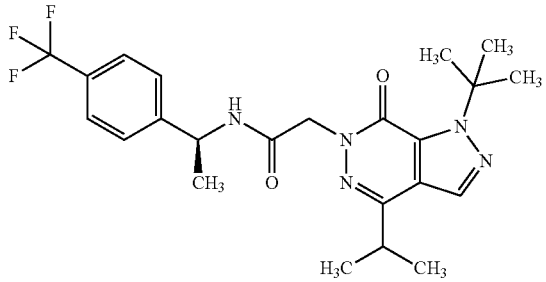 [SMILES: CC(C)c1nn(CC(=O)N[C@@H](C)c2ccc(C(F)(F)F)cc2)c(=O)c2c1cnn2C(C)(C)C]

The title compound was prepared like EXAMPLE 11, using 1-(tert-butyl)-4-isopropyl-1,6-dihydro-7H-pyrazolo[3,4-d]pyridazin-7-one and (S)-2-bromo-N-(1-(4-(trifluoromethyl)phenyl)ethyl)acetamide, and was obtained as a white solid (48 mg, 81%). $^1$H NMR (500 MHz, DMSO-$d_6$) δ ppm 1.27 (dd, J=6.8, 5.4 Hz, 6H), 1.40 (d, J=7.3 Hz, 3H), 1.74 (s, 9 FT), 3.16-3.25 (m, 1H), 4.78 (s, 2H), 499 (quin, J=7.3 Hz, 1H), 7.57 (d, J=8.8 Hz, 2H), 7.65 (d, J=7.8 Hz, 2H), 8.23 (s, 1H), 8.69 (d, J=7.8 Hz, 1H); ESI-MS [M+H]$^+$ 464.3.

Example 13: (S)-2-(1-(tert-butyl)-4-methyl-7-oxo-1,7-dihydro-6H-pyrazolo[3,4-d]pyridazin-6-yl)-N-(1-(p-tolyl)ethyl)acetamide

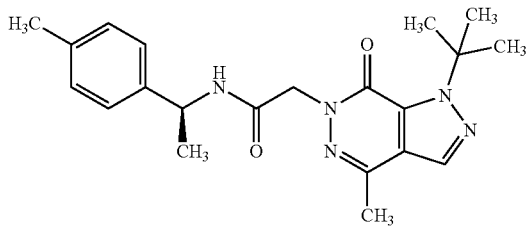 [SMILES: Cc1ccc([C@H](C)NC(=O)Cn2nc(C)c3cnn(C(C)(C)C)c3c2=O)cc1]

The title compound was prepared like EXAMPLE 11, using 1-(tert-butyl)-4-methyl-1,6-dihydro-7H-pyrazolo[3,4-d]pyridazin-7-one and (S)-2-bromo-N-(1-(p-tolyl)ethyl)acetamide, and was obtained as a white solid (23 mg, 63%). $^1$H NMR (500 MHz, DMSO-$d_6$) δ ppm 1.35 (d, J=6.8 Hz, 3H), 1.74 (s, 9H), 2.27 (s, 3H), 2.42-2.45 (m, 3H), 4.75 (s, 2H), 4.89 (quin, J=7.2 Hz, 1H), 7.11 (d, J=7.8 Hz, 2H), 7.22 (d, J=7.8 Hz, 2H), 8.10-8.14 (m, 1H), 8.49 (d, J=7.8 Hz, 1H); ESI-MS m/z [M+H]$^+$ 382.3.

Example 14: (S)-2-(1-(tert-butyl)-4-methyl-7-oxo-1,7-dihydro-6H-pyrazolo[3,4-d]pyridazin-6-yl)-N-(1-(4-(trifluoromethyl)phenyl)ethyl)acetamide

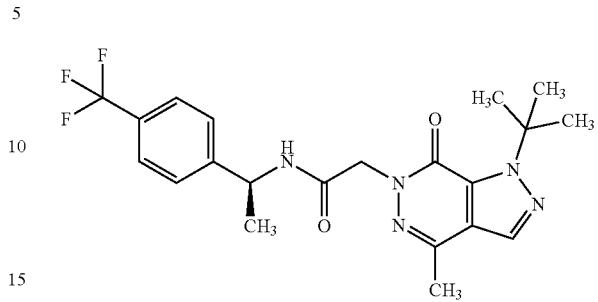

The title compound was prepared like EXAMPLE 11, using 1-(tert-butyl)-4-methyl-1,6-dihydro-7H-pyrazolo[3,4-d]pyridazin-7-one and (S)-2-bromo-N-(1-(4-(trifluoromethyl)phenyl)ethyl)acetamide, and was obtained as a white solid (19 mg, 45%). $^1$H NMR (500 MHz, DMSO-$d_6$) δ ppm 1.40 (d, J=6.8 Hz, 3H), 1.74 (s, 9H), 2.44 (s, 3H), 4.73-4.83 (m, 2H), 4.99 (quin, J=7.2 Hz, 1H), 7.57 (d, J=8.3 Hz, 2H), 7.66 (d, J=8.3 Hz, 2H), 8.12 (s, 1H), 8.69 (d, J=7.8 Hz, 1H); ESI-MS m/z [M+H]$^+$ 436.2.

Example 15: (S)-2-(1-(tert-butyl)-4-methyl-7-oxo-1,7-dihydro-6H-pyrazolo[3,4-d]pyridazin-6-yl)-N-(1-(4-(trifluoromethoxy)phenyl)ethyl)acetamide

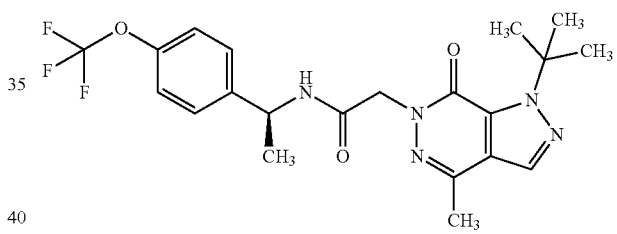

The title compound was prepared like EXAMPLE 11, using 1-(tert-butyl)-4-methyl-1,6-dihydro-7H-pyrazolo[3,4-d]pyridazin-7-one and (S)-2-bromo-N-(1-(4-(trifluoromethoxy)phenyl)ethyl)acetamide, and was obtained as a white solid (22 mg, 50%). $^1$H NMR (500 MHz, DMSO-$d_6$) δ ppm 1.38 (d, J=6.8 Hz, 3H), 1.74 (s, 9H), 2.44 (s, 3H), 4.71-4.82 (m, 2H), 4.95 (quin, J=7.1 Hz, 1H), 7.29 (d, J=7.8 Hz, 2H), 7.44-7.50 (m, 2H), 8.12 (s, 1H), 8.62 (d, J=7.8 Hz, 1H); ESI-MS m/z [M+H]$^+$ 452.2.

Example 16: (S)-2-(1-(tert-butyl)-4-methyl-7-oxo-1,7-dihydro-6H-pyrazolo[3,4-d]pyridazin-6-yl)-N-(1-(2-fluoro-4-methylphenyl)ethyl)acetamide

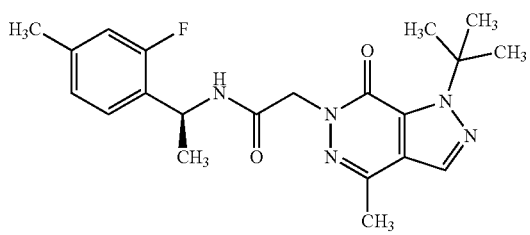 [SMILES: Cc1ccc([C@H](C)NC(=O)Cn2nc(C)c3cnn(C(C)(C)C)c3c2=O)c(F)c1]

The title compound was prepared like EXAMPLE 11, using 1-(tert-butyl)-4-methyl-1,6-dihydro-7H-pyrazolo[3,4-d]pyridazin-7-one and (S)-2-bromo-N-(1-(2-fluoro-4-methylphenyl)ethyl)acetamide, and was obtained as a white solid (21 mg, 54%). ¹H NMR (500 MHz, DMSO-$d_6$) δ ppm 1.35 (d, J=6.8 Hz, 3H), 1.74 (s, 9H), 2.28 (s, 3H), 2.44 (s, 3H), 4.76 (s, 2H), 5.09 (quirt, 17.2 Hz, 1H), 6.9:3-7.00 (m, 2H), 7.32 (t, J=8.1 Hz, 1H), 8.11-8.14 (m, 1H), 8.60 (d, J=7.8 Hz, 1H); ESI-MS m/z [M+H]⁺ 400.3.

Example 17: (S)-2-(1-isopropyl-3-methyl-4-oxo-1,4-dihydro-5H-pyrazolo[3,4-d]pyridazin-5-yl)-N-(1-(4-methoxyphenyl)ethyl)acetamide

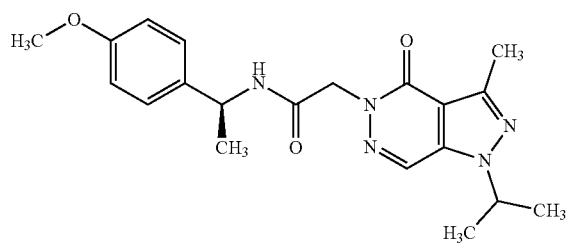 [SMILES: COc1ccc([C@H](C)NC(=O)Cn2ncc3c(c(C)nn3C(C)C)c2=O)cc1]

The title compound was prepared like EXAMPLE 11, using 1-isopropyl-3-methyl-1,5-dihydro-4H-pyrazolo[3,4-d]pyridazin-4-one and (S)-2-bromo-N-(1-(4-methoxyphenyl)ethyl)acetamide, and was obtained as a white solid (16 mg, 56%). ¹H NMR (500 MHz, DMSO-$d_6$) δ ppm 1.34 (d, J=7.3 Hz, 3H), 1.45 (d, J=6.8 Hz, 6H), 2.48 (s, 3H), 3.72 (s, 3H), 4.65-4.76 (m, 2H), 4.86 (quin, J=7.2 Hz, 1H), 4.91-4.99 (m, 1H), 6.85-6.90 (m, 2H), 7.20-7.27 (m, 2H), 8.46 (d, J=7.8 Hz, 1H), 8.55 (s, 1H); ESI-MS m/z [M+H]⁺ 384.2.

Example 18: (S)-2-(3-cyclopropyl-1-isopropyl-4-oxo-1,4-dihydro-5H-pyrazolo[3,4-d]pyridazin-5-yl)-N-(1-(4-methoxyphenyl)ethyl)acetamide

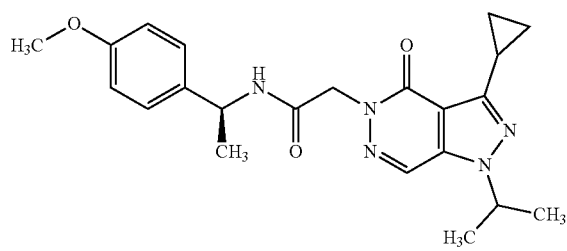 [SMILES: COc1ccc([C@H](C)NC(=O)Cn2ncc3c(c(C4CC4)nn3C(C)C)c2=O)cc1]

The title compound was prepared like EXAMPLE 11, using 3-cyclopropyl-1-isopropyl-1,5-dihydro-4H-pyrazolo[3,4-d]pyridazin-4-one and (S)-2-bromo-N-(1-(4-methoxyphenyl)ethyl)acetamide, and was obtained as a white solid (16 mg, 54%). ¹H NMR (500 MHz, DMSO-$d_6$) δ ppm 0.95-1.01 (m, 4H), 1.34 (d, J=6.8 Hz, 3H), 1.42 (d, J=6.3 Hz, 6H), 2.39-2.45 (m, 1H), 3.72 (s, 3H), 4.65-4.77 (m, 2H), 4.83-4.96 (m, 2H), 6.85-6.89 (m, 2H), 7.21-7.26 (m, 2H), 8.46 (d, J=7.8 Hz, 1H), 8.53 (s, 1H); ESI-MS m/z [M+H]⁺ 410.2.

Example 19: (S)-2-(1,3-dimethyl-4-oxo-1,4-dihydro-5H-pyrazolo[3,4-d]pyridazin-5-yl)-N-(1-(2-fluoro-4-methoxyphenyl)ethyl)acetamide

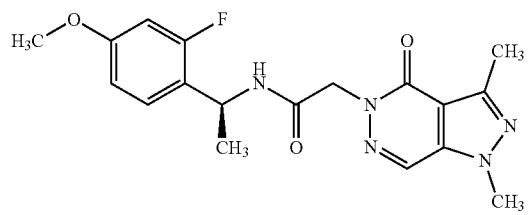 [SMILES: COc1ccc([C@H](C)NC(=O)Cn2ncc3c(c(C)nn3C)c2=O)c(F)c1]

The title compound was prepared like EXAMPLE 11, using 1,3-dimethyl-1,5-dihydro-4H-pyrazolo[3,4-d]pyridazin-4-one and (S)-2-bromo-N-(1-(2-fluoro-4-methoxyphenyl)ethyl)acetamide, and was obtained as a white solid (14 mg, 44%). ¹H NMR (500 MHz, DMSO-$d_6$) δ ppm 1.33 (d, J=6.8 Hz, 3H), 2.47 (s, 3H), 3.74 (s, 3H), 3.99 (s, 3H), 4.67-4.76 (m, 2H), 5.06 (quin, J=7.2 Hz, 1H), 6.74-6.80 (m, 2H), 7.27-7.35 (m, 1H), 8.47 (s, 1H), 8.55 (d, J=7.8 Hz, 1H); ESI-MS m/z [M+H]+ 374.2.

Example 20: (S)—N-(1-(p-tolyl)ethyl)-2-(1,3,4-trimethyl-7-oxo-1,7-dihydro-6H-pyrazolo[3,4-d]pyridazin-6-yl)acetamide

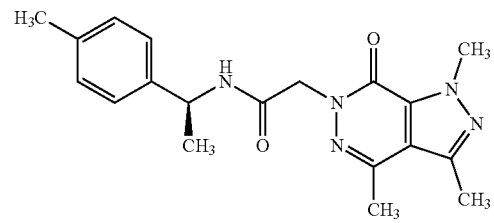 [SMILES: Cc1ccc([C@H](C)NC(=O)Cn2nc(C)c3c(C)nn(C)c3c2=O)cc1]

The title compound was prepared like EXAMPLE 11, using 1,3,4-trimethyl-1,6-dihydro-7H-pyrazolo[3,4-d]pyridazin-7-one and (S)-2-bromo-N-(1-(p-tolyl)ethyl)acetamide, and was obtained as a white solid (9 mg, 45%). ¹H NMR (500 MHz, DMSO-$d_6$) δ ppm 1.33 (d, J=6.8 Hz, 3H), 2.25 (s, 3H), 2.45 (s, 3H), 2.49 (s, 3H), 4.15 (s, 3H), 4.67 (s, 2H), 4.86 (quin, J=7.2 Hz, 1H), 7.09-7.14 (m, 2H), 7.17-7.21 (m, 2H), 8.48 (d, J=8.3 Hz, 1H); ESI-MS m/z [M+H]⁺ 354.1.

Example 21: (S)-2-(1-isopropyl-3,4-dimethyl-7-oxo-1,7-dihydro-6H-pyrazolo[3,4-d]pyridazin-6-yl)-N-(1-(p-tolyl)ethyl)acetamide

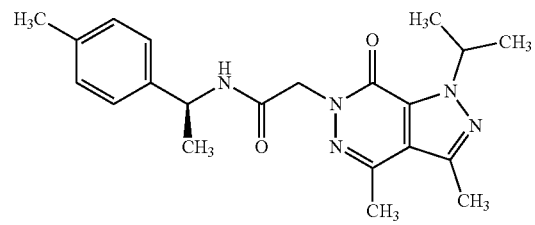 [SMILES: Cc1ccc([C@H](C)NC(=O)Cn2nc(C)c3c(C)nn(C(C)C)c3c2=O)cc1]

The title compound was prepared like EXAMPLE 11, using 1-isopropyl-3,4-dimethyl-1,6-dihydro-7H-pyrazolo[3, 4-d]pyridazin-7-one and (S)-2-bromo-N-(1-(p-tolyl)ethyl)acetamide to give the title compound as a white solid (16 mg, 73%). $^1$H NMR (500 MHz, DMSO-d6) δ ppm 1.33 (d, J=7.3 Hz, 3H), 1.41 (d, J=6.8 Hz, 6H), 2.25 (s, 3H), 2.43-2.45 (m, 3H), 2.52 (s, 3H), 4.68 (s, 2H), 4.86 (quin, J=7 Hz, 1H), 5.50-5.58 (m, 1H), 7.11 (d, J=7.8 Hz, 2H), 7.19 (d, J=8.3 Hz, 2H), 8.48 (d, J=8.3 Hz, 1H); ESI-MS m/z [M+H]$^+$ 382.1.

Example 22: (S)-2-(1-cyclopropyl-3,4-dimethyl-7-oxo-1,7-dihydro-6H-pyrazolo[3,4-d]pyridazin-6-yl)-N-(1-(p-tolyl)ethyl)acetamide

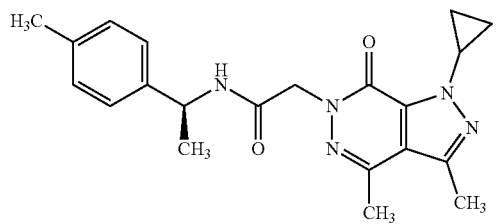

The title compound was prepared like EXAMPLE 11, using 1-cyclopropyl-3,4-dimethyl-1,6-dihydro-7H-pyrazolo[3,4-d]pyridazin-7-one and (S)-2-bromo-N-(1-(p-tolyl)ethyl)acetamide, and was obtained as a white solid (17 mg, 74%). $^1$H NMR (500 MHz, DMSO-d$_6$) δ ppm 1.00-1.06 (m, 2H), 1.12-1.18 (m, 2H), 1.33 (d, J=7.3 Hz, 3H), 2.25 (s, 3H), 2.45 (s, 3H), 2.49 (s, 3H), 4.56 (tt, J=7.6, 3.9 Hz, 1H), 4.69 (s, 2H), 4.87 (quin, J=7.3 Hz, 1H), 7.09-7.14 (m, 2H), 7.19 (d, J=8.3 Hz, 2H), 8.48 (d, J=8.3 Hz, 1H); ESI-MS m/z [M+H]$^+$ 380.1.

Example 23: (S)-2-(1-isopropyl-3-methyl-7-oxo-1,7-dihydro-6H-pyrazolo[3,4-d]pyridazin-6-yl)-N-(1-p-tolyl)ethyl)acetamide

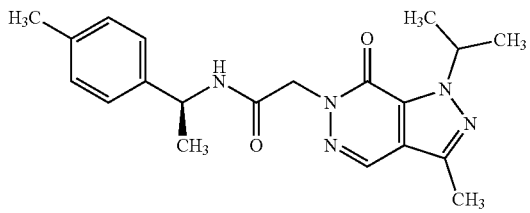 [SMILES: Cc1ccc([C@H](C)NC(=O)Cn2ncc3c(C)nn(C(C)C)c3c2=O)cc1]

The title compound was prepared like EXAMPLE 11, using 1-isopropyl-3-methyl-1,6-dihydro-7H-pyrazolo[3,4-d]pyridazin-7-one and (S)-2-bromo-N-(1-(p-tolyl)ethyl)acetamide, and was obtained as a white solid (15 mg, 69%). $^1$H NMR (500 MHz, DMSO-d$_6$) δ ppm 1.33 (d, J=6.83 Hz, 3H), 1.43 (d, J=6.83 Hz, 6H), 2.25 (s, 3H), 2.44-2.45 (m, 3H), 4.74 (d, J=0.98 Hz, 2H), 4.87 (t, J=7.20 Hz, 1H), 5.49 (quin, J=6.83 Hz, 1H), 7.08-7.13 (m, 2H), 7.16-7.21 (m, 2H), 8.33 (s, 1H), 8.51 (d, J=7.81 Hz, 1H); ESI-MS m/z [M+H]$^+$ 368.1.

Example 24: (S)—N-(1-(4-chloro-2-fluorophenyl)ethyl)-2-(1-cyclopropyl-3-methyl-4-oxo-1,4-dihydro-5H-pyrazolo[3,4-d]pyridazin-5-yl)acetamide

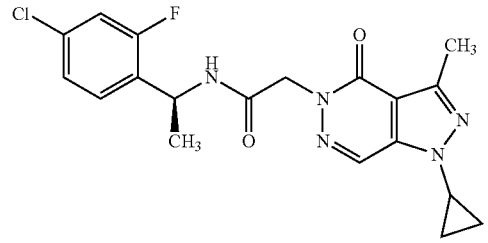 [SMILES: Cc1nn(C2CC2)c2cnn(CC(=O)N[C@@H](C)c3ccc(Cl)cc3F)c(=O)c12]

The title compound was prepared like EXAMPLE 1, using 1-cyclopropyl-3-methyl-1,5-dihydro-4H-pyrazolo[3,4-d]pyridazin-4-one and (S)-2-bromo-N-(1-(4-chloro-2-fluorophenyl)ethyl)acetamide, and was obtained as a white solid (17 mg, 83%). $^1$H NMR (500 MHz, DMSO-d$_6$) δ ppm 1.06-1.13 (m, 4H), 1.34 (d, J=7.08 Hz, 3H), 2.44 (s, 3H), 3.83-3.88 (m, 1H), 4.69-4.78 (m, 2H), 5.03-5.10 (m, 1H), 7.28 (dd, J=8.42, 2.07 Hz, 1H), 7.37 (dd, J=10.25, 1.95 Hz, 1H), 7.40-7.45 (m, 1H), 8.48 (s, 1H), 8.69 (d, J=7.57 Hz, 1H); ESI-MS m/z [M+H]$^+$ 404.0.

Example 25: (S)-2-(1-cyclopropyl-3-methyl-4-oxo-1,4-dihydro-5H-pyrazolo[3,4-d]pyridazin-5-yl)-N-(1-(3-fluorophenyl)ethyl)acetamide

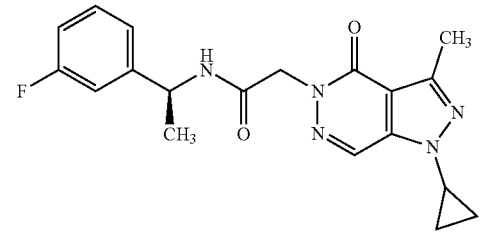 [SMILES: Cc1nn(C2CC2)c2cnn(CC(=O)N[C@@H](C)c3cccc(F)c3)c(=O)c12]

The title compound was prepared like EXAMPLE 11, using 1-cyclopropyl-3-methyl-1,5-dihydro-4H-pyrazolo[3,4-d]pyridazin-4-one and (S)-2-bromo-N-(1-(3-fluorophenyl)ethyl)acetamide, and was obtained as a white solid (18 mg, 85%). NMR (500 MHz, DMSO-d$_6$) δ ppm 1.07-1.13 (m, 4H), 1.35 (d, J=7.08 Hz, 3H), 2.45 (s, 3H), 3.83-3.89 (m, 1H), 4.74 (s, 2H), 4.92 (t, J=7.32 Hz, 1H), 7.01-7.06 (m, 1H), 7.12-7.17 (m, 2H), 7.35 (td, J=8.05, 6.35 Hz, 1H), 8.49 (s, 1H), 8.58 (d, J=7.81 Hz, 1H); ESI-MS m/z [M+H]$^+$ 370.0.

Example 26: (S)-2-(1-cyclopropyl-3-methyl-4-oxo-1,4-dihydro-5H-pyrazolo[3,4-d]pyridazin-5-yl)-N-(1-(2,5-dimethylphenyl)ethyl)acetamide

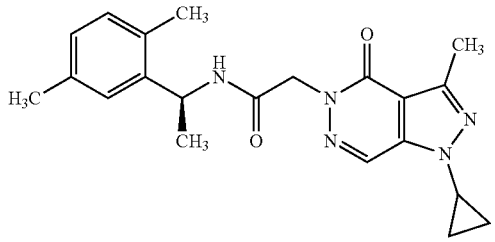 [SMILES: Cc1ccc(C)c([C@H](C)NC(=O)Cn2ncc3c(c(C)nn3C3CC3)c2=O)c1]

The title compound was prepared like EXAMPLE 11, using 1-cyclopropyl-3-methyl-1,5-dihydro-4H-pyrazolo[3,4-d]pyridazin-4-one and (S)-2-bromo-N-(1-(2,5-dimethylphenyl)ethyl)acetamide, and was obtained as a white solid (14 mg, 66%). $^1$H NMR (500 MHz, DMSO-$d_6$) δ ppm 1.04-1.12 (m, 4H), 1.32 (d, J=6.83 Hz, 3H), 2.16 (s, 3H), 2.19 (s, 3H), 2.45 (s, 3H), 3.85 (tt, J=7.20, 3.66 Hz, 1H), 4.71 (s, 2H), 4.82 (t, J=7.32 Hz, 1H), 6.98-7.02 (m, 1H), 7.04-7.09 (m, 2H), 8.44-8.50 (m, 2H); ESI-MS m/z [M+H]$^+$ 380.1.

Example 27: (S)-2-(1,3-dimethyl-7-oxo-1,7-dihydro-6H-pyrazolo[3,4-d]pyridazin-6-yl)-N-(1-(p-tolyl)ethyl)acetamide

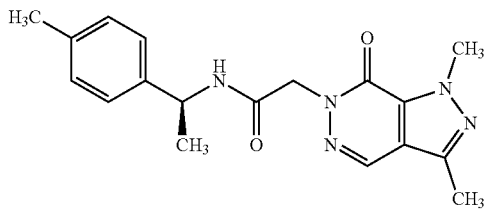 [SMILES: Cc1ccc([C@H](C)NC(=O)Cn2ncc3c(C)nn(C)c3c2=O)cc1]

The title compound was prepared like EXAMPLE 11, using 1,3-dimethyl-1,6-dihydro-7H-pyrazolo[3,4-d]pyridazin-7-one and (S)-2-bromo-N-(1-(p-tolyl)ethyl)acetamide, and was obtained as a white solid (12 mg, 60%). $^1$H NMR (500 MHz, DMSO-$d_6$) δ ppm 1.33 (d, J=6.8 Hz, 3H), 2.25 (s, 3H), 2.42-2.45 (m, 3H), 4.17 (s, 3H), 4.73 (d, J=2.2 Hz, 2H), 4.86 (t. J=7.3 Hz, 1H), 7.11 (d, J=8.3 Hz, 2H), 7.19 (d, J=8.1 Hz, 2H), 8.32 (s, 1H), 8.50 (d, 8.1 Hz, 1H); ESI-MS m/z [M+H]$^+$ 340.0.

Example 28: (S)-2-(1-cyclopropyl-3-methyl-7-oxo-1,7-dihydro-6H-pyrazolo[3,4-d]pyridazin-6-yl)-N-(1-(p-tolyl)ethyl)acetamide

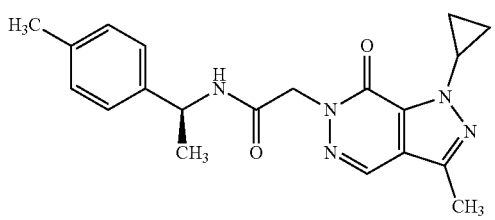 [SMILES: Cc1ccc([C@H](C)NC(=O)Cn2ncc3c(C)nn(C4CC4)c3c2=O)cc1]

The title compound was prepared like EXAMPLE 11, using 1-cyclopropyl-3-methyl-1,6-dihydro-7H-pyrazolo[3,4-d]pyridazin-7-one and (S)-2-bromo-N-(1-(p-tolyl)ethyl)acetamide, and was obtained as a white solid (13 mg, 61%). $^1$H NMR (500 MHz, DMSO-$d_6$) δ ppm 1.02-1.08 (m, 2H), 1.14-1.19 (m, 2H), 1.33 (d, J=7.08 Hz, 3H), 2.25 (s, 3H), 2.41 (s, 3H), 4.52 (tt, J=7.47, 3.87 Hz, 1H), 4.75 (d, J=1.71 Hz, 2H), 4.87 (t, J=7.20 Hz, 1H), 7.11 (d, J=8.30 Hz, 2H), 7.19 (d, J=8.05 Hz, 2H), 8.31 (s, 1H), 8.51 (d, J=7.81 Hz, 1H); ESI-MS m/z [M+H]$^+$ 366.1.

Example 29: (S)-2-(1,7-dimethyl-4-oxo-1,4-dihydro-5H-imidazo[4,5-d]pyridazin-5-yl)-N-(1-(p-tolyl)ethyl)acetamide

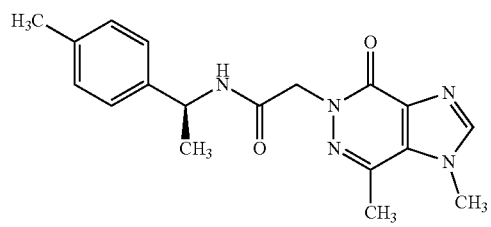 [SMILES: Cc1ccc([C@H](C)NC(=O)Cn2nc(C)c3c(ncn3C)c2=O)cc1]

The title compound was prepared like EXAMPLE 11, using 1,7-dimethyl-1,5-dihydro-4H-imidazo[4,5-d]pyridazin-4-one and (S)-2-bromo-N-(1-(p-tolyl)ethyl)acetamide, and was obtained as a white solid (5 mg, 26%). $^1$H NNW. (500 MHz, DMSO-$d_6$) δ ppm 1.33 (d, J=7.08 Hz, 3H), 2.25 (s, 3H), 2.58 (s, 3H), 3.99 (s, 3H), 4.66-4.75 (m, 2H), 4.86 (t, J=7.44 Hz, 1H), 7.11 (d, J=8.30 Hz, 2H), 7.18-7.21 (m, 2H), 8.20 (s, 1H), 8.46 (d, J=8.05 Hz, 1H); ESI-MS m/z [M+H]$^+$ 340.1.

Example 30: (S)-2-(1-cyclopropyl-3-methyl-4-oxo-1,4-dihydro-5H-pyrazolo[3,4-d]pyridazin-5-yl)-N-(1-(2,3-difluorophenyl)ethyl)acetamide

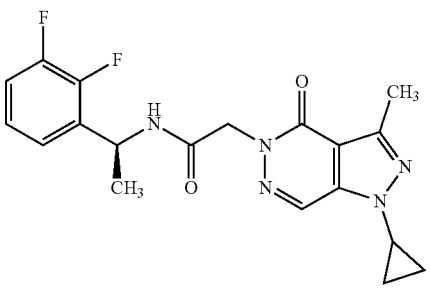 [SMILES: Cc1nn(C2CC2)c2cnn(CC(=O)N[C@@H](C)c3cccc(F)c3F)c(=O)c12]

The title compound was prepared like EXAMPLE 11, using 1-cyclopropyl-3-methyl-1,5-dihydro-4H-pyrazolo[3,4-d]pyridazin-4-one and (S)-2-bromo-N-(1-(2,3-difluorophenyl)ethyl)acetamide, and was obtained as a white solid (16 mg, 74%). $^1$H NMR (500 MHz, DMSO-6/6) δ ppm 1.06-1.13 (m, 4H), 1.37 (d, J=7.08 Hz, 3H), 2.44 (s, 3H), 3.85 (tt, J=7.23, 3.75 Hz, 1H), 4.69-4.79 (m, 2H), 5.12 (t, J=7.08 Hz, 1H), 7.16-7.24 (m, 2H), 7.26-7.34 (m, 1H), 8.48 (s, 1H), 8.72 (d, 1-7.57 Hz, 1H); ESI-MS m/z [M+H]$^+$ 388.0.

Example 31: (S)-2-(1-cyclopropyl-3-methyl-4-oxo-1,4-dihydro-5H-pyrazolo[3,4-d]pyridazin-5-yl)-N-(1-(4-methoxy-3-methylphenyl)ethyl)acetamide

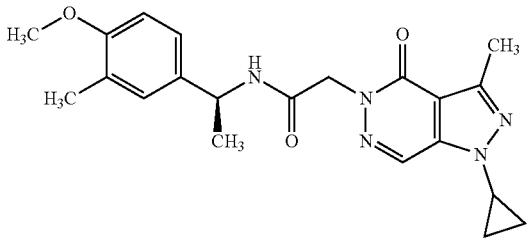 [SMILES: COc1ccc([C@H](C)NC(=O)Cn2ncc3c(c(C)nn3C3CC3)c2=O)cc1C]

The title compound was prepared like EXAMPLE 11, using 1-cyclopropyl-3-methyl-1,5-dihydro-4H-pyrazolo[3,4-d]pyridazin-4-one and (S)-2-bromo-N-(1-(4-methoxy-3-methylphenyl)ethyl)acetamide, and was obtained as a white solid (12 mg, 57%). ESI-MS m/z [M+H]$^+$ 396.0.

Example 32: (S)-2-(1-cyclopropyl-3-methyl-4-oxo-1,4-dihydro-5H-pyrazolo[3,4-d]pyridazin-5-yl)-N-(5-(trifluoromethyl)pyridin-2-yl)ethyl)acetamide

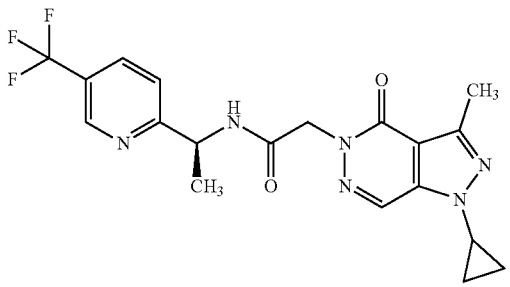 [SMILES: Cc1nn(C2CC2)c2cnn(CC(=O)N[C@@H](C)c3ccc(C(F)(F)F)cn3)c(=O)c12]

The title compound was prepared like EXAMPLE 11, using 1-cyclopropyl-3-methyl-1,5-dihydro-4H-pyrazolo[3,4-d]pyridazin-4-one and (S)-2-bromo-N-(1-(5-(trifluoromethyl)pyridin-2-yl)ethyl)acetamide, and was obtained as a white solid (12 mg, 28%). $^1$H NMR (500 MHz, DMSO-d$_6$) δ ppm 1.07-1.13 (m, 4H), 1.41 (d, J=7.08 Hz, 3H), 2.45 (s, 3H), 3.82-3.88 (m, 1H), 4.73-4.82 (m, 2H), 5.00 (t, J=7.44 Hz, 1H), 7.61 (d, J=8.30 Hz, 1H), 8.19 (dd, J=8.30, 2.44 Hz, 1H), 8.49 (d, J=0.73 Hz, 1H), 8.76 (d, J=7.32 Hz, 1H), 8.88-8.91 (m, 1H); ESI-MS m/z [M+H]$^+$ 421.0.

Example 33: (S)-2-(1-methyl-4-oxo-1,4-dihydro-5H-pyrazolo[3,4-d]pyridazin-5-yl)-N-(1-(p-tolyl)ethyl)acetamide

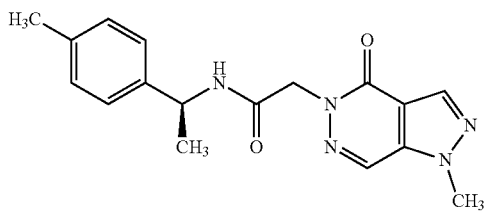 [SMILES: Cc1ccc([C@H](C)NC(=O)Cn2ncc3c(cnn3C)c2=O)cc1]

To a solution of (S)-2-bromo-N-(1-(p-tolyl)ethyl)acetamide (23.88 mg, 0.093 mmol) in DMF (466 µL) were added 1-methyl-1,5-dihydro-4H-pyrazolo[3,4-d]pyridazin-4-one (14 mg, 0.093 mmol) and K$_2$CO$_3$ (25.8 mg, 0.186 mmol). The reaction mixture was stirred at WI for 18 hours and then diluted in MT, filtered through a hydrophilic PTFE 0.45 µm filter (Millipore® Millex-LCR) and purified by HPLC (Method B). The product-containing fractions were combined, concentrated in a rotary evaporator at 45° C., and dried in vacuo to give the title compound as a white solid (9.2 mg 30%). $^1$H NMR (500 MHz, DMSO-d$_6$) δ ppm 1.35 (d, J=7.3 Hz, 3H), 2.27 (s, 3H), 4.11 (s, 3H), 4.71-4.81 (m, 2H), 4.88 (quin, J=7.2 Hz, 1H), 7.13 (d, J=7.8 Hz, 2H), 7.19-7.23 (m, 2H), 8.22 (s, 1H), 8.50 ((i, J=8.3 Hz, 1H), 8.59 (s, 1H); ESI-MS m/z [M+H]$^+$ 326.3.

Example 34: (S)-2-(1-methyl-4-oxo-1,4-dihydro-5H-pyrazolo[3,4-d]pyridazin-5-yl)-N-(1-(4-(trifluoromethyl)phenyl)ethyl)acetamide

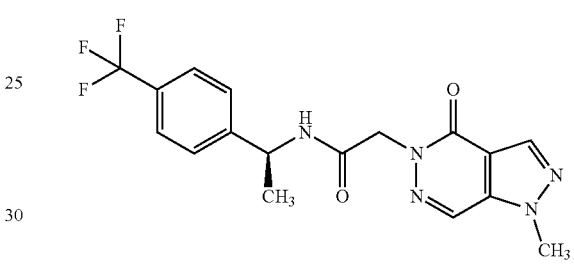

The title compound was prepared like EXAMPLE 33, using 1-methyl-1,5-dihydro-4H-pyrazolo[3,4-d]pyridazin-4-one and (S)-2-bromo-N-(1-(4-(trifluoromethyl)phenyl)ethyl)acetamide; and was obtained as a white solid (13 mg, 37%). $^1$H NMR (500 MHz, DMSO-16) δ ppm 1.39 (d, J=6.8 Hz, 3H), 4.11 (s, 3H), 4.75-4.85 (m, 2H), 4.98 (quin, J=7.2 Hz, 1H), 7.55 (d, J=8.3 Hz, 2H), 7.69 (d, J=7.8 Hz, 2H), 8.22 (d, J=1.0 Hz, 1H), 8.59 (s, 1H), 8.69 (d, J=7.8 Hz, 1H); ESI-MS m/z [M+H]$^+$ 380.1.

Example 35: (S)—N-(1-(2-fluoro-4-methylphenyl)ethyl)-2-(1-methyl-4-oxo-1,4-dihydro-5H-pyrazolo[3,4-d]pyridazin-5-yl)acetamide

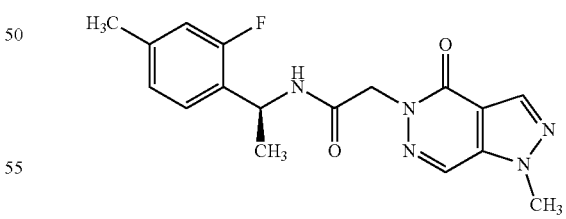

The title compound was prepared like EXAMPLE 33, using 1-methyl-1,5-dihydro-4H-pyrazolo[3,4-d]pyridazin-4-one and (S)-2-bromo-N-(1-(2-fluoro-4-methylphenyl)ethyl)acetamide, and was obtained as a white solid (12 mg, 37%). NMR (500 MHz; DMSO-d$_6$) δ ppm 1.34 (d, J=6.8 Hz, 3H), 2.28 (s, 3H), 4.10 (s, 3H), 4.73-4.83 (m, 2H), 5.09 (quin, J=7.2 Hz, 1H), 6.94-7.03 (m, 2H), 7.29 (t, J=8.1 Hz, 1H), 8.22 (d, J=1.0 Hz, 1H), 8.57-8.63 (m, 2H); ESI-MS m/z [M+H]$^+$ 344.2.

Example 36: (S)-2-(1,3-dimethyl-4-oxo-1,4-dihydro-5H-pyrazolo[3,4-d]pyridazin-5-yl)-N-(1-(p-tolyl)ethyl)acetamide

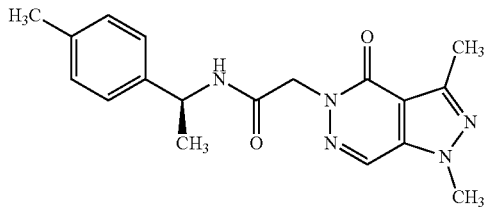 [SMILES: Cc1ccc([C@H](C)NC(=O)Cn2ncc3c(c(C)nn3C)c2=O)cc1]

The title compound was prepared like EXAMPLE 33, using 1,3-dimethyl-1,5-dihydro-4H-pyrazolo[3,4-d]pyridazin-4-one and (S)-2-bromo-N-(1-(p-tolyl)ethyl)acetamide, and was obtained as a white solid (11 mg, 47%). $^1$H NMR (500 MHz, DMSO-d6) δ ppm 1.35 (d, J=7.3 Hz, 3H), 2.27 (s, 3H), 2.48 (s, 3H), 4.00 (s, 3H), 4.67-4.77 (m, 2H), 4.88 (quin, J=7.2 Hz, 1H), 7.10-7.16 (m, 2H), 7.21 (d, J=7.8 Hz, 2H), 8.46-8.51 (m, 2H); ESI-MS m/z [M+H]$^+$ 340.2.

Example 37: (S)-2-(1,3-dimethyl-4-oxo-1,4-dihydro-5H-pyrazolo[3,4-d]pyridazin-5-yl)-N-(1-(4-(trifluoromethyl)phenyl)ethyl)acetamide

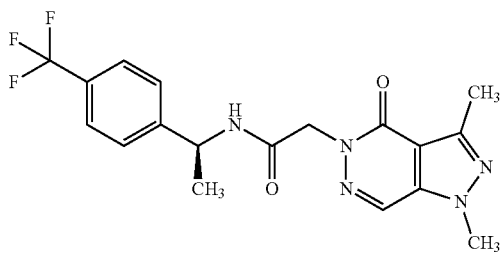 [SMILES: Cc1nn(C)c2cnn(CC(=O)N[C@@H](C)c3ccc(C(F)(F)F)cc3)c(=O)c12]

The title compound was prepared like EXAMPLE 33, using 1,3-dimethyl-1,5-dihydro-4H-pyrazolo[3,4-d]pyridazin-4-one and (S)-2-bromo-N-(1-(4-(trifluoromethyl)phenyl)ethyl)acetamide, and was obtained as a white solid (9 mg, 36%). $^1$H NMR (500 MHz, DMSO-d$_6$) δ ppm 1.39 (d, J=7.3 Hz, 3H), 2.48 (s, 3H), 4.00 (s, 3H), 4.70-4.82 (m, 2H), 4.98 (quip, J=7.2 Hz, 1H), 7.52-7.59 (m, 2H), 7.70 (d, J=8.3 Hz, 2H), 8.47-8.51 (m, 1H), 8.68 (d, J=7.3 Hz, 1H); ESI-MS m/z [M+H]$^+$ 394.2.

Example 38: (S)-2-(3-cyclopropyl-1-methyl-4-oxo-1,4-dihydro-5H-pyrazolo[3,4-d]pyridazin-5-yl)-N-(1-(p-tolyl)ethyl)acetamide

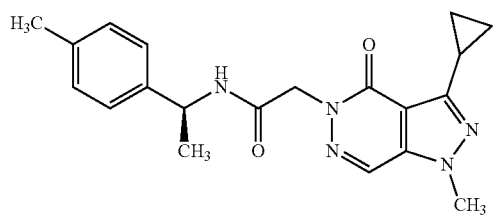 [SMILES: Cc1ccc([C@H](C)NC(=O)Cn2ncc3c(c(C4CC4)nn3C)c2=O)cc1]

The title compound was prepared like EXAMPLE 33, using 3-cyclopropyl-1-methyl-1,5-dihydro-4H-pyrazolo[3,4-d]pyridazin-4-one and (S)-2-bromo-N-(1-(p-tolyl)ethyl)acetamide, and was obtained as a white solid (8 mg, 37%). ESI-MS m/z [M+H]$^+$ 366.2.

Example 39: (S)-2-(1,4-dimethyl-7-oxo-1,7-dihydro-6-pyrazolo[3,4-d]pyridazin-6-yl)-N-(1-(p-totyl)ethyl)acetamide

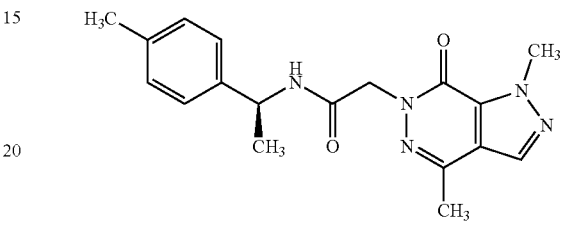

The title compound was prepared like EXAMPLE 33, using 1,4-dimethyl-1,6-dihydro-7H-pyrazolo[3,4-d]pyridazin-7-one and (S)-2-bromo-N-(1-(p-tolyl)ethyl)acetamide, and was obtained as a white solid (7 mg, 44%) $^1$H NMR (500 MHz, DMSO-d$_6$) δ ppm 1.35 (d, J=7.3 Hz, 3H), 2.26-2.29 (m, 3H), 2.42-2.44 (m, 3H), 4.26 (s, 3H), 4.63-4.77 (m, 2H), 4.88 (quin, J=7.2 Hz, 1H), 7.13 (d, J=7.8 Hz, 2H), 7.18-7.25 (m, 2H), 8.16 (s, 1H), 8.49 (d, J=7.8 Hz, 1H); m/z [M+H]$^+$ 340.1.

Example 40: (S)-2-(1,4-dimethyl-7-oxo-1,7-dihydro-6H-pyrazolo[3,4-d]pyridazin-6-yl)-N-(1-(4-(trifluoromethyl)phenyl)ethyl)acetamide

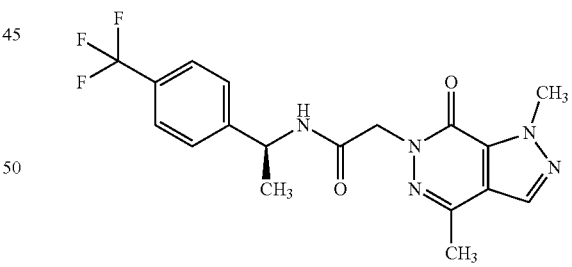

The title compound was prepared like EXAMPLE 33, using 1,4-dimethyl-1,6-dihydro-7H-pyrazolo[3,4-d]pyridazin-7-one and (S)-2-bromo-N-(1-(4-(trifluoromethyl)phenyl)ethyl)acetamide, and was obtained as a white solid (8 mg, 39%). $^1$H NAIR (500 MHz, DMSO-d$_6$) δ ppm 1.40 (d, J=6.8 Hz, 3H), 2.43 (s, 3H), 4.26 (s, 3H), 4.75 (s, 2H), 4.99 (quin, J=7.1 Hz, 1H), 7.55 (d, J=8.3 Hz, 2H), 7.70 (d, J=8.3 Hz, 2H), 8.16 (s, 1H), 8.65-8.70 (m, 1H); ESI-MS m/z [M+H]$^+$ 394.1.

Example 41: (S)-2-(1,4-dimethyl-7-oxo-1,7-dihydro-6H-pyrazolo[3,4-d]pyridazin-6-yl)-N-(1-(2-fluoro-4-methylphenyl)ethyl)acetamide

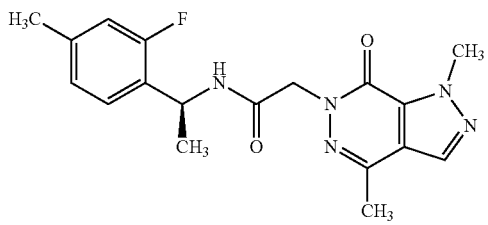 [SMILES: Cc1ccc([C@H](C)NC(=O)Cn2nc(C)c3cnn(C)c3c2=O)c(F)c1]

The title compound was prepared like EXAMPLE 33, using 1,4-dimethyl-1,6-dihydro-7H-pyrazolo[3,4-d]pyridazin-7-one and (S)-2-bromo-N-(1-(2-fluoro-4-methylphenyl)ethyl)acetamide, and was obtained as a white solid (6 mg, 37%). $^1$H NMR (500 MHz, DMSO-d$_6$) δ ppm 1.35 (d, J=7.3 Hz, 3H), 2.29 (s, 3H), 2.41-2.43 (m, 3H), 4.26 (s, 3H), 4.72 (s, 2H), 5.09 (quin, J=7.2 HZ, 1H), 6.94-7.02 (m, 2H), 7.29 (t, J=8.1 Hz, 1H), 8.14-8.17 (m, 1H), 8.57-8.62 (m, 1H); ESI-MS m/z [M+H]$^+$ 358.1.

Example 42: (S)-2-(4-cyclopropyl-7-oxo-1-phenyl-1,7-dihydro-6H-pyrazolo[3,4-d]pyridazin-6-yl)-N-(1-(2-fluoro-4-methylphenyl)ethyl)acetamide

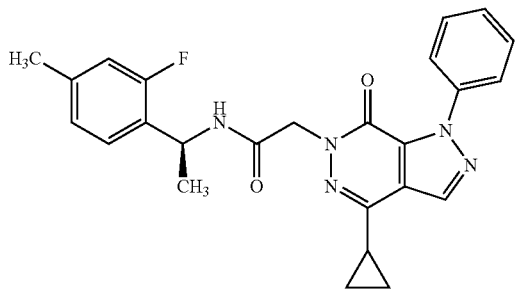 [SMILES: Cc1ccc([C@H](C)NC(=O)Cn2nc(C3CC3)c3cnn(-c4ccccc4)c3c2=O)c(F)c1]

To a solution of (S)-2-bromo-N-(1-(2-fluoro-4-methylphenyl)ethyl)acetamide (32.6 mg, 0.119 mmol) in MT (0.6 mL) were added 4-cyclopropyl-1-phenyl-1,6-dihydro-7H-pyrazolo[3,4-d]pyridazin-7-one (30 mg, 0.119 mmol) and K$_2$CO$_3$ (32.9 mg, 0,238 mmol). The reaction mixture was stirred at 28-45° C. for 18 hours and then diluted in DMF, filtered through a hydrophilic PTFE 0.45 μm filter (Millipore® Millex-LCR) and purified by HPLC (Method A). The product-containing fraction was concentrated under reduced pressure to give the title compound as a white solid (24.7 mg, 47%). $^1$H NMR (500 MHz, CDCl$_3$) δ ppm 1.02-1.09 (m, 2H), 1.09-1.17 (m, 2H), 1.45 (d, J=6.83 Hz, 3H), 2.13-2.21-(m, 1H), 2.31 (s, 3H), 4.70-4.90 (m, 2H), 5.16-5.25 (m, 1H), 6.42-6.49 (m, 1H), 6.78-6.85 (m, 1H), 6.85-6.89 (m, 1H), 7.08-7.14 (m, 1H), 7.44-7.54 (m, 3H), 7.67-7.71 (m, 2H), 8.19 (s, 1H); ESI-MS m/z [M+H]$^+$ 446.2.

Example 43: (S)-2-(4-cyclopropyl-7-oxo-1-phenyl-1,7-dihydro-6H-pyrazolo[3,4-d]pyridazin-6-yl)-N-(1-(p-tolyl)ethyl)acetamide

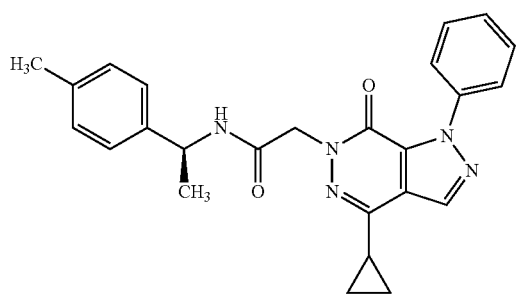 [SMILES: Cc1ccc([C@H](C)NC(=O)Cn2nc(C3CC3)c3cnn(-c4ccccc4)c3c2=O)cc1]

The title compound was prepared like EXAMPLE 42, using 4-cyclopropyl-1-phenyl-1,6-dihydro-7H-pyrazolo[3,4-d]pyridazin-7-one and (S)-2-bromo-N-(1-(p-tolyl)ethyl)acetamide, and was obtained as a white solid (24.8 mg, 49%). ESI-MS m/z [M+H]$^+$ 428.3.

Example 44: (S)-2-(4-cyclopropyl-7-oxo-1-phenyl-1,7-dihydro-6H-pyrazolo[3,4-d]pyridazin-6-yl)-N-(1-(4-(trifluoromethyl)phenyl)ethyl)acetamide

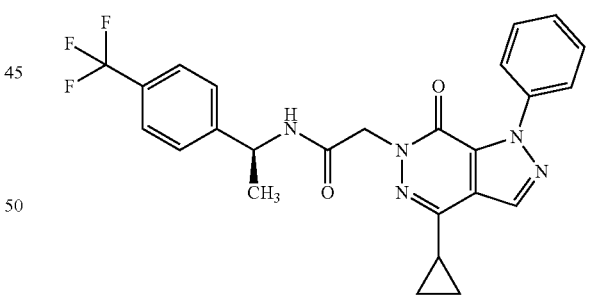

The title compound was prepared like EXAMPLE 42, using 4-cyclopropyl-1-phenyl-1,6-dihydro-7H-pyrazolo[3,4-d]pyridazin-7-one and (S)-2-bromo-N-(1-(4-(trifluoromethyl)phenyl)ethyl)acetamide, and was obtained as a white solid (16.8 mg, 29%). $^1$H NMR (500 MHz, CDCl$_3$) δ ppm 1.05-1.16 (m, 4H), 1.47 (d, J=7.32 Hz, 3H), 2.13-2.21 (m, 1H), 4.77-4.91 (m, 2H), 5.11-5.19 (m, 1H), 6.29-6.38 (m, 1H), 7.36-7.40 (m, 2H), 7.46-7.57 (m, 5H), 7.66-7.70 (m, 2H), 8.20 (s, 1H); ESI-MS m/z [M+H]$^+$ 482.3.

Example 45: (S)-2-(4-cyclopropyl-7-oxo-1-phenyl-1,7-dihydro-6H-pyrazolo[3,4-d]pyridazin-6-yl)-N-(1-(4-(trifluoromethoxy)phenyl)ethyl)acetamide

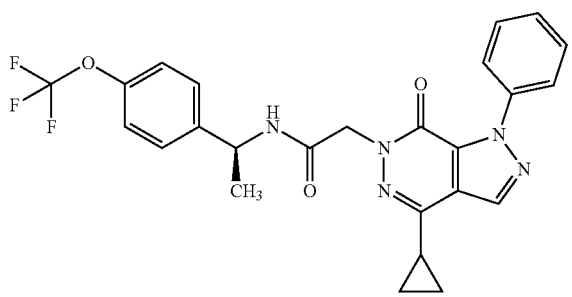 [SMILES: C[C@H](NC(=O)Cn1nc(C2CC2)c2cnn(-c3ccccc3)c2c1=O)c1ccc(OC(F)(F)F)cc1]

The title compound was prepared like EXAMPLE 42, using 4-cyclopropyl-1-phenyl-1,6-dihydro-7H-pyrazolo[3,4-d]pyridazin-7-one and (S)-2-bromo-N-(1-(4-(trifluoromethoxy)phenyl)ethyl)acetamide, and was obtained as a white solid (21.7 mg, 37%). ESI-MS m/z [M+H]$^+$ 498.2.

Example 46: (S)-2-(1-isopropyl-3-methyl-4-oxo-1,4-dihydro-5H-pyrazolo[3,4-d]pyridazin-5-yl)-N-(1-(p-tolyl)ethyl)acetamide

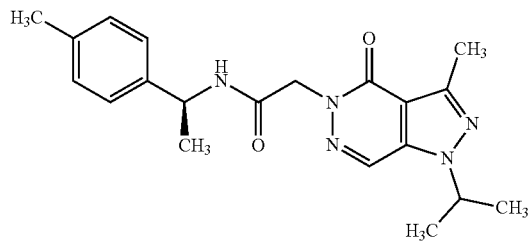 [SMILES: Cc1ccc([C@H](C)NC(=O)Cn2ncc3c(c(C)nn3C(C)C)c2=O)cc1]

The title compound was prepared like EXAMPLE 42, using 1-isopropyl-3-methyl-1,5-dihydro-4H-pyrazolo[3,4-d]pyridazin-4-one and (S)-2-bromo-N-(1-(p-tolyl)ethyl)acetamide, and was obtained as a white solid (17.3 mg, 60%). $^1$H NMR (500 MHz, CDCl$_3$) δ ppm 1.48 (d, J=6.83 Hz, 3H), 1.59 (d, J=6.83 Hz, 6H), 2.32 (s, 3H), 2.66 (s, 3H), 4.63-4.72 (m, 1H), 4.81-4.89 (m, 2H), 5.11 (quin, J=7.20 Hz, 1H), 6.35 (br s, 1H), 7.08-7.15 (m, 2H), 7.15-7.21 (m, 2H), 8.11 (s, 1H); ESI-MS m/z [M+H]$^+$ 368.2.

Example 47: (S)-2-(1,3-dimethyl-4-oxo-1,4-dihydro-5H-pyrazolo[3,4-d]pyridazin-5-yl)-N-(1-(4-(trifluoromethoxy)phenyl)ethyl)acetamide

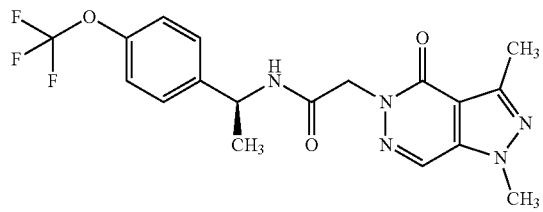 [SMILES: Cc1nn(C)c2cnn(CC(=O)N[C@@H](C)c3ccc(OC(F)(F)F)cc3)c(=O)c12]

The title compound was prepared like EXAMPLE 42, using 1,3-dimethyl-5-dihydro-4H-pyrazolo[3,4-d]pyridazin-4-one and (S)-2-bromo-N-(1-(4-(trifluoromethoxy)phenyl)ethyl)acetamide, and was obtained as a white solid (18.2 mg, 38%). $^1$H NMR (500 MHz, CD$_3$OD) δ ppm 1.49 (d, J=6.83 Hz, 3H), 2.56 (s, 3H), 4.02 (s, 3H), 4.86-4.89 (m, 2H), 5.02-5.10 (m, 1H), 7.23 (d, J=8.30 Hz, 2H), 7.41-7.48 (m, 2H), 8.33-8.37 (m, 1H), 8.68 (d, J=7.32 Hz, 1H); ESI-MS m/z [M+H]$^+$ 410.1.

Example 48: (S)-2-(1,3-dimethyl-4-oxo-1,4-dihydro-5H-pyrazolo[3,4-d]pyridazin-5-yl)-N-(1-(4-methoxyphenyl)ethyl)acetamide

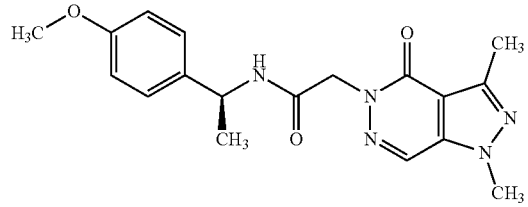 [SMILES: COc1ccc([C@H](C)NC(=O)Cn2ncc3c(c(C)nn3C)c2=O)cc1]

The title compound was prepared like EXAMPLE 42, using 1,3-dimethyl-1,5-dihydro-4H-pyrazolo[3,4-d]pyridazin-4-one and (S)-2-bromo-N-(1-(4-methoxyphenyl)ethyl)acetamide, and was obtained as a white solid (12.2 mg, 43%). ESI-MS m/z [M+H]$^+$ 356.2.

Example 49: (S)—N-(1-(2-fluoro-4-methylphenyl)ethyl)-2-(3-isopropyl-1-methyl-4-oxo-1,4-dihydro-5H-pyrazolo[3,4-d]pyridazin-5-yl)acetamide

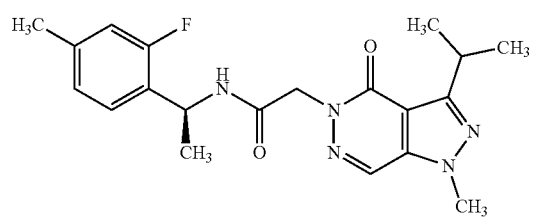 [SMILES: Cc1ccc([C@H](C)NC(=O)Cn2ncc3c(c(C(C)C)nn3C)c2=O)c(F)c1]

The title compound was prepared like EXAMPLE 42, using 3-isopropyl-1-methyl-1,5-dihydro-4H-pyrazolo[3,4-d]pyridazin-4-one and (S)-2-bromo-N-(1-(2-fluoro-4-methylphenyl)ethyl)acetamide, and was obtained as a solid (19.5 mg, 50%). ESI-MS m/z [M+H]$^+$ 386.2.

Example 50: (S)-2-(3-isopropyl-1-methyl-4-oxo-1,4-dihydro-5H-pyrazolo[3,4-d]pyridazin-5-yl)-N-(1-(4-(trifluoromethoxy)phenyl)ethyl)acetamide

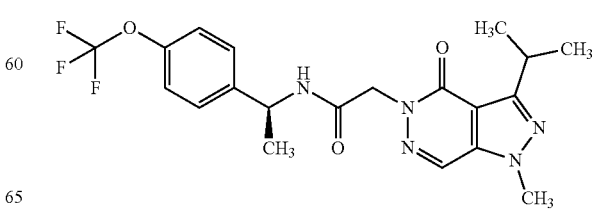

The title compound was prepared like EXAMPLE 42, using 3-isopropyl-1-methyl-1,5-dihydro-4H-pyrazolo[3,4-d]pyridazin-4-one and (S)-2-bromo-N-(1-(4-(trifluoromethoxy)phenyl)ethyl)acetamide, and was obtained as a solid (25.5 mg, 59%). ¹H NMR (500 MHz, CD₃OD) δ ppm 1.31-1.40 (m, 6H), 1.47-1.52 (m, 3H), 3.43-3.56 (m, 1H), 4.03 (s, 3H), 4.88 (d, J=2.44 Hz, 2H), 5.01-5.11 (m, 1H), 7.18-7.26 (m, 2H), 7.41-7.48 (m, 2H), 8.35 (s, 1H), 8.67 (d, J=7.32 Hz, 1H); ESI-MS m/z [M+H]⁺ 438.2.

Example 51: (S)-2-(3-isopropyl-1-methyl-4-oxo-1,4-dihydro-5H-pyrazolo[3,4-d]pyridazin-5-yl)-N-(1-(p-tolyl)ethyl)acetamide

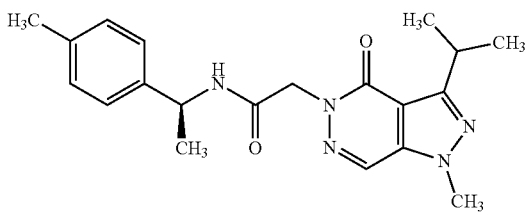 [SMILES: Cc1ccc([C@H](C)NC(=O)Cn2ncc3c(c(C(C)C)nn3C)c2=O)cc1]

The title compound was prepared like EXAMPLE 42, using 3-isopropyl-1-methyl-1,5-dihydro-4H-pyrazolo[3,4-d]pyridazin-4-one and (S)-2-bromo-N-(1-(p-tolyl)ethyl)acetamide, and was obtained as a solid (17.9 mg, 48%). ESI-MS m/z [M+H]⁺ 368.2.

Example 52: (S)-2-(3-isopropyl-1-methyl-4-oxo-1,4-dihydro-5H-pyrazolo-[3,4-d]pyridazin-5-yl)-N-(1-(4-(trifluoromethyl)phenyl)ethyl)acetamide

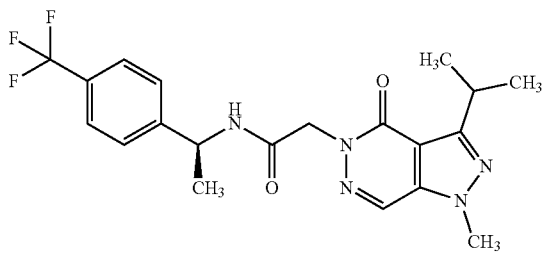 [SMILES: CC(C)c1nn(C)c2cnn(CC(=O)N[C@@H](C)c3ccc(C(F)(F)F)cc3)c(=O)c12]

The title compound was prepared like EXAMPLE 42, using 3-isopropyl-1-methyl-1,5-dihydro-4H-pyrazolo[3,4-d]pyridazin-4-one and (S)-2-bromo-N-(1-(4-(trifluoromethyl)phenyl)ethyl)acetamide, and was obtained as a solid (24.1 mg, 58%). ESI-MS m/z [M+H]⁺422.2.

Example 53: (S)-2-(3-isopropyl-1-methyl-4-oxo-1,4-dihydro-5H-pyrazolo[3,4-d]pyridazin-5-yl)-N-(1-(4-methoxyphenyl)ethyl)acetamide

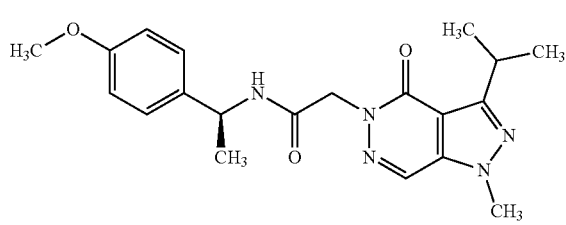 [SMILES: COc1ccc([C@H](C)NC(=O)Cn2ncc3c(c(C(C)C)nn3C)c2=O)cc1]

The title compound was prepared like EXAMPLE 42, using 3-isopropyl-1-methyl-1,5-dihydro-4H-pyrazolo[3,4-d]pyridazin-4-one and (S)-2-bromo-N-(1-(4-methoxyphenyl)ethyl)acetamide, and was obtained as solid (14.2 mg, 37%). ¹H NMR (500 MHz, CD₃OD) δ ppm 1.33-1.39 (m, 6H), 1.45-1.50 (m, 3H), 3.45-3.56 (m, 1H), 3.77 (s, 3H), 4.04 (s, 3H), 4.83-4.89 (m, 2H), 4.97-5.06 (m, 1H), 6.82-6.91 (m, 2H), 7.22-7.31 (m, 2H), 8.35 (s, 1H), 8.51 (d, J=7.81 Hz, 1H); ESI-MS m/z [M+H]⁺ 384.2.

Example 54: (S)—N-(1-(2-fluoro-4-methylphenyl)ethyl)-2-(1-isopropyl-3,7-dimethyl-4-oxo-1,4-dihydro-5H-pyrazolo[3,4-d]pyridazin-5-yl)acetamide

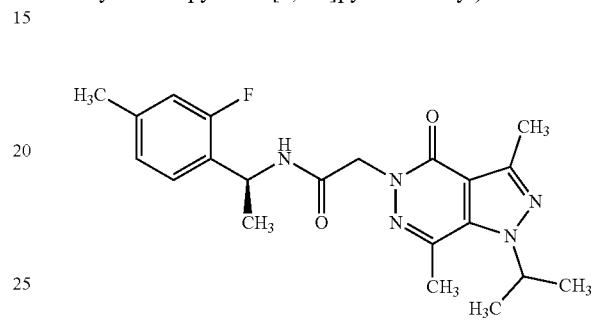

The title compound was prepared like EXAMPLE 42, using 1-isopropyl-3,7-dimethyl-1,5-dihydro-4H-pyrazolo[3,4-d]pyridazin-4-one and (S)-2-bromo-N-(1-(2-fluoro-4-methylphenyl)ethyl)acetamide, and was obtained as a solid (26.6 mg, 71%). ¹H NMR (500 MHz, CD₃OD) δ ppm 1.46 (d, J=6.83 Hz, 3H), 1.55 (d, J=6.35 Hz, 6H), 2.31 (s, 3H), 2.57 (s, 3H), 2.65 (d, J=1.46 Hz, 3H), 4.76-4.89 (m, 2H), 5.04-5.13 (m, 1H), 5.19-5.26 (m, 1H), 6.87 (d, J=11.72 Hz, 1H), 6.93-7.00 (m, 1H), 7.23-7.30 (m, 1H); ESI-MS m/z [M+H]⁺ 400.2.

Example 55: (S)-2-(1-isopropyl-3,7-dimethyl-4-oxo-1,4-dihydro-5H-pyrazolo[3,4-d]pyridazin-5-yl)-N-(1-(p-tolyl)ethyl)acetamide

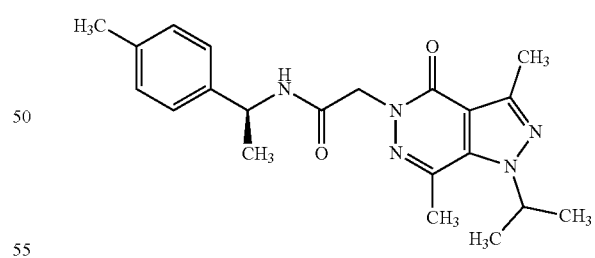

The title compound was prepared like EXAMPLE 42, using 1-isopropyl-3,7-dimethyl-1,5-dihydro-4H-pyrazolo[3,4-d]pyridazin-4-one and (S)-2-bromo-N-(1-(p-tolyl)ethyl)acetamide, and was obtained as a solid (0.8 mg, 2%). ¹H NMR (500 MHz, CD₃OD) δ ppm 1.46 (d, J=6.83 Hz, 3H), 1.55 (d, J=6.35 Hz, 6H), 2.30 (s, 3H), 2.57 (s, 3H), 2.65 (s, 3H), 4.81 (d, J=9.76 Hz, 2H), 4.98-5.04 (m, 1H), 5.06-5.13 (m, 1H), 7.13 (d, J=7.81 Hz, 2H), 7.22 (d, J=8.30 Hz, 2H), 8.52 (d, J=6.83 Hz, 1H); ESI-MS m/z [M+H]⁺ 382.2.

Example 56: (S)-2-(1-isopropyl-3,7-dimethyl-4-oxo-1,4-dihydro-5H-pyrazolo[3,4-d]pyridazin-5-yl)-N-(1-(4-(trifluoromethyl)phenyl)ethyl)acetamide

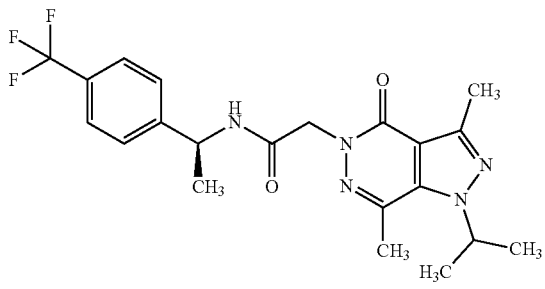

The title compound was prepared like EXAMPLE 42, using 1-isopropyl-3,7-dimethyl-1,5-dihydro-4H-pyrazolo[3,4-d]pyridazin-4-one and (S)-2-bromo-N-(1-(4-(trifluoromethyl)phenyl)ethyl)acetamide, and was obtained as a solid (20.2 mg, 50%). ESI-MS m/z [M+H]+ 436.2.

Example 57: (S)-2-(1-isopropyl-3,7-dimethyl-4-oxo-1,4-dihydro-5H-pyrazolo[3,4-d]pyridazin-5-yl)-N-(1-(4-methoxyphenyl)ethyl)acetamide

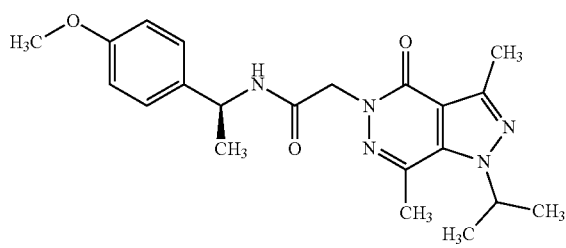

The title compound was prepared like EXAMPLE 42, using 1-isopropyl-3,7-dimethyl-1,5-dihydro-4H-pyrazolo[3,4-d]pyridazin-4-one and (S)-2-bromo-N-(1-(4-methoxyphenyl)ethyl)acetamide, and was obtained as a solid (2.1 mg, 6%). ESI-MS m/z [M+H]+ 398.2.

Example 58: (S)-2-(1-cyclopropyl-3-methyl-7-oxo-1,7-dihydro-6H-pyrazolo[3,4-d]pyridazin-6-yl)-N-(1-(5-(trifluoromethyl)pyridin-2-yl)ethyl)acetamide

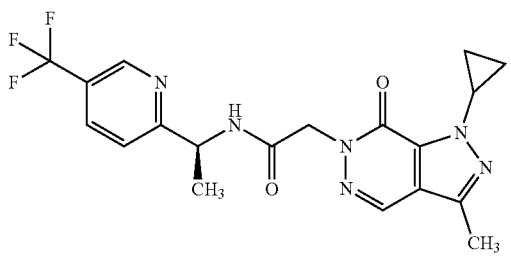

The title compound was prepared like EXAMPLE 42, using 1-cyclopropyl-3-methyl-1,6-dihydro-7H-pyrazolo[3,4-d]pyridazin-7-one and (S)-2-bromo-N-(1-(5-(trifluoromethyl)pyridin-2-yl)ethyl)acetamide, and was obtained as a solid (9.5 mg, 35%). ESI-MS m/z [M+H]+ 421.1.

Example 59: (S)-2-(1-isopropyl-3,4-dimethyl-7-oxo-1,7-dihydro-6H-pyrazolo[3,4-d]pyridazin-6-yl)-N-(1-(5-(trifluoromethyl)pyridin-2-yl)ethyl)acetamide

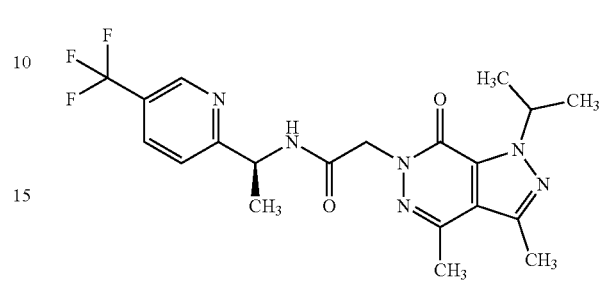

The title compound was prepared like EXAMPLE 42, using 1-isopropyl-3,4-dimethyl-1,6-dihydro-7H-pyrazolo[3,4-d]pyridazin-7-one and (S)-2-bromo-N-(1-(5-(trifluoromethyl)pyridin-2-yl)ethyl)acetamide, and was obtained as a solid (2.5 mg, 9%). $^1$H NMR (500 MHz, CDCl$_3$) δ ppm 1.48-1.55 (m, 9H), 2.55 (s, 3H), 2.60 (s, 3H), 4.82-4.94 (m, 2H), 5.21-5.31 (m, 1H), 5.61-5.72 (m, 1H), 7.34-7.41 (m, 1H), 7.42-7.48 (m, 1H), 7.92-7.97 (m, 1H), 8.73-8.78 (m, 1H); ESI-MS [M+H]+ 437.1.

Example 60: (S)-2-(1,3-dimethyl-7-oxo-1,7-dihydro-6H-pyrazolo[3,4-d]pyridazin-6-yl)-N-(1-(5-(trifluoromethyl)pyridin-2-yl)ethyl)acetamide

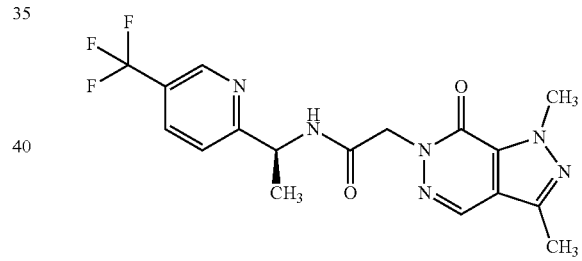

The title compound was prepared like EXAMPLE 42, using 1,3-dimethyl-1,6-dihydro-7H-pyrazolo[3,4-d]pyridazin-7-one and (S)-2-bromo-N-(1-(5-(trifluoromethyl)pyridin-2-yl)ethyl)acetamide, and was obtained as a solid (4.0 mg, 16%). ESI-MS m/z [M+H]+ 395.1.

Example 61: N-(1-(chroman-6-yl)ethyl)-2-(1-cyclopropyl-3,4-dimethyl-7-oxo-1,7-dihydro-6H-pyrazolo[3,4-d]pyridazin-6-yl)acetamide

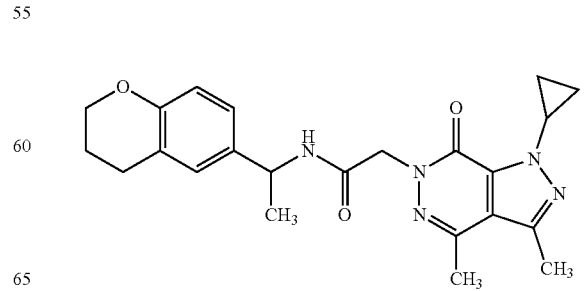

The title compound was prepared like EXAMPLE 42, using 1-cyclopropyl-3,4-dimethyl-1,6-dihydro-7H-pyrazolo[3,4-d]pyridazin-7-one and 2-bromo-N-(1-(chroman-6-yl)ethyl)acetamide, and was obtained as a solid (0.8 mg, 3%). ESI-MS m/z [M+H]+ 422.2.

Example 62: (S)-2-(1-cyclopropyl-3-methyl-4-oxo-1,4-dihydro-5H-pyrrolo[2,3-d]pyridazin-5-yl)-N-(1-(3-fluoro-4-methylphenyl)ethyl)acetamide

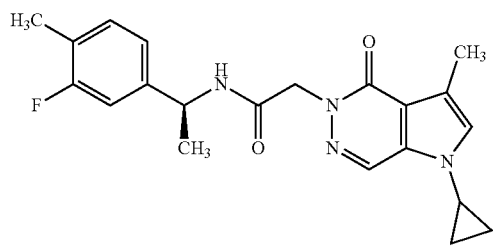

The title compound was prepared like EXAMPLE 42, using 1-cyclopropyl-3-methyl-1,5-dihydro-4H-pyrrolo[2,3-d]pyridazin-4-one and (S)-2-bromo-N-(1-(3-fluoro-4-methylphenyl)ethyl)acetamide, and was obtained as a solid (18.8 mg, 62%). $^1$H NMR (400 MHz, CDCl$_3$) δ ppm 1.02-1.17 (m, 4H), 1.45 (d, J=7.03 Hz, 3H), 2.23 (d, J=1.76 Hz, 3H), 2.46 (d, J=0.88 Hz, 3H), 3.39 (tt, J=7.12, 3.67 Hz, 1H), 4.85 (d, J=14.68 Hz, 1H), 4.95 (d, J=14.81 Hz, 1H), 5.09 (t, J=7.28 Hz, 1H), 6.64-6.75 (m, 1H), 6.88 (d, J=0.88 Hz, 1H), 6.91 (dd, J=10.85, 1.57 Hz, 1H), 6.97 (dd, J=7.84, 1.69 Hz, 1H), 7.10 (t, J=7.91 Hz, 1H), 8.22 (s, 1H); ESI-MS m/z [M+H]+ 383.2.

Example 63: (S)—N-(1-(4-chloro-2-methylphenyl)ethyl)-2-(1-cyclopropyl-3-methyl-4-oxo-1,4-dihydro-5H-pyrrolo[2,3-d]pyridazin-5-yl)acetamide

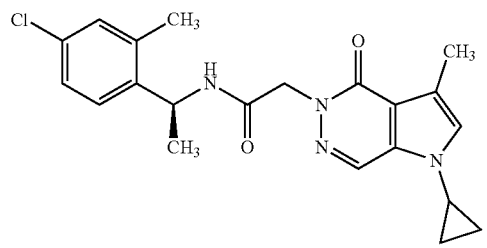

The title compound was prepared like EXAMPLE 42, using 1-cyclopropyl-3-methyl-1,5-dihydro-4H-pyrrolo[2,3-d]pyridazin-4-one and (S)-2-bromo-N-(1-(4-chloro-2-methylphenyl)ethyl)acetamide, and was obtained as a solid (22.7 mg, 72%). ESI-MS m/z [M+H]+ 399.1.

Example 64: (S)-2-(1-cyclopropyl-3-methyl-4-oxo-1,4-dihydro-5H-pyrrolo[2,3-d]pyridazin-5-yl)-N-(1-mesitylethyl)acetamide

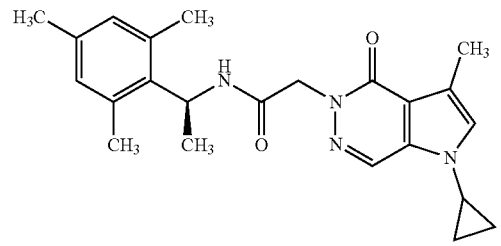

The title compound was prepared like EXAMPLE 42, using 1-cyclopropyl-3-methyl-1,5-dihydro-4H-pyrrolo[2,3-d]pyridazin-4-one and (S)-2-bromo-N-(1-mesitylethyl)acetamide, and was obtained as a solid (20.2 mg, 65%). $^1$H NMR (400 MHz, CDCl$_3$) δ ppm 0.98-1.07 (m, 2H), 1.07-1.16 (m, 2H), 1.46 (d, J=7.28 Hz, 3H), 2.21 (s, 3H), 2.36 (s, 6H), 2.44 (s, 3H), 3.38 (tt, J=7.11, 3.62 Hz, 1H), 4.80-4.94 (m, 2H), 5.51 (t, J=7.28 Hz, 1H), 6.77 (s, 2H), 6.85 (s, 1H), 6.96 (br, d, J=6.65 Hz, 1H), 8.18 (s, 1H); ESI-MS m/z [M+H]+ 393.2.

Example 65: (S)-2-(1-cyclopropyl-3-methyl-4-oxo-1,4-dihydro-5H-pyrrolo[2,3-d]pyridazin-5-yl)-N-(1-(2,4-dimethylphenyl)ethyl)acetamide

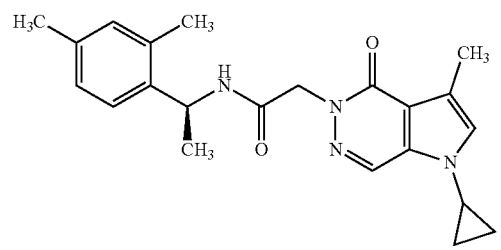

The title compound was prepared like EXAMPLE 42, using 1-cyclopropyl-3-methyl-1,5-dihydro-4H-pyrrolo[2,3-d]pyridazin-4-one and (S)-2-bromo-N-(1-(2,4-dimethylphenyl)ethyl)acetamide, and was obtained as a solid (19.9 mg, 66%). ESI-MS m/z [M+H]+ 379.2.

Example 66: (S)—N-(1-(2-chloro-4-fluorophenyl)ethyl)-2-(1-cyclopropyl-3-methyl-4-oxo-1,4-dihydro-5H-pyrrolo[2,3-d]pyridazin-5-yl)acetamide

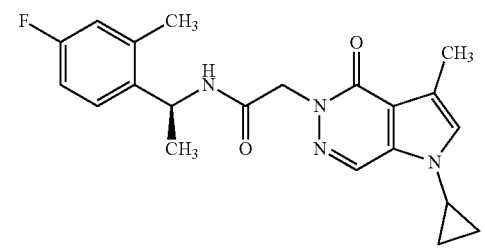

The title compound was prepared like EXAMPLE 42, using 1-cyclopropyl-3-methyl-1,5-dihydro-4H-pyrrolo[2,3- d]pyridazin-4-one and (S)-2-bromo-N-(1-(2-chloro-4-fluorophenyl)ethyl)acetamide, and was obtained as a solid (17.7 mg, 55%). $^1$H NMR (400 MHz, CDCl$_3$) δ ppm 1.02-1.10 (m, 2H), 1.10-1.18 (m, 2H), 1.45 (d, J=6.90 Hz, 3H), 2.46 (d, J=1.00 Hz, 3H), 3.40 (tt, J=7.12, 3.67 Hz, 1H), 4.84-4.96 (m, 2H), 5.34 (t, J=7.15 Hz, 1H), 6.89 (d, J=1.00 Hz, 1H), 6.92 (dd, J=8.28, 2.64 Hz, 1H), 6.98 (br d, J=6.78 Hz, 1H), 7.06 (dd, J=8.47, 2.57 Hz, 1H), 7.27-7.32 (m, 1H), 8.22 (s, 1H); ESI-MS [M+H]$^+$ 403.1.

Example 67: (S)—N-(1-(4-chloro-2-methoxyphenyl)propan-2-yl)-2-(1-cyclopropyl-3-methyl-4-oxo-1,4-dihydro-5H-pyrrolo[2,3-d]pyridazin-5-yl)acetamide

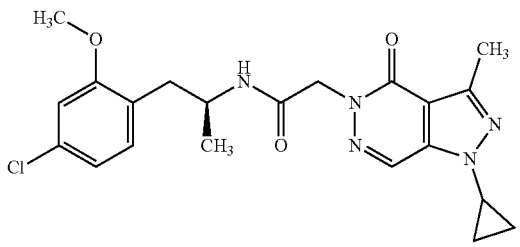

The title compound was prepared like EXAMPLE 42, using 1-cyclopropyl-3-methyl-1,5-dihydro-4H-pyrrolo[2,3-d]pyridazin-4-one and (S)-2-bromo-N-(1-(4-chloro-Z-methoxyphenyl)propan-2-yl)acetamide, and was obtained as a solid (20.7 mg, 61%). ESI-MS m/z [M+H]$^+$ 429.1.

Example 68: (S)-2-(1-cyclopropyl-3,4-dimethyl-7-oxo-1,7-dihydro-6H-pyrazolo[3,4-d]pyridazin-6-yl)-N-(1-(3-fluoro-4-methylphenyl)ethyl)acetamide

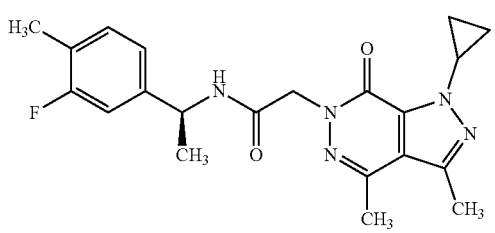

The title compound was prepared like EXAMPLE 42, using 1-cyclopropyl-3,4-dimethyl-1,6-dihydro-7H-pyrazolo[3,4-d]pyridazin-7-one and (S)-2-bromo-N-(1-(3-fluoro-4-methylphenyl)ethyl)acetamide, and was obtained as a solid (10.4 mg, 36%). ESI-MS m/z [M+H]$^+$ 398.2.

Example 69: (S)-2-(1-cyclopropyl-3,4-dimethyl-7-oxo-1,7-dihydro-6H-pyrazolo[3,4-d]pyridazin-6-yl)-N-(1-(2-fluoro-4-methylphenyl)ethyl)acetamide

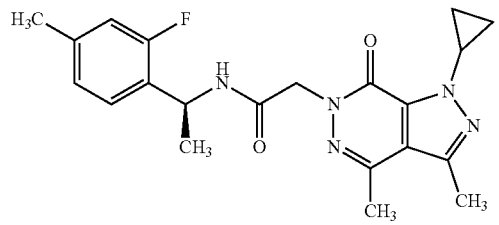

The title compound was prepared like EXAMPLE 42, using 1-cyclopropyl-3,4-dimethyl-1,6-dihydro-7H-pyrazolo[3,4-d]pyridazin-7-one and (S)-2-bromo-N-(1-(2-fluoro-4-methylphenyl)ethyl)acetamide, and was obtained as a solid (10.1 mg, 35%). $^1$H NMR (400 MHz, CDCl$_3$) δ ppm 1.05-1.19 (m, 2H), 1.30-1.41 (m, 2H), 1.48 (d, J=6.90 Hz, 3H), 2.33 (s, 3H), 2.54 (s, 3H), 2.56 (s, 3H), 4.57 (tt, J=7.59, 3.89 Hz, 1H), 4.85 (y, J=15.18 Hz, 2H), 5.21-5.30 (m, 1H), 6.61 (br d, J=8.28 Hz, 1H), 6.84 (d, J=11.92 Hz, 1H), 6.89 (d, J=7.65 Hz, 1H), 7.15 (t, J=7.84 Hz, 1H); ESI-MS m/z [M+H]$^+$ 398.2.

Example 70: (S)-2-(1-cyclopropyl-3,4-dimethyl-7-oxo-1,7-dihydro-6H-pyrazolo[3,4-d]pyridazin-6-yl)-N-(1-mesitylethyl)acetamide

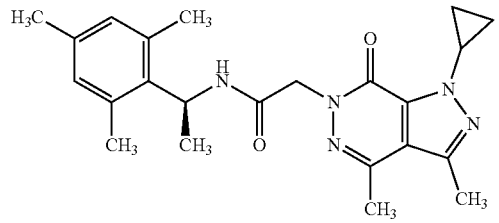 [SMILES: Cc1cc(C)c([C@H](C)NC(=O)Cn2nc(C)c3c(C)nn(C4CC4)c3c2=O)c(C)c1]

The title compound was prepared like EXAMPLE 42, using 1-cyclopropyl-3,4-dimethyl-1,6-dihydro-7H-pyrazolo[3,4-d]pyridazin-7-one and (S)-2-bromo-N-(1-mesitylethyl)acetamide, and was obtained as a solid (12.3 mg, 41%). ESI-MS m/z [M+H]$^+$ 408.2.

Example (S)—N-(1-(2-chloro-4-fluorophenyl)ethyl)-2-(1-cyclopropyl-3,4-dimethyl-7-oxo-1,7-dihydro-6H-pyrazolo[3,4-d]pyridazin-6-yl)acetamide

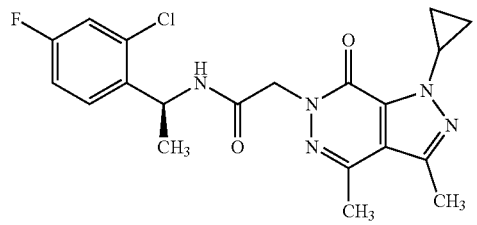 [SMILES: Cc1nn(CC(=O)N[C@@H](C)c2ccc(F)cc2Cl)c(=O)c2c1c(C)nn2C1CC1]

The title compound was prepared like EXAMPLE 42, using 1-cyclopropyl-3,4-dimethyl-1,6-dihydro-7H-pyrazolo[3,4-d]pyridazin-7-one and (S)-2-bromo-N-(1-(2-chloro-4-fluorophenyl)ethyl)acetamide, and was obtained as a solid (14.3 mg, 47%). NMR (400 MHz, CDCl₃) δ ppm 1.08-1.17 (m, 2H), 1.28-1.41 (m, 2H), 1.49 (d, J=7.03 Hz, 3H), 2.55 (s, 3H), 2.56 (s, 3H), 4.58 (tt, J=7.58, 3.84 Hz, 1H), 4.86 (q, J=15.06 Hz, 2H), 5.36 (quin, J=7.06 Hz, 1H), 6.62 (br d, J=6.90 Hz, 1H), 6.95 (td, J=8.28, 2.64 Hz, 1H), 7.09 (dd, J=8.41, 2.64 Hz, 1H), 7.31 (dd, J=8.72, 6.09 Hz, 1H); ESI-MS m/z [M+H]⁺ 418.1.

Example 72: (S)-2-(1,7-dimethyl-4-oxo-1,4-dihydro-5H-pyrazolo[3,4-d]pyridazin-5-yl)-N-(1-(4-(trifluoromethyl)phenyl)ethyl)acetamide

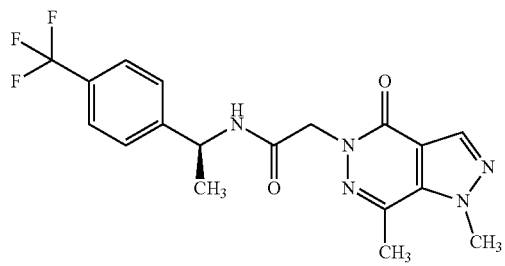 [SMILES: Cc1nn(CC(=O)N[C@@H](C)c2ccc(C(F)(F)F)cc2)c(=O)c2cnn(C)c12]

A 4 mL vial equipped with a stir bar was charged with K₂CO₃ (33 mg, 0.24 mmol) and (S)-2-bromo-N-(1-(4-(trifluoromethyl)phenyl)ethyl)acetamide (45 mg, 0.15 mmol). A solution of 1,7-dimethyl-1,5-dihydro-4H-pyrazolo[3,4-d]pyridazin-4-one (20 mg, 0.12 mmol) in DMF (0.5 mL) was added and the vial was capped. The reaction mixture was stirred at 40° C. for 18 h and then filtered through a 0.45 μm frit and purified by HPLC (Method B) to give the title compound (7.4 mg, 15%). ¹H NMR (500 MHz, CD₃CN) δ ppm 1.52 (d, J=6.83 Hz, 3H), 2.72 (s, 3H), 4.28 (s, 3H), 4.89 (d, J=3.42 Hz, 2H), 5.07-5.14 (m, 1H), 7.53-7.59 (m, 2H), 7.64 (d, J=8.30 Hz, 2H), 8.14 (s, 1H); ESI-MS m/z [M+H]⁺ 394.1.

Example 73: (S)-2-(1,7-dimethyl-4-oxo-1,4-dihydro-5H-pyrazolo[3,4-d]pyridazin-5-yl)-N-(1-(4-(trifluoromethoxy)phenyl)ethyl)acetamide

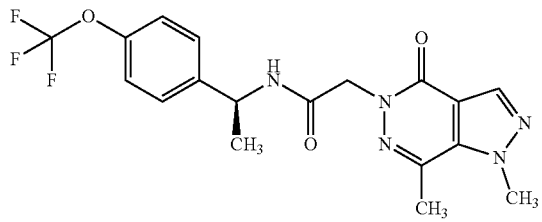 [SMILES: Cc1nn(CC(=O)N[C@@H](C)c2ccc(OC(F)(F)F)cc2)c(=O)c2cnn(C)c12]

The title compound (13.4 mg, 27%) was prepared like EXAMPLE 72, using 1,7-dimethyl-1,5-dihydro-4H-pyrazolo[3,4-d]pyridazin-4-one and (S)-2-bromo-N-(1-(4-(trifluoromethoxy)phenyl)ethyl)acetamide. ¹H NMR (500 MHz, CD₃OD) δ ppm 1.50 (d, J=6.83 Hz, 3H), 2.72 (s, 3H), 4.28 (s, 3H), 4.87 (d, J=3.91 Hz, 2H), 5.04-5.11 (m, 1H), 7.24 (dd, J=8.79, 0.98 Hz, 2H), 7.44-7.49 (m, 2H), 8.14 (s, 1H); ESI-MS m/z [M+H]⁺ 410.1.

Example 74: (S)-2-(1,7-dimethyl-4-oxo-1,4-dihydro-5H-pyrazolo[3,4-d]pyridazin-5-yl)-N-(1-(p-tolyl)ethyl)acetamide

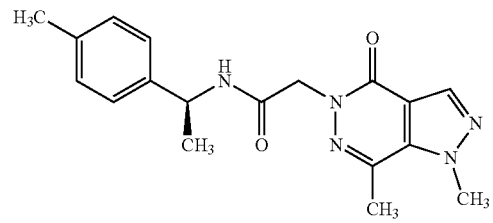 [SMILES: Cc1ccc([C@H](C)NC(=O)Cn2nc(C)c3c(cnn3C)c2=O)cc1]

The title compound (6.9 mg, 17%) was prepared like EXAMPLE 72, using 1,7-dimethyl-1,5-dihydro-4H-pyrazolo[3,4-d]pyridazin-4-one and (S)-2-bromo-N-(1-(p-tolyl)ethyl)acetamide, ESI-MS m/z [M+H]⁺ 340.1.

Example 75: (S)-2-(1-isopropyl-7-methyl-4-oxo-1,4-dihydro-5H-pyrazolo[3,4-d]pyridazin-5-yl)-N-(1-(4-(trifluoromethyl)phenyl)ethyl)acetamide

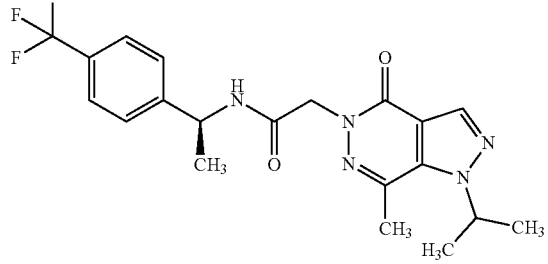

The title compound (7.7 mg, 18%) was prepared like EXAMPLE 72, using 1-isopropyl-7-methyl-1,5-dihydro-4H-pyrazolo[3,4-d]pyridazin-4-one and (S)-2-bromo-N-(1-(4-(trifluoromethyl)phenyl)ethyl)acetamide, ESI-MS m/z [M+H]⁺ 422.1.

Example 76: (S)-2-(1-isopropyl-7-methyl-4-oxo-1,4-dihydro-5H-pyrazolo[3,4-d]pyridazin-5-yl)-N-(1-(4-(trifluoromethoxy)phenyl)ethyl)acetamide

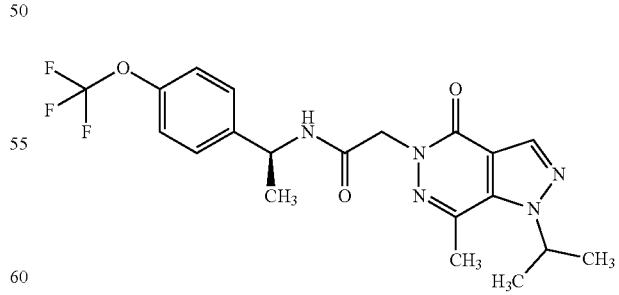

The title compound (4.2 mg, 9.2%) was prepared like EXAMPLE 72, using 1-isopropyl-7-methyl-1,5-dihydro-4H-pyrazolo[3,4-d]pyridazin-4-one and (S)-2-bromo-N-(1-(4-(trifluoromethoxy)phenyl)ethyl)acetamide. ESI-MS m/z [M+H]⁺ 438.2.

Example 77: (S)-2-(1-isopropyl-7-methyl-4-oxo-1,4-dihydro-5H-pyrazolo[3,4-d]pyridazin-5-yl)-N-(1-(p-tolyl)ethyl)acetamide

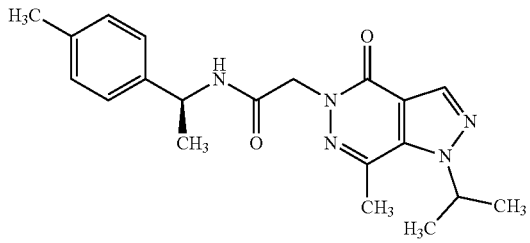 [SMILES: Cc1ccc([C@H](C)NC(=O)Cn2nc(C)c3c(cnn3C(C)C)c2=O)cc1]

The title compound (9.6 mg, 25%) was prepared like EXAMPLE 72, using 1-isopropyl-7-methyl-1,5-dihydro-4H-pyrazolo[3,4-d]pyridazin-4-one and (S)-2-bromo-N-(1-(p-tolyl)ethyl)acetamide. $^1$H NMR (500 MHz, CD$_3$OD) δ ppm 1.47 (d, J=6.83 Hz, 3H), 1.60 (d, J=6.83 Hz, 6H), 2.31 (s, 3H), 2.72 (s, 3H), 4.86-4.88 (m, 2H), 4.99-5.05 (m, 1H), 5.15-5.24 (m, 1H), 7.14 (d, J=8.30 Hz, 2H), 7.22-7.25 (m, 2H), 8.18-8.22 (m, 1H); ESI-MS [M+H]$^+$ 368.2.

Example 78: (S)-2-(1-cyclopropyl-7-methyl-4-oxo-1,4-dihydro-5H-pyrazolo[3,4-d]pyridazin-5-yl)-N-(1-(4-(trifluoromethyl)phenyl)ethyl)acetamide

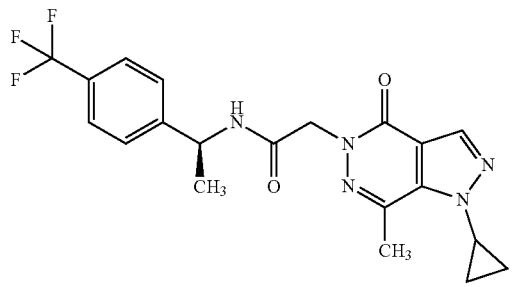 [SMILES: Cc1nn(CC(=O)N[C@@H](C)c2ccc(C(F)(F)F)cc2)c(=O)c2cnn(C3CC3)c12]

The title compound (4.9 mg, 11%) was prepared like EXAMPLE 72, using 1-cyclopropyl-7-methyl-1,5-dihydro-4H-pyrazolo[3,4-d]pyridazin-4-one and (S)-2-bromo-N-(1-(4-(trifluoromethyl)phenyl)ethyl)acetamide. $^1$H NMR (500 MHz, CD$_3$OD) δ ppm 1.24 (d, J=4.80 Hz, 2H), 1.38 (s, 2H), 1.51 (d, J=7.07 Hz, 3H), 2.82 (s, 3H), 3.96-4.04 (m, 1H), 4.88 (d, J=2.53 Hz, 2H), 5.06-5.15 (m, 1H), 7.52-7.57 (m, 2H), 7.62 (s, 2H), 8.08 (s, 1H); ESI-MS m/z [M+H]$^+$ 420.4.

Example 79: (S)-2-(1-cyclopropyl-7-methyl-4-oxo-1,4-dihydro-5/1-pyrazolo[3,4-d]pyridazin-5-yl)-N-(1-(4-(trifluoromethoxy)phenyl)ethyl)acetamide

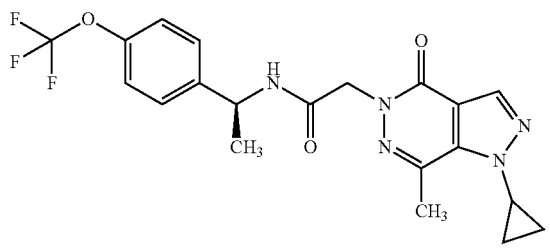 [SMILES: Cc1nn(CC(=O)N[C@@H](C)c2ccc(OC(F)(F)F)cc2)c(=O)c2cnn(C3CC3)c12]

The title compound (2.9 mg, 6.3%) was prepared like EXAMPLE 72, using 1-cyclopropyl-7-methyl-1,5-dihydro-4H-pyrazolo[3,4-d]pyridazin-4-one and (S)-2-bromo-N-(1-(4-(trifluoromethoxy)phenyl)ethyl)acetamide. ESI-MS m/z [M+H]$^+$ 436.4.

Example 80: (S)-2-(1-cyclopropyl-7-methyl-4-oxo-1,4-dihydro-5H-pyrazolo[3,4-d]pyridazin-5-yl)-N-(1-(p-tolyl)ethyl)acetamide

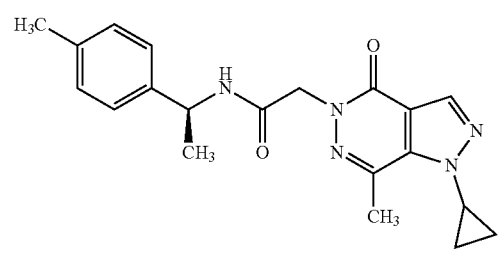 [SMILES: Cc1ccc([C@H](C)NC(=O)Cn2nc(C)c3c(cnn3C3CC3)c2=O)cc1]

The title compound (2.5 mg, 6.5%) was prepared like EXAMPLE 72, using 1-cyclopropyl-7-methyl-1,5-dihydro-4H-pyrazolo[3,4-d]pyridazin-4-one and (S)-2-bromo-N-(1-(p-tolyl)ethyl)acetamide. $^1$H NMR (500 MHz, CD$_3$OD) δ ppm 1.20-1.27 (m, 2H), 1.36-1.40 (m, 2H), 1.46 (d, J=7.07 Hz, 3H), 2.30 (s, 3H), 2.82 (s, 3H), 3.97-4.04 (m, 1H), 4.98-5.05 (m, 1H), 7.13 (d, J=7.83 Hz, 2H), 7.23 (d, J=8.08 Hz, 2H), 8.08 (s, 1H); ESI-MS m/z [M+H]$^+$ 366.4.

Example 81: (S)-2-(1-cyclopropyl-7-methyl-4-oxo-1,4-dihydro-5H-pyrazolo[3,4-d]pyridazin-5-yl)-N-(1-(2-fluoro-4-methylphenyl)ethyl)acetamide

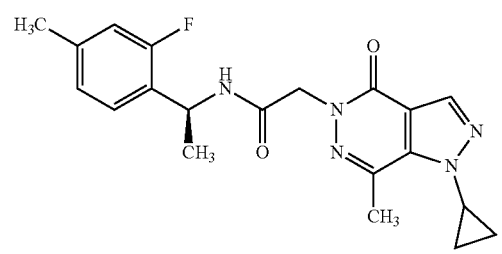 [SMILES: Cc1ccc([C@H](C)NC(=O)Cn2nc(C)c3c(cnn3C3CC3)c2=O)c(F)c1]

The title compound (3.9 mg, 9.4%) was prepared like EXAMPLE 72, using 1-cyclopropyl-7-methyl-1,5-dihydro-4H-pyrazolo[3,4-d]pyridazin-4-one and (S)-2-bromo-N-(1-(2-fluoro-4-methylphenyl)ethyl)acetamide. ESI-MS m/z [M+H]$^+$ 384.4.

Example 82: (S)-2-(1,7-dimethyl-4-oxo-1,4-dihydro-5H-pyrazolo[3,4-d]pyridazin-5-yl)-N-(2-fluoro-4-methylphenyl)ethyl)acetamide

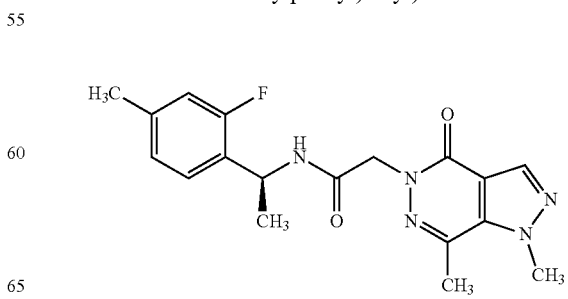

A 4 ml, vial equipped with a stir bar was charged with K₂CO₃ (34 mg, 0.24 mmol) and (S)-2-bromo-N-(1-(2-fluoro-4-methylphenyl)ethyl)acetamide (40 mg, 0.15 mmol). A solution of 1,7-dimethyl-1,5-dihydro-4H-pyrazolo[3,4-d]pyridazin-4-one (20 mg, 0.12 mmol) in NMP (0.5 mL) was added and the vial was capped. The reaction mixture was stirred at 50° C. for 18 hours and then filtered through a 0.45 μm frit and purified by HPLC (Method B) to give the title compound as a white solid (322 mg, 7.4%). ¹H NMR (500 MHz, CD₃CN) δ ppm 1.43-1.45 (m, 3H), 2.17 (s, 2H), 2.34 (s, 3H), 2.68 (s, 3H), 4.23 (s, 3H), 4.75 (s, 2H), 5.16-5.23 (m, 1H), 6.91 (d, J=11.72 Hz, 1H), 6.99 (d, J=7.81 Hz, 2H), 7.25 (t, J=8.05 Hz, 1H), 8.07 (s, 1H); ESI-MS m/z [M+H]⁺ 358.1.

Example 83: (S)—N-(1-(2-fluoro-4-methylphenyl)ethyl)-2-(1-isopropyl-7-methyl-4-oxo-1,4-dihydro-5H-pyrazolo[3,4-d]pyridazin-5-yl)acetamide

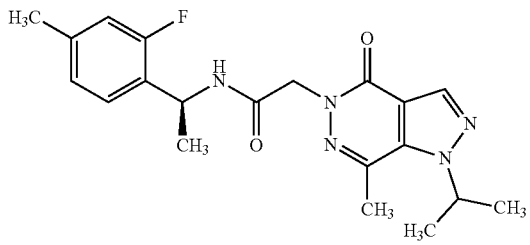 [SMILES: Cc1ccc([C@H](C)NC(=O)Cn2nc(C)c3c(cnn3C(C)C)c2=O)c(F)c1]

The title compound (10.5 mg, 26%) was prepared like EXAMPLE 82, using 1-isopropyl-7-methyl-1,5-dihydro-4H-pyrazolo[3,4-d]pyridazin-4-one and (S)-2-bromo-N-(1-(2-fluoro-4-methylphenyl)ethyl)acetamide. ¹H NMR (500 MHz, CDCl₃) δ ppm 1.46 (d. J=6.83 Hz, 3H), 1.63 (d, J=6.83 Hz, 6H), 2.31 (s, 3H), 2.69 (s, 3H), 4.84 (d, J=2.93 Hz, 2H), 5.00-5.09 (m, 1H), 5.18-5.27 (m, 1H), 6.73-6.79 (m, 1H), 6.80-6.84 (m, 1H), 6.86-6.90 (m, 1H), 7.14 (s, 1H), 8.26 (s, 1H); ESI-MS m/z [M+H]⁺ 386.1.

Example 84: 5-(2-(2-(4-chlorophenyl)pyrrolidin-1-yl)-2-oxoethyl)-3-cyclopropyl-1-methyl-1,5-dihydro-4H-pyrazolo[3,4-d]pyridazin-4-one

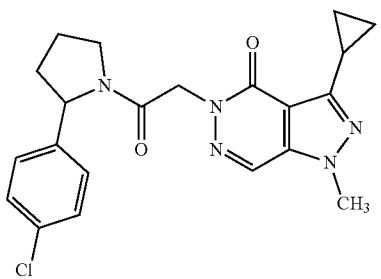 [SMILES: Cn1nc(C2CC2)c2c(=O)n(CC(=O)N3CCCC3c3ccc(Cl)cc3)ncc21]

The title compound (9.4 mg, 28%) was prepared like EXAMPLE 82, using 3-cyclopropyl-1-methyl-1,5-dihydro-4H-pyrazolo[3,4-d]pyridazin-4-one and 2-bromo-1-(2-(4-chlorophenyl)pyrrolidin-1-yl)ethan-1-one. ESI-MS m/z [M+H]⁺ 412.1.

Example 85: 6-(2-(2-(4-chlorophenyl)pyrrolidin-1-yl)-2-oxoethyl)-1-cyclopropyl-3-methyl-1,6-dihydro-7H-pyrazolo[3,4-d]pyridazin-7-one

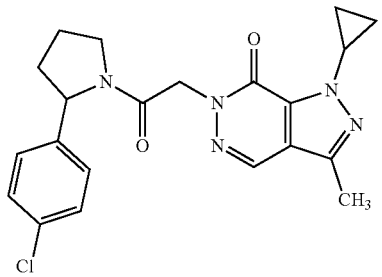 [SMILES: Cc1nn(C2CC2)c2c(=O)n(CC(=O)N3CCCC3c3ccc(Cl)cc3)ncc12]

The title compound (10 mg, 30%) was prepared like EXAMPLE 82, using 1-cyclopropyl-3-methyl-1,6-dihydro-7H-pyrazolo[3,4-d]pyridazin-7-one and 2-bromo-1-(2-(4-chlorophenyl)pyrrolidin-1-yl)ethan-1-one. ESI-MS m/z [M+H]⁺ 412.1.

Example 86: (S)-2-(1-isopropyl-4-oxo-1,4-dihydro-5H-pyrazolo[3,4-d]pyridazin-5-yl)-N-(1-(4-(trifluoromethyl)phenyl)ethyl)acetamide

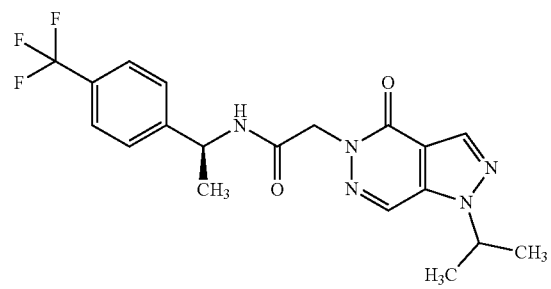 [SMILES: CC(C)n1ncc2c(=O)n(CC(=O)N[C@@H](C)c3ccc(C(F)(F)F)cc3)ncc21]

A 4 mL vial equipped with a stir bar was charged with Cs₂CO₃ (73 mg, 0.22 mmol) and (S)-2-bromo-N-(1-(4-(trifluoromethyl)phenyl)ethyl)acetamide (42 mg, 0.14 mmol). A solution of 1-isopropyl-1,5-dihydro-4H-pyrazolo[3,4-d]pyridazin-4-one (20 mg, 0.11 mmol) in DMF (0.5 mL) was added and the vial was capped. The reaction mixture was stirred at 60° C. for 18 hours and then filtered through a 0.45 μm frit and purified by HPLC (Method B) to give the title compound (31 mg, 68%). NMR (500 MHz, CD₃OD) δ ppm 1.52 (d, J=6.83 Hz, 3H), 1.58 (d, J=6.83 Hz, 6H), 4.94 (d, J=4.88 Hz, 2H), 5.01 (s, 1H), 5.07-5.15 (m, 1H), 7.53-7.58 (m, 2H), 7.63 (d, J=8.30 Hz, 2H), 8.21 (s, 1H), 8.53 (s, 1H); ESI-MS m/z [M+H]⁺ 408.1.

Example 87: (S)-2-(1-isopropyl-4-oxo-1,4-dihydro-5H-pyrazolo[3,4-d]pyridazin-5-yl)-N-(1-(4-(trifluoromethoxy)phenyl)ethyl)acetamide

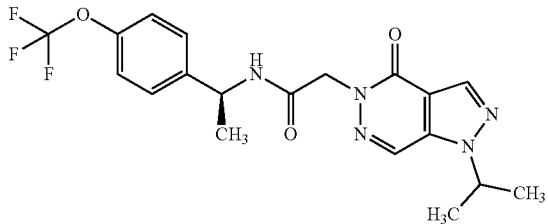 [SMILES: CC(C)n1ncc2c(=O)n(CC(=O)N[C@@H](C)c3ccc(OC(F)(F)F)cc3)ncc21]

The title compound (23 mg, 48%) was prepared like EXAMPLE 86, using 1-isopropyl-1,5-dihydro-4H-pyrazolo[3,4-d]pyridazin-4-one and (S)-2-bromo-N-(1-(4-(trifluoromethoxy)phenyl)ethyl)acetamide. ESL-MS m/z [M+H]+ 424.1.

Example 88: (S)—N-(1-(2-fluoro-4-methylphenyl)ethyl)-2-(1-isopropyl-4-oxo-1,4-dihydro-5H-pyrazolo[3,4-d]pyridazin-5-yl)acetamide

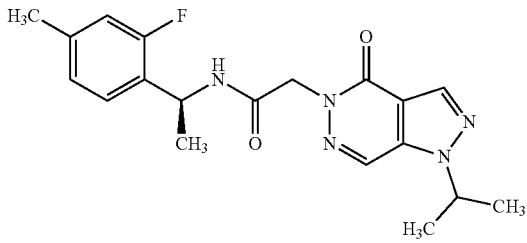 [SMILES: Cc1ccc([C@H](C)NC(=O)Cn2ncc3c(cnn3C(C)C)c2=O)c(F)c1]

The title compound (30 mg, 73%) was prepared like EXAMPLE 86, using 1-isopropyl-1,5-dihydro-4H-pyrazolo[3,4-d]pyridazin-4-one and (S)-2-bromo-N-(1-(2-fluoro-4-methylphenyl)ethyl)acetamide. $^1$H NMR (500 MHz, CD$_3$OD) δ ppm 1.44-1.48 (m, 3H), 1.58 (d, J=6.35 Hz, 6H), 2.32 (s, 3H), 4.88-4.97 (m, 2H), 4.97-5.04 (m, 1H), 5.20-5.27 (m, 1H), 6.85-6.90 (m, 1H), 6.97 (d, J=7.81 Hz, 1H), 7.27 (t, J=8.05 Hz, 1H), 8.20 (s, 1H), 8.52 (s, 1H); ESI-MS m/z [M+H]+ 372.2.

Example 89: (S)-2-(1-isopropyl-4-oxo-1,4-dihydro-5H-pyrazolo[3,4-d]pyridazin-5-yl)-N-(1-(p-tolyl)ethyl)acetamide

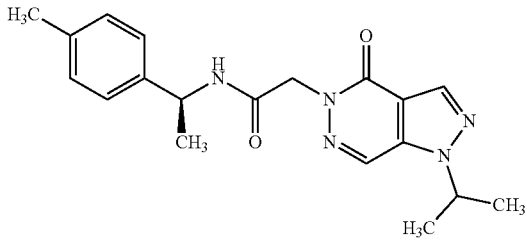

A solution of 1-isopropyl-1,5-dihydro-4H-pyrazolo[3,4-d]pyridazin-4-one (0.500 g, 2.81 mmol) and (S)-2-bromo-N-(1-(p-tolyl)ethyl)acetamide (0.719 g, 2.81 mmol) in DMA (15 mL) was cooled in an ice bath. To the cooled solution was added Cs$_2$CO$_3$ (1.371 g, 4.21 mmol) in one portion and the ice bath was allowed to warm to RT. The mixture was stirred overnight and then ice water (60 mL) was slowly added, dropwise. The mixture was stirred vigorously in an ice bath for 1 hour, filtered, washed with water; and recrystallized from EtOAc to give the title compound as a colorless solid (0.493 g, 50%). $^1$H NMR (400 MHz, DMSO-d$_6$) δ ppm 8.65 (d, J=0.75 Hz, 1H), 8.50 (d, J=7.91 Hz; 1H), 8.25 (s, 1H), 7.17-7.25 (m, 2H), 7.09-7.16 (m, 2H), 5.05 (spt, J=6.67 Hz, 1H), 4.88 (quin, J=7.22 Hz, 1H), 4.70-4.82 (m, 2H), 2.27 (s, 3H), 1.49 (d, J=6.65 Hz, 6H), 1.35 (d, J=6.90 Hz, 3H); ESI-MS m/z [M+H]+ 354.4.

Example 90: (S)-2-(1-cyclopropyl-4-oxo-1,4-dihydro-5H-pyrazolo[3,4-d]pyridazin-5-yl)-N-(1-(2-fluoro-4-methylphenyl)ethyl)acetamide

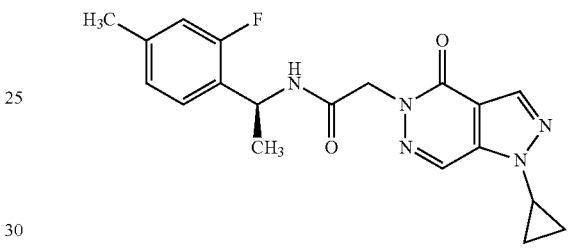

To a solution of (S)-2-bromo-N-(1-(2-fluoro-4-methylphenyl)ethyl)acetamide (15 mg, 0.054 mmol) in DMF (0.6 mL) was added 1-cyclopropyl-1,5-dihydro-4H-pyrazolo[3,4-d]pyridazin-4-one (8 mg, 0.045 mmol) and K$_2$CO$_3$ (16 mg, 0.114 mmol). The reaction mixture was stirred at 28-45° C. for 18 hours and then diluted in DMF, filtered through a hydrophilic PTFE 0.45 μm filter (Millipore® Millex-LCR) and purified by HPLC (Method B). The product-containing fraction was concentrated under reduced pressure to give the title compound as a white solid (9.6 mg, 57%). $^1$H NMR (500 MHz, CDCl$_3$) δ ppm 1.21-1.27 (m, 2H), 1.28-1.33 (m, 2H), 1.47 (d, J=6.83 Hz, 3H), 2.31 (s, 3H), 3.65-3.72 (m, 1H), 4.89 (s, 2H), 5.18-5.27 (m, 1H), 6.49-6.57 (m, 1H), 6.80-6.86 (m, 1H), 6.86-6.90 (m, 1H), 7.10-7.16 (m, 1H), 8.17 (d, J=0.98 Hz, 1H) (d, J=0.98 Hz, 1H); ESI-MS m/z [M+H]+ 370.1.

Example 91: (S)-2-(1-cyclopropyl-4-oxo-1,4-dihydro-5H-pyrazolo[3,4-d]pyridazin-5-yl)-N-(1-(p-tolyl)ethyl)acetamide

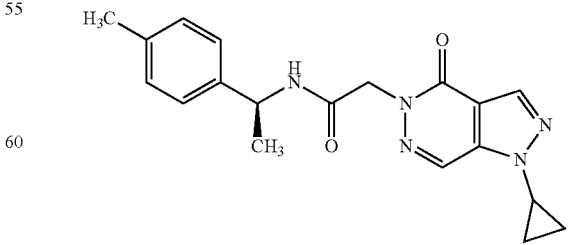

The title compound was prepared like EXAMPLE 90, using 1-cyclopropyl-1,5-dihydro-4H-pyrazolo[3,4-d]

pyridazin-4-one and (S)-2-bromo-N-(1-(p-tolyl)ethyl)acetamide, and was obtained as a white solid (33.4 mg, 84%). ¹H NMR (500 MHz, CDCl₃) δ ppm 1.21-1.27 (m, 2H), 1.27-1.32 (m, 2H), 1.48 (d, J=7.32 Hz, 3H), 2.32 (s, 3H), 3.65-3.72 (m, 1H), 4.88 (s, 2H), 5.07-5.14 (m, 1H), 6.26-6.33 (m, 1H), 7.10-7.15 (m, 2H), 7.17-7.21 (m, 2H), 8.15-8.17 (m, 1H), 8.31-8.34 (m, 1H); ESI-MS m/z [M+H]⁺ 352.2.

Example 92: (S)—N-(1-(2-fluoro-4-methylphenyl)ethyl)-2-(1-isopropyl-3-methyl-4-oxo-1,4-dihydro-5H-pyrazolo[3,4-d]pyridazin-5-yl)acetamide

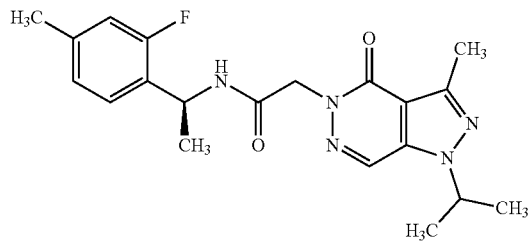 [SMILES: Cc1ccc([C@H](C)NC(=O)Cn2ncc3c(c(C)nn3C(C)C)c2=O)c(F)c1]

The title compound was prepared like EXAMPLE 90, using 1-isopropyl-3-methyl-1,5-dihydro-4H-pyrazolo[3,4-d]pyridazin-4-one and (S)-2-bromo-N-(1-(2-fluoro-4-methylphenyl)ethyl)acetamide, and was obtained as a white solid (18.5 mg, 62%). ¹H NMR (500 MHz, CDCl₃) δ ppm 1.47 (d, J=6.83 Hz, 3H), 1.60 (d, J=6.83 Hz, 6H), 2.31 (s, 3H), 2.66 (s, 3H), 4.64-4.75 (m, 1H), 4.85 (d, J=1.46 Hz, 2H), 5.19-5.28 (m, 1H), 6.48-6.58 (m, 1H), 6.79-6.85 (m, 1H), 6.85-6.91 (m, 1H), 7.10-7.15 (m, 1H), 8.11 (s, 1H); ESI-MS m/z [M+H]⁺ 386.2.

Example 93: (S)-2-(1-isopropyl-3-methyl-4-oxo-1,4-dihydro-5H-pyrazolo[3,4-d]pyridazin-5-yl)-N-(1-(4-(trifluoromethoxy)phenyl)ethyl)acetamide

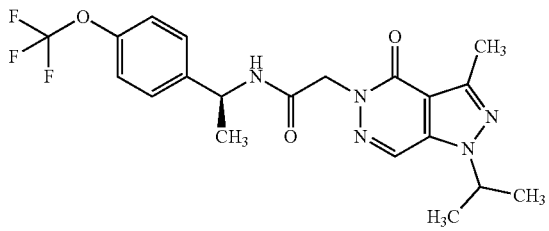 [SMILES: Cc1nn(C(C)C)c2cnn(CC(=O)N[C@@H](C)c3ccc(OC(F)(F)F)cc3)c(=O)c12]

The title compound was prepared like EXAMPLE 90, using 1-isopropyl-3-methyl-1,5-dihydro-4H-pyrazolo[3,4-d]pyridazin-4-one and (S)-2-bromo-N-(1-(4-(trifluoromethoxy)phenyl)ethyl)acetamide, and was obtained as a white solid (23.3 mg, 68%). ESI-MS m/z [M+H]⁺ 438.1.

Example 94: (S)-2-(1-isopropyl-3-methyl-4-oxo-1,4-dihydro-5H-pyrazolo[3,4-d]pyridazin-5-yl)-N-(1-(4-(trifluoromethyl)phenyl)ethyl)acetamide

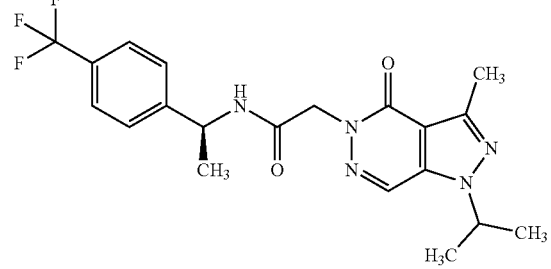

The title compound was prepared like EXAMPLE 90, using 1-isopropyl-3-methyl-1,5-dihydro-4H-pyrazolo[3,4-d]pyridazin-4-one and (S)-2-bromo-N-(1-(4-(trifluoromethyl)phenyl)ethyl)acetamide, and was obtained as a white solid (21.3 mg, 65%). ESI-MS m/z [M+H]⁺ 422.1.

Example 95: (S)-2-(3-cyclopropyl-1-isopropyl-4-oxo-1,4-dihydro-5H-pyrazolo[3,4-d]pyridazin-5-yl)-N-(1-(2-fluoro-4-methylphenyl)ethyl)acetamide

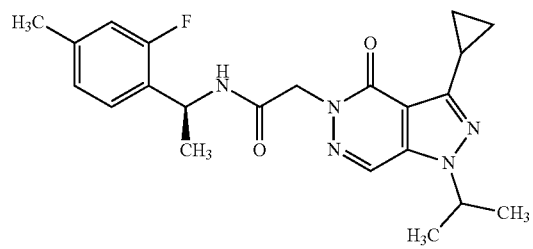 [SMILES: Cc1ccc([C@H](C)NC(=O)Cn2ncc3c(c(C4CC4)nn3C(C)C)c2=O)c(F)c1]

The title compound was prepared like EXAMPLE 90, using 3-cyclopropyl-1-isopropyl-1,5-dihydro-4H-pyrazolo[3,4-d]pyridazin-4-one and (S)-2-bromo-N-(1-(2-fluoro-4-methylphenyl)ethyl)acetamide, and was obtained as a white solid (12.2 mg, 43%). ESI-MS m/z [M+H]⁺ 412.2.

Example 96: (S)-2-(3-cyclopropyl-1-isopropyl-4-oxo-1,4-dihydro-5H-pyrazolo[3,4-d]pyridazin-5-yl)-N-(1-(4-(trifluoromethoxy)phenyl)ethyl)acetamide

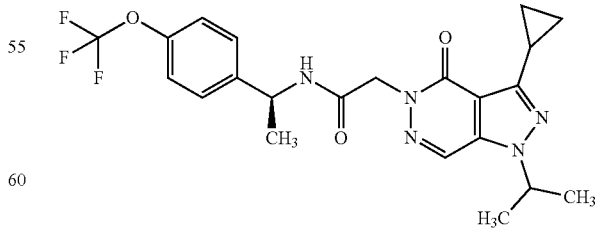

The title compound was prepared like EXAMPLE 90, using 3-cyclopropyl-1-isopropyl-1,5-dihydro-4H-pyrazolo[3,4-d]pyridazin-4-one and (S)-2-bromo-N-(1-(4-(trifluoromethoxy)phenyl)ethyl)acetamide, and was obtained as a white solid (15.6 mg, 49%). ¹H NMR (500 MHz, CDCl₃) δ ppm 1.02-1.08 (m, 2H), 1.09-1.16 (m, 2H), 1.48 (d, J=6.83 Hz, 3H), 1.55 (d, J=6.83 Hz, 6H), 2.51-2.60 (m, 1H), 4.67 (t, J=6.83 Hz, 1H), 4.81-4.92 (m, 2H), 5.13 (quip, J=7.08 Hz, 1H), 6.49-6.57 (m, 1H), 7.15 (d, J=8.30 Hz, 2H), 7.32 (d, J=8.79 Hz, 2H), 8.10 (s, 1H); ESI-MS m/z [M+H]⁺ 464.2.

Example 97: (S)-2-(3-cyclopropyl-1-isopropyl-4-oxo-1,4-dihydro-5H-pyrazolo[3,4-d]pyridazin-5-yl)-N-(1-(p-tolyl)ethyl)acetamide

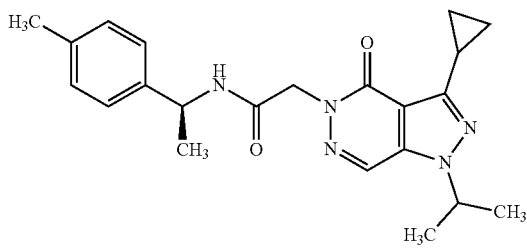 [SMILES: Cc1ccc([C@H](C)NC(=O)Cn2ncc3c(c(C4CC4)nn3C(C)C)c2=O)cc1]

The title compound was prepared like EXAMPLE 90, using 3-cyclopropyl-1-isopropyl-1,5-dihydro-4H-pyrazolo[3,4-d]pyridazin-4-one and (S)-2-bromo-N-(1-(p-tolyl)ethyl)acetamide, and was obtained as a white solid (3.6 mg, 13%). ESI-MS m/z [M+H]⁺ 394.2.

Example 98: (S)-2-(3-cyclopropyl-1-isopropyl-4-oxo-1,4-dihydro-5H-pyrazolo[3,4-d]pyridazin-5-yl)-N-(1-(4-(trifluoromethyl)phenyl)ethyl)acetamide

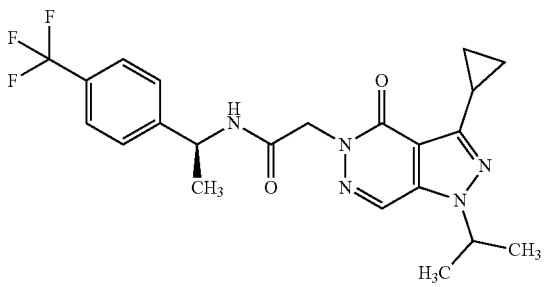 [SMILES: CC(C)n1nc(C2CC2)c2c(=O)n(CC(=O)N[C@@H](C)c3ccc(C(F)(F)F)cc3)ncc21]

The title compound was prepared like EXAMPLE 90, using 3-cyclopropyl-1-isopropyl-1,5-dihydro-4H-pyrazolo[3,4-d]pyridazin-4-one and (S)-2-bromo-N-(1-(4-(trifluoromethyl)phenyl)ethyl)acetamide, and was obtained as a white solid (9.2 mg, 30%). ¹H NMR (500 MHz, CDCl₃) δ ppm 1.02-1.09 (m, 2H), 1.10-1.16 (m, 2H), 1.50 (d, J=7.32 Hz, 3H), 1.56 (d, J=6.83 Hz, 6H), 2.56 (tt, J=8.36, 5.31 Hz, 1H), 4.67 (spt, J=6.67 Hz, 1H), 4.82-4.93 (m, 2H), 5.16 (quin, J=7.08 Hz, 1H), 6.58-6.66 (m, 1H), 7.41 (d, J=7.81 Hz, 2H), 7.56 (d, J=7.81 Hz, 2H), 8.10 (s, 1H); [M+H]⁺ 448.2.

Example 99: (S)-2-(1,3-dimethyl-4-oxo-1,4-dihydro-5H-pyrazolo[3,4-d]pyridazin-5-yl)-N-(2-fluoro-4-methylphenyl)ethyl)acetamide

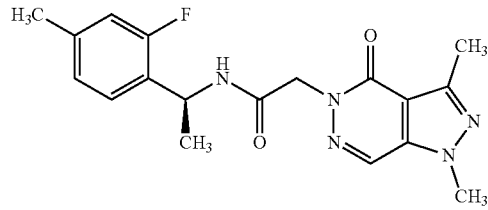 [SMILES: Cc1ccc([C@H](C)NC(=O)Cn2ncc3c(c(C)nn3C)c2=O)c(F)c1]

The title compound was prepared like EXAMPLE 90, using 1,3-dimethyl-1,5-dihydro-4H-pyrazolo[3,4-d]pyridazin-4-one and (S)-2-bromo-N-(1-(2-fluoro-4-methylphenyl)ethyl)acetamide, and was obtained as a white solid (5.5 mg, 17%). ESI-MS m/z [M+H]⁺ 358.2.

Example 100: (S)-2-(1-isopropyl-3,7-dimethyl-4-oxo-1,4-dihydro-5H-pyrazolo[3,4-d]pyridazin-5-yl)-N-(1-(4-(trifluoromethoxy)phenyl)ethyl)acetamide

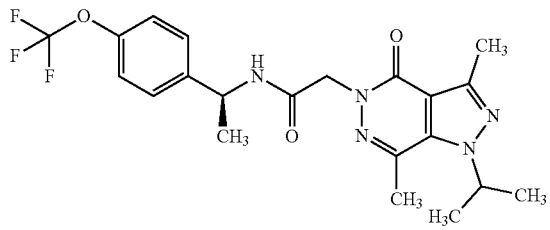 [SMILES: Cc1nn(C(C)C)c2c(C)nn(CC(=O)N[C@@H](C)c3ccc(OC(F)(F)F)cc3)c(=O)c12]

The title compound was prepared like EXAMPLE 90, using 1-isopropyl-3,7-dimethyl-1,5-dihydro-4H-pyrazolo[3,4-d]pyridazin-4-one and (S)-2-bromo-N-(1-(4-(trifluoromethoxy)phenyl)ethyl)acetamide, and was obtained as a solid (4.7 mg, 14%). ESI-MS m/z [M+H]⁺ 452.2.

Example 101: (S)-2-(1-cyclopropyl-3,4-dimethyl-7-oxo-1,7-dihydro-6H-pyrazolo[3,4-d]pyridazin-6-yl)-N-(1-(5-(trifluoromethyl)pyridin-2-yl)ethyl)acetamide

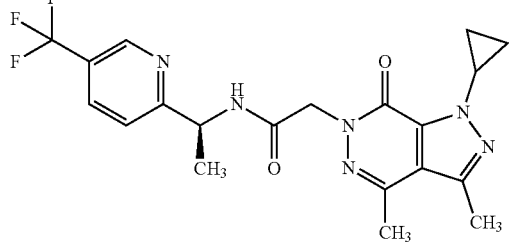

The title compound was prepared like EXAMPLE 90, using 1-cyclopropyl-3,4-dimethyl-1,6-dihydro-7H-pyrazolo[3,4-d]pyridazin-7-one and (S)-2-bromo-N-(1-(5-(trifluoromethyl)pyridin-2-yl)ethyl)acetamide, and was obtained as a solid (0.9 mg, 3%). ESI-MS m/z [M+H]⁺ 435.2.

Example 102: (S)—N-(1-(5-(trifluoromethyl)pyridin-2-yl)ethyl)-2-(1,3,4-trimethyl-7-oxo-1,7-dihydro-6H-pyrazolo[3,4-d]pyridazin-6-yl)acetamide

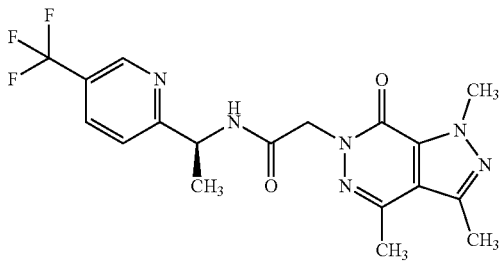 [SMILES: Cc1nn(CC(=O)N[C@@H](C)c2ccc(C(F)(F)F)cn2)c(=O)c2c1c(C)nn2C]

The title compound was prepared like EXAMPLE 90, using 1,3,4-trimethyl-1,6-dihydro-7H-pyrazolo[3,4-d]pyridazin-7-one and (S)-2-bromo-N-(1-(5-(trifluoromethyl)pyridin-2-yl)ethyl)acetamide, and was obtained as a solid (0.7 mg, 3%). ESI-MS m/z [M+H]⁺ 409.1.

Example 103: (S)-2-(1-isopropyl-3-methyl-7-oxo-1,7-dihydro-6H-pyrazolo[3,4-d]pyridazin-6-yl)-N-(1-(5-(trifluoromethyl)pyridin-2-yl)ethyl)acetamide

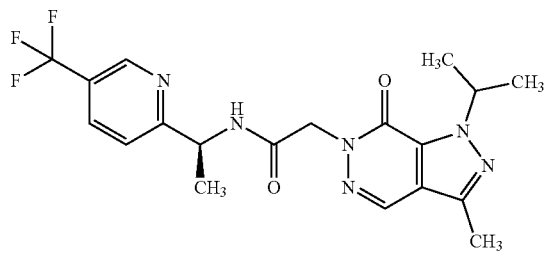 [SMILES: Cc1nn(C(C)C)c2c(=O)n(CC(=O)N[C@@H](C)c3ccc(C(F)(F)F)cn3)ncc12]

The title compound was prepared like EXAMPLE 90, using 1-isopropyl-3-methyl-1,6-dihydro-7H-pyrazolo[3,4-d]pyridazin-7-one and (S)-2-bromo-N-(1-(5-(trifluoromethyl)pyridin-2-yl)ethyl)acetamide, and was obtained as a solid (2.7 mg, 10%). ¹H NMR (500 MHz, CDCl₃) δ ppm 1.48-1.53 (m, 3H), 1.53-1.58 (m, 6H), 2.53 (s, 3H), 4.90-4.99 (m, 2H), 5.21-5.31 (m, 1H), 5.58-5.70 (m, 1H), 7.13-7.22 (m, 1H), 7.37-7.42 (m, 1H), 7.88-7.93 (m, 1H), 8.13 (s, 1H), 8.71-8.76 (m, 1H); ESI-MS m/z [M+H]⁺ 423.1.

Example 104: N-(1-(chroman-6-yl)ethyl)-2-(1-cyclopropyl-3-methyl-4-oxo-1,4-dihydro-5H-pyrazolo[3,4-d]pyridazin-5-yl)acetamide

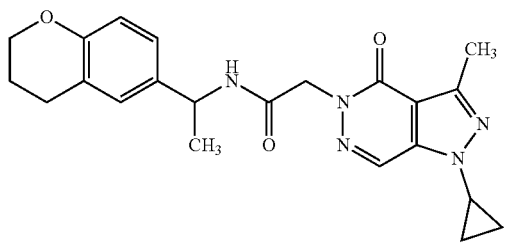 [SMILES: Cc1nn(C2CC2)c2cnn(CC(=O)NC(C)c3ccc4c(c3)CCCO4)c(=O)c12]

The title compound was prepared like EXAMPLE 90, using 1-cyclopropyl-3-methyl-1,5-dihydro-4H-pyrazolo[3,4-d]pyridazin-4-one and 2-bromo-N-(1-(chroman-6-yl)ethyl)acetamide, and was obtained as a solid (6.3 nig, 23%). ¹H NMR (500 MHz, CDCl₃) δ ppm 1.18-1.24 (m, 4H), 1.46 (d, J=6.83 Hz, 3H), 1.94-2.03 (m, 2H), 2.63 (d, J=0.98 Hz, 3H), 2.74 (t, J=6.47 Hz, 2H), 3.53-3.61 (m, 1H), 4.13-4.19 (m, 2H), 4.80-4.89 (m, 2H), 4.99-5.09 (m, 1H), 6.25 (br d, J=7.32 Hz, 1H), 6.69-6.74 (m, 1H), 6.97 (s, 1H), 7.00 (dd, J=8.30, 1.71 Hz, 1H), 8.24 (d, J=0.98 Hz, 1H); ESI-MS m/z [M+H]⁺ 408.2.

Example 105: 2-(1-cyclopropyl-3,4-dimethyl-7-oxo-1,7-dihydro-6H-pyrazolo[3,4-d]pyridazin-6-yl)-N-(1-(2,3-dihydrobenzo[b][1,4]dioxin-6-yl)ethyl)acetamide

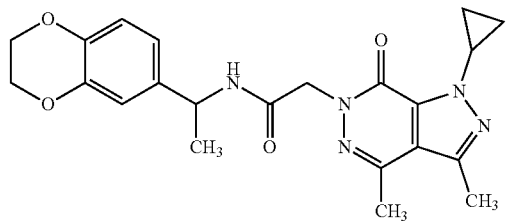 [SMILES: Cc1nn(CC(=O)NC(C)c2ccc3c(c2)OCCO3)c(=O)c2c1c(C)nn2C1CC1]

The title compound was prepared like EXAMPLE 90, using 1-cyclopropyl-3,4-dimethyl-1,6-dihydro-7H-pyrazolo[3,4-d]pyridazin-7-one and 2-bromo-N-(1-(2,3-dihydrobenzo[b][1,4]dioxin-6-yl)ethyl)acetamide, and was obtained as a solid (5.2 mg, 18%). ¹H NMR (500 MHz, CDCl₃) δ ppm 1.06-1.14 (m, 2H), 1.27-1.36 (m, 2H), 1.45 (d, J=6.83 Hz, 3H), 2.52 (s, 3H), 2.56 (s, 3H), 4.24 (s, 4H), 4.51-4.59 (m, 1H), 4.81-4.90 (m, 2H), 5.01-5.09 (m, 1H), 6.26 (br s, 1H), 6.73-6.84 (m, 3H); ESI-MS m/z [M+H]⁺ 424.2.

Example 106: 2-(1-cyclopropyl-3-methyl-4-oxo-1,4-dihydro-5H-pyrazolo[3,4-d]pyridazin-5-yl)-N-(1-(2,3-dihydrobenzo[b][1,4]dioxin-6-yl)ethyl)acetamide

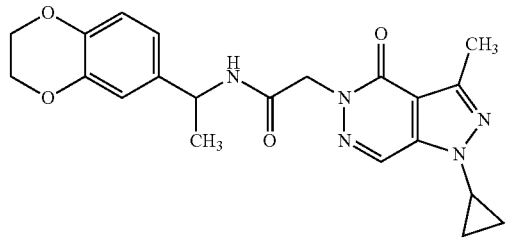 [SMILES: Cc1nn(C2CC2)c2cnn(CC(=O)NC(C)c3ccc4c(c3)OCCO4)c(=O)c12]

The title compound was prepared like EXAMPLE 90, using 1-cyclopropyl-3-methyl-1,5-dihydro-4H-pyrazolo[3,4-d]pyridazin-4-one and 2-bromo-N-(1-(2,3-dihydrobenzo[b][1,4]dioxin-6-yl)ethyl)acetamide, and was obtained as a solid (15.7 mg, 58%). ¹H NMR (400 MHz, DMSO-d₆) δ ppm 1.08-1.19 (m, 4H), 1.33 (d, J=7.07 Hz, 3H), 2.48 (s, 3H), 3.89 (dt, J=7.26, 3.32 Hz, 1H), 4.20-4.26 (m, 4H), 4.67-4.76 (m, 2H), 4.78-4.86 (m, 1H), 6.75-6.84 (m, 3H), 8.48 (d, J=7.83 Hz, 1H), 8.52 (s, 1H); ESI-MS m/z [M+H]⁺ 410.2.

Example 107: (S)-2-(1-cyclopropyl-3-methyl-4-oxo-1,4-dihydro-5H-pyrazolo[3,4-d]pyridazin-5-yl)-N-(1-(4-(trifluoromethyl)phenyl)ethyl)acetamide

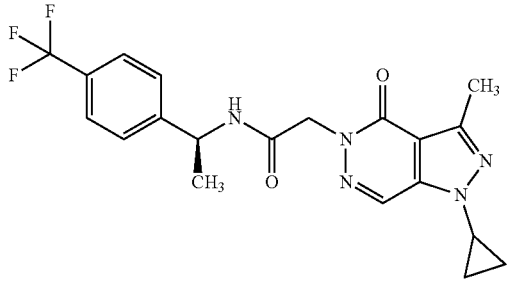

A slurry of (S)-2-bromo-N-(1-(4-(trifluoromethyl)phenyl)ethyl)acetamide (4.03 g, 13.00 mmol), 1-cyclopropyl-3-methyl-1,5-dihydro-4H-pyrazolo[3,4-d]pyridazin-4-one (2.52 g, 13.26 mmol) and K$_2$CO$_3$ (2.69 g, 19.49 mmol) in DMF (40 mL) was stirred at 20° C. for 22 hours. The mixture was taken up in EtOAc (400 mL) and washed with water (400 mL) brine (300 mL). The organic layer was dried over MgSO$_4$ and concentrated in vacuo to provide a white solid, which was recrystallized from EtOAc to give the title compound as a white solid (4.08 g, 75%). $^1$H NMR (400 MHz, DMSO-d$_6$) δ ppm 1.06-1.17 (m, 4H), 1.40 (d, J=7.03 Hz, 3H), 2.46 (s, 3H), 3.81-3.91 (m, 1H), 4.69-4.84 (m, 2H), 4.99 (quin, J=7.09 Hz, 1H), 7.55 (d, J=8.41 Hz, 2H), 7.69 (d, J=8.16 Hz, 2H), 8.49 (s, 1H), 8.64 (d, J=7.53 Hz, 1H); ESI-MS m/z [M+H]$^+$ 420.3.

Example 108: (S)-2-(1-cyclopropyl-3-methyl-4-oxo-1,4-dihydro-5H-pyrazolo[3,4-d]pyridazin-5-yl)-N-(1-(2-fluoro-4-methylphenyl)ethyl)acetamide

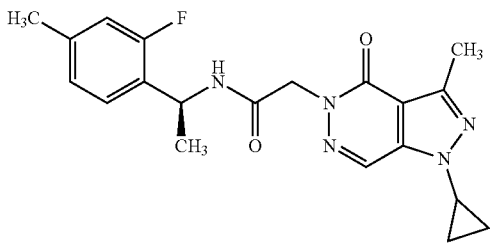 [SMILES: Cc1ccc([C@H](C)NC(=O)Cn2ncc3c(c(C)nn3C3CC3)c2=O)c(F)c1]

A 4 mL vial equipped with a stir bar and charged with Cs$_2$CO$_3$ (51 mg, 0.16 mmol) and (S)-2-bromo-N-(1-(2-fluoro-4-methylphenyl)ethyl)acetamide (26 mg, 0.095 mmol). A solution of 1-cyclopropyl-3-methyl-1,5-dihydro-4H-pyrazolo[3,4-d]pyridazin-4-one (15 mg, 0.079 mmol) in DUE (0.5 mL) was added and the vial was capped. The reaction mixture was stirred at 40° C. for 18 hours and then filtered through a 0.45 μm frit and purified by HPLC (Method B) to give the title compound (7.1 mg, 23%). ESI-MS m/z [M+H]$^+$ 384.4.

Example 109: (S)-2-(1-cyclopropyl-3-methyl-4-oxo-1,4-dihydro-5H-pyrazolo[3,4-d]pyridazin-5-yl)-N-(1-(4-(trifluoromethoxy)phenyl)ethyl)acetamide

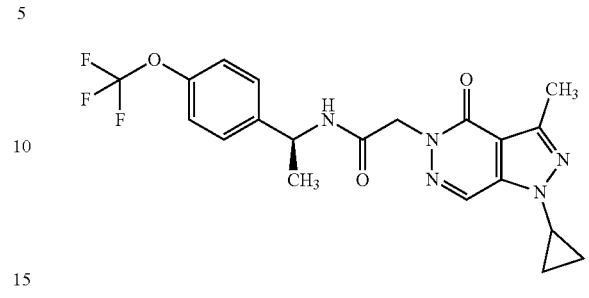

The title compound (27 mg, 78%) was prepared like EXAMPLE 108, using 1-cyclopropyl-3-methyl-1,5-dihydro-4H-pyrazolo[3,4-d]pyridazin-4-one and (S)-2-bromo-N-(1-(4-(trifluoromethoxy)phenyl)ethyl)acetamide. ESI-MS m/z [M+H]$^+$ 436.1.

Example 110: (S)-2-(1-cyclopropyl-3-methyl-4-oxo-1,4-dihydro-5H-pyrazolo[3,4-d]pyridazin-5-yl)-N-(1-(4-methoxyphenyl)ethyl)acetamide

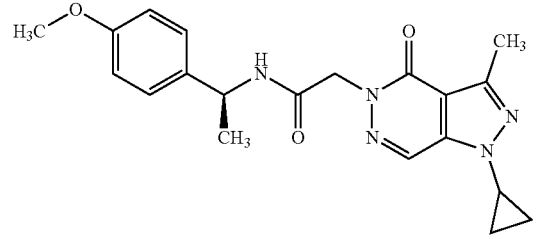

The title compound (18 mg, 60%) was prepared like EXAMPLE 108, using 1-cyclopropyl-3-methyl-1,5-dihydro-4H-pyrazolo[3,4-d]pyridazin-4-one and (S)-2-bromo-N-(1-(4-methoxyphenyl)ethyl)acetamide. $^1$H NMR (500 MHz, CD$_3$CN) δ ppm 1.13 (br s, 4H), 1.36-1.42 (m, 3H), 2.50 (s, 3H), 3.61-3.68 (m, 1H), 3.75 (s, 3H), 4.76 (d, J=6.35 Hz, 2H), 4.89-4.97 (m, 1H), 6.87 (d, J=8.79 Hz, 2H), 7.23 (d, J=8.30 Hz, 2H), 8.33 (s, 1H); ESI-MS m/z [M+H]$^+$ 382.2.

Example 111: (S)—N-(1-(2-fluoro-4-methylphenyl)ethyl)-2-(1,3,7-trimethyl-4-oxo-1,4-dihydro-5H-pyrazolo[3,4-d]pyridazin-5-yl)acetamide

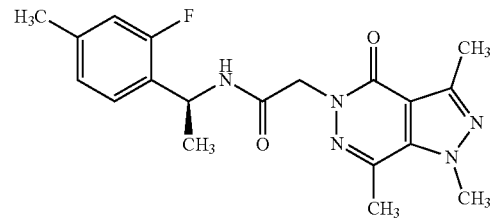 [SMILES: Cc1ccc([C@H](C)NC(=O)Cn2nc(C)c3c(c(C)nn3C)c2=O)c(F)c1]

The title compound (14 mg, 45%) was prepared like EXAMPLE 108, using 1,3,7-trimethyl-1,5-dihydro-4/1- pyrazolo[3,4-d]pyridazin-4-one and (S)-2-bromo-N-(1-(2-fluoro-4-methylphenyl)ethyl)acetamide. ESI-MS m/z [M+H]+ 372.2.

Example 112: (S)—N-(1-(4-(trifluoromethoxy)phenyl)ethyl)-2-(1,3,7-trimethyl-4-oxo-1,4-dihydro-5H-pyrazolo[3,4-d]pyridazin-5-yl)acetamide

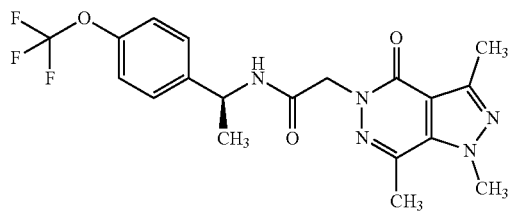 [SMILES: Cc1nn(C)c2c(C)nn(CC(=O)N[C@@H](C)c3ccc(OC(F)(F)F)cc3)c(=O)c12]

The title compound (10 mg, 29%) was prepared like EXAMPLE 108, using 1,3,7-trimethyl-1,5-dihydro-4H-pyrazolo[3,4-d]pyridazin-4-one and (S)-2-bromo-N-(1-(4-(trifluoromethoxy)phenyl)ethyl)acetamide. ESI-MS m/z [M+H]+ 424.1.

Example 113: (S)—N-(1-(p-tolyl)ethyl)-2-(1,3,7-trimethyl-4-oxo-1,4-dihydro-5H-pyrazolo[3,4-d]pyridazin-5-yl)acetamide

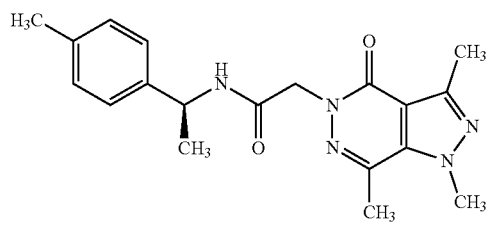 [SMILES: Cc1ccc([C@H](C)NC(=O)Cn2nc(C)c3c(c(C)nn3C)c2=O)cc1]

The title compound (5.3 mg 18%) was prepared like EXAMPLE 108, using 1,3,7-trimethyl-1,5-dihydro-4H-pyrazolo[3,4-d]pyridazin-4-one and (S)-2-bromo-N-(1-(p-tolyl)ethyl)acetamide. ESI-MS m/z [M+H]+ 354.1.

Example 114: (S)—N-(1-(4-(trifluoromethyl)phenyl)ethyl)-2-(1,3,7-trimethyl-4-oxo-1,4-dihydro-5H-pyrazolo[3,4-d]pyridazin-5-yl)acetamide

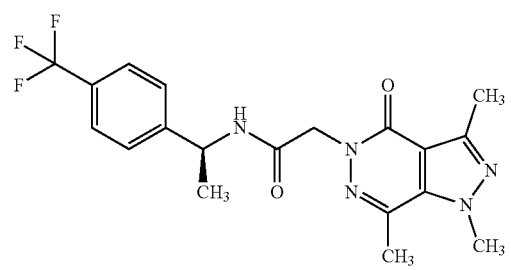 [SMILES: Cc1nn(C)c2c(C)nn(CC(=O)N[C@@H](C)c3ccc(C(F)(F)F)cc3)c(=O)c12]

The title compound (2.8 mg, 8.2%) was prepared like EXAMPLE 108, using 1,3,7-trimethyl-1,5-dihydro-4H-pyrazolo[3,4-d]pyridazin-4-one and (S)-2-bromo-N-(1-(4-(trifluoromethyl)phenyl)ethyl)acetamide. ESI-MS m/z [M+H]+ 408.1.

Example 115: (S)-2-(3-cyclopropyl-1-methyl-4-oxo-1,4-dihydro-5H-pyrazolo[3,4-d]pyridazin-5-yl)-N-(1-(4-(trifluoromethyl)phenyl)ethyl)acetamide

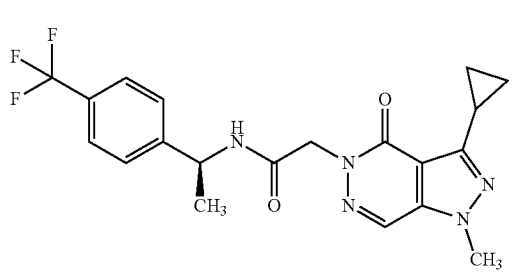 [SMILES: C[C@H](NC(=O)Cn1ncc2c(c(C3CC3)nn2C)c1=O)c1ccc(C(F)(F)F)cc1]

The title compound (27 mg, 83%) was prepared like EXAMPLE 108, using 3-cyclopropyl-1-methyl-1,5-dihydro-4H-pyrazolo[3,4-d]pyridazin-4-one and (S)-2-bromo-N-(1-(4-(trifluoromethyl)phenyl)ethyl)acetamide. ESI-MS m/z [M+]+ 420.1.

Example 116: (S)-2-(3-cyclopropyl-1-methyl-4-oxo-1,4-dihydro-5H-pyrazolo[3,4-d]pyridazin-5-yl)-N-(1-(4-methoxyphenyl)ethyl)acetamide

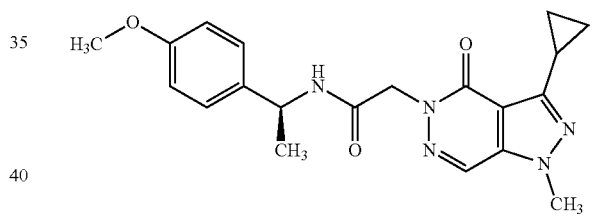

The title compound (22 mg, 72%) was prepared like EXAMPLE 108, using 3-cyclopropyl-1-methyl-1,5-dihydro-4H-pyrazolo[3,4-d]pyridazin-4-one and (S)-2-bromo-N-(1-(4-methoxyphenyl)ethyl)acetamide. ESI-MS m/z [M+H]+ 382.2.

Example 117: (S)-2-(3-cyclopropyl-1,7-dimethyl-4-oxo-1,4-dihydro-5H-pyrazolo[3,4-d]pyridazin-5-yl)-N-(1-(2-fluoro-4-methylphenyl)ethyl)acetamide

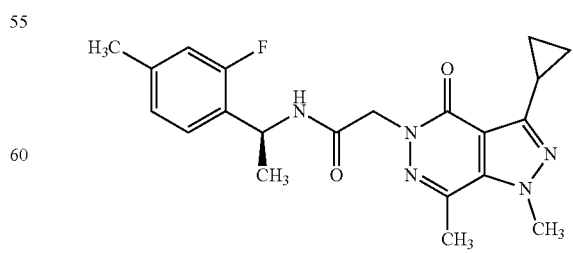

The title compound (19 mg, 64%) was prepared like EXAMPLE 108, using 3-cyclopropyl-1,7-dimethyl-1,5-dihydro-4H-pyrazolo[3,4-d]pyridazin-4-one and (S)-2-bromo-N-(1-(2-fluoro-4-methylphenyl)ethyl)acetamide. ESI-MS m/z [M+H]+ 398.1.

Example 118: (S)-2-(3-cyclopropyl-1,7-dimethyl-4-oxo-1,4-dihydro-5H-pyrazolo[3,4-d]pyridazin-5-yl)-N-(1-(4-(trifluoromethoxy)phenyl)ethyl)acetamide

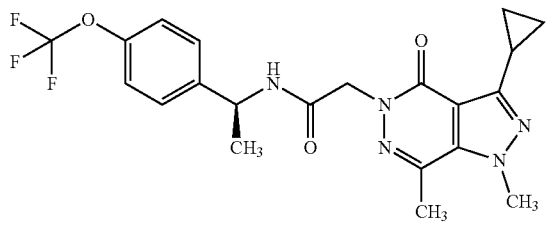 [SMILES: Cc1nn(CC(=O)N[C@@H](C)c2ccc(OC(F)(F)F)cc2)c(=O)c2c(C3CC3)nn(C)c12]

The title compound (16 mg, 49%) was prepared like EXAMPLE 108, using 3-cyclopropyl-1,7-dimethyl-1,5-dihydro-4H-pyrazolo[3,4-d]pyridazin-4-one and (S)-2-bromo-N-(1-(4-(trifluoromethoxy)phenyl)ethyl)acetamide. ESI-MS [M+H]+ 450.1.

Example 119: (S)-2-(3-cyclopropyl-1,7-dimethyl-4-oxo-1,4-dihydro-5H-pyrazolo[3,4-d]pyridazin-5-yl)-N-(1-(p-tolyl)ethyl)acetamide

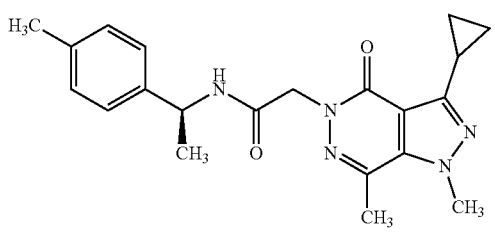 [SMILES: Cc1ccc([C@H](C)NC(=O)Cn2nc(C)c3c(c(C4CC4)nn3C)c2=O)cc1]

The title compound (19 mg, 69%) was prepared like EXAMPLE 108, using 3-cyclopropyl-1,7-dimethyl-1,5-dihydro-4H-pyrazolo[3,4-d]pyridazin-4-one and (S)-2-bromo-N-(1-(p-tolyl)ethyl)acetamide. $^1$H NMR (500 MHz, CD$_3$CN) δ ppm 0.97-1.05 (m, 4H), 1.34-1.38 (m, 1H), 1.41 (d, J=6.83 Hz, 3H), 2.33 (s, 3H), 2.56 (s, 1H), 2.60 (s, 3H), 4.07 (s, 3H), 4.70 (s, 2H), 4.94-5.01 (m, 1H), 6.94-6.99 (m, 1H), 7.14-7.17 (m, 2H), 7.22 (s, 2H); ESI-MS m/z [M+H]+ 380.2.

Example 120: (S)-2-(3-cyclopropyl-1,7-dimethyl-4-oxo-1,4-dihydro-5H-pyrazolo[3,4-d]pyridazin-5-yl)-N-(1-(4-(trifluoromethyl)phenyl)ethyl)acetamide

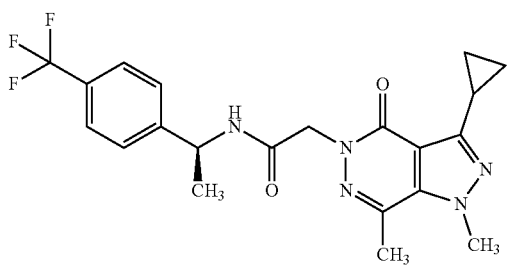 [SMILES: Cc1nn(CC(=O)N[C@@H](C)c2ccc(C(F)(F)F)cc2)c(=O)c2c(C3CC3)nn(C)c12]

The title compound (19 mg, 59%) was prepared like EXAMPLE 108, using 3-cyclopropyl-1,7-dimethyl-1,5-dihydro-4H-pyrazolo[3,4-d]pyridazin-4-one and (S)-2-bromo-N-(1-(4-(trifluoromethyl)phenyl)ethyl)acetamide. ESI-MS m/z [M+H]+ 434.1.

Example 121: (S)-2-(3-cyclopropyl-1,7-dimethyl-4-oxo-1,4-dihydro-5H-pyrazolo[3,4-d]pyridazin-5-yl)-N-(1-(4-methoxyphenyl)ethyl)acetamide

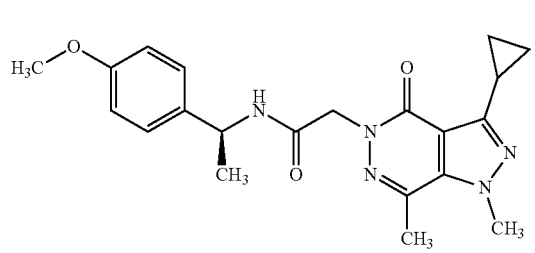 [SMILES: COc1ccc([C@H](C)NC(=O)Cn2nc(C)c3c(c(C4CC4)nn3C)c2=O)cc1]

The title compound (20 mg, 70%) was prepared like EXAMPLE 108, using 3-cyclopropyl-1,7-dimethyl-1,5-dihydro-4H-pyrazolo[3,4-d]pyridazin-4-one and (S)-2-bromo-N-(1-(4-methoxyphenyl)ethyl)acetamide. ESI-MS m/z [M+H]+ 396.2.

Example 122: (S)-2-(1-cyclopropyl-3-methyl-4-oxo-1,4-dihydro-5H-pyrazolo[3,4-d]pyridazin-5-yl)-N-(1-(p-tolyl)ethyl)acetamide

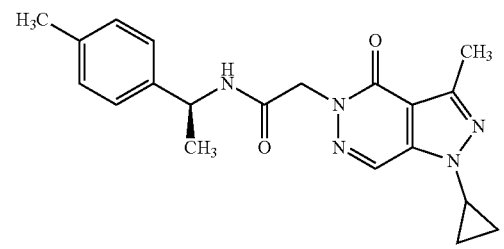 [SMILES: Cc1ccc([C@H](C)NC(=O)Cn2ncc3c(c(C)nn3C3CC3)c2=O)cc1]

The title compound (7.9 mg, 27%) was prepared like EXAMPLE 108, using 1-cyclopropyl-3-methyl-1,5-dihydro-4H-pyrazolo[3,4-d]pyridazin-4-one and (S)-2-bromo-N-(1-(p-tolyl)ethyl)acetamide, EST-MS m/z [M+H]+ 366.4.

Example 123: (S)—N-(1-(4-methoxyphenyl)ethyl)-2-(1,3,7-trimethyl-4-oxo-1,4-dihydro-5H-pyrazolo[3,4-d]pyridazin-5-yl)acetamide

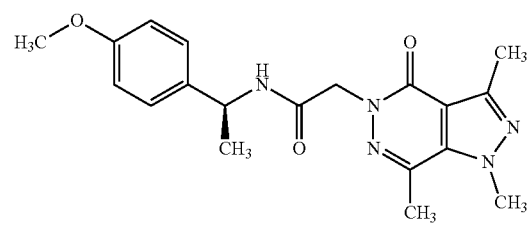 [SMILES: COc1ccc([C@H](C)NC(=O)Cn2nc(C)c3c(c(C)nn3C)c2=O)cc1]

The title compound (5.2 mg, 17%) was prepared like EXAMPLE 108, using 7-trimethyl-1,5-dihydro-4H-pyrazolo[3,4-d]pyridazin-4-one and (S)-2-bromo-N-(1-(4-methoxyphenyl)ethyl)acetamide. EST-MS m/z [M+H]+ 370.3.

Example 124: (S)-2-(3-cyclopropyl-1-methyl-4-oxo-1,4-dihydro-5H-pyrazolo[3,4-d]pyridazin-5-yl)-N-(1-(2-fluoro-4-methylphenyl)ethyl)acetamide

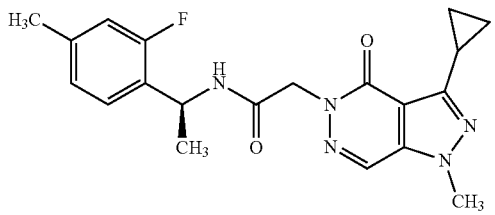 [SMILES: Cc1ccc([C@H](C)NC(=O)Cn2ncc3c(c(C4CC4)nn3C)c2=O)c(F)c1]

The title compound (5.0 mg, 17%) was prepared like EXAMPLE 108, using 3-cyclopropyl-1-methyl-1,5-dihydro-4H-pyrazolo[3,4-d]pyridazin-4-one and (S)-2-bromo-N-(1-(2-fluoro-4-methylphenyl)ethyl)acetamide. ESI-MS m/z [M+H]+ 384.4.

Example 125: (S)-2-(3-cyclopropyl-1-methyl-4-oxo-1,4-dihydro-5H-pyrazolo[3,4-d]pyridazin-5-yl)-N-(1-(4-(trifluoromethoxy)phenyl)ethyl)acetamide

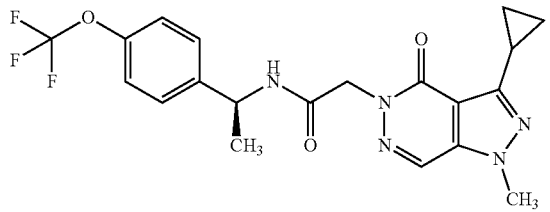 [SMILES: C[C@H](NC(=O)Cn1ncc2c(c(C3CC3)nn2C)c1=O)c1ccc(OC(F)(F)F)cc1]

The title compound (12 mg, 35%) was prepared like EXAMPLE 108, using 3-cyclopropyl-1-methyl-1,5-dihydro-4H-pyrazolo[3,4-d]pyridazin-4-one and (S)-2-bromo-N-(1-(4-(trifluoromethoxy)phenyl)ethyl)acetamide. ESI-MS m/z [M+H]+ 436.3.

Example 126: (S)—N-(1-(2,6-difluorophenyl)ethyl)-2-(1,3-dimethyl-4-oxo-1,4-dihydro-5H-pyrazolo[3,4-d]pyridazin-5-yl)acetamide

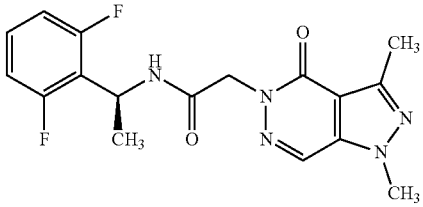 [SMILES: Cc1nn(C)c2cnn(CC(=O)N[C@@H](C)c3c(F)cccc3F)c(=O)c12]

To a vial containing 1,3-dimethyl-1,5-dihydro-4H-pyrazolo[3,4-d]pyridazin-4-one (32.8 mg, 0.200 mmol) in DMF (1 mL) was added (S)-2-bromo-N-(1-(2,6-difluorophenyl) ethyl)acetamide (55.6 mg, 0.2 mmol) and K₂CO₃ (33.2 mg, 0.240 mmol). The mixture was stirred for 3 hours at 60° C. and then diluted in DMF (1 mL), filtered through Millipore® Millex-LCR resin and purified by HPLC (Method B). The product-containing fractions were combined, concentrated in vacuo and lyophilized to give the title compound as an off-white solid (15 mg, 21%). ¹H NMR (500 MHz, DMSO-d₆) δ ppm 1.47 (d, J=7.32 Hz, 3H), 2.46 (s, 3H), 3.99 (s, 3H), 4.63-4.68 (m, 1H), 4.73-4.78 (m, 1H), 5.22 (quin, J=7.08 Hz, 1H), 7.02-7.09 (m, 2H), 7.30-7.38 (m, 1H), 8.46 (s, 1H), 8.67 (d, J=6.83 Hz, 1H); ESI-MS m/z [M+H]+ 362.2.

Example 127: (S)-2-(1-cyclopropyl-3-methyl-4-oxo-1,4-dihydro-5H-pyrazolo[3,4-d]pyridazin-5-yl)-N-(1-(2-fluoro-4-methoxyphenyl)ethyl)acetamide

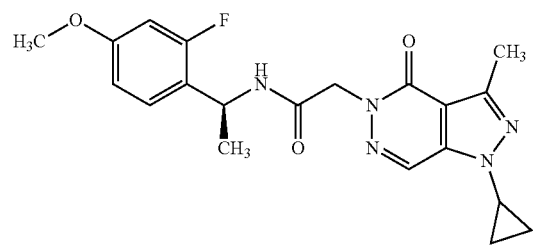 [SMILES: COc1ccc([C@H](C)NC(=O)Cn2ncc3c(c(C)nn3C3CC3)c2=O)c(F)c1]

A 4 mL vial equipped with a stir bar was charged with K₂CO₃ (29 mg, 0.21 mmol) and (S)-2-bromo-N-(1-(2-fluoro-4-methoxyphenyl)ethyl)acetamide (37 mg, 0.13 mmol). A solution of 1-cyclopropyl-3-methyl-1,5-dihydro-4H-pyrazolo[3,4-d]pyridazin-4-one (20 mg, 0.11 mmol) in DMF (0.5 mL) was added and the vial was capped. The reaction mixture was stirred at 60° C. for 18 hours and then filtered through a 0.45 μm frit and purified by HPLC (Method A) to give the title compound (4.2 mg, 10%). ESI-MS [M+H]+ 400.1.

Example 128: (S)-2-(1-cyclopropyl-3-methyl-4-oxo-1,4-dihydro-5H-pyrazolo[3,4-d]pyridazin-5-yl)-N-(1-(2,4-difluorophenyl)ethyl)acetamide

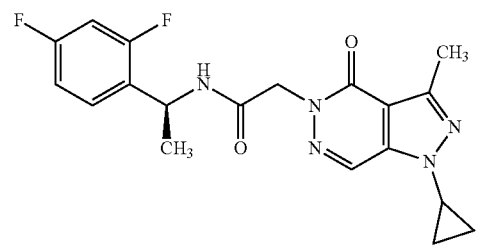

The title compound (10 mg, 25%) was prepared like EXAMPLE 127, using 1-cyclopropyl-3-methyl-1,5-dihydro-4H-pyrazolo[3,4-d]pyridazin-4-one and (S)-2-bromo-N-(1-(2,4-difluorophenyl)ethyl)acetamide. ¹H NMR (500 MHz, CDCl₃) δ ppm 1.19-1.26 (m, 4H), 1.47 (d, J=6.83 Hz, 3H), 2.62 (s, 3H), 3.56-3.62 (m, 1H), 4.87 (s, 2H), 5.19-5.27 (m, 1H), 6.63-6.70 (m, 1H), 6.73-6.83 (m, 2H), 7.20-7.28 (m, 1H), 8.25 (s, 1H); ESI-MS m/z [M+H]+ 388.2.

Example 129: (S)-2-(1-cyclopropyl-3-methyl-4-oxo-1,4-dihydro-5H-pyrazolo[3,4-d]pyridazin-5-yl)-N-(1-(3-fluoro-4-methoxyphenyl)ethyl)acetamide

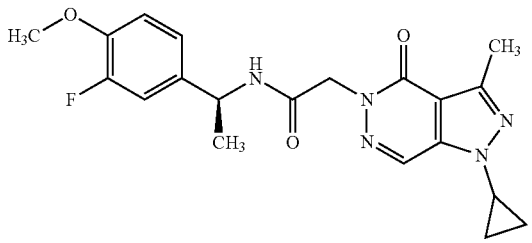 [SMILES: COc1ccc([C@H](C)NC(=O)Cn2ncc3c(c(C)nn3C3CC3)c2=O)cc1F]

The title compound (4.0 mg 10%) was prepared like EXAMPLE 127, using 1-cyclopropyl-3-methyl-1,5-dihydro-4H-pyrazolo[3,4-d]pyridazin-4-one and (S)-2-bromo-N-(1-(3-fluoro-4-methoxyphenyl)ethyl)acetamide. ESI-MS m/z [M+H]$^+$ 400.2.

Example 130: (S)-2-(1-cyclopropyl-3-methyl-4-oxo-1,4-dihydro-5H-pyrazolo[3,4-d]pyridazin-5-yl)-N-(1-(3-fluoro-4-methylphenyl)ethyl)acetamide

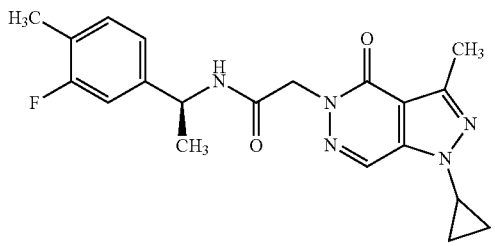

The title compound (15 mg, 38%) was prepared like EXAMPLE 127, using 1-cyclopropyl-3-methyl-1,5-dihydro-4H-pyrazolo[3,4-d]pyridazin-4-one and (S)-2-bromo-N-(1-(3-fluoro-4-methylphenyl)ethyl)acetamide. $^1$H NMR (500 MHz, CDCl$_3$) δ ppm 1.17-1.26 (m, 4H), 1.44 (d, J=7.32 Hz, 3H), 2.22 (s, 3H), 2.62 (s, 3H), 3.56-3.61 (m, 1H), 4.86 (d, J=5.86 Hz, 2H), 5.04-5.11 (m, 1H), 6.49 (d, J=7.32 Hz, 1H), 6.90 (d, J=10.74 Hz, 1H), 6.96 (d, J=1.95 Hz, 1H), 7.09 (s, 1H), 8.24 (s, 1H); ESI-MS m/z [M+H]$^+$ 384.1.

Example 131: (S)—N-(1-(2-chloro-4-fluorophenyl)ethyl)-2-(1-cyclopropyl-3-methyl-4-oxo-1,4-dihydro-5H-pyrazolo[3,4-d]pyridazin-5-yl)acetamide

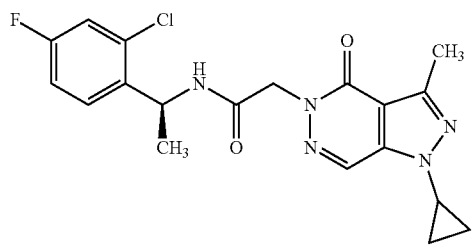 [SMILES: Cc1nn(C2CC2)c2cnn(CC(=O)N[C@@H](C)c3ccc(F)cc3Cl)c(=O)c12]

The title compound (19 mg, 44%) was prepared like EXAMPLE 127, using 1-cyclopropyl-3-methyl-1,5-dihydro-4H-pyrazolo[3,4-d]pyridazin-4-one and (S)-2-bromo-N-(1-(2-chloro-4-fluorophenyl)ethyl)acetamide. ESI-MS m/z [M+H]$^+$ 404.1.

Example 132: (S)-2-(1-cyclopropyl-3-methyl-4-oxo-1,4-dihydro-5H-pyrazolo[3,4-d]pyridazin-5-yl)-N-(1-(4-fluoro-3-methoxyphenyl)ethyl)acetamide

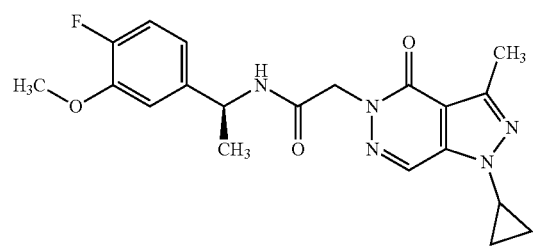 [SMILES: COc1cc([C@H](C)NC(=O)Cn2ncc3c(c(C)nn3C3CC3)c2=O)ccc1F]

The title compound (11 mg, 27%) was prepared like EXAMPLE 127, using 1-cyclopropyl-3-methyl-1,5-dihydro-4H-pyrazolo[3,4-d]pyridazin-4-one and (S)-2-bromo-N-(1-(4-fluoro-3-methoxyphenyl)ethyl)acetamide. ESI-MS m/z [M+H]$^+$ 400.1.

Example 133: (S)-2-(1-cyclopropyl-3-methyl-4-oxo-1,4-dihydro-5H-pyrazolo[3,4-d]pyridazin-5-yl)-N-(1-(2,4,6-trifluorophenyl)ethyl)acetamide

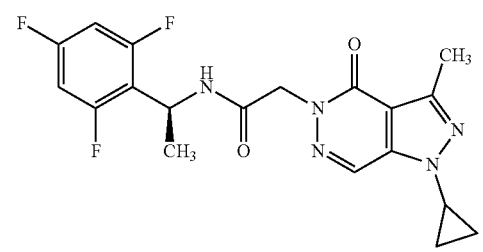 [SMILES: Cc1nn(C2CC2)c2cnn(CC(=O)N[C@@H](C)c3c(F)cc(F)cc3F)c(=O)c12]

The title compound (9.0 mg, 21%) was prepared like EXAMPLE 127, using 1-cyclopropyl-3-methyl-1,5-dihydro-4H-pyrazolo[3,4-d]pyridazin-4-one and (S)-2-bromo-N-(1-(2,4,6-trifluorophenyl)ethyl)acetamide. ESI-MS m/z [M+H]$^+$ 406.1.

Example 134: (S)-2-(1-cyclopropyl-3-methyl-4-oxo-1,4-dihydro-5H-pyrazolo[3,4-d]pyridazin-5-yl)-N-(1-(4-fluoro-3-methylphenyl)ethyl)acetamide

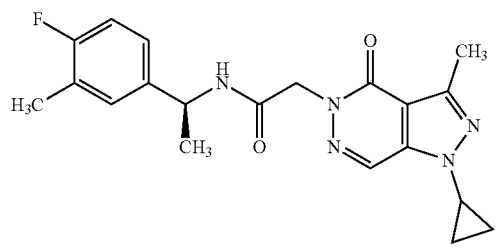 [SMILES: Cc1cc([C@H](C)NC(=O)Cn2ncc3c(c(C)nn3C3CC3)c2=O)ccc1F]

The title compound (14 mg, 35%) was prepared like EXAMPLE 127, using 1-cyclopropyl-3-methyl-1,5-dihydro-4H-pyrazolo[3,4-d]pyridazin-4-one and (S)-2-bromo-N-(1-(4-fluoro-3-methylphenyl)ethyl)acetamide. ESI-MS m/z [M+H]+ 384.2.

Example 135: (S)-2-(1-cyclopropyl-3-methyl-4-oxo-1,4-dihydro-5H-pyrazolo[3,4-d]pyridazin-5-yl)-N-(1-(3,5-difluorophenyl)ethyl)acetamide

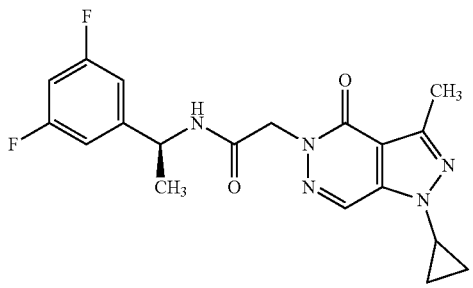 [SMILES: Cc1nn(C2CC2)c2cnn(CC(=O)N[C@@H](C)c3cc(F)cc(F)c3)c(=O)c12]

The title compound (22 mg, 54%) was prepared like EXAMPLE 127, using 1-cyclopropyl-3-methyl-1,5-dihydro-4H-pyrazolo[3,4-d]pyridazin-4-one and (S)-2-bromo-N-(1-(3,5-difluorophenyl)ethyl)acetamide. ESI-MS m/z [M+H]+ 388.1.

Example 136: (S)—N-(1-(2-chloro-6-fluorophenyl)ethyl)-2-(1-cyclopropyl-3-methyl-4-oxo-1,4-dihydro-5H-pyrazolo[3,4-d]pyridazin-5-yl)acetamide

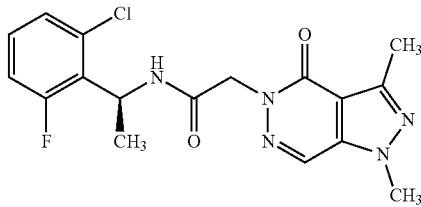 [SMILES: Cc1nn(C)c2cnn(CC(=O)N[C@@H](C)c3c(F)cccc3Cl)c(=O)c12]

The title compound (15 mg, 35%) was prepared like EXAMPLE 127, using 1-cyclopropyl-3-methyl-1,5-dihydro-4H-pyrazolo[3,4-d]pyridazin-4-one and (S)-2-bromo-N-(1-(2-chloro-6-fluorophenyl)ethyl)acetamide, ESI-MS m/z [M+H]+ 404.1.

Example 137: (S)-2-(1,7-dimethyl-4-oxo-1,4-dihydro-5H-imidazo[4,5-d]pyridazin-5-yl)-N-(1-(5-(trifluoromethyl)pyridin-2-yl)ethyl)acetamide

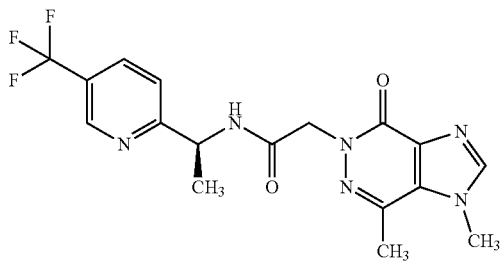 [SMILES: Cc1nn(CC(=O)N[C@@H](C)c2ccc(C(F)(F)F)cn2)c(=O)c2ncn(C)c12]

A solution of (S)-2-bromo-N-(1-(5-(trifluoromethyl)pyridin-2-yl)ethyl)acetamide (20 mg, 0.064 mmol) and sodium hydride (7.67 mg, 0.192 mmol) in DMF (total volume: 0.5 mL) was stirred at 0° C. for 1 hour. Next, 1,7-dimethyl-1,5-dihydro-4H-imidazo[4,5-d]pyridazin-4-one (10.55 mg, 0.064 mmol) was added. The mixture was stirred at RT for 30 minutes and then diluted in DMF, filtered through a hydrophilic PTFE 0.45 μm filter (Millipore® Millex-LCR) and purified by HPLC (Method A). The product-containing fraction was concentrated under reduced pressure to give the title compound as a solid (16.2 mg 64%). $^1$H NMR (500 MHz, CDCl$_3$) δ ppm 1.52-1.63 (m, 3H), 2.68 (s, 3H), 4.09 (s, 3H), 4.97 (s, 2H), 5.22-5.35 (m, 1H), 7.78 (d, J=8.30 Hz, 1H), 8.21 (dd, J=8.30, 1.95 Hz, 1H), 8.25-8.32 (m, 2H), 8.92 (s, 1H); ESI-MS m/z [M+H]+ 395.1.

Example 138: (S)-2-(3-methyl-4-oxo-3,4-dihydro-5H-imidazo[4,5-d]pyridazin-5-yl)-N-(1-(p-tolyl)ethyl)acetamide

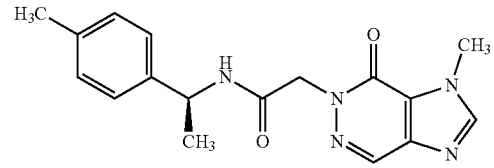 [SMILES: Cc1ccc([C@H](C)NC(=O)Cn2ncc3ncn(C)c3c2=O)cc1]

To a vial containing 3-methyl-3,5-dihydro-4H-imidazo[4,5-d]pyridazin-4-one (30.0 mg, 0.200 mmol) in DMF (1 mL) were added (S)-2-bromo-N-(1-(p-tolyl)ethyl)acetamide (51.2 mg, 0.2 mmol) and K$_2$CO$_3$ (33.2 mg, 0.240 mmol). The mixture was stirred at RT overnight and then at 60° C. for 3 hours. The solution was subsequently diluted in DMF (1 mL), filtered through Millipore® Millex-LCR resin and purified by HPLC (Method B). The product-containing fractions were combined, concentrated iii vacuo and lyophilized to give the title compound as an off-white solid (30.4 mg, 46.7%). $^1$H NMR. (500 MHz, DMSO-d$_6$) δ ppm 1.33-1.37 (m, 3H), 2.26-2.28 (m, 3H), 4.02-4.04 (m, 3H), 4.74-4.81 (m, 2H), 4.83-4.93 (m, 1H), 7.11-7.16 (m, 2H), 7.19-7.24 (m, 2H), 8.34 (s, 1H), 8.37 (s, 1H), 8.51-8.57 (m, 1H); ESI-MS m/z [M+H]+ 326.3.

Example 139: (S)-2-(3-methyl-4-oxo-3,4-dihydro-5H-imidazo[4,5-d]pyridazin-5-yl)-N-(1-(4-(trifluoromethyl)phenyl)ethyl)acetamide

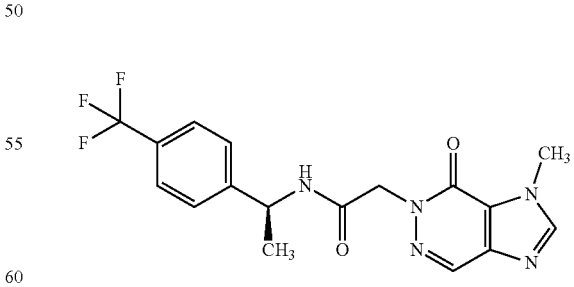

To a vial containing 3-methyl-3,5-dihydro-4H-imidazo[4,5-d]pyridazin-4-one (30.0 mg, 0.200 mmol) in DMF (1 mL) were added (S)-2-bromo-N-(1-(4-(trifluoromethyl)phenyl)ethyl)acetamide (62.0 mg, 0.2 mmol) and K$_2$CO$_3$ (33.2 mg, 0.240 mmol). The mixture was stirred at RT overnight and then at 60° C. for 3 hours. The solution was subsequently diluted in DMF (1 mL), filtered through Millipore® Millex-LCR resin and purified by HPLC (Method B). The product-containing fractions were combined, concentrated iii vacuo and lyophilized to give the title compound as an off-white solid (38 mg, 50%). ¹H NMR. (500 MHz, DMSO-d₆) δ ppm 1.38-1.42 (m, 3H), 4.02-4.04 (m, 3H), 4.78-4.85 (m, 2H), 4.93-5.03 (m, 1H), 7.53-7.58 (m, 2H), 7.68-7.73 (m, 2H), 8.34-8.35 (m, 1H), 8.38-8.39 (m, 1H), 8.69-8.76 (m, 1H); ESI-MS m/z [M+H]⁺ 380.2.

Example 140: (S)-2-(1-methyl-4-oxo-1,4-dihydro-5H-imidazo[4,5-d]pyridazin-5-yl)-N-(1-(p-tolyl)ethyl)acetamide

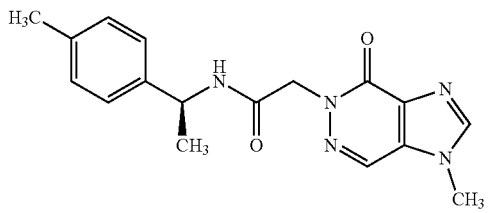 [SMILES: Cc1ccc([C@H](C)NC(=O)Cn2ncc3c(ncn3C)c2=O)cc1]

To a vial containing 1-methyl-1,5-dihydro-4H-imidazo[4,5-d]pyridazin-4-one (30.0 mg, 0.200 mmol) in MT (1 mL) were added (S)-2-bromo-N-(1-(p-tolyl)ethyl)acetamide (51.2 mg, 0.2 mmol) and K₂CO₃ (33.2 mg, 0.240 mmol). The mixture was stirred at 60° C. for 3 hours and then diluted in DMF (1 mL), filtered through Millipore® Millex-LCR resin and purified by HPLC (Method B). The product-containing fractions were combined, concentrated in vacuo and lyophilized to give the title compound as an off-white solid (6.4 mg, 9.8%). ¹H NMR (500 MHz, DMSO-d₆) δ ppm 1.34-1.36 (m, 3H), 2.27-2.28 (m, 3H), 3.90-3.90 (m, 3H), 4.78-4.80 (m, 2H), 4.86-4.90 (m, 1H), 7.12-7.14 (m, 2H), 7.21 (d, J=8.05 Hz, 2H), 8.25-8.28 (m, 1H), 8.48-8.49 (m, 1H), 8.50-8.53 (m, 1H); ESI-MS m/z [M+H]⁺ 326.2.

Example 141: (S)-2-(1-methyl-4-oxo-1,4-dihydro-5H-imidazo[4,5-d]pyridazin-5-yl)-N-(1-(4-(trifluoromethyl)phenyl)ethyl)acetamide

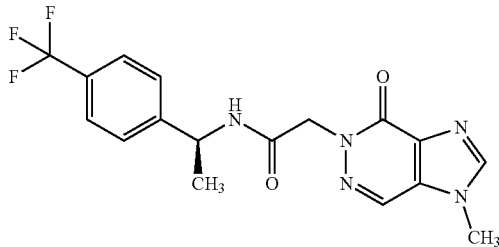 [SMILES: C[C@H](NC(=O)Cn1ncc2c(ncn2C)c1=O)c1ccc(C(F)(F)F)cc1]

To a vial containing 1-methyl-1,5-dihydro-4H-imidazo[4,5-d]pyridazin-4-one (30.0 mg, 0.200 mmol) in DMF (1 mL) were added (S)-2-bromo-N-(1-(4-(trifluoromethyl)phenyl)ethyl)acetamide (62.0 mg, 0.2 mmol) and K₂CO₃ (33.2 mg, 0.240 mmol). The mixture was stirred at 60° C. for 3 hours and then diluted in DMF (1 mL), filtered through Millipore® Millex-LCR resin and purified by HPLC (Method B), The product-containing fractions were combined, concentrated in vacuo and lyophilized to give the title compound as an off-white solid (8.7 mg, 11%). ¹H NMR (500 MHz, DMSO-d₆) δ ppm 1.40 (d, J=7.08 Hz, 3H), 3.90-3.90 (m, 3H), 4.82-4.84 (m, 2H), 4.96-5.01 (m, 1H), 7.55-7.57 (m, 2H), 7.68-7.70 (m, 2H), 8.26-8.28 (m, 1H), 8.48-8.50 (m, 1H), 8.69-8.72 (m, 1H); ESI-MS m/z [M+H]⁺ 380.2.

Example 142: (S)-2-(3-cyclopropyl-1-methyl-7-oxo-1,7-dihydro-6H-pyrazolo[3,4-d]pyridazin-6-yl)-N-(1-(4-(trifluoromethyl)phenyl)ethyl)acetamide

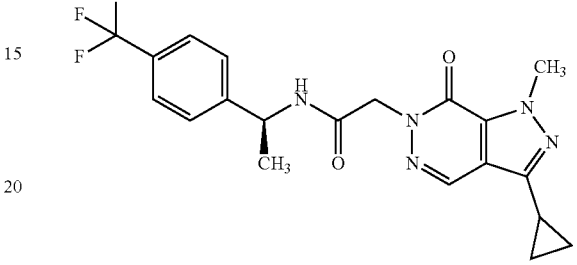

To a solution of 3-cyclopropyl-1-methyl-1,6-dihydro-7H-pyrazolo[3,4-d]pyridazin-7-one (35 mg, 0.184 mmol) in anhydrous DMF (1 mL) were added (S)-2-bromo-N-(1-(4-(trifluoromethyl)phenyl)ethyl)acetamide (57.1 mg, 0.184 mmol) and K₂CO₃ (76 mg, 0.552 mmol). The reaction mixture was stirred at 45° C. for 18 hours and then purified by HPLC (Method B) to give the title compound as an off-white solid (6 mg, 8%). ¹H NMR (400 MHz, CDCl₃) δ ppm 0.96-1.12 (m, 4H), 1.50 (d, J=7.03 Hz, 3H), 2.05-2.13 (m, 1H), 4.28 (s, 3H), 4.88 (s, 2H), 5.13-5.24 (m, 1H), 6.26-6.42 (m, 1H), 7.41 (d, J=8.28 Hz, 2H), 7.57 (d, J=8.28 Hz, 2H), 8.16 (s, 1H); ESI-MS [M+H]⁺ 420.1.

Example 143: (S)-2-(3-cyclopropyl-1-methyl-7-oxo-1,7-dihydro-6H-pyrazolo[3,4-d]pyridazin-6-yl)-N-(1-(4-(trifluoromethoxy)phenyl)ethyl)acetamide

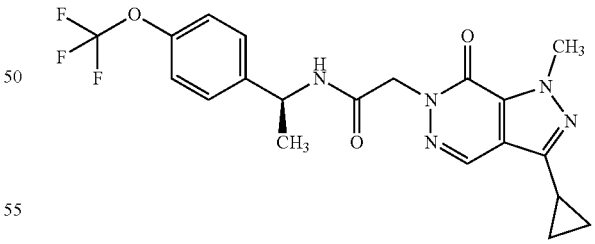

The title compound was prepared like EXAMPLE 42, using 1-cyclopropyl-3-methyl-1,5-dihydro-4H-pyrazolo[3,4-d]pyridazin-4-one and (S)-2-bromo-N-(1-(4-(trifluoromethoxy)phenyl)ethyl)acetamide, and was obtained as a white solid (30 mg, 37%). ¹H NMR (400 MHz, CDCl₃) δ ppm 0.99 (br d, J=3.01 Hz, 4H), 1.46 (d, J=6.78 Hz, 3H), 2.01-2.12 (m, 1H), 4.24 (s, 3H), 4.83 (s, 2H), 5.07-5.16 (m, 1H), 6.71-6.78 (m, 1H), 7.09-7.17 (m, 2H), 7.31 (d, J=8.28 Hz, 2H), 8.13 (s, 1H); ESI-MS m/z [M+H]⁺ 436.1.

Example 144: (S)-2-(1-cyclopropyl-3-methyl-4-oxo-1,4-dihydro-5H-pyrrolo[2,3-d]pyridazin-5-yl)-N-(1-(4-(trifluoromethyl)phenyl)ethyl)acetamide

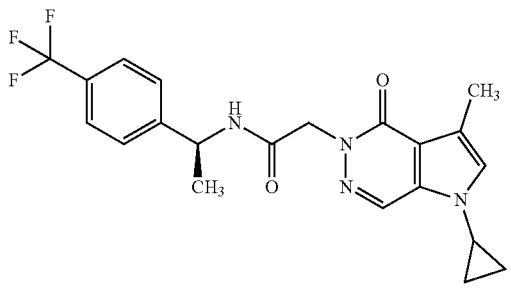 [SMILES: Cc1cn(C2CC2)c2cnn(CC(=O)N[C@@H](C)c3ccc(C(F)(F)F)cc3)c(=O)c12]

A mixture of 1-cyclopropyl-3-methyl-1,5-dihydro-4H-pyrrolo[2,3-d]pyridazin-4-one (21 mg, 0.111 (S)-2-bromo-N-(1-(4-(trifluoromethyl)phenyl)ethyl)acetamide (68.8 mg, 0.222 mmol) and $K_2CO_3$ (46.0 mg, 0.333 mmol) in DMF (555 μL) was stirred for 5 hours at RT. The reaction mixture was then diluted with methanol and purified by HPLC (Method B) to give the title compound as a white solid (27 mg, 58%). $^1$H NMR (400 MHz, CDCl$_3$) δ ppm 1.00-1.06 (m, 2H), 1.11-1.17 (m, 2H), 1.44-1.51 (m, 3H), 2.45 (d, J=1.00 Hz, 3H), 3.31-3.43 (m, 1H), 4.77-4.99 (m, 2H), 5.08-5.25 (m, 1H), 6.75-6.86 (m, 1H), 6.88 (d, J=1.00 Hz, 1H), 7.40 (s, 2H), 7.53 (d, J=8.16 Hz, 2H), 8.21 (s, 1H); ESI-MS m/z [M+H]$^+$ 419.3.

Example 145: (S)-2-(1-cyclopropyl-3-methyl-4-oxo-1,4-dihydro-5H-pyrrolo[2,3-d]pyridazin-5-yl)-N-(1-(4-methoxyphenyl)ethyl)acetamide

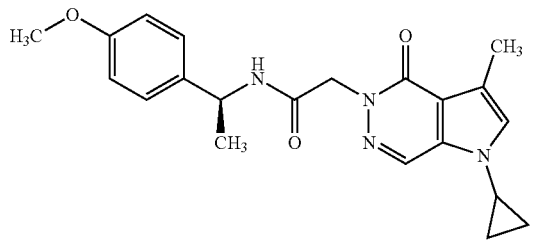 [SMILES: COc1ccc([C@H](C)NC(=O)Cn2ncc3c(c(C)cn3C3CC3)c2=O)cc1]

The title compound was prepared like EXAMPLE 144, using 1-cyclopropyl-3-methyl-1,5-dihydro-4H-pyrrolo[2,3-d]pyridazin-4-one and (S)-2-bromo-N-(1-(4-methoxyphenyl)ethyl)acetamide, and was obtained as a white solid (12.4 mg, 51%). $^1$H NMR (400 MHz, DMSO-d$_6$) δ ppm 0.90-1.09 (m, 4H), 1.35 (d, J=6.90 Hz, 3H), 2.29 (d, J=0.88 Hz, 3H), 3.09-3.15 (m, 1H), 3.44-3.60 (m, 1H), 3.73 (s, 3H), 4.61-4.73 (m, 2H), 4.79-4.93 (m, 1H), 6.80-6.93 (m, 2H), 7.04-7.15 (m, 1H), 7.20-7.30 (m, 2H), 8.18-8.32. (m, 1H); ESI-MS m/z [M+H]$^+$ 381.0.

Example 146: (S)-2-(1-cyclopropyl-3-methyl-4-oxo-1,4-dihydro-5H-pyrrolo[2,3-d]pyridazin-5-yl)-N-(1-phenylethyl)acetamide

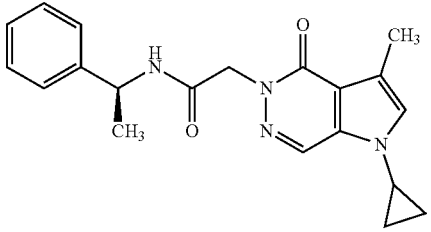 [SMILES: Cc1cn(C2CC2)c2cnn(CC(=O)N[C@@H](C)c3ccccc3)c(=O)c12]

The title compound was prepared like EXAMPLE 144, using 1-cyclopropyl-3-methyl-1,5-dihydro-4H-pyrrolo[2,3-d]pyridazin-4-one and (S)-2-bromo-N-(1-phenylethyl)acetamide, and was obtained as a white solid (11.3 mg, 34%). $^1$H NMR. (400 MHz, DMSO-d$_6$) δ ppm 0.96-1.01 (m, 2H), 1.02-1.09 (m, 2H), 1.35-1.42 (m, 3H), 2.29-2.31 (m, 3H), 3.52-3.62 (m, 1H), 4.68-4.79 (m, 2H), 4.90-5.00 (m, 1H), 7.13-7.17 (m, 1H), 7.22-7.28 (m, 1H), 7.35 (s, 4H), 8.28 (s, 1H), 8.44-8.51 (m, 1H); ESI-MS m/z [M+H]$^+$ 351.2.

Example 147: (S)-2-(1-cyclopropyl-3-methyl-4-oxo-1,4-dihydro-5H-pyrrolo[2,3-d]pyridazin-5-yl)-N-(1-(p-tolyl)ethyl)acetamide

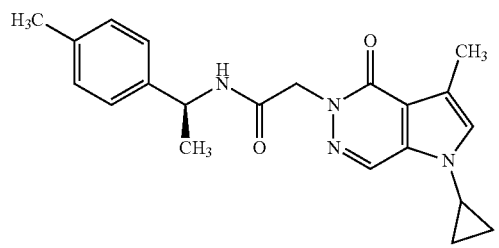 [SMILES: Cc1ccc([C@H](C)NC(=O)Cn2ncc3c(c(C)cn3C3CC3)c2=O)cc1]

The title compound was prepared like EXAMPLE 144, using 1-cyclopropyl-3-methyl-1,5-dihydro-4H-pyrrolo[2,3-d]pyridazin-4-one and (S)-2-bromo-N-(1-(p-tolyl)ethyl)acetamide, and was obtained as a white solid (17.3 mg, 50%). $^1$H NMR (400 MHz, DMSO-d$_6$) δ ppm 0.93-1.10 (m, 4H), 1.35 (d, J=6.90 Hz, 3H), 2.23-2.35 (m, 6H), 3.48-3.61 (m, 1H), 4.64-4.75 (m, 2H), 4.83-4.96 (m, 1H), 7.13 (s, 3H), 7.20 (s, 2H), 8.26 (s, 1H), 8.35-8.43 (m, 1H); ESI-MS m/z [M+H]$^+$ 365.2.

Example 148: (S)-2-(3-cyclopropyl-1-methyl-7-oxo-1,7-dihydro-6H-pyrazolo[3,4-d]pyridazin-6-yl)-N-(1-(3-fluorophenyl)ethyl)acetamide

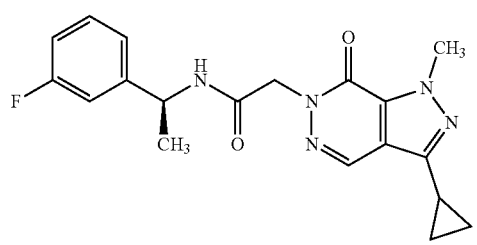 [SMILES: C[C@H](NC(=O)Cn1ncc2c(C3CC3)nn(C)c2c1=O)c1cccc(F)c1]

To a solution of 3-cyclopropyl-1-meth-1,6-dihydro-7H-pyrazolo[3,4-d]pyridazin-7-one (20 mg, 0.105 mmol) in anhydrous DMF (1 mL) were added (S)-2-bromo-N-(1-(3-fluorophenyl)ethyl)acetamide (30.1 mg, 0.116 mmol) and $K_2CO_3$ (43.6 mg, 0.315 mmol). The reaction mixture was stirred at RT for 18 hours and then purified by HPLC (Method B) to give the title compound as a white solid (11 mg, 28%). $^1$H NMR (400 MHz, $CD_3OD$) δ ppm 0.73-0.82 (m, 2H), 0.83-0.93 (m, 2H), 1.25-1.32 (m, 3H), 1.85-1.97 (m, 1H), 4.04 (s, 3H), 4.67 (d, J=1.76 Hz, 2H), 4.81-4.92 (m, 1H), 6.67-6.76 (m, 1H), 6.82-6.86 (m, 1H), 6.88-6.94 (m, 1H), 7.04-7.14 (m, 1H), 7.97 (s, 1H); ESI-MS m/z [M+H]$^+$ 370.3.

Example 149: (S)-2-(3-cyclopropyl-1-methyl-7-oxo-1,7-dihydro-6H-pyrazolo[3,4-d]pyridazin-6-yl)-N-(1-(p-tolyl)ethyl)acetamide

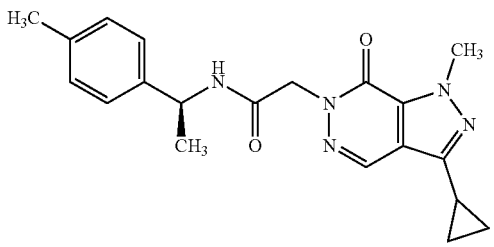 [SMILES: Cc1ccc([C@H](C)NC(=O)Cn2ncc3c(C4CC4)nn(C)c3c2=O)cc1]

The title compound was prepared like EXAMPLE 148, using 3-cyclopropyl-1-methyl-1,6-dihydro-7H-pyrazolo[3,4-d]pyridazin-7-one and (S)-2-bromo-N-(1-(p-tolyl)ethyl)acetamide, and was obtained as a white solid (14 mg, 36%). $^1$H NMR (400 MHz, $CD_3OD$) δ ppm 0.94-0.99 (m, 2H), 1.03-1.09 (m, 2H), 1.45 (d, J=7.03 Hz, 3H), 2.12 (tt, J=8.34, 5.08 Hz, 1H), 2.29 (s, 3H), 4.21 (s, 3H), 4.78-4.91 (m, 2H), 5.01 (q, J=7.03 Hz, 1H), 7.07-7.12 (m, 2H), 7.16-7.23 (m, 2H), 8.18 (s, 1H); ESI-MS m/z [M+H]$^+$ 366.3.

Example 150: (S)—N-(1-(2-chloro-6-fluorophenyl)ethyl)-2-(3-cyclopropyl-1-methyl-7-oxo-1,7-dihydro-6H-pyrazolo[3,4-d]pyridazin-6-yl)acetamide

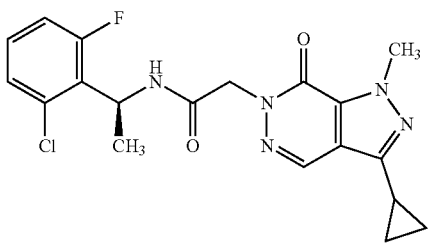 [SMILES: C[C@H](NC(=O)Cn1ncc2c(C3CC3)nn(C)c2c1=O)c1c(F)cccc1Cl]

The title compound was prepared like EXAMPLE 148, using 3-cyclopropyl-1-methyl-1,6-dihydro-7H-pyrazolo[3,4-d]pyridazin-7-one and (S)-2-bromo-N-(1-(2-chloro-6-fluorophenyl)ethyl)acetamide, and was obtained as a white solid (21 mg, 50%). $^1$H NMR (400 MHz, DMSO-$d_6$) δ ppm 0.82-0.88 (m, 2H), 0.95-1.00 (m, 2H), 1.40 (d, J=7.03 Hz, 3H), 2.13-2.21 (m, 1H), 4.07 (s, 3H), 4.59-4.66 (m, 1H), 4.71-4.77 (m, 1H), 5.31 (t, J=6.78 Hz, 1H), 7.06-7.15 (m, 1H), 7.17-7.29 (m, 1H), 8.26 (s, 1H), 8.65 (d, J=7.03 Hz, 1H); ESI-MS m/z [M+H]$^+$ 404.3.

Example 151: (S)-2-(3-cyclopropyl-1-methyl-7-oxo-1,7-dihydro-6H-pyrazolo[3,4-d]pyridazin-6-yl)-N-(1-(3-fluoro-4-methylphenyl)ethyl)acetamide

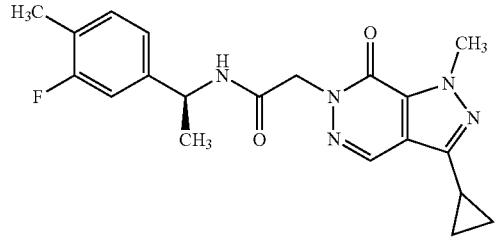 [SMILES: Cc1ccc([C@H](C)NC(=O)Cn2ncc3c(C4CC4)nn(C)c3c2=O)cc1F]

The title compound was prepared like EXAMPLE 148, using 3-cyclopropyl-1-methyl-1,6-dihydro-7H-pyrazolo[3,4-d]pyridazin-7-one and (S)-2-bromo-N-(1-(3-fluoro-4-methylphenyl)ethyl)acetamide, and was obtained as a white solid (10 mg, 15%). $^1$H NMR (400 MHz, $CDCl_3$) δ ppm 0.97-1.13 (m, 4H), 1.47 (d, J=6.78 Hz, 3H), 2.06-2.13 (m, 1H), 2.24 (d, J=1.76 Hz, 3H), 4.29 (s, 3H), 4.80-4.93 (m, 2H), 5.11 (dt, J=14.49, 7.18 Hz, 1H), 6.12-6.21 (m, 1H), 6.90-7.00 (m, 2H), 7.12 (t, J=7.78 Hz, 1H), 8.16 (s, 1H), ESI-MS m/z [M+H]$^+$ 384.2.

Example 152: (S)-2-(3-cyclopropyl-1-methyl-7-oxo-1,7-dihydro-6H-pyrazolo[3,4-d]pyridazin-6-yl)-N-(1-(2-fluoro-4-methylphenyl)ethyl)acetamide

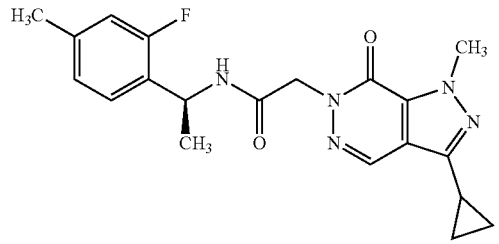 [SMILES: Cc1ccc([C@H](C)NC(=O)Cn2ncc3c(C4CC4)nn(C)c3c2=O)c(F)c1]

The title compound was prepared like EXAMPLE 148, using 3-cyclopropyl-1-methyl-1,6-dihydro-7H-pyrazolo[3,4-d]pyridazin-7-one and (S)-2-bromo-N-(1-(2-fluoro-4-methylphenyl)ethyl)acetamide, and was obtained as a white solid (21 mg, 32%). $^1$H NMR (400 MHz, $CDCl_3$) δ ppm 0.99-1.12 (m, 4H), 1.46-1.51 (m, 3H), 2.13 (br s, 1H), 2.32 (s, 3H), 4.28 (s, 3H), 4.81-4.89 (m, 2H), 5.21-5.28 (m, 1H), 6.40 (td, J=5.40, 2.01 Hz, 1H), 6.81-6.91 (m, 2H), 7.13 (t, J=7.91 Hz, 1H), 8.15 (s, 1H); ESI-MS m/z [M+H]$^+$ 384.2.

Example 153: (S)-2-(1-methyl-7-oxo-1,7-dihydro-6H-pyrrolo[2,3-d]pyridazin-6-yl)-N-(1-phenylethyl)acetamide

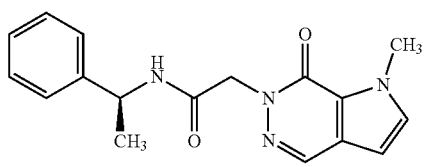 [SMILES: C[C@H](NC(=O)Cn1ncc2ccn(C)c2c1=O)c1ccccc1]

The title compound was prepared like EXAMPLE 148, using 1-methyl-1,6-dihydro-7H-pyrrolo[2,3-d]pyridazin-7-one and (S)-2-brume-N-(1-phenylethyl)acetamide, and was obtained as a white solid (36 mg, 79%). ¹H NMR (400 MHz, CDCl₃) δ ppm 1.46 (d, J=6.78 Hz, 3H), 4.15 (s, 3H), 4.89 (d, J=2.01 Hz, 2H), 5.15 (quin, J=7.15 Hz, 1H), 6.40 (d, J=3.01 Hz, 1H), 6.55 (br d, J=7.28 Hz, 1H), 7.06 (d, J=2.76 Hz, 1H), 7.17-7.23 (m, 1H), 7.26-7.34 (m, 4H), 8.10 (s, 1H); ESI-MS m/z [M+H]⁺ 311.2.

Example 154: (S)—N-(1-(3-fluorophenyl)ethyl)-2-(1,3,4-trimethyl-7-oxo-1,7-dihydro-6H-pyrazolo[3,4-d]pyridazin-6-yl)acetamide

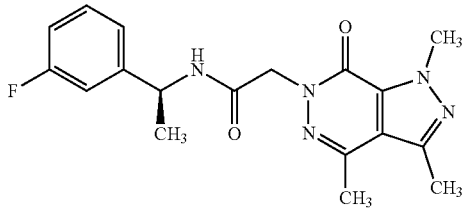 [SMILES: Cc1nn(CC(=O)N[C@@H](C)c2cccc(F)c2)c(=O)c2c1c(C)nn2C]

The title compound was prepared like EXAMPLE 148, using 1,3,4-trimethyl-1,6-dihydro-7H-pyrazolo[3,4-d]pyridazin-7-one and (S)-2-bromo-N-(1-(3-fluorophenyl)ethyl)acetamide, and was obtained as a white solid (5 mg, 4%). ¹H NMR (400 MHz, CDCl₃) δ ppm 1.45 (d, J=7.03 Hz, 3H), 2.53 (d, J=11.29 Hz, 6H), 4.28 (s, 3H), 4.72-4.89 (m, 2H), 5.06-5.17 (m, 1H), 6.30 (br d, J=7.78 Hz, 1H), 6.85-6.98 (m, 2H), 7.04 (dd, J=7.78, 0.75 Hz, 1H), 7.24 (s, 1H); ESI-MS m/z [M+H]⁺ 358.3.

Example 155: (S)-2-(1-cyclobutyl-3-methyl-4-oxo-1,4-dihydro-5H-pyrazolo[3,4-d]pyridazin-5-yl)-N-(1-(4-(trifluoromethyl)phenyl)ethyl)acetamide

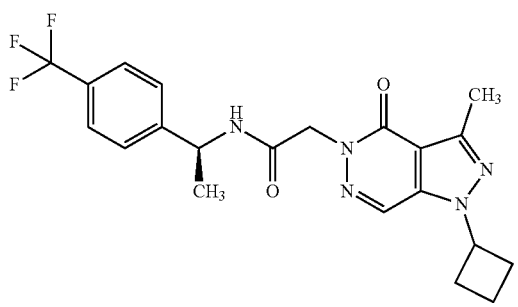 [SMILES: Cc1nn(C2CCC2)c2cnn(CC(=O)N[C@@H](C)c3ccc(C(F)(F)F)cc3)c(=O)c12]

A slurry of 1-cyclobutyl-5-(hydroxymethyl)-3-methyl-1,5-dihydro-4H-pyrazolo[3,4-d]pyridazin-4-one (23.12 mg, 0.099 mmol) and K₂CO₃ (26.7 mg, 0.193 mmol) in DMF (0.8 mL) was stirred at 20° C. for 2 hours. Next, (S)-2-bromo-N-(1-(4-(trifluoromethyl)phenyl)ethyl)acetamide (30 mg, 0.097 mmol) was added and the mixture stirred at 20° C. for 18 hours. The mixture was then diluted with methanol (0.1 mL), filtered through a syringe filter, rinsed with DMF (0.2 mL) and methanol (0.2 mL) and purified by preparative HPLC (Method B) to give the title compound as a white solid (14 mg, 33%). ¹H NMR (400 MHz, DMSO-d₆) δ ppm 1.39 (d, J=7.03 Hz, 3H), 1.74-1.94 (m, 2H), 2.38-2.47 (m, 2H), 2.52 (s, 3H), 2.54-2.65 (m, 2H), 4.68-4.83 (m, 2H), 4.98 (quin, J=7.18 Hz, 1H), 5.23 (quin, J=8.22 Hz, 1H), 7.55 (d, J=8.16 Hz, 2H), 7.69 (d, J=8.16 Hz, 2H), 8.50 (s, 1H), 8.63 (d, J=7.53 Hz, 1H); ESI-MS m/z [M+H]⁺ 434.4.

Example 156: (S)-2-(1-(bicyclo[1.1.1]pentan-1-yl)-3-methyl-4-oxo-1,4-dihydro-5H-pyrazolo[3,4-d]pyridazin-5-yl)-N-(1-(4-(trifluoromethyl)phenyl)ethyl)acetamide

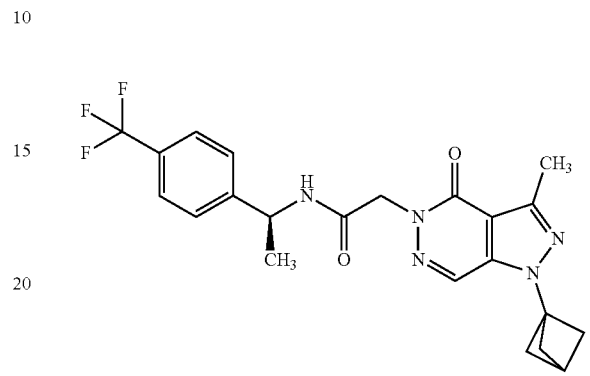

The title compound was prepared like EXAMPLE 155, using 1-(bicyclo[1.1.1]pentan-1-yl)-5-(hydroxymethyl)-3-methyl-1,5-dihydro-4H-pyrazolo[3,4-d]pyridazin-4-one and (S)-2-bromo-N-(1-(4-(trifluoromethyl)phenyl)ethyl)acetamide, and was obtained as a white solid (27 mg, 72%). ¹H NMR (400 MHz, DMSO-d₆) δ ppm 1.40 (d, J=7.15 Hz, 3H), 2.42 (s, 6H), 2.49 (br s, 3H), 2.71 (s, 1H), 4.70-4.84 (m, 2H), 4.99 (quin, J=7.09 Hz, 1H), 7.55 (d, J=8.41 Hz, 2H), 7.69 (d, J=8.16 Hz, 2H), 8.49 (s, 1H), 8.65 (d, J=7.65 Hz, 1H); ESL-MS m/z [M+H]⁺ 446.3.

Example 157: (S)-2-(1-(tert-butyl)-3-methyl-4-oxo-1,4-dihydro-5H-pyrazolo[3,4-d]pyridazin-5-yl)-N-(1-(4-(trifluoromethyl)phenyl)ethyl)acetamide

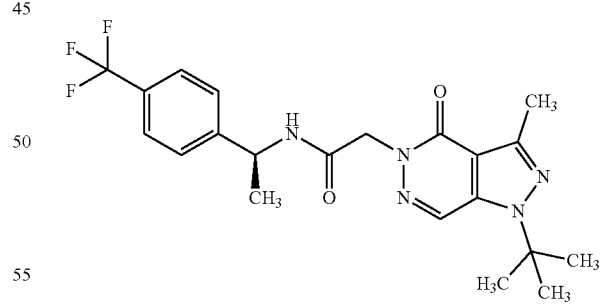

The title compound was prepared like EXAMPLE 155, using 1-(tert-butyl)-3-methyl-1,5-dihydro-4H-pyrazolo[3,4-d]pyridazin-4-one and (S)-2-bromo-N-(1-(4-(trifluoromethyl)phenyl)ethyl)acetamide, and was obtained as a white solid (21 mg, 60%). ¹H NMR (400 MHz, DMSO) δ ppm 1.40 (d, J=7.15 Hz, 3H), 1.67 (s, 9H), 2.49 (s, 3H), 4.68-4.84 (m, 2H), 4.98 (quin, J=7.03 Hz, 1H), 7.55 (d, J=8.16 Hz, 2H), 7.69 (d, J=8.16 Hz, 2H), 8.64 (s, 1H), 8.68 (d, J=7.65 Hz, 1H); ESI-MS m/z [M+H]⁺ 436.3.

Example 158: (S)-2-(3-cyclopropyl-1-methyl-7-oxo-1,7-dihydro-6H-pyrrolo[2,3-d]pyridazin-6-yl)-N-(1-(p-tolyl)ethyl)acetamide

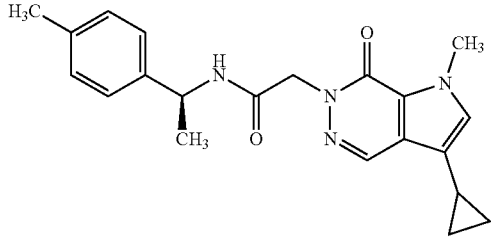 [SMILES: Cc1ccc([C@H](C)NC(=O)Cn2ncc3c(C4CC4)cn(C)c3c2=O)cc1]

A mixture of 3-cyclopropyl-1-methyl-1,6-dihydro-7H-pyrrolo[2,3-d]pyridazin-7-one (15 mg, 0.079 mmol), (S)-2-bromo-N-(1-(p-tolyl)ethyl)acetamide (40.6 mg, 0.159 mmol) and K$_2$CO$_3$ (21.91 mg, 0.159 mmol) in DMF (396 µL) was stirred for 5 hours at RT. The reaction mixture was then diluted with methanol and purified by HPLC (Method B) to give the title compound as a solid (8.6 mg, 30%). $^1$H NMR (400 MHz, CD$_3$OD) δ ppm 0.54-0.69 (m, 2H), 0.86-1.01 (m, 2H), 1.46 (d, J=6.90 Hz, 3H), 1.82-1.97 (m, 1H), 2.30 (s, 3H), 4.00-4.09 (m, 3H), 4.81-4.89 (m, 3H), 4.96-5.07 (m, 1H), 6.98-7.03 (m, 1H), 7.09-7.16 (m, 2H), 7.19-7.27 (m, 2H), 8.23 (s, 1H); ESI-MS m/z [M+H]$^+$ 365.3.

Example 159: (S)-2-(3-cyclopropyl-1-methyl-7-oxo-1,7-dihydro-6H-pyrrolo[2,3-d]pyridazin-6-yl)-N-(1-(4-(trifluoromethyl)phenyl)ethyl)acetamide

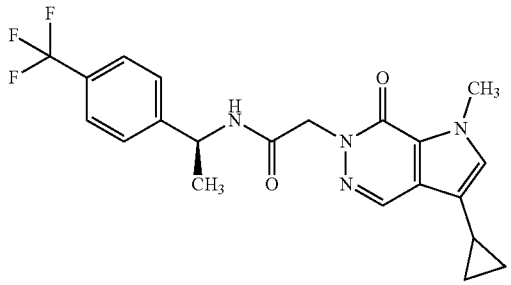 [SMILES: C[C@H](NC(=O)Cn1ncc2c(C3CC3)cn(C)c2c1=O)c1ccc(C(F)(F)F)cc1]

The title compound was prepared like 158, using 3-cyclopropyl-1-methyl-1,6-dihydro-7H-pyrrolo[2,3-d]pyridazin-7-one and (S)-2-bromo-N-(1-(4-(trifluoromethyl)phenyl)ethyl)acetamide, and was obtained as an oil (18.7 mg, 56%). $^1$H NMR (400 MHz, DMSO-d$_6$) δ ppm 0.51-0.66 (m, 2H), 0.80-0.97 (m, 2H), 1.40 (d, J=7.03 Hz, 3H), 1.87-2.01 (m, 1H), 3.99 (s, 3H), 4.63-4.83 (m, 2H), 4.93-5.09 (m, 1H), 7.15 (s, 1H), 7.57 (s, 2H), 7.68 (s, 2H), 8.20 (s, 1H), 8.57-8.65 (m, 1H); ESI-MS m/z [M+H]$^+$ 419.3.

Example 160: (R)-2-(1-cyclopropyl-3-methyl-4-oxo-1,4-dihydro-5H-pyrazolo[3,4-d]pyridazin-5-yl)-N-(1-(4-(trifluoromethyl)phenyl)ethyl)acetamide

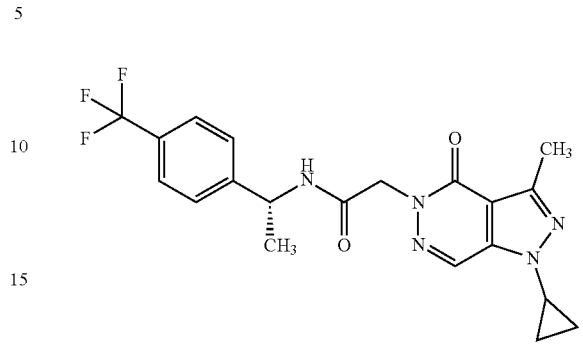

To a 100 mL round-bottom flask charged with 1-cyclopropyl-3-methyl-1,5-dihydro-4H-pyrazolo[3,4-d]pyridazin-4-one (1.8 g, 9.46 mmol), (R)-2-chloro-N-(1-(4-(trifluoromethyl)phenyl)ethyl)acetamide (2.51 g, 9.46 mmol) and DMA (20 mL) was added K$_2$CO$_3$ (1.962 g, 14.20 mmol). The reaction mixture was stirred at RT for 18 hours and then water (80 mL) was added. A precipitate was isolated by filtration, washed with water (20 mL×2) and dried under reduced pressure overnight at 50° C. to give the title compound as an off-white solid (3.74 g, 94%). $^1$H NMR (400 MHz, DMSO-d$_6$) δ ppm 1.12 (br d, J=4.95 Hz, 4H), 1.39 (d, J=6.97 Hz, 3H), 2.46 (s, 3H), 3.80-3.94 (m, 1H), 4.06-4.13 (m, 1H), 4.77 (d, J=3.12 Hz, 2H), 4.91-5.11 (m, 1H), 7.55 (d, J=7.98 Hz, 2H), 7.69 (d, J=7.98 Hz, 2H), 8.50 (s, 1H), 8.62-8.80 (m, 1H); ESI-MS m/z [M+H]$^+$ 420.2.

Example 161: (S)—N-(1-(4-chlorophenyl)ethyl)-2-(1-methyl-7-oxo-1,7-dihydro-6H-pyrrolo[2,3-d]pyridazin-6-yl)acetamide

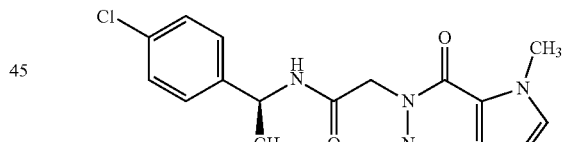

A 4 mL vial equipped with a stir bar was charged with K$_2$CO$_3$ (48 mg, 0.35 mmol) and (S)-2-bromo-N-(1-(4-chlorophenyl)ethyl)acetamide (39 mg, 0.14 mmol), A solution of 1-methyl-1,6-dihydro-7H-pyrrolo[2,3-d]pyridazin-7-one (25 mg, 0.17 mmol) in DMF (0.5 mL) was added and the vial was capped. The reaction mixture was stirred at 45° C. for 18 hours and then filtered through a 0.45 µm frit and purified by HPLC (Method A) to give the title compound (28 mg, 59%). $^1$H NMR (400 MHz, CD$_3$OD) δ ppm 1.45-1.50 (m, 3H), 4.11-4.16 (m, 3H), 4.83-4.92 (m, 2H), 4.99-5.08 (m, 1H), 6.46-6.51 (m, 1H), 7.29-7.36 (m, 5H), 8.13-8.19 (m, 1H), 8.47-8.58 (m, 1H); ESI-MS m/z [M+H]$^+$ 345.1.

Example 162: (S)-2-(1-methyl-7-oxo-1,7-dihydro-6H-pyrrolo[2,3-d]pyridazin-6-yl)-N-(1-(p-tolyl)ethyl)acetamide

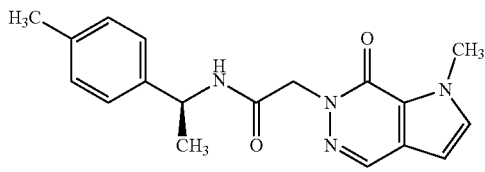 [SMILES: Cc1ccc([C@H](C)NC(=O)Cn2ncc3ccn(C)c3c2=O)cc1]

The title compound (16 mg, 35%), was prepared like EXAMPLE 161, using methyl-1,6-dihydro-7H-pyrrolo[2,3-d]pyridazin-7-one and (S)-2-bromo-N-(1-(p-tolyl)ethyl)acetamide, ESI-MS m/z [M+H]$^+$ 325.1.

Example 163: (S)—N-(1-(4-methoxyphenyl)ethyl)-2-(1-methyl-7-oxo-1,7-dihydro-6H-pyrrolo[2,3-d]pyridazin-6-yl)acetamide

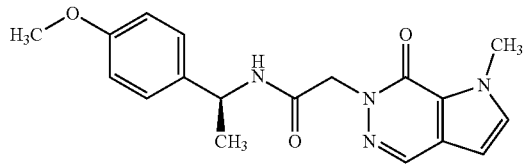 [SMILES: COc1ccc([C@H](C)NC(=O)Cn2ncc3ccn(C)c3c2=O)cc1]

The title compound (17 mg, 36%) was prepared like EXAMPLE 161, using 1-methyl-1,6-dihydro-7H-pyrrolo[2,3-d]pyridazin-7-one and (S)-2-bromo-N-(1-(4-methoxyphenyl)ethyl)acetamide. ESI-MS m/z [M+H]$^+$ 341.1.

Example 164: (S)-2-(1-methyl-7-oxo-1,7-dihydro-6H-pyrrolo[2,3-d]pyridazin-6-yl)-N-(1-(4-(trifluoromethyl)phenyl)ethyl)acetamide

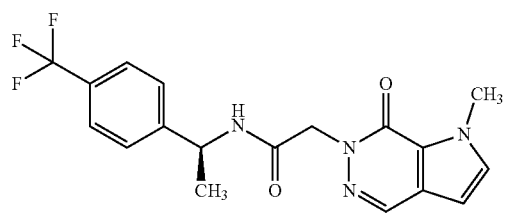 [SMILES: C[C@H](NC(=O)Cn1ncc2ccn(C)c2c1=O)c1ccc(C(F)(F)F)cc1]

The title compound (25 mg, 48%) was prepared like EXAMPLE 161, using 1-methyl-1,6-dihydro-7H-pyrrolo[2,3-d]pyridazin-7-one and (S)-2-bromo-N-(1-(4-(trifluoromethyl)phenyl)ethyl)acetamide. $^1$H NMR (400 MHz, CD$_3$OD) δ ppm 1.48-1.54 (m, 3H), 4.11-4.16 (m, 3H), 4.85-4.95 (m, 2H), 5.06-5.16 (m, 1H), 6.47-6.52 (m, 1H), 7.28-7.33 (m, 1H), 7.51-7.56 (m, 2H), 7.59-7.64 (m, 2H), 8.13-8.19 (m, 1H), 8.15-8.17 (m, 1H), 8.55-8.69 (m, 1H); ESI-MS [M+H]$^+$ 379.1.

Example 165: (S)—N-(1-(2-fluoro-4-methylphenyl)ethyl)-2-(1-methyl-7-oxo-1,7-dihydro-6H-pyrrolo[2,3-d]pyridazin-6-yl)acetamide

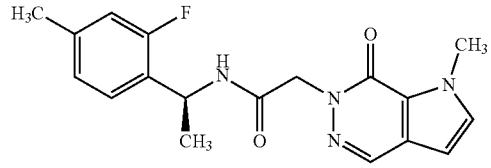 [SMILES: Cc1ccc([C@H](C)NC(=O)Cn2ncc3ccn(C)c3c2=O)c(F)c1]

The title compound (35 mg, 73%) was prepared like EXAMPLE 161, using 1-methyl-1,6-dihydro-7H-pyrrolo[2,3-d]pyridazin-7-one and (S)-2-bromo-N-(1-(2-fluoro-4-methylphenyl)ethyl)acetamide. ESI-MS m/z [M+H]$^+$ 343.1.

Example 166: (S)-2-(1-isopropyl-4-oxo-1,4-dihydro-5H-pyrazolo[3,4-d]pyridazin-5-yl)-N-(1-(4-(methyl-d$_3$)phenyl)ethyl)acetamide

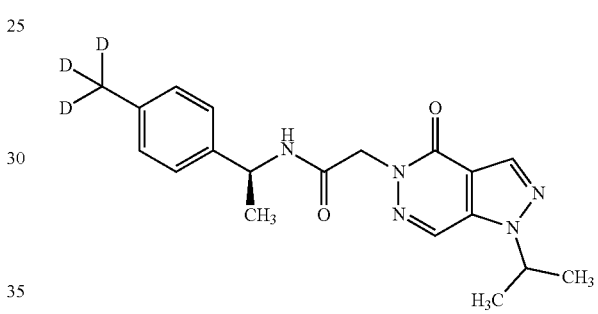

A solution of (S)-2-bromo-N-(1-(4-(methyl-d$_3$)phenyl)ethyl)acetamide (20 mg, 0.077 mmol) in DMA (0.5 mL) was added to K$_2$CO$_3$ (21 mg, 0.15 mmol) and 1-isopropyl-1,5-dihydro-4H-pyrazolo[3,4-d]pyridazin-4-one (15 mg, 0.085 mmol) in a 4 mL vial equipped with a stir bar. The vial was capped. The reaction mixture was stirred at 26° C. for 18 hours and then filtered through a 0.45 μm frit and purified by HPLC (Method B) to give the title compound (21.8 mg, 79%). ESI-MS m/z [M+H]$^+$ 357.1.

Example 167: (S)-2-(1-cyclopropyl-3-methyl-4-oxo-1,4-dihydro-5H-pyrazolo[3,4-d]pyridazin-5-yl)-N-(1-(4-(methyl-d$_3$)phenyl)ethyl)acetamide

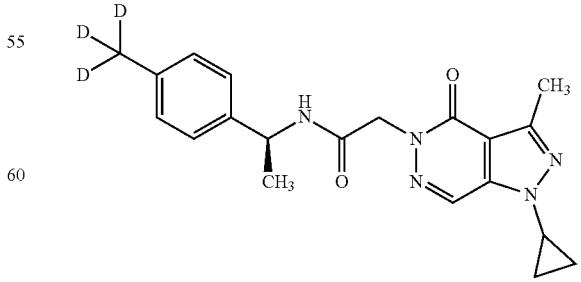

A solution of (S)-2-bromo-N-(1-(4-(methyl-d$_3$)phenyl)ethyl)acetamide (20 mg, 0.077 mmol) in DMA (0.5 mL) was added to K₂CO₃ (21 mg, 0.15 mmol) and 1-cyclopropyl-3-methyl-1,5-dihydro-4H-pyrazolo[3,4-d]pyridazin-4-one (16 mg, 0.085 mmol) in a 4 mL vial equipped with a stir bar. The vial was capped. The reaction mixture was stirred at 26° C. for 18 hours and then filtered through a 0.45 µm frit and purified by HPLC (Method B) to give the title compound (19.8 mg, 69%). ¹H NMR (400 MHz, DMSO-d₆) δ ppm 1.05-1.20 (m, 4H), 1.35 (d, J=690 Hz, 3H), 2.47 (s, 3H), 3.84-3.91 (m, 1H), 4.69-4.79 (m, 2H), 4.88 (quin, J=7.34 Hz, 1H), 7.11-7.16 (m, 2H), 7.17-7.25 (m, 2H), 8.52 (d, J=8.24 Hz, 2H), 8.51 (s, 1H); ESI-MS ink [M+H]⁺ 369.1.

Example 168: (S)-2-(1-isopropyl-3-methyl-4-oxo-1,4-dihydro-5H-pyrazolo[3,4-d]pyridazin-5-yl)-N-(1-(4-(Methyl-d₃)phenyl)ethyl)acetamide

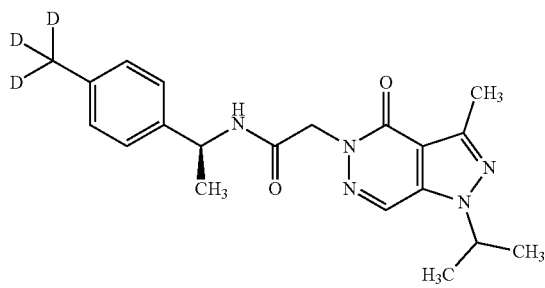 [SMILES: [2H]C([2H])([2H])c1ccc([C@H](C)NC(=O)Cn2ncc3c(c(C)nn3C(C)C)c2=O)cc1]

A solution of (S)-2-bromo-N-(1-(4-(methyl-d₃)phenyl)ethyl)acetamide (8 mg, 0.031 mmol) in DMA (0.5 mL) was added to K₂CO₃ (8.5 mg, 0.062 mmol) and 1-isopropyl-3-methyl-1,5-dihydro-4H-pyrazolo[3,4-d]pyridazin-4-one (6.5 mg, 0.034 mmol) in a 4 mL vial equipped with a stir bar. The mixture was capped. The reaction mixture was stirred at 26° C. for 18 hours and then filtered through a 0.45 µm frit and purified by HPLC (Method B) to give the title compound (4.7 mg, 41%). EST-MS m/z [M+H]⁺ 371.2.

Example 169: (S)-2-(1-methyl-4-oxo-3-(trifluoromethyl)-1,4-dihydro-5H-pyrazolo[3,4-d]pyridazin-5-yl)-N-(1-(p-tolyl)ethyl)acetamide

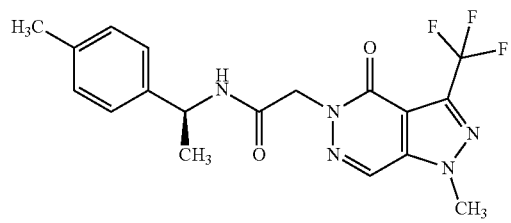

To a 4 mL vial equipped with a stir bar was added 1-methyl-3-(trifluoromethyl)-1,5-dihydro-4H-pyrazolo[3,4-d]pyridazin-4-one (22.4 mg, 0.103 mmol), (S)-2-bromo-N-(1-(p-tolyl)ethyl)acetamide (25.0 mg, 0.0980 mmol), K₂CO₃ (16.0 mg, 0.117 mmol) and DMF (326 µL). The vial was capped, and the resulting slurry was stirred at 20° C. for 23 hours. The reaction mixture was diluted with MeOH/DMF, filtered through a 0.45 µm Millipore® Millex-FH Phobic PTFE syringe filter and purified by preparative HPLC (Method B) to give the title compound as a white solid (22.3 mg, 58%). ¹H NMR (400 MHz, DMSO-d₆) δ ppm 1.36 (d, J=7.03 Hz, 3H), 2.27 (s, 3H), 4.18 (s, 3H), 4.73-4.83 (m, 2H), 4.89 (quin, J=7.15 Hz, 1H), 7.10-7.15 (m, 2H), 7.19-7.23 (m, 2H), 8.52 (d, J=7.91 Hz, 1H), 8.68 (s, 1H); ESI-MS m/z [M+H]⁺ 394.2.

Example 170: (S)—N-(1-(2-fluoro-4-methylphenyl)ethyl)-2-(1-methyl-4-oxo-3-(trifluoromethyl)-1,4-dihydro-5H-pyrazolo[3,4-d]pyridazin-5-yl)acetamide

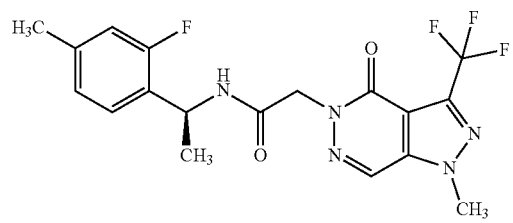 [SMILES: Cc1ccc([C@H](C)NC(=O)Cn2ncc3c(c(C(F)(F)F)nn3C)c2=O)c(F)c1]

The title compound was prepared like EXAMPLE 169, using 1-methyl-3-(trifluoromethyl)-1,5-dihydro-4H-pyrazolo[3,4-d]pyridazin-4-one and (S)-2-bromo-N-(1-(2-fluoro-4-methylphenyl)ethyl)acetamide, and was obtained as a white solid (28.2 mg, 72%). ¹H NMR (400 MHz, DMSO-d₆) δ ppm 1.35 (d, =7.03 Hz, 3H), 2.28 (s, 3H), 4.18 (s, 3H), 4.74-4.86 (m, 2H), 5.10 (quin, J=7.15 Hz, 1H), 6.93-7.03 (m, 2H), 7.25-7.33 (m, 1H), 8.62 (d, J=7.65 Hz, 1H), 8.68 (s, 1H); ESI-MS m/z [M+H]⁺ 412.1.

Example 171: (S)—N-(1-(3-fluoro-4-methylphenyl)ethyl)-2-(1-methyl-4-oxo-3-(trifluoromethyl)-1,4-dihydro-5H-pyrazolo[3,4-d]pyridazin-5-yl)acetamide

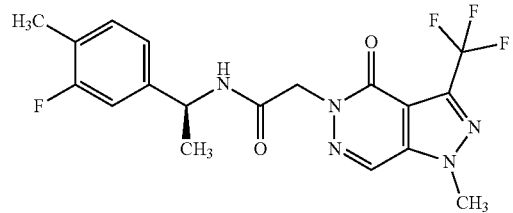 [SMILES: Cc1ccc([C@H](C)NC(=O)Cn2ncc3c(c(C(F)(F)F)nn3C)c2=O)cc1F]

The title compound was prepared like EXAMPLE 169, using 1-methyl-3-(trifluoromethyl)-1,5-dihydro-4H-pyrazolo[3,4-d]pyridazin-4-one and (S)-2-bromo-N-(1-(3-fluoro-4-methylphenyl)ethyl)acetamide, and was obtained as a white solid (20.7 mg, 54%). ¹H NMR (400 MHz, DMSO-d₆) δ ppm 1.36 (d, =7.03 Hz, 3H), 2.20 (d, J=1.51 Hz, 3H), 4.18 (s, 3H), 4.76-4.84 (m, 2H), 4.90 (quin, J=7.18 Hz, 1H), 7.02-7.11 (m, 2H), 7.22 (t, J=7.91 Hz, 1H), 8.57 (d, J=7.78 Hz, 1H), 8.69 (s, 1H); EST-MS m/z [M+H]⁺ 412.1.

Example 172: (S)-2-(1-methyl-4-oxo-3-(trifluoromethyl)-1,4-dihydro-5H-pyrazolo[3,4-d]pyridazin-5-yl)-N-(1-(4-(trifluoromethyl)phenyl)ethyl)acetamide

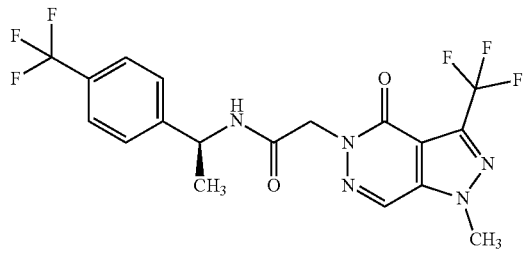 [SMILES: C[C@H](NC(=O)Cn1ncc2c(c(C(F)(F)F)nn2C)c1=O)c1ccc(C(F)(F)F)cc1]

The title compound was prepared like EXAMPLE 169, using 1-methyl-3-(trifluoromethyl)-1,5-dihydro-4H-pyrazolo[3,4-d]pyridazin-4-one and (S)-2-bromo-N-(1-(4-(trifluoromethyl)phenyl)ethyl)acetamide, and was obtained as a white solid (25.8 mg, 61%). $^{1}$H NMR (400 MHz, DMSO-$d_6$) δ ppm 1.40 (d, J=7.15 Hz, 3H), 4.18 (s, 3H), 4.77-4.87 (m, 2H), 4.99 (quin, J=7.09 Hz, 1H), 7.55 (d, J=8.41 Hz, 2H), 7.68 (d, J=8.16 Hz, 2H), 8.69 (s, 1H), 8.71 (d, J=7.53 Hz, 1H); ESI-MS m/z [M+H]+ 448.1.

Example 173: (S)—N-(cyclopropyl(phenyl)methyl)-2-(1-cyclopropyl-3-methyl-4-oxo-1,4-dihydro-5H-pyrazolo[3,4-d]pyridazin-5-yl)acetamide

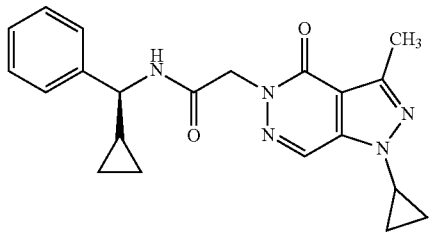 [SMILES: Cc1nn(C2CC2)c2cnn(CC(=O)N[C@H](c3ccccc3)C3CC3)c(=O)c12]

A solution of 1-cyclopropyl-3-methyl-1,5-dihydro-4H-pyrazolo[3,4-d]pyridazin-4-one (17 mg, 0.090 mmol) in NMP (0.6 mL) was added to $K_2CO_3$ (21 mg, 0.15 mmol) and (S)-2-promo-N-(cyclopropyl(phenyl)methyl)acetamide (20 mg, 0.075 mmol) in a 4 mL vial equipped with a stir bar. The vial was capped. The reaction mixture was stirred at 40° C. for 18 hours and then filtered through a 0.45 μm frit and purified by HPLC (Method B) to give the title compound (16.5 mg, 59%). $^{1}$H NMR (400 MHz, $CD_3OD$) δ ppm 0.37-0.49 (m, 2H), 0.59-0.67 (m, 2H), 1.17-1.28 (m, 5H), 2.54-2.59 (m, 3H), 3.71-3.80 (m, 1H), 4.32-4.38 (m, 1H), 4.91-4.98 (m, 2H), 7.2.2-7.29 (m, 1H), 7.31-7.36H), 7.38-7.44 (in, 2H), 8.44-8.48 (m, 1H); ESI-MS m/z [M+H]+ 378.1.

Example 174: (S)-2-(1-methyl-7-oxo-1,7-dihydro-6H-pyrrolo[2,3-d]pyridazin-1-yl)-N-(1-(4-(methyl-$d_3$)phenyl)ethyl)acetamide

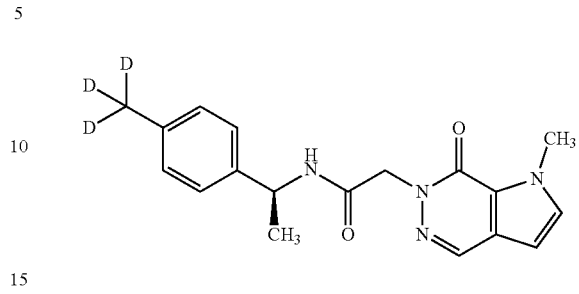

A mixture of (S)-3-bromo-N-(1-(4-(methyl-$d_3$)phenyl)ethyl)acetamide (20 mg, 0.08 mmol), 1-methyl-1,6-dihydro-7H-pyrrolo[2,3-d]pyridazin-7-one (9 mg, 0.06 mmol), potassium carbonate (21 mg, 0.15 mmol) and NMP (1 mL) was stirred at 40° C. for 18 hours and was then purified by HPLC (Method B) to give the title compound (7 mg, 28%). ESI-MS m/z [M+H]+ 328.1.

Table 5, below, lists biological assay data (GPR139 activation and GPR139 binding affinity) for some of the compounds described in the examples, where larger $pEC_{50}$ and pKi values represent higher activation (potency) and binding affinity, respectively. The example compounds shown in Table 5 were tested in accordance with the assays described in the section entitled Biological Activity, above.

TABLE 5

| | GPR139 Potency ($pEC_{50}$) and Binding Affinity (pKi) | |
|---|---|---|
| Ex. No. | $pEC_{50}$ | pKi |
| 1 | 7.29 | 7.26 |
| 2 | 7.25 | 6.06 |
| 3 | ≤5.00 | 7.14 |
| 4 | ≤5.00 | 7.04 |
| 5 | 6.65 | 7.03 |
| 6 | ≤5.00 | 7.63 |
| 7 | ≤5.00 | 6.79 |
| 8 | ≤5.00 | 7.56 |
| 9 | 7.02 | — |
| 10 | 7.10 | 6.92 |
| 11 | 5.56 | 6.97 |
| 12 | 5.67 | 7.47 |
| 13 | 6.99 | 7.68 |
| 14 | 6.21 | 7.43 |
| 15 | 6.21 | 7.24 |
| 16 | 6.70 | 7.96 |
| 17 | 7.24 | 5.53 |
| 18 | 6.77 | 6.45 |
| 19 | 7.17 | 5.97 |
| 20 | 7.38 | 6.75 |
| 21 | 6.94 | 7.55 |
| 22 | 6.98 | 8.04 |
| 23 | 6.78 | 6.99 |
| 24 | 7.33 | 7.01 |
| 25 | 7.63 | 6.21 |
| 26 | 6.03 | 4.41 |
| 27 | 6.62 | 6.66 |
| 28 | 7.28 | 7.49 |
| 29 | 6.29 | 4.52 |
| 30 | 7.14 | 6.59 |
| 31 | 7.24 | 4.93 |
| 32 | 6.21 | 4.52 |
| 33 | 7.18 | 5.28 |
| 34 | 7.15 | 5.22 |
| 35 | 7.10 | 5.99 |
| 36 | 7.41 | 6.60 |
| 37 | 7.58 | 6.45 |

TABLE 5-continued

GPR139 Potency (pEC$_{50}$) and Binding Affinity (pKi)

| Ex. No. | pEC$_{50}$ | pKi |
|---|---|---|
| 38 | 7.26 | 7.14 |
| 39 | 7.44 | 6.64 |
| 40 | 7.48 | 6.60 |
| 41 | 7.46 | 7.13 |
| 42 | ≤5.00 | 7.71 |
| 43 | 6.15 | 7.05 |
| 44 | 5.44 | 6.98 |
| 45 | ≤5.00 | 6.65 |
| 46 | 7.11 | — |
| 47 | 7.43 | 6.79 |
| 48 | 7.48 | 5.72 |
| 49 | 7.31 | 7.64 |
| 50 | 6.78 | 6.90 |
| 51 | 7.49 | 6.87 |
| 52 | 7.17 | 6.69 |
| 53 | 7.26 | 5.99 |
| 54 | 6.97 | 7.06 |
| 55 | 7.08 | 6.42 |
| 56 | 6.67 | 6.32 |
| 57 | 6.88 | 5.51 |
| 58 | 7.13 | 5.87 |
| 59 | 6.46 | 6.13 |
| 60 | 6.67 | 4.52 |
| 61 | 6.85 | 7.38 |
| 62 | 7.60 | 8.67 |
| 63 | 7.07 | 8.70 |
| 64 | 6.92 | 8.68 |
| 65 | 7.17 | 8.43 |
| 66 | 7.10 | 9.10 |
| 67 | 7.07 | 8.41 |
| 68 | 7.16 | 9.46 |
| 69 | 7.16 | 9.35 |
| 70 | 6.75 | 9.12 |
| 71 | 7.03 | 9.40 |
| 72 | 7.26 | 5.72 |
| 73 | 7.20 | 5.46 |
| 74 | 7.03 | 5.61 |
| 75 | 6.21 | 5.63 |
| 76 | 5.99 | — |
| 77 | 7.04 | — |
| 78 | 7.10 | — |
| 79 | 6.59 | — |
| 80 | 6.60 | 5.78 |
| 81 | 6.84 | 6.48 |
| 82 | 7.38 | 6.26 |
| 83 | 7.03 | — |
| 84 | 6.39 | 7 02 |
| 85 | 6.13 | 7.26 |
| 86 | 7.08 | — |
| 87 | 6.90 | — |
| 88 | 7.11 | 6.17 |
| 89 | 7.35 | 5.66 |
| 90 | 7.23 | — |
| 91 | 7.23 | — |
| 92 | 7.24 | 7.00 |
| 93 | 6.63 | 6.41 |
| 94 | 6.97 | 6.51 |
| 95 | 6.93 | — |
| 96 | 6.30 | — |
| 97 | 7.31 | — |
| 98 | 6.56 | — |
| 99 | 6.91 | 7.02 |
| 100 | 6.44 | — |
| 101 | 6.40 | 6.55 |
| 102 | 6.68 | 4.82 |
| 103 | 6.66 | 5.00 |
| 104 | 7.21 | 6.10 |
| 105 | 6.97 | 7.01 |
| 106 | 7.24 | 5.70 |
| 107 | 7.37 | 6.61 |
| 108 | 7.46 | 7.12 |
| 109 | 6.55 | — |
| 110 | 7.16 | 5.78 |
| 111 | 6.83 | 7.37 |
| 112 | 6.21 | 6.58 |
| 113 | 6.82 | 6.75 |
| 114 | 6.88 | 6.69 |
| 115 | 6.65 | 7.23 |
| 116 | 7.13 | 6.47 |
| 117 | 7.30 | 8.68 |
| 118 | 7.16 | 7.63 |
| 119 | 7.47 | 8.10 |
| 120 | 6.74 | 7.76 |
| 121 | 6.89 | 7.13 |
| 122 | 7.08 | 6.61 |
| 123 | 5.67 | 5.84 |
| 124 | 7.22 | 8.15 |
| 125 | 6.91 | 7.32 |
| 126 | 6.49 | 6.02 |
| 127 | 7.59 | 6.03 |
| 128 | 7.17 | 6.59 |
| 129 | 7.27 | 6.14 |
| 130 | 7.75 | 7.42 |
| 131 | 7.38 | 7.37 |
| 132 | 6.15 | 5.65 |
| 133 | 6.53 | 6.50 |
| 134 | 7.62 | 6.23 |
| 135 | 7.85 | 6.88 |
| 136 | 7.04 | 7.09 |
| 137 | 5.58 | 4.52 |
| 138 | 6.44 | 4.52 |
| 139 | 6.59 | 5.42 |
| 140 | 6.28 | 4.52 |
| 141 | 6.34 | 5.23 |
| 142 | 7.02 | 6.64 |
| 143 | 6.93 | 6.75 |
| 144 | 7.08 | 7.70 |
| 145 | 7.53 | 7.05 |
| 146 | 7.29 | 7.46 |
| 147 | 7.48 | 8.12 |
| 148 | 7.70 | 6.23 |
| 149 | 7.58 | 6.66 |
| 150 | 7.32 | 7.11 |
| 151 | 7.69 | 7.22 |
| 152 | 7.54 | 6.96 |
| 153 | 7.05 | 5.76 |
| 154 | 7.67 | 6.31 |
| 155 | 7.06 | 6.75 |
| 156 | 6.97 | 6.48 |
| 157 | 6.90 | 6.63 |
| 158 | 7.24 | 7.32 |
| 159 | 7.00 | 7.10 |
| 160 | 6.53 | 4.52 |
| 161 | 8.07 | 6.98 |
| 162 | 7.88 | 6.71 |
| 163 | 7.81 | 5.75 |
| 164 | 7 97 | 6.70 |
| 165 | 7.90 | 7.15 |
| 166 | 7.27 | 5.63 |
| 167 | 7.20 | 6.50 |
| 168 | 7.36 | 6.42 |
| 169 | 7.29 | 7.12 |
| 170 | 7.14 | 7.68 |
| 171 | 7.38 | 7.62 |
| 172 | 7.03 | 6.75 |
| 173 | — | 4.52 |
| 174 | 7.75 | 6.63 |

As used in this specification and the appended claims, singular articles such as "a," "an," and "the," may refer to a single object or to a plurality of objects unless the context clearly indicates otherwise. Thus, for example, reference to a composition containing "a compound" may include a single compound or two or more compounds. The above description is intended to be illustrative and not restrictive. Many embodiments will be apparent to those of skill in the art upon reading the above description. Therefore, the scope of the disclosure should be determined with reference to the appended claims and includes the full scope of equivalents to which such claims are entitled. The disclosures of all articles and references cited in the disclosure, including patents, patent applications and publications, are herein incorporated by reference in their entirety and for all purposes.

What is claimed is:
1. A compound of Formula 1,

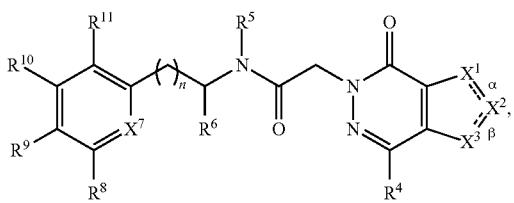

a tautomer thereof, or a pharmaceutically acceptable salt of the compound or tautomer, wherein:
α is a single bond, β is a double bond, $X^1$ is $NR^{1N}$, and either (i) $X^2$ is N and $X^3$ is $CR^{3C}$
or (ii) $X^2$ is $CR^2$ and $X^3$ is selected from N and $CR^{3C}$; or
α is a double bond, β is a single bond, $X^3$ is $NR^{3N}$ and either (i) $X^1$ is N and $X^2$ is $CR^2$; or
(ii) $X^1$ is $CR^1C$ and $X^2$ is selected from N and $CR^2$;
n is selected from 0 and 1;
$R^{1C}$, $R^2$, $R^{3C}$ and $R^4$ are each independently selected from
  (a) hydrogen; and
  (b) $C_{1-6}$ alkyl and $C_{3-8}$ cycloalkyl, each unsubstituted or substituted with 1 to 3 substituents independently selected from halo;
$R^{1N}$ and $R^{3N}$ are each independently selected from $C_{1-6}$ alkyl, $C_{3-8}$ cycloalkyl and $C_{6-10}$ aryl, each unsubstituted or substituted with 1 to 3 substituents independently selected from halo;
$R^5$ is selected from hydrogen and $C_{1-6}$ alkyl, and
$R^6$ is selected from $C_{1-6}$ alkyl and $C_{3-8}$ cycloalkyl; or
$R^5$ and $R^6$, together with the nitrogen and carbon atoms to which they are each respectively attached, form a $C_{3-6}$ heterocyclic ring, the heterocyclic ring being monocyclic and having one ring atom which is a heteroatom;
$X^7$ is selected from N and $CR^7$;
$R^7$ is selected from
  (a) hydrogen, halo, cyano, hydroxy and amino; and
  (b) $C_{1-6}$ alkyl and $C_{1-6}$ alkoxy, each unsubstituted or substituted with 1 to 3 substituents independently selected from halo;
$R^8$ and $R^9$ are each independently selected from
  (a) hydrogen, halo, cyano, hydroxy and amino; and
  (b) $C_{1-6}$ alkyl and $C_{1-6}$ alkoxy, each unsubstituted or substituted with 1 to 3 substituents independently selected from halo; or
$R^8$ and $R^9$, together with the carbon atoms to which they are attached, form a $C_{4-5}$ heterocyclic ring, the heterocyclic ring having one or two ring atoms that are heteroatoms, each of heteroatoms being independently selected from N, O and S;
$R^{10}$ and $R^{11}$ are each independently selected from
  (a) hydrogen, halo, cyano, hydroxy and amino; and
  (b) $C_{1-6}$ alkyl and $C_{1-6}$ alkoxy, each unsubstituted or substituted with 1 to 3 substituents independently selected from halo.

2. The compound, tautomer or pharmaceutically acceptable salt of claim 1, wherein α is a single bond, β is a double bond, $X^1$ is $NR^{1N}$, and either (i) $X^2$ is N and $X^3$ is $CR^{3C}$ or (ii) $X^2$ is $CR^2$ and $X^3$ is selected from N and $CR^{3C}$.

3. The compound, tautomer or pharmaceutically acceptable salt of claim 2, wherein $R^{1N}$ is selected from $C_{1-4}$ alkyl, cyclopropyl and phenyl.

4. The compound, tautomer or pharmaceutically acceptable salt of claim 2, wherein $X^2$ is N and $X^3$ is $CR^{3C}$.

5. The compound, tautomer or pharmaceutically acceptable salt of claim 2, wherein $R^{3C}$ is selected from hydrogen, $C_{1-4}$ alkyl and cyclopropyl.

6. The compound, tautomer or pharmaceutically acceptable salt of claim 1, wherein α is a double bond, β is a single bond, $X^3$ is $NR^{3N}$ and either (i) $X^1$ is N and $X^2$ is $CR^2$ or (ii) $X^1$ is $CR^1C$ and $X^2$ is selected from N and $CR^2$.

7. The compound, tautomer or pharmaceutically acceptable salt of claim 6, wherein $R^{3N}$ is selected from $C_{1-4}$ alkyl and $C_{3-6}$ cycloalkyl.

8. The compound, tautomer or pharmaceutically acceptable salt of claim 6, wherein $X^1$ is $CR^{1C}$ and $X^2$ is selected from N and $CR^2$.

9. The compound, tautomer or pharmaceutically acceptable salt of claim 6, wherein $X^1$ is $CR^{1C}$ and $X^2$ is N.

10. The compound, tautomer or pharmaceutically acceptable salt of claim 9, wherein $R^{1C}$ is selected from hydrogen, $C_{1-4}$ alkyl and cyclopropyl.

11. The compound, tautomer or pharmaceutically acceptable salt of claim 1, wherein $R^2$ is hydrogen.

12. The compound, tautomer or pharmaceutically acceptable salt of claim 1, wherein $R^4$ is selected from hydrogen, $C_{1-4}$ alkyl and cyclopropyl.

13. The compound, tautomer or pharmaceutically acceptable salt of claim 1, wherein $R^5$ is hydrogen.

14. The compound, tautomer or pharmaceutically acceptable salt of claim 1, wherein Re is methyl.

15. The compound, tautomer or pharmaceutically acceptable salt of claim 1, wherein n is 0.

16. The compound, tautomer or pharmaceutically acceptable salt of claim 1, wherein $X^7$ is $CR^7$.

17. The compound, tautomer or pharmaceutically acceptable salt of claim 16, wherein $R^7$ is selected from
  (a) hydrogen and halo; and
  (b) $C_{1-6}$ alkyl and $C_{1-6}$ alkoxy, each unsubstituted or substituted with 1 to 3 substituents independently selected from halo.

18. The compound, tautomer or pharmaceutically acceptable salt of claim 1, wherein $R^8$ is selected from
  (a) hydrogen and halo; and
  (b) $C_{1-6}$ alkyl and $C_{1-6}$ alkoxy, each unsubstituted or substituted with 1 to 3 substituents independently selected from halo.

19. The compound, tautomer or pharmaceutically acceptable salt of claim 1, wherein $R^9$ is selected from
  (a) hydrogen and halo; and
  (b) $C_{1-6}$ alkyl and $C_{1-6}$ alkoxy, each unsubstituted or substituted with 1 to 3 substituents independently selected from halo.

20. The compound, tautomer or pharmaceutically acceptable salt of claim 1, wherein $R^{10}$ is selected from hydrogen, halo and $C_{1-4}$ alkyl which is unsubstituted or substituted with 1 to 3 substituents independently selected from halo.

21. The compound, tautomer or pharmaceutically acceptable salt of claim 1, wherein $R^{11}$ is selected from hydrogen, halo and $C_{1-4}$ alkyl which is unsubstituted or substituted with 1 to 3 substituents independently selected from halo.

22. The compound of claim 1, which is selected from the following compounds:
- (S)-2-(4-methyl-7-oxo-1-phenyl-1,7-dihydro-6H-pyrazolo[3,4-d]pyridazin-6-yl)-N-(1-(p-tolyl)ethyl) acetamide;
- (S)-N-(1-(4-methoxyphenyl)ethyl)-2-(4-methyl-7-oxo-1-phenyl-1,7-dihydro-6H-pyrazolo[3,4-d]pyridazin-6-yl) acetamide;
- (S)-2-(4-isopropyl-7-oxo-1-phenyl-1,7-dihydro-6H-pyrazolo[3,4-d]pyridazin-6-yl)-N-(1-(p-tolyl)ethyl) acetamide;
- (S)-2-(4-isopropyl-7-oxo-1-phenyl-1,7-dihydro-6H-pyrazolo[3,4-d]pyridazin-6-yl)-N-(1-(4-(trifluoromethyl)phenyl)ethyl) acetamide;
- (S)-2-(4-methyl-7-oxo-1-phenyl-1,7-dihydro-6H-pyrazolo[3,4-d]pyridazin-6-yl)-N-(1-(4-(trifluoromethoxy)phenyl)ethyl) acetamide;
- (S)-N-(1-(2-fluoro-4-methylphenyl)ethyl)-2-(4-methyl-7-oxo-1-phenyl-1,7-dihydro-6H-pyrazolo[3,4-d]pyridazin-6-yl) acetamide;
- (S)-2-(4-isopropyl-7-oxo-1-phenyl-1,7-dihydro-6H-pyrazolo[3,4-d]pyridazin-6-yl)-N-(1-(4-(trifluoromethoxy)phenyl)ethyl) acetamide;
- (S)-N-(1-(2-fluoro-4-methylphenyl)ethyl)-2-(4-isopropyl-7-oxo-1-phenyl-1,7-dihydro-6H-pyrazolo[3,4-d]pyridazin-6-yl) acetamide;
- (S)-2-(1-(tert-butyl)-4-methyl-7-oxo-1,7-dihydro-6H-pyrazolo[3,4-d]pyridazin-6-yl)-N-(1-(4-methoxyphenyl)ethyl) acetamide;
- (S)-N-(1-(3-fluoro-4-methoxyphenyl)ethyl)-2-(3-isopropyl-1,7-dimethyl-4-oxo-1H-pyrazolo[3,4-d]pyridazin-5(4H)-yl) acetamide;
- (S)-2-(1-(tert-butyl)-4-isopropyl-7-oxo-1,7-dihydro-6H-pyrazolo[3,4-d]pyridazin-6-yl)-N-(1-(p-tolyl)ethyl) acetamide;
- (S)-2-(1-(tert-butyl)-4-isopropyl-7-oxo-1,7-dihydro-6H-pyrazolo[3,4-d]pyridazin-6-yl)-N-(1-(4-(trifluoromethyl)phenyl)ethyl) acetamide;
- (S)-2-(1-(tert-butyl)-4-methyl-7-oxo-1,7-dihydro-6H-pyrazolo[3,4-d]pyridazin-6-yl)-N-(1-(p-tolyl)ethyl) acetamide;
- (S)-2-(1-(tert-butyl)-4-methyl-7-oxo-1,7-dihydro-6H-pyrazolo[3,4-d]pyridazin-6-yl)-N-(1-(4-(trifluoromethyl)phenyl)ethyl) acetamide;
- (S)-2-(1-(tert-butyl)-4-methyl-7-oxo-1,7-dihydro-6H-pyrazolo[3,4-d]pyridazin-6-yl)-N-(1-(4-(trifluoromethoxy)phenyl)ethyl) acetamide;
- (S)-2-(1-(tert-butyl)-4-methyl-7-oxo-1,7-dihydro-6H-pyrazolo[3,4-d]pyridazin-6-yl)-N-(1-(2-fluoro-4-methylphenyl)ethyl) acetamide;
- (S)-2-(1-isopropyl-3-methyl-4-oxo-1,4-dihydro-5H-pyrazolo[3,4-d]pyridazin-5-yl)-N-(1-(4-methoxyphenyl)ethyl) acetamide;
- (S)-2-(3-cyclopropyl-1-isopropyl-4-oxo-1,4-dihydro-5H-pyrazolo[3,4-d]pyridazin-5-yl)-N-(1-(4-methoxyphenyl)ethyl) acetamide;
- (S)-2-(1,3-dimethyl-4-oxo-1,4-dihydro-5H-pyrazolo[3,4-d]pyridazin-5-yl)-N-(1-(2-fluoro-4-methoxyphenyl)ethyl) acetamide;
- (S)-N-(1-(p-tolyl)ethyl)-2-(1,3,4-trimethyl-7-oxo-1,7-dihydro-6H-pyrazolo[3,4-d]pyridazin-6-yl) acetamide;
- (S)-2-(1-isopropyl-3,4-dimethyl-7-oxo-1,7-dihydro-6H-pyrazolo[3,4-d]pyridazin-6-yl)-N-(1-(p-tolyl)ethyl) acetamide;
- (S)-2-(1-cyclopropyl-3,4-dimethyl-7-oxo-1,7-dihydro-6H-pyrazolo[3,4-d]pyridazin-6-yl)-N-(1-(p-tolyl)ethyl) acetamide;
- (S)-2-(1-isopropyl-3-methyl-7-oxo-1,7-dihydro-6H-pyrazolo[3,4-d]pyridazin-6-yl)-N-(1-(p-tolyl)ethyl) acetamide;
- (S)-N-(1-(4-chloro-2-fluorophenyl)ethyl)-2-(1-cyclopropyl-3-methyl-4-oxo-1,4-dihydro-5H-pyrazolo[3,4-d]pyridazin-5-yl) acetamide;
- (S)-2-(1-cyclopropyl-3-methyl-4-oxo-1,4-dihydro-5H-pyrazolo[3,4-d]pyridazin-5-yl)-N-(1-(3-fluorophenyl)ethyl) acetamide;
- (S)-2-(1-cyclopropyl-3-methyl-4-oxo-1,4-dihydro-5H-pyrazolo[3,4-d]pyridazin-5-yl)-N-(1-(2,5-dimethylphenyl)ethyl) acetamide;
- (S)-2-(1,3-dimethyl-7-oxo-1,7-dihydro-6H-pyrazolo[3,4-d]pyridazin-6-yl)-N-(1-(p-tolyl)ethyl) acetamide;
- (S)-2-(1-cyclopropyl-3-methyl-7-oxo-1,7-dihydro-6H-pyrazolo[3,4-d]pyridazin-6-yl)-N-(1-(p-tolyl)ethyl) acetamide;
- (S)-2-(1,7-dimethyl-4-oxo-1,4-dihydro-5H-imidazo[4,5-d]pyridazin-5-yl)-N-(1-(p-tolyl)ethyl) acetamide;
- (S)-2-(1-cyclopropyl-3-methyl-4-oxo-1,4-dihydro-5H-pyrazolo[3,4-d]pyridazin-5-yl)-N-(1-(2,3-difluorophenyl)ethyl) acetamide;
- (S)-2-(1-cyclopropyl-3-methyl-4-oxo-1,4-dihydro-5H-pyrazolo[3,4-d]pyridazin-5-yl)-N-(1-(4-methoxy-3-methylphenyl)ethyl) acetamide;
- (S)-2-(1-cyclopropyl-3-methyl-4-oxo-1,4-dihydro-5H-pyrazolo[3,4-d]pyridazin-5-yl)-N-(1-(5-(trifluoromethyl)pyridin-2-yl)ethyl) acetamide;
- (S)-2-(1-methyl-4-oxo-1,4-dihydro-5H-pyrazolo[3,4-d]pyridazin-5-yl)-N-(1-(p-tolyl)ethyl) acetamide;
- (S)-2-(1-methyl-4-oxo-1,4-dihydro-5H-pyrazolo[3,4-d]pyridazin-5-yl)-N-(1-(4-(trifluoromethyl)phenyl)ethyl) acetamide;
- (S)-N-(1-(2-fluoro-4-methylphenyl)ethyl)-2-(1-methyl-4-oxo-1,4-dihydro-5H-pyrazolo[3,4-d]pyridazin-5-yl) acetamide;
- (S)-2-(1,3-dimethyl-4-oxo-1,4-dihydro-5H-pyrazolo[3,4-d]pyridazin-5-yl)-N-(1-(p-tolyl)ethyl) acetamide;
- (S)-2-(1,3-dimethyl-4-oxo-1,4-dihydro-5H-pyrazolo[3,4-d]pyridazin-5-yl)-N-(1-(4-(trifluoromethyl)phenyl)ethyl) acetamide;
- (S)-2-(3-cyclopropyl-1-methyl-4-oxo-1,4-dihydro-5H-pyrazolo[3,4-d]pyridazin-5-yl)-N-(1-(p-tolyl)ethyl) acetamide;
- (S)-2-(1,4-dimethyl-7-oxo-1,7-dihydro-6H-pyrazolo[3,4-d]pyridazin-6-yl)-N-(1-(p-tolyl)ethyl) acetamide;
- (S)-2-(1,4-dimethyl-7-oxo-1,7-dihydro-6H-pyrazolo[3,4-d]pyridazin-6-yl)-N-(1-(4-(trifluoromethyl)phenyl)ethyl) acetamide;
- (S)-2-(1,4-dimethyl-7-oxo-1,7-dihydro-6H-pyrazolo[3,4-d]pyridazin-6-yl)-N-(1-(2-fluoro-4-methylphenyl)ethyl) acetamide;
- (S)-2-(4-cyclopropyl-7-oxo-1-phenyl-1,7-dihydro-6H-pyrazolo[3,4-d]pyridazin-6-yl)-N-(1-(2-fluoro-4-methylphenyl)ethyl) acetamide;
- (S)-2-(4-cyclopropyl-7-oxo-1-phenyl-1,7-dihydro-6H-pyrazolo[3,4-d]pyridazin-6-yl)-N-(1-(p-tolyl)ethyl) acetamide;
- (S)-2-(4-cyclopropyl-7-oxo-1-phenyl-1,7-dihydro-6H-pyrazolo[3,4-d]pyridazin-6-yl)-N-(1-(4-(trifluoromethyl)phenyl)ethyl) acetamide;
- (S)-2-(4-cyclopropyl-7-oxo-1-phenyl-1,7-dihydro-6H-pyrazolo[3,4-d]pyridazin-6-yl)-N-(1-(4-(trifluoromethoxy)phenyl)ethyl) acetamide;
- (S)-2-(1-isopropyl-3-methyl-4-oxo-1,4-dihydro-5H-pyrazolo[3,4-d]pyridazin-5-yl)-N-(1-(p-tolyl)ethyl) acetamide;

(S)-2-(1,3-dimethyl-4-oxo-1,4-dihydro-5H-pyrazolo[3,4-d]pyridazin-5-yl)-N-(1-(4-(trifluoromethoxy)phenyl)ethyl) acetamide;

(S)-2-(1,3-dimethyl-4-oxo-1,4-dihydro-5H-pyrazolo[3,4-d]pyridazin-5-yl)-N-(1-(4-methoxyphenyl)ethyl) acetamide;

(S)-N-(1-(2-fluoro-4-methylphenyl)ethyl)-2-(3-isopropyl-1-methyl-4-oxo-1,4-dihydro-5H-pyrazolo[3,4-d]pyridazin-5-yl) acetamide;

(S)-2-(3-isopropyl-1-methyl-4-oxo-1,4-dihydro-5H-pyrazolo[3,4-d]pyridazin-5-yl)-N-(1-(4-(trifluoromethoxy)phenyl)ethyl) acetamide;

(S)-2-(3-isopropyl-1-methyl-4-oxo-1,4-dihydro-5H-pyrazolo[3,4-d]pyridazin-5-yl)-N-(1-(p-tolyl)ethyl) acetamide;

(S)-2-(3-isopropyl-1-methyl-4-oxo-1,4-dihydro-5H-pyrazolo[3,4-d]pyridazin-5-yl)-N-(1-(4-(trifluoromethyl)phenyl)ethyl) acetamide;

(S)-2-(3-isopropyl-1-methyl-4-oxo-1,4-dihydro-5H-pyrazolo[3,4-d]pyridazin-5-yl)-N-(1-(4-methoxyphenyl)ethyl) acetamide;

(S)-N-(1-(2-fluoro-4-methylphenyl)ethyl)-2-(1-isopropyl-3,7-dimethyl-4-oxo-1,4-dihydro-5H-pyrazolo[3,4-d]pyridazin-5-yl) acetamide;

(S)-2-(1-isopropyl-3,7-dimethyl-4-oxo-1,4-dihydro-5H-pyrazolo[3,4-d]pyridazin-5-yl)-N-(1-(p-tolyl)ethyl) acetamide;

(S)-2-(1-isopropyl-3,7-dimethyl-4-oxo-1,4-dihydro-5H-pyrazolo[3,4-d]pyridazin-5-yl)-N-(1-(4-(trifluoromethyl)phenyl)ethyl) acetamide;

(S)-2-(1-isopropyl-3,7-dimethyl-4-oxo-1,4-dihydro-5H-pyrazolo[3,4-d]pyridazin-5-yl)-N-(1-(4-methoxyphenyl)ethyl) acetamide;

(S)-2-(1-cyclopropyl-3-methyl-7-oxo-1,7-dihydro-6H-pyrazolo[3,4-d]pyridazin-6-yl)-N-(1-(5-(trifluoromethyl) pyridin-2-yl)ethyl) acetamide;

(S)-2-(1-isopropyl-3,4-dimethyl-7-oxo-1,7-dihydro-6H-pyrazolo[3,4-d]pyridazin-6-yl)-N-(1-(5-(trifluoromethyl) pyridin-2-yl)ethyl) acetamide;

(S)-2-(1,3-dimethyl-7-oxo-1,7-dihydro-6H-pyrazolo[3,4-d]pyridazin-6-yl)-N-(1-(5-(trifluoromethyl) pyridin-2-yl)ethyl) acetamide;

N-(1-(chroman-6-yl)ethyl)-2-(1-cyclopropyl-3,4-dimethyl-7-oxo-1,7-dihydro-6H-pyrazolo[3,4-d]pyridazin-6-yl) acetamide;

(S)-2-(1-cyclopropyl-3-methyl-4-oxo-1,4-dihydro-5H-pyrrolo[2,3-d]pyridazin-5-yl)-N-(1-(3-fluoro-4-methylphenyl)ethyl) acetamide;

(S)-N-(1-(4-chloro-2-methylphenyl)ethyl)-2-(1-cyclopropyl-3-methyl-4-oxo-1,4-dihydro-5H-pyrrolo[2,3-d]pyridazin-5-yl) acetamide;

(S)-2-(1-cyclopropyl-3-methyl-4-oxo-1,4-dihydro-5H-pyrrolo[2,3-d]pyridazin-5-yl)-N-(1-mesitylethyl) acetamide;

(S)-2-(1-cyclopropyl-3-methyl-4-oxo-1,4-dihydro-5H-pyrrolo[2,3-d]pyridazin-5-yl)-N-(1-(2,4-dimethylphenyl)ethyl) acetamide;

(S)-N-(1-(2-chloro-4-fluorophenyl)ethyl)-2-(1-cyclopropyl-3-methyl-4-oxo-1,4-dihydro-5H-pyrrolo[2,3-d]pyridazin-5-yl) acetamide;

(S)-N-(1-(4-chloro-2-methoxyphenyl) propan-2-yl)-2-(1-cyclopropyl-3-methyl-4-oxo-1,4-dihydro-5H-pyrrolo[2,3-d]pyridazin-5-yl) acetamide;

(S)-2-(1-cyclopropyl-3,4-dimethyl-7-oxo-1,7-dihydro-6H-pyrazolo[3,4-d]pyridazin-6-yl)-N-(1-(3-fluoro-4-methylphenyl)ethyl) acetamide;

(S)-2-(1-cyclopropyl-3,4-dimethyl-7-oxo-1,7-dihydro-6H-pyrazolo[3,4-d]pyridazin-6-yl)-N-(1-(2-fluoro-4-methylphenyl)ethyl) acetamide;

(S)-2-(1-cyclopropyl-3,4-dimethyl-7-oxo-1,7-dihydro-6H-pyrazolo[3,4-d]pyridazin-6-yl)-N-(1-mesitylethyl) acetamide;

(S)-N-(1-(2-chloro-4-fluorophenyl)ethyl)-2-(1-cyclopropyl-3,4-dimethyl-7-oxo-1,7-dihydro-6H-pyrazolo[3,4-d]pyridazin-6-yl) acetamide;

(S)-2-(1,7-dimethyl-4-oxo-1,4-dihydro-5H-pyrazolo[3,4-d]pyridazin-5-yl)-N-(1-(4-(trifluoromethyl)phenyl)ethyl) acetamide;

(S)-2-(1,7-dimethyl-4-oxo-1,4-dihydro-5H-pyrazolo[3,4-d]pyridazin-5-yl)-N-(1-(4-(trifluoromethoxy)phenyl)ethyl) acetamide;

(S)-2-(1,7-dimethyl-4-oxo-1,4-dihydro-5H-pyrazolo[3,4-d]pyridazin-5-yl)-N-(1-(p-tolyl)ethyl) acetamide;

(S)-2-(1-isopropyl-7-methyl-4-oxo-1,4-dihydro-5H-pyrazolo[3,4-d]pyridazin-5-yl)-N-(1-(4-(trifluoromethyl)phenyl)ethyl) acetamide;

(S)-2-(1-isopropyl-7-methyl-4-oxo-1,4-dihydro-5H-pyrazolo[3,4-d]pyridazin-5-yl)-N-(1-(4-(trifluoromethoxy)phenyl)ethyl) acetamide;

(S)-2-(1-isopropyl-7-methyl-4-oxo-1,4-dihydro-5H-pyrazolo[3,4-d]pyridazin-5-yl)-N-(1-(p-tolyl)ethyl) acetamide;

(S)-2-(1-cyclopropyl-7-methyl-4-oxo-1,4-dihydro-5H-pyrazolo[3,4-d]pyridazin-5-yl)-N-(1-(4-(trifluoromethyl)phenyl)ethyl) acetamide;

(S)-2-(1-cyclopropyl-7-methyl-4-oxo-1,4-dihydro-5H-pyrazolo[3,4-d]pyridazin-5-yl)-N-(1-(4-(trifluoromethoxy)phenyl)ethyl) acetamide;

(S)-2-(1-cyclopropyl-7-methyl-4-oxo-1,4-dihydro-5H-pyrazolo[3,4-d]pyridazin-5-yl)-N-(1-(p-tolyl)ethyl) acetamide;

(S)-2-(1-cyclopropyl-7-methyl-4-oxo-1,4-dihydro-5H-pyrazolo[3,4-d]pyridazin-5-yl)-N-(1-(2-fluoro-4-methylphenyl)ethyl) acetamide;

(S)-2-(1,7-dimethyl-4-oxo-1,4-dihydro-5H-pyrazolo[3,4-d]pyridazin-5-yl)-N-(1-(2-fluoro-4-methylphenyl)ethyl) acetamide;

(S)-N-(1-(2-fluoro-4-methylphenyl)ethyl)-2-(1-isopropyl-7-methyl-4-oxo-1,4-dihydro-5H-pyrazolo[3,4-d]pyridazin-5-yl) acetamide;

5-(2-(2-(4-chlorophenyl) pyrrolidin-1-yl)-2-oxoethyl)-3-cyclopropyl-1-methyl-1,5-dihydro-4H-pyrazolo[3,4-d]pyridazin-4-one;

6-(2-(2-(4-chlorophenyl) pyrrolidin-1-yl)-2-oxoethyl)-1-cyclopropyl-3-methyl-1,6-dihydro-7H-pyrazolo[3,4-d]pyridazin-7-one;

(S)-2-(1-isopropyl-4-oxo-1,4-dihydro-5H-pyrazolo[3,4-d]pyridazin-5-yl)-N-(1-(4-(trifluoromethyl)phenyl)ethyl) acetamide;

(S)-2-(1-isopropyl-4-oxo-1,4-dihydro-5H-pyrazolo[3,4-d]pyridazin-5-yl)-N-(1-(4-(trifluoromethoxy)phenyl)ethyl) acetamide;

(S)-N-(1-(2-fluoro-4-methylphenyl)ethyl)-2-(1-isopropyl-4-oxo-1,4-dihydro-5H-pyrazolo[3,4-d]pyridazin-5-yl) acetamide;

(S)-2-(1-isopropyl-4-oxo-1,4-dihydro-5H-pyrazolo[3,4-d]pyridazin-5-yl)-N-(1-(p-tolyl)ethyl) acetamide;

(S)-2-(1-cyclopropyl-4-oxo-1,4-dihydro-5H-pyrazolo[3,4-d]pyridazin-5-yl)-N-(1-(2-fluoro-4-methylphenyl)ethyl) acetamide;

(S)-2-(1-cyclopropyl-4-oxo-1,4-dihydro-5H-pyrazolo[3,4-d]pyridazin-5-yl)-N-(1-(p-tolyl)ethyl) acetamide;

(S)-N-(1-(2-fluoro-4-methylphenyl)ethyl)-2-(1-isopropyl-3-methyl-4-oxo-1,4-dihydro-5H-pyrazolo[3,4-d]pyridazin-5-yl) acetamide;

(S)-2-(1-isopropyl-3-methyl-4-oxo-1,4-dihydro-5H-pyrazolo[3,4-d]pyridazin-5-yl)-N-(1-(4-(trifluoromethoxy)phenyl)ethyl) acetamide;

(S)-2-(1-isopropyl-3-methyl-4-oxo-1,4-dihydro-5H-pyrazolo[3,4-d]pyridazin-5-yl)-N-(1-(4-(trifluoromethyl)phenyl)ethyl) acetamide;

(S)-2-(3-cyclopropyl-1-isopropyl-4-oxo-1,4-dihydro-5H-pyrazolo[3,4-d]pyridazin-5-yl)-N-(1-(2-fluoro-4-methylphenyl)ethyl) acetamide;

(S)-2-(3-cyclopropyl-1-isopropyl-4-oxo-1,4-dihydro-5H-pyrazolo[3,4-d]pyridazin-5-yl)-N-(1-(4-(trifluoromethoxy)phenyl)ethyl) acetamide;

(S)-2-(3-cyclopropyl-1-isopropyl-4-oxo-1,4-dihydro-5H-pyrazolo[3,4-d]pyridazin-5-yl)-N-(1-(p-tolyl)ethyl) acetamide;

(S)-2-(3-cyclopropyl-1-isopropyl-4-oxo-1,4-dihydro-5H-pyrazolo[3,4-d]pyridazin-5-yl)-N-(1-(4-(trifluoromethyl)phenyl)ethyl) acetamide;

(S)-2-(1,3-dimethyl-4-oxo-1,4-dihydro-5H-pyrazolo[3,4-d]pyridazin-5-yl)-N-(1-(2-fluoro-4-methylphenyl)ethyl) acetamide;

(S)-2-(1-isopropyl-3,7-dimethyl-4-oxo-1,4-dihydro-5H-pyrazolo[3,4-d]pyridazin-5-yl)-N-(1-(4-(trifluoromethoxy)phenyl)ethyl) acetamide;

(S)-2-(1-cyclopropyl-3,4-dimethyl-7-oxo-1,7-dihydro-6H-pyrazolo[3,4-d]pyridazin-6-yl)-N-(1-(5-(trifluoromethyl) pyridin-2-yl)ethyl) acetamide;

(S)-N-(1-(5-(trifluoromethyl) pyridin-2-yl)ethyl)-2-(1,3,4-trimethyl-7-oxo-1,7-dihydro-6H-pyrazolo[3,4-d]pyridazin-6-yl) acetamide;

(S)-2-(1-isopropyl-3-methyl-7-oxo-1,7-dihydro-6H-pyrazolo[3,4-d]pyridazin-6-yl)-N-(1-(5-(trifluoromethyl) pyridin-2-yl)ethyl) acetamide;

N-(1-(chroman-6-yl)ethyl)-2-(1-cyclopropyl-3-methyl-4-oxo-1,4-dihydro-5H-pyrazolo[3,4-d]pyridazin-5-yl) acetamide;

2-(1-cyclopropyl-3,4-dimethyl-7-oxo-1,7-dihydro-6H-pyrazolo[3,4-d]pyridazin-6-yl)-N-(1-(2,3-dihydrobenzo[b][1,4]dioxin-6-yl)ethyl) acetamide;

2-(1-cyclopropyl-3-methyl-4-oxo-1,4-dihydro-5H-pyrazolo[3,4-d]pyridazin-5-yl)-N-(1-(2,3-dihydrobenzo[b][1,4]dioxin-6-yl)ethyl) acetamide;

(S)-2-(1-cyclopropyl-3-methyl-4-oxo-1,4-dihydro-5H-pyrazolo[3,4-d]pyridazin-5-yl)-N-(1-(4-(trifluoromethyl)phenyl)ethyl) acetamide;

(S)-2-(1-cyclopropyl-3-methyl-4-oxo-1,4-dihydro-5H-pyrazolo[3,4-d]pyridazin-5-yl)-N-(1-(2-fluoro-4-methylphenyl)ethyl) acetamide;

(S)-2-(1-cyclopropyl-3-methyl-4-oxo-1,4-dihydro-5H-pyrazolo[3,4-d]pyridazin-5-yl)-N-(1-(4-(trifluoromethoxy)phenyl)ethyl) acetamide;

(S)-2-(1-cyclopropyl-3-methyl-4-oxo-1,4-dihydro-5H-pyrazolo[3,4-d]pyridazin-5-yl)-N-(1-(4-methoxyphenyl)ethyl) acetamide;

(S)-N-(1-(2-fluoro-4-methylphenyl)ethyl)-2-(1,3,7-trimethyl-4-oxo-1,4-dihydro-5H-pyrazolo[3,4-d]pyridazin-5-yl) acetamide;

(S)-N-(1-(4-(trifluoromethoxy)phenyl)ethyl)-2-(1,3,7-trimethyl-4-oxo-1,4-dihydro-5H-pyrazolo[3,4-d]pyridazin-5-yl) acetamide;

(S)-N-(1-(p-tolyl)ethyl)-2-(1,3,7-trimethyl-4-oxo-1,4-dihydro-5H-pyrazolo[3,4-d]pyridazin-5-yl) acetamide;

(S)-N-(1-(4-(trifluoromethyl)phenyl)ethyl)-2-(1,3,7-trimethyl-4-oxo-1,4-dihydro-5H-pyrazolo[3,4-d]pyridazin-5-yl) acetamide;

(S)-2-(3-cyclopropyl-1-methyl-4-oxo-1,4-dihydro-5H-pyrazolo[3,4-d]pyridazin-5-yl)-N-(1-(4-(trifluoromethyl)phenyl)ethyl) acetamide;

(S)-2-(3-cyclopropyl-1-methyl-4-oxo-1,4-dihydro-5H-pyrazolo[3,4-d]pyridazin-5-yl)-N-(1-(4-methoxyphenyl)ethyl) acetamide;

(S)-2-(3-cyclopropyl-1,7-dimethyl-4-oxo-1,4-dihydro-5H-pyrazolo[3,4-d]pyridazin-5-yl)-N-(1-(2-fluoro-4-methylphenyl)ethyl) acetamide;

(S)-2-(3-cyclopropyl-1,7-dimethyl-4-oxo-1,4-dihydro-5H-pyrazolo[3,4-d]pyridazin-5-yl)-N-(1-(4-(trifluoromethoxy)phenyl)ethyl) acetamide;

(S)-2-(3-cyclopropyl-1,7-dimethyl-4-oxo-1,4-dihydro-5H-pyrazolo[3,4-d]pyridazin-5-yl)-N-(1-(p-tolyl)ethyl) acetamide;

(S)-2-(3-cyclopropyl-1,7-dimethyl-4-oxo-1,4-dihydro-5H-pyrazolo[3,4-d]pyridazin-5-yl)-N-(1-(4-(trifluoromethyl)phenyl)ethyl) acetamide;

(S)-2-(3-cyclopropyl-1,7-dimethyl-4-oxo-1,4-dihydro-5H-pyrazolo[3,4-d]pyridazin-5-yl)-N-(1-(4-methoxyphenyl)ethyl) acetamide;

(S)-2-(1-cyclopropyl-3-methyl-4-oxo-1,4-dihydro-5H-pyrazolo[3,4-d]pyridazin-5-yl)-N-(1-(p-tolyl)ethyl) acetamide;

(S)-N-(1-(4-methoxyphenyl)ethyl)-2-(1,3,7-trimethyl-4-oxo-1,4-dihydro-5H-pyrazolo[3,4-d]pyridazin-5-yl) acetamide;

(S)-2-(3-cyclopropyl-1-methyl-4-oxo-1,4-dihydro-5H-pyrazolo[3,4-d]pyridazin-5-yl)-N-(1-(2-fluoro-4-methylphenyl)ethyl) acetamide;

(S)-2-(3-cyclopropyl-1-methyl-4-oxo-1,4-dihydro-5H-pyrazolo[3,4-d]pyridazin-5-yl)-N-(1-(4-(trifluoromethoxy)phenyl)ethyl) acetamide;

(S)-N-(1-(2,6-difluorophenyl)ethyl)-2-(1,3-dimethyl-4-oxo-1,4-dihydro-5H-pyrazolo[3,4-d]pyridazin-5-yl) acetamide;

(S)-2-(1-cyclopropyl-3-methyl-4-oxo-1,4-dihydro-5H-pyrazolo[3,4-d]pyridazin-5-yl)-N-(1-(2-fluoro-4-methoxyphenyl)ethyl) acetamide;

(S)-2-(1-cyclopropyl-3-methyl-4-oxo-1,4-dihydro-5H-pyrazolo[3,4-d]pyridazin-5-yl)-N-(1-(2,4-difluorophenyl)ethyl) acetamide;

(S)-2-(1-cyclopropyl-3-methyl-4-oxo-1,4-dihydro-5H-pyrazolo[3,4-d]pyridazin-5-yl)-N-(1-(3-fluoro-4-methoxyphenyl)ethyl) acetamide;

(S)-2-(1-cyclopropyl-3-methyl-4-oxo-1,4-dihydro-5H-pyrazolo[3,4-d]pyridazin-5-yl)-N-(1-(3-fluoro-4-methylphenyl)ethyl) acetamide;

(S)-N-(1-(2-chloro-4-fluorophenyl)ethyl)-2-(1-cyclopropyl-3-methyl-4-oxo-1,4-dihydro-5H-pyrazolo[3,4-d]pyridazin-5-yl) acetamide;

(S)-2-(1-cyclopropyl-3-methyl-4-oxo-1,4-dihydro-5H-pyrazolo[3,4-d]pyridazin-5-yl)-N-(1-(4-fluoro-3-methoxyphenyl)ethyl) acetamide;

(S)-2-(1-cyclopropyl-3-methyl-4-oxo-1,4-dihydro-5H-pyrazolo[3,4-d]pyridazin-5-yl)-N-(1-(2,4,6-trifluorophenyl)ethyl) acetamide;

(S)-2-(1-cyclopropyl-3-methyl-4-oxo-1,4-dihydro-5H-pyrazolo[3,4-d]pyridazin-5-yl)-N-(1-(4-fluoro-3-methylphenyl)ethyl) acetamide;

(S)-2-(1-cyclopropyl-3-methyl-4-oxo-1,4-dihydro-5H-pyrazolo[3,4-d]pyridazin-5-yl)-N-(1-(3,5-difluorophenyl)ethyl) acetamide;

(S)-N-(1-(2-chloro-6-fluorophenyl)ethyl)-2-(1-cyclopropyl-3-methyl-4-oxo-1,4-dihydro-5H-pyrazolo[3,4-d]pyridazin-5-yl) acetamide;

(S)-2-(1,7-dimethyl-4-oxo-1,4-dihydro-5H-imidazo[4,5-d]pyridazin-5-yl)-N-(1-(5-(trifluoromethyl) pyridin-2-yl)ethyl) acetamide;

(S)-2-(3-methyl-4-oxo-3,4-dihydro-5H-imidazo[4,5-d]pyridazin-5-yl)-N-(1-(p-tolyl)ethyl) acetamide;

(S)-2-(3-methyl-4-oxo-3,4-dihydro-5H-imidazo[4,5-d]pyridazin-5-yl)-N-(1-(4-(trifluoromethyl)phenyl)ethyl) acetamide;

(S)-2-(1-methyl-4-oxo-1,4-dihydro-5H-imidazo[4,5-d]pyridazin-5-yl)-N-(1-(p-tolyl)ethyl) acetamide;

(S)-2-(1-methyl-4-oxo-1,4-dihydro-5H-imidazo[4,5-d]pyridazin-5-yl)-N-(1-(4-(trifluoromethyl)phenyl)ethyl) acetamide;

(S)-2-(3-cyclopropyl-1-methyl-7-oxo-1,7-dihydro-6H-pyrazolo[3,4-d]pyridazin-6-yl)-N-(1-(4-(trifluoromethyl)phenyl)ethyl) acetamide;

(S)-2-(3-cyclopropyl-1-methyl-7-oxo-1,7-dihydro-6H-pyrazolo[3,4-d]pyridazin-6-yl)-N-(1-(4-(trifluoromethoxy)phenyl)ethyl) acetamide;

(S)-2-(1-cyclopropyl-3-methyl-4-oxo-1,4-dihydro-5H-pyrrolo[2,3-d]pyridazin-5-yl)-N-(1-(4-(trifluoromethyl)phenyl)ethyl) acetamide;

(S)-2-(1-cyclopropyl-3-methyl-4-oxo-1,4-dihydro-5H-pyrrolo[2,3-d]pyridazin-5-yl)-N-(1-(4-methoxyphenyl)ethyl) acetamide;

(S)-2-(1-cyclopropyl-3-methyl-4-oxo-1,4-dihydro-5H-pyrrolo[2,3-d]pyridazin-5-yl)-N-(1-phenylethyl) acetamide;

(S)-2-(1-cyclopropyl-3-methyl-4-oxo-1,4-dihydro-5H-pyrrolo[2,3-d]pyridazin-5-yl)-N-(1-(p-tolyl)ethyl) acetamide;

(S)-2-(3-cyclopropyl-1-methyl-7-oxo-1,7-dihydro-6H-pyrazolo[3,4-d]pyridazin-6-yl)-N-(1-(3-fluorophenyl)ethyl) acetamide;

(S)-2-(3-cyclopropyl-1-methyl-7-oxo-1,7-dihydro-6H-pyrazolo[3,4-d]pyridazin-6-yl)-N-(1-(p-tolyl)ethyl) acetamide;

(S)-N-(1-(2-chloro-6-fluorophenyl)ethyl)-2-(3-cyclopropyl-1-methyl-7-oxo-1,7-dihydro-6H-pyrazolo[3,4-d]pyridazin-6-yl) acetamide;

(S)-2-(3-cyclopropyl-1-methyl-7-oxo-1,7-dihydro-6H-pyrazolo[3,4-d]pyridazin-6-yl)-N-(1-(3-fluoro-4-methylphenyl)ethyl) acetamide;

(S)-2-(3-cyclopropyl-1-methyl-7-oxo-1,7-dihydro-6H-pyrazolo[3,4-d]pyridazin-6-yl)-N-(1-(2-fluoro-4-methylphenyl)ethyl) acetamide;

(S)-2-(1-methyl-7-oxo-1,7-dihydro-6H-pyrrolo[2,3-d]pyridazin-6-yl)-N-(1-phenylethyl) acetamide;

(S)-N-(1-(3-fluorophenyl)ethyl)-2-(1,3,4-trimethyl-7-oxo-1,7-dihydro-6H-pyrazolo[3,4-d]pyridazin-6-yl) acetamide;

(S)-2-(1-cyclobutyl-3-methyl-4-oxo-1,4-dihydro-5H-pyrazolo[3,4-d]pyridazin-5-yl)-N-(1-(4-(trifluoromethyl)phenyl)ethyl) acetamide;

(S)-2-(1-(bicyclo[1.1.1]pentan-1-yl)-3-methyl-4-oxo-1,4-dihydro-5H-pyrazolo[3,4-d]pyridazin-5-yl)-N-(1-(4-(trifluoromethyl)phenyl)ethyl) acetamide;

(S)-2-(1-(tert-butyl)-3-methyl-4-oxo-1,4-dihydro-5H-pyrazolo[3,4-d]pyridazin-5-yl)-N-(1-(4-(trifluoromethyl)phenyl)ethyl) acetamide;

(S)-2-(3-cyclopropyl-1-methyl-7-oxo-1,7-dihydro-6H-pyrrolo[2,3-d]pyridazin-6-yl)-N-(1-(p-tolyl)ethyl) acetamide;

(S)-2-(3-cyclopropyl-1-methyl-7-oxo-1,7-dihydro-6H-pyrrolo[2,3-d]pyridazin-6-yl)-N-(1-(4-(trifluoromethyl)phenyl)ethyl) acetamide;

(R)-2-(1-cyclopropyl-3-methyl-4-oxo-1,4-dihydro-5H-pyrazolo[3,4-d]pyridazin-5-yl)-N-(1-(4-(trifluoromethyl)phenyl)ethyl) acetamide;

(S)-N-(1-(4-chlorophenyl)ethyl)-2-(1-methyl-7-oxo-1,7-dihydro-6H-pyrrolo[2,3-d]pyridazin-6-yl) acetamide;

(S)-2-(1-methyl-7-oxo-1,7-dihydro-6H-pyrrolo[2,3-d]pyridazin-6-yl)-N-(1-(p-tolyl)ethyl) acetamide;

(S)-N-(1-(4-methoxyphenyl)ethyl)-2-(1-methyl-7-oxo-1,7-dihydro-6H-pyrrolo[2,3-d]pyridazin-6-yl) acetamide;

(S)-2-(1-methyl-7-oxo-1,7-dihydro-6H-pyrrolo[2,3-d]pyridazin-6-yl)-N-(1-(4-(trifluoromethyl)phenyl)ethyl) acetamide;

(S)-N-(1-(2-fluoro-4-methylphenyl)ethyl)-2-(1-methyl-7-oxo-1,7-dihydro-6H-pyrrolo[2,3-d]pyridazin-6-yl) acetamide;

(S)-2-(1-isopropyl-4-oxo-1,4-dihydro-5H-pyrazolo[3,4-d]pyridazin-5-yl)-N-(1-(4-(methyl-d3)phenyl)ethyl) acetamide;

(S)-2-(1-cyclopropyl-3-methyl-4-oxo-1,4-dihydro-5H-pyrazolo[3,4-d]pyridazin-5-yl)-N-(1-(4-(methyl-d3)phenyl)ethyl) acetamide;

(S)-2-(1-isopropyl-3-methyl-4-oxo-1,4-dihydro-5H-pyrazolo[3,4-d]pyridazin-5-yl)-N-(1-(4-(methyl-d3)phenyl)ethyl) acetamide;

(S)-2-(1-methyl-4-oxo-3-(trifluoromethyl)-1,4-dihydro-5H-pyrazolo[3,4-d]pyridazin-5-yl)-N-(1-(p-tolyl)ethyl) acetamide;

(S)-N-(1-(2-fluoro-4-methylphenyl)ethyl)-2-(1-methyl-4-oxo-3-(trifluoromethyl)-1,4-dihydro-5H-pyrazolo[3,4-d]pyridazin-5-yl) acetamide;

(S)-N-(1-(3-fluoro-4-methylphenyl)ethyl)-2-(1-methyl-4-oxo-3-(trifluoromethyl)-1,4-dihydro-5H-pyrazolo[3,4-d]pyridazin-5-yl) acetamide;

(S)-2-(1-methyl-4-oxo-3-(trifluoromethyl)-1,4-dihydro-5H-pyrazolo[3,4-d]pyridazin-5-yl)-N-(1-(4-(trifluoromethyl)phenyl)ethyl) acetamide;

(S)-N-(cyclopropyl (phenyl)methyl)-2-(1-cyclopropyl-3-methyl-4-oxo-1,4-dihydro-5H-pyrazolo[3,4-d]pyridazin-5-yl) acetamide;

(S)-2-(1-methyl-7-oxo-1,7-dihydro-6H-pyrrolo[2,3-d]pyridazin-6-yl)-N-(1-(4-(methyl-d3)phenyl)ethyl) acetamide;

a tautomer of any one of the aforementioned compounds, and a pharmaceutically acceptable salt of any one of the aforementioned compounds or tautomer thereof.

23. A pharmaceutical composition comprising:
a compound, tautomer or pharmaceutically acceptable salt as defined in claim 1; and
a pharmaceutically acceptable excipient.

24. A compound, tautomer or pharmaceutically acceptable salt as defined in claim 1 for use as a medicament.

25. A method for activating GPR139 in a subject in need thereof, the method comprising administering to the subject a compound, tautomer or pharmaceutically acceptable salt as defined in claim 1.

26. A method of reversing, alleviating, or inhibiting the progress of a disease, disorder or condition, or reversing, alleviating, or inhibiting the progress of one or more symptoms of such a disease, disorder or condition in a subject in need thereof, wherein the method comprises administering to the subject a compound, tautomer or pharmaceutically acceptable salt as defined in claim 1, wherein the disease, disorder or condition is associated with GPR139.

27. A method of reversing, alleviating, or inhibiting the progress of a disease, disorder or condition, or reversing, alleviating, or inhibiting the progress of one or more symptoms of such a disease, disorder or condition in a subject in need thereof, wherein the method comprises administering to the subject a compound, tautomer or pharmaceutically acceptable salt as defined in claim 1, wherein the disease, disorder or condition is selected from schizophrenia, autism spectrum disorder, sleep disorders, depression, bipolar disorder, cognitive impairment, attention deficit hyperactivity disorder, post-traumatic stress disorder, substance use disorder, substance abuse, drug addiction, eating disorders, obsessive compulsive disorder, anxiety disorders, epilepsy, pain, fibromyalgia, Alzheimer's disease and Parkinson's disease.

28. A combination comprising a compound, tautomer or pharmaceutically acceptable salt as defined in claim 1, and at least one additional pharmacologically active agent.

* * * * *

UNITED STATES PATENT AND TRADEMARK OFFICE
CERTIFICATE OF CORRECTION

PATENT NO. : 12,370,192 B2
APPLICATION NO. : 17/753803
DATED : July 29, 2025
INVENTOR(S) : Holger Monenschein et al.

It is certified that error appears in the above-identified patent and that said Letters Patent is hereby corrected as shown below:

In the Claims

Claim 14, Column 172, Line 37:
"Re"
Should read as
--$R^6$--.

Claim 22, Column 180, Lines 20-22:
"(S)-2-(1-isopropyl-4-oxo-1,4-dihydro-5H-pyrazolo[3,4-d]pyridazin-5-yl)-N-(1-(4-(methyl-d3)phenyl)ethyl) acetamide;"
Should read as:
--(S)-2-(1-isopropyl-4-oxo-1,4-dihydro-5H-pyrazolo[3,4-d]pyridazin-5-yl)-N-(1-(4-(methyl-$d_3$)phenyl)ethyl)acetamide;--.

Claim 22, Colum 180, Lines 23-25:
"(S)-2-(1-cyclopropyl-3-methyl-4-oxo-1,4-dihydro-5H-pyrazolo[3,4-d]pyridazin-5-yl)-N-(1-(4-(methyl-d3)phenyl)ethyl) acetamide;"
Should read as:
--(S)-2-(1-cyclopropyl-3-methyl-4-oxo-1,4-dihydro-5H-pyrazolo[3,4-d]pyridazin-5-yl)-N-(1-(4-(methyl-$d_3$)phenyl)ethyl)acetamide;--.

Claim 22, Column 180, Lines 26-28:
"(S)-2-(1-isopropyl-3-methyl-4-oxo-1,4-dihydro-5H-pyrazolo[3,4-d]pyridazin-5-yl)-N-(1-(4-(methyl-d3)phenyl)ethyl) acetamide;"
Should read as:
--(S)-2-(1-isopropyl-3-methyl-4-oxo-1,4-dihydro-5H-pyrazolo[3,4-d]pyridazin-5-yl)-N-(1-(4-(methyl-$d_3$)phenyl)ethyl)acetamide;--.

Signed and Sealed this
Twenty-third Day of September, 2025

John A. Squires
*Director of the United States Patent and Trademark Office*

Claim 22, Column 180, Lines 44-46:
"(S)-2-(1-methyl-7-oxo-1,7-dihydro-6H-pyrrolo[2,3-d]pyridazin-6-yl)-N-(1-(4-(methyl-d3)phenyl)ethyl) acetamide;"
Should read as:
--(S)-2-(1-methyl-7-oxo-1,7-dihydro-6H-pyrrolo[2,3-d]pyridazin-6-yl)-N-(1-(4-(methyl-$d_3$)phenyl)ethyl)acetamide;--.